(12) United States Patent
Letourneau et al.

(10) Patent No.: US 11,583,538 B2
(45) Date of Patent: *Feb. 21, 2023

(54) SUBSTITUTED PYRROLO[1,2-A]PYRAZINES AND PYRROLO[1,2-A][1,4]DIAZEPINES AS TREX1 INHIBITORS

(71) Applicant: Venenum Biodesign, LLC, Hamilton, NJ (US)

(72) Inventors: Jeffrey J. Letourneau, East Windsor, NJ (US); Kiruthika Selvarangan Elamparuthi, Princeton Junction, NJ (US); Chia-Yu Huang, West Windsor, NJ (US); Venugopalareddy Bommireddy Venkata, Princeton Junction, NJ (US)

(73) Assignee: VENENUM BIODESIGN, LLC, Hamilton, NJ (US)

( * ) Notice: Subject to any disclaimer, the term of this patent is extended or adjusted under 35 U.S.C. 154(b) by 114 days.

This patent is subject to a terminal disclaimer.

(21) Appl. No.: 17/064,320

(22) Filed: Oct. 6, 2020

(65) Prior Publication Data
US 2021/0015829 A1    Jan. 21, 2021

Related U.S. Application Data

(63) Continuation-in-part of application No. 16/829,655, filed on Mar. 25, 2020, now Pat. No. 11,306,098.

(60) Provisional application No. 62/830,626, filed on Apr. 8, 2019.

(51) Int. Cl.
A61K 31/4985   (2006.01)
A61K 31/551    (2006.01)
C07D 487/04    (2006.01)
A61P 35/00     (2006.01)
A61K 45/06     (2006.01)

(52) U.S. Cl.
CPC ........ A61K 31/551 (2013.01); A61K 31/4985 (2013.01); A61K 45/06 (2013.01); A61P 35/00 (2018.01); C07D 487/04 (2013.01)

(58) Field of Classification Search
CPC . A61K 31/4985; A61K 31/551; C07D 487/04
USPC ............. 514/211.09, 249; 540/567; 544/349
See application file for complete search history.

(56) References Cited

FOREIGN PATENT DOCUMENTS

| WO | 2008032162 A1 | 3/2008 | |
| WO | 2007028654 A1 | 3/2017 | |
| WO | 2019055913 A1 | 3/2019 | |
| WO | WO-2020210032 A1 * | 10/2020 | ......... A61K 31/5517 |

OTHER PUBLICATIONS

Jordan, V. C. Nature Reviews: Drug Discovery, Feb. 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Pub med Compound Record for CI D 10048055, '1-Butyl-4-( dimethylamino )-3-( 1, 1-dioxo-4H-1$1"{6},2,4-benzothiadiazin-3-yl)-1,8-naphthyridin-2-one', U.S. National Library of Medicine, Oct. 25, 2006 (Oct. 25, 2006), pp. 1-8 (https://pubchem.ncbi.ntm.nih.gov/compound/10048055); p. 2 Oct. 25, 2006.
Pubmed Compound Record for CID 21250308, 'Ethyl 4-(3-((4-cyanophenyt)methyl]-1-methyl-2-oxoquinoxalin-5-yl]-5-oxo-5-pyrrotidin-1-ylpentanoate', U.S. National Library of Medicine, Dec. 5, 2007 (Dec. 5, 2007), pp. 1-8 (https://pubchem.ncbi.nlm.nih.gov/compound/21250308); p. 2 Dec. 5, 2007.
Pubmed Compound Record for CID 130002996, 'CID 130002996', U.S. National Library of Medicine, Oct. 7, 2017 (Oct. 7, 2017), pp. 1-6 (https://pubchem.ncbi.nlm.nih.gov/compound/130002996); p. 2 Oct. 7, 2017.
Ablasser, et al., Trex1 Deficiency Triggers Cell-Autonomous Immunity in a cGAS-Dependent Manner 2014.

(Continued)

Primary Examiner — Douglas M Willis
(74) Attorney, Agent, or Firm — Heslin Rothenberg Farley & Mesiti, P.C.

(57) ABSTRACT

The present invention provides compounds of Formula I:

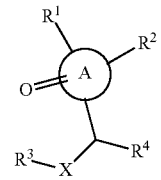

wherein

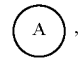

X, $R^1$, $R^2$, $R^3$ and $R^4$ are as defined herein, or a stereoisomer, tautomer, pharmaceutically acceptable salt, prodrug ester or solvate form thereof, wherein all of the variables are as defined herein. These compounds are effective at modulating the TREX1 protein and thus can be used as medicaments for treating or preventing disorders affected by the inhibition of TREX1.

22 Claims, 1 Drawing Sheet

(56) References Cited

OTHER PUBLICATIONS

Stetson, et al., Trex1 Prevents Cell-Intrinsic Initiation Of Autoimmunity 2008.
Vanpouille-Box, et al., DNA exonuclease Trex1 regulates radiotheraphy-induced tumour immunigenicity 2017.
Yan, Immune Diseases Associated with TREX1 and STING Dysfunction 2017.
Yang, Trex1 Exonuclease Degrades ssDNA to Prevent Chronic Checkpoint Activation and Autoimmune Disease 2007.

* cited by examiner

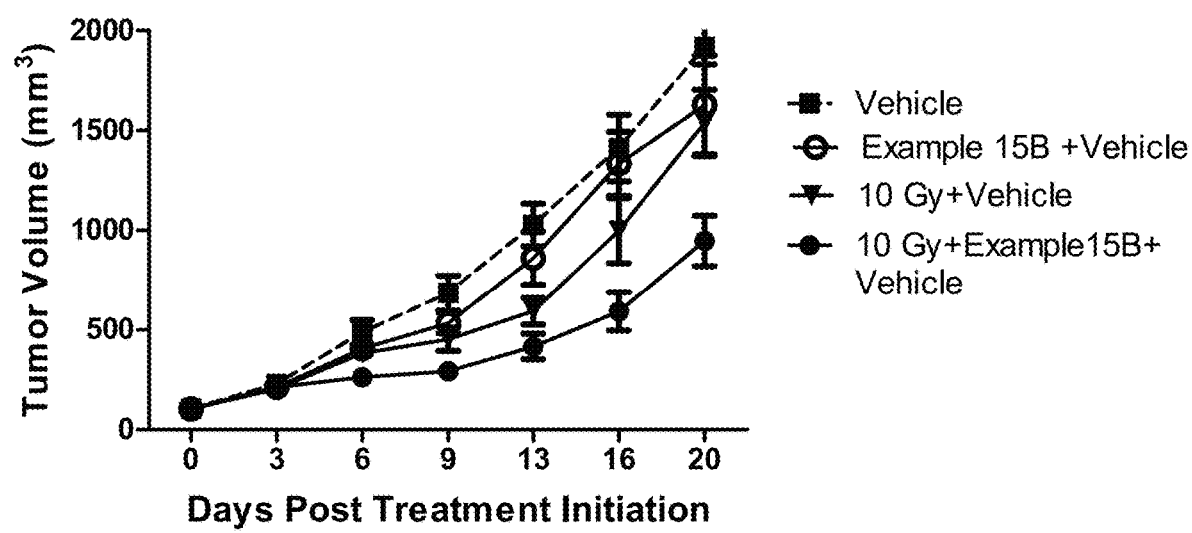

SUBSTITUTED PYRROLO[1,2-A]PYRAZINES AND PYRROLO[1,2-A][1,4]DIAZEPINES AS TREX1 INHIBITORS

CROSS REFERENCE TO RELATED APPLICATIONS

This application is a continuation-in-part of U.S. application Ser. No. 16/829,655, filed Mar. 25, 2020. U.S. application Ser. No. 16/829,655 claims the benefit under 35 U.S.C. § 119 (e) to U.S. Provisional Application No. 62/830,626, filed on Apr. 8, 2019. The contents of both applications are incorporated by reference herein in their entirety.

FIELD OF THE INVENTION

The present invention provides novel cyclic compounds, and analogues thereof, which are three prime repair exonuclease 1 (TREX1) inhibitors and are useful in preventing or treating disorders associated with TREX1. This invention also relates to pharmaceutical compositions containing these compounds and methods of using the same.

BACKGROUND OF THE INVENTION

Three-prime repair exonuclease 1 (gene name TREX-1), also called Deoxyribonuclease III or DNase III, is an enzyme that degrades deoxyribonucleic acid by cleaving the 3' terminal base of a DNA polymer. TREX1 can digest single-stranded and double-stranded DNA containing a mismatched 3' overhang. TREX1 is an endoplasmic reticulum-associated cytosolic protein and can also be found in the nucleus.

TREX1 functions to prevent cell-intrinsic initiation of autoimmunity by degrading cytosolic self DNA from endogenous retroelements (Stetson, D. B et al. (2008) Cell. 134(4). 587-598). TREX 1 prevents chronic ATM-dependent checkpoint activation by processing ssDNA polynucleotide species arising from the processing of aberrant DNA replication intermediates (Yang Y. G. et. al. (2007) Cell 131(5), 873-86). Cytosolic DNA fragments and retroelements are sensed by pattern recognition receptors, such as cyclic GMP-AMP synthase (gene name cGAS). When cGAS binds DNA its enzyme activity is greatly enhanced and it produces cyclic GMP-AMP which serves as a secondary messenger that binds to and activates Stimulator of Interferon Genes (STING) and thereby initiating a type 1 interferon immune response (Wu J. et al., (2012) Science. 339(6121), 826-30; Sun L. et al., (2012). Science. 339(6121). TREX1 DNA degrading activity can attenuate such responses as a check to prevent excessive type 1 interferon responses.

Defects in TREX1 have numerous biological consequences. Defects in TREX1 function are associated with type 1 interferon driven systemic inflammatory and autoimmune conditions. These include Familial Chilblain Lupus, Aicardi-Goutie'res syndrome (AGS), Retinal Vasculopathy and Cerebral leukodystrophy (RVCL) (Ablasser, A. et al. (2014) J. Immun. 192, 5993-5997). Similar to activating mutations of STING (Jeremiah, N. et al. (2014) JCI, 124 (12), 5516-5520), inactivating mutations in TREX1 (Yan, N. et al. (2017) J. Interfer. Cyt. Res. 2017 37(5), 198-206) are associated with type 1 interferon-driven systemic inflammatory and autoimmune conditions. It follows then that TREX1 inhibitors should have the same therapeutic consequence as STING agonists in the context of cancer immunotherapy. TREX1 inhibitors can be used in combinatorial strategies to maximizing the immunogenicity of radiation therapy (Van-pouille-Box (2017) Nature Commun. 8, 81658). Inactivating mutations in TREX1 confers resistance to RNA viruses, including HIV, VSV, influenza, West Nile and Sendai viruses. Therefore, TREX1 inhibition could be used in antiviral therapy as well.

The potential therapeutic benefits of enhancing both innate and adaptive immunity make TREX1 an attractive therapeutic target that demonstrates impressive activity by itself and can also be combined with other immunotherapies.

SUMMARY OF THE INVENTION

In one aspect the invention relates to a compound of Formula I:

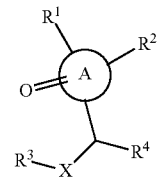

or a stereoisomer, tautomer, pharmaceutically acceptable salt, solvate or prodrug thereof, wherein:

A is a 6 to 7-membered monocyclic heterocyclyl or a 8- to 12-membered bicyclic heterocyclyl, wherein the heterocyclyl contains at least two N atoms;

X is independently selected from $-C(=O)-NR^5-$; $-C(=O)-NHet$, $-C(=O)-NR^5-S(=O)_2-$; $-C_1-C_6$ alkyl-$NR^5-S(=O)_2-$; $-C_1-C_6$ alkyl-$NR^5-C(=O)-$; and a 5-membered nitrogen containing heteroaryl, wherein NHet is a 5 to 7-membered nitrogenous monocyclic heterocyclyl or a 9- to 12-membered nitrogenous bicyclic heterocyclyl attached at a nitrogen, wherein said nitrogenous heterocycle may be optionally substituted with one or more substituents selected from the group consisting of =O, OH, CN, halo, $C_1-C_4$ alkyl, $C_1-C_4$ alkoxy, halo-$C_1-C_4$ alkyl or halo-$C_1-C_4$ alkoxy;

or, X and $R^4$, taken together may form a 5 to 7-membered monocyclic heterocycle, said heterocycle optionally substituted with one or more substituents chosen independently from =O, $-C(=O)R^{25}$, $-SO_2R^{25}$, and $R^{25}$;

$R^1$ is independently selected from $-C_1-C_6$ alkyl-$NR^5R^6$ and $-NR^5R^6$;

$R^2$ is independently selected from $C_1-C_6$ alkyl, $C_6-C_{10}$ aryloxy-$C_1-C_6$-alkyl, $C_6-C_{10}$ aryl-S-$C_1-C_6$-alkyl, $C_6-C_{10}$ aryl-S(=O)-$C_1-C_6$-alkyl, $C_6-C_{10}$ aryl-S(=O)$_2$-$C_1-C_6$-alkyl, $C_6-C_{10}$ aryl-$C_1-C_6$-alkyl, a 5- to 10-membered heteroaryl-oxy-$C_1-C_6$-alkyl, a 5- to 10-membered heteroaryl-S-$C_1-C_6$-alkyl, a 5- to 10-membered heteroaryl-S(=O)-$C_1-C_6$-alkyl, a 5- to 10-membered heteroaryl-S(=O)$_2$-$C_1-C_6$-alkyl and a 5- to 10-membered heteroaryl-$C_1-C_6$-alkyl, wherein any aryl and heteroaryl may be optionally substituted with one or more substituents selected from the group consisting of OH, CN, halo, $C_1-C_4$ alkyl, $C_1-C_4$ alkoxy, halo-$C_1-C_4$ alkyl or halo-$C_1-C_4$ alkoxy;

$R^3$ is independently selected from $C_1-C_6$ alkyl, $C_6-C_{10}$ aryl, $C_6-C_{10}$ aryl-$C_1-C_6$-alkyl, a 5- to 10-membered heteroaryl-$C_1-C_6$-alkyl, and $C_3-C_6$ cycloalkyl-$C_1-C_6$-alkyl; and, when either (a) X is NHet and NHet is a dichloro substituted bicyclic heterocycle, or
(b) X and $R^4$, taken together form a heterocycle substituted with one or more substituents chosen independently from =O, —C(=O)$R^{25}$, —SO$_2$$R^{25}$, and $R^{25}$, then $R^3$ may additionally be H; wherein any cycloalkyl, aryl and heteroaryl, may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_6$ alkoxy;

$R^4$, when it does not form a heterocycle together with X, is $C_1$-$C_6$ alkyl, optionally substituted with one or more substituents selected from the group consisting of OH, CN, —C(=O)OH, —C(=O)O$R^{27}$, —C(=O)N$R^8$$R^9$; —N$R^8$$R^9$; —O—N$R^8$$R^9$; —S(=O)$_2$OH; —S(=O)$_2$N$R^8$$R^9$; —N$R^8$—S(=O)$_2$—$R^9$; —C(=O)N$R^8$—S(=O)$_2$—$R^9$; —C(=O)N$R^8$—S(=O)$_2$—N$R^{28}$$R^{29}$; —N$R^{28}$—C(=O)N$R^8$—S(=O)$_2$—$R^9$; —N$R^{28}$—C(=O)N$R^8$$R^9$; N$R^{28}$—C(=NH)N$R^8$$R^9$, —S(=O)$_2$—$R^9$; —S(=O)—$R^9$; —S—$R^9$; $C_6$-$C_{10}$ aryl, or a 5-membered nitrogen-containing heteroaryl, wherein the aryl and heteroaryl may be optionally substituted with one or more substituents selected from the group consisting of OH, =O, CN, halo, $C_1$-$C_4$ alkyl, $C_1$-$C_4$ alkoxy, halo-$C_1$-$C_4$ alkyl or halo-$C_1$-$C_4$ alkoxy;

$R^5$, at each occurrence, is independently selected from H, $C_1$-$C_6$ alkyl and halo $C_1$-$C_6$ alkyl;

$R^6$ is independently selected from H, $C_1$-$C_6$ alkyl, halo $C_1$-$C_6$ alkyl and —C(=O)$R^7$;

$R^7$ is independently selected from $C_1$-$C_6$ alkyl and $C_1$-$C_6$ alkoxy;

$R^8$ is independently selected from H, $C_1$-$C_4$ alkyl, $C_1$-$C_4$ alkoxy, halo-$C_1$-$C_4$-alkyl, —C(=O)—$C_1$-$C_4$ alkyl, and halo-$C_1$-$C_4$ alkoxy;

$R^9$ is independently selected from H, OH, $C_1$-$C_4$ alkyl, $C_1$-$C_4$ alkoxy, $C_3$-$C_6$ cycloalkyl and $C_6$-$C_{10}$ aryl, wherein the alkyl, alkoxy, cycloalkyl and aryl may be optionally substituted with one or more substituents selected from the group consisting of OH, =O, CN, halo, $C_1$-$C_4$ alkyl, $C_1$-$C_4$ alkoxy, halo-$C_1$-$C_4$ alkyl or halo-$C_1$-$C_4$ alkoxy;

$R^{25}$ is selected from substituted $C_6$-$C_{10}$ aryl, $C_6$-$C_{10}$ aryl-$C_1$-$C_6$-alkyl, a 5- to 10-membered heteroaryl-$C_1$-$C_6$-alkyl, and $C_3$-$C_6$ cycloalkyl-$C_1$-$C_6$-alkyl, wherein substituents are selected from the group consisting of OH, CN, halo, $C_1$-$C_4$ alkyl, $C_1$-$C_4$ alkoxy, halo-$C_1$-$C_4$ alkyl, halo-$C_1$-$C_6$ alkoxy, and $C_1$-$C_6$ alkyl optionally substituted with one or more substituents selected from the group consisting of OH, CN, —C(=O)OH, —C(=O)O$R^{27}$, —C(=O)N$R^8$$R^9$; —N$R^8$$R^9$; —O—N$R^8$$R^9$; —S(=O)$_2$OH; —S(=O)$_2$N$R^8$$R^9$; —N$R^8$—S(=O)$_2$—$R^9$; —C(=O)N$R^8$—S(=O)$_2$—$R^9$; —C(=O)N$R^8$—S(=O)$_2$—N$R^{28}$$R^{29}$; —N$R^{28}$—C(=O)N$R^8$—S(=O)$_2$—$R^9$; —N$R^{28}$—C(=O)N$R^8$$R^9$; —S(=O)$_2$—$R^9$; —S(=O)—$R^9$; —S—$R^9$; $C_6$-$C_{10}$ aryl;

$R^{27}$ is chosen from $C_1$-$C_6$ alkyl, —$C_1$-$C_6$ alkylC(=O)N$R^8$$R^9$, $R^{28}$ is independently selected from H, $C_1$-$C_4$ alkyl, $C_1$-$C_4$ alkoxy, halo-$C_1$-$C_4$-alkyl and halo-$C_1$-$C_4$ alkoxy; and $R^{29}$ is independently selected from H, $C_1$-$C_4$ alkyl, $C_1$-$C_4$ alkoxy, halo-$C_1$-$C_4$-alkyl and halo-$C_1$-$C_4$ alkoxy.

In another aspect the invention relates to a pharmaceutical composition, which comprises a pharmaceutically acceptable carrier and a compound of formula I as described above, or stereoisomers, tautomers, pharmaceutically acceptable salts, or solvates thereof, alone or in combination with another therapeutic agent.

In another aspect the invention relates to a method for the treatment or prophylaxis of a disorder, disease, syndrome, or condition, wherein the disease, syndrome, or condition is affected by the inhibition of TREX1, comprising administering to a subject in need thereof a therapeutically effective amount of a compound of formula I, or a stereoisomer, tautomer, pharmaceutically acceptable salt, solvate or prodrug thereof.

The present invention also relates to processes and intermediates for making the compounds of formula I or stereoisomers, tautomers, pharmaceutically acceptable salts, solvates, or prodrug esters thereof.

The present invention also relates to the use of the compounds of formula I or stereoisomers, tautomers, pharmaceutically acceptable salts, solvates, or prodrug esters thereof, for the manufacture of a medicament for the treatment or prophylaxis of a disorder, disease, syndrome, or condition affected by the inhibition of TREX1.

Other features and advantages of the invention will be apparent from the following detailed description and claims.

BRIEF DESCRIPTION OF THE DRAWINGS

FIG. 1 is a graph of tumor volume versus days post treatment for four treatments: (1) vehicle, (2) example 15B plus vehicle, (3) 10 Gray units (GY) of radiation plus vehicle and (4) 10 GY plus example 15B plus vehicle.

DETAILED DESCRIPTION

In one embodiment, the present invention provides cyclic compounds, stereoisomers, tautomers, salts, solvates or prodrugs thereof, of Formula I having the structure:

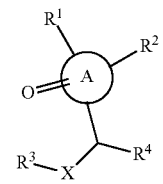

as described above.

In some embodiments A is an 8- to 11-membered bicyclic heterocyclyl, wherein the bicyclic heterocyclyl contains at least two N atoms. In other embodiments, A is an 8- to 10-membered bicyclic heterocyclyl, wherein the bicyclic heterocyclyl contains at least two N atoms. In some embodiments, A is

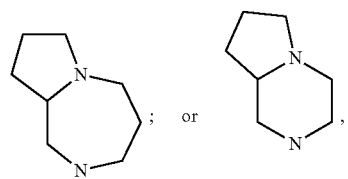 [SMILES: C1CNCC2CCCN2C1 ; C1CC2CNCCN2C1]

and in, narrower embodiments, A is an 8-aminooctahydro-1H-pyrrolo[1,2-a][1,4]diazepin-1-one of formula Ia:

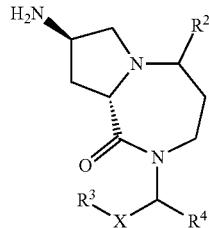

or an 7-aminohexahydropyrrolo[1,2-a]pyrazin-1(2H)-one of formula Ib:

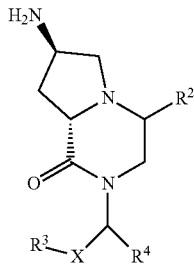

In some embodiments A is a 6- to 7-membered monocyclic heterocyclyl, wherein the heterocyclyl contains at least two N atoms.

In some embodiments, X is independently selected from —C(=O)—NR$^5$—; —C(=O)—NR$^5$—S(=O)$_2$—; —C$_1$-C$_6$ alkyl-NR$^5$—C(=O)—; and a 5-membered nitrogen containing heteroaryl. In some embodiments, X is chosen from —C(=O)NR$^5$—, —C(=O)—NR$^5$—S(=O)$_2$—, and —C(=O)—NHet-. In some embodiments, X is selected from —C(=O)—NR$^5$—; —C$_1$-C$_6$ alkyl-NR$^5$—C(=O)—; and a 5-membered nitrogen containing heteroaryl. In other embodiments, X is selected from —C(=O)—NR$_5$—; and —C$_1$-C$_6$ alkyl-NR$_5$—C(=O)—. In other embodiments, X is —C(=O)—NR$^5$—.

In some embodiments, X and R$^4$, taken together, form a 5 to 7-membered monocyclic heterocycle, and the heterocycle is optionally substituted with one or more substituents chosen independently from =O, —C(=O)R$^{25}$, SO$_2$R$^{25}$, and R$^{25}$. Examples of such X/R$^4$ heterocycles include nitrogenous heterocycles such as

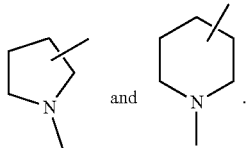

In some embodiments, R$^2$ is chosen from C$_6$-C$_{10}$ aryl-C$_1$-C$_6$-alkyl and 5- to 10-membered heteroaryl-C$_1$-C$_6$-alkyl, wherein aryl and heteroaryl may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_4$ alkoxy. In some embodiments, R$^2$ is phenethyl. In still other embodiments R$^2$ is selected from C$_1$-C$_6$ alkyl, C$_6$-C$_{10}$ aryloxy-C$_1$-C$_6$-alkyl, C$_6$-C$_{10}$ aryl-S—C$_1$-C$_6$-alkyl, C$_6$-C$_{10}$ aryl-S(=O)$_2$—C$_1$-C$_6$-alkyl and C$_6$-C$_{10}$ aryl-C$_1$-C$_6$-alkyl, wherein any aryl may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_4$ alkoxy. In some embodiments, R$^2$ is selected from C$_1$-C$_6$ alkyl, C$_6$-C$_{10}$ aryloxy-C$_1$-C$_6$-alkyl, C$_6$-C$_{10}$ aryl-S—C$_1$-C$_6$-alkyl and C$_6$-C$_{10}$ aryl-C$_1$-C$_6$-alkyl, wherein any aryl may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_4$ alkoxy. In other embodiments, R$^2$ is selected from C$_1$-C$_6$ alkyl and C$_6$-C$_{10}$ aryl-C$_1$-C$_6$-alkyl, wherein the aryl may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_4$ alkoxy.

In other embodiments, R$^3$ is selected from C$_1$-C$_6$ alkyl, C$_6$-C$_{10}$ aryl, C$_6$-C$_{10}$ aryl-C$_1$-C$_6$-alkyl, and a 5- to 10-membered heteroaryl-C$_1$-C$_6$-alkyl, wherein any C$_6$-C$_{10}$ aryl and heteroaryl, may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_6$ alkoxy. In yet another embodiment, R$^3$ is selected from C$_1$-C$_6$ alkyl, C$_6$-C$_{10}$ aryl, C$_6$-C$_{10}$ aryl-C$_1$-C$_6$-alkyl, a 5-membered heteroaryl-C$_1$-C$_6$-alkyl, and a 6-membered heteroaryl-C$_1$-C$_6$-alkyl, wherein any aryl and heteroaryl, may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_6$ alkoxy. In yet another embodiment, R$^3$ is selected from C$_1$-C$_6$ alkyl, C$_6$-C$_{10}$ aryl, and C$_6$-C$_{10}$ aryl-C$_1$-C$_6$-alkyl, wherein any aryl may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_6$ alkoxy. In embodiments in which X is —C(=O)NH— or X and R$^4$ together form a 5 to 7-membered monocyclic heterocycle, R$^3$ may be chosen from

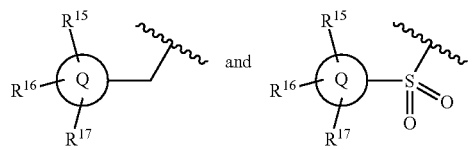

wherein Q is a phenyl or pyridine ring, and R$^{15}$, R$^{16}$, and R$^{17}$ are chosen independently from hydrogen, halogen, (C$_1$-C$_6$) alkoxy, (C$_1$-C$_6$)alkyl, halo(C$_1$-C$_6$)alkyl, and halo(C$_1$-C$_6$) alkoxy.

In some embodiments, R$^4$ is C$_1$-C$_6$ alkyl, optionally substituted with a substituent selected from the group consisting of CN, —C(=O)OH, —C(=O)OR$^{27}$, —NHC(=NH)NH$_2$, —NR$^8$—S(=O)$_2$—R$^9$; and —C(=O)NR$^8$R$^9$. In particular embodiments, R$^4$ is C$_1$-C$_6$ alkyl, optionally substituted with one or more substituents selected from the group consisting of OH, CN, —C(=O)OH, —C(=O)NR$^8$R$^9$; C$_6$-C$_{10}$ aryl, or a 5-membered nitrogen containing heteroaryl, wherein the aryl and heteroaryl may be optionally substituted with OH, =O, CN, halo, C$_1$-C$_4$ alkyl, C$_1$-C$_4$ alkoxy, halo-C$_1$-C$_4$ alkyl or halo-C$_1$-C$_4$ alkoxy; R$^8$ is selected from H, C$_1$-C$_4$ alkyl, C$_1$-C$_4$ alkoxy, halo-C$_1$-C$_4$-alkyl and halo-C$_1$-C$_4$ alkoxy; and R$^9$ is selected from H, C$_1$-C$_4$ alkyl, C$_1$-C$_4$ alkoxy, halo-C$_1$-C$_4$-alkyl and halo-C$_1$-C$_4$ alkoxy.

In exemplary embodiments, the 5-membered nitrogen containing heteroaryl in the definition of R$_4$ is selected from the group consisting of

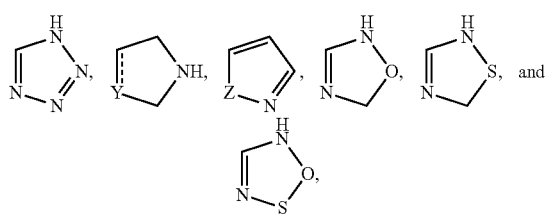

wherein Y is O, S, N or C and Z is O, S, or N(CH$_3$).

In a particular embodiment, A is a 8- to 11-membered bicyclic heterocyclyl, wherein the bicyclic heterocyclyl contains at least two N atoms; X is independently selected from —C(=O)—NR$^5$—; —C(=O)—NR$^5$—S(=O)$_2$—; —C$_1$-C$_6$ alkyl-NR$^5$—C(=O)—; and a 5-membered nitrogen containing heteroaryl; R$^1$ is selected from —C$_1$-C$_6$ alkyl-NR$^5$R$^6$ and —NR$^5$R$^6$; R$^2$ is selected from C$_1$-C$_6$ alkyl, C$_6$-C$_{10}$ aryloxy-C$_1$-C$_6$-alkyl, C$_6$-C$_{10}$ aryl-S—C$_1$-C$_6$-alkyl, C$_6$-C$_{10}$ aryl-S(=O)—C$_1$-C$_6$-alkyl, C$_6$-C$_{10}$ aryl-S(=O)$_2$—C$_1$-C$_6$-alkyl and C$_6$-C$_{10}$ aryl-C$_1$-C$_6$-alkyl, wherein any aryl may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_4$ alkoxy; R$^3$ is independently selected from C$_1$-C$_6$ alkyl, C$_6$-C$_{10}$ aryl, C$_6$-C$_{10}$ aryl-C$_1$-C$_6$-alkyl, and a 5- to 10-membered heteroaryl-C$_1$-C$_6$-alkyl, wherein any C$_6$-C$_{10}$ aryl and heteroaryl, may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_6$ alkoxy; R$^4$ is C$_1$-C$_6$ alkyl, optionally substituted with one or more substituents selected from the group consisting of OH, CN, —C(=O)OH, —C(=O)NR$^8$R$^9$; C$_6$-C$_{10}$ aryl, or a 5-membered nitrogen containing heteroaryl, wherein the aryl or heteroaryl may be optionally substituted with OH, =O, CN, halo, C$_1$-C$_4$ alkyl, C$_1$-C$_4$ alkoxy, halo-C$_1$-C$_4$ alkyl or halo-C$_1$-C$_4$ alkoxy; R$^5$, is selected from H, C$_1$-C$_6$ alkyl and halo C$_1$-C$_6$ alkyl; R$^6$ is selected from H, C$_1$-C$_6$ alkyl, halo C$_1$-C$_6$ alkyl and —C(=O)R$^7$; R$^7$ is selected from C$_1$-C$_6$ alkyl and C$_1$-C$_6$ alkoxy; R$^8$ is selected from H, C$_1$-C$_4$ alkyl, C$_1$-C$_4$ alkoxy, and halo-C$_1$-C$_4$-alkyl; and R$^9$ is selected from H, C$_1$-C$_4$ alkyl, C$_1$-C$_4$ alkoxy, and halo-C$_1$-C$_4$-alkyl.

In yet another embodiment, A is a 8- to 10-membered bicyclic heterocyclyl, wherein the bicyclic heterocyclyl contains at least two N atoms; X is selected from —C(=O)—NR$^5$—; —C$_1$-C$_6$ alkyl-NR$^5$—C(=O)—; and a 5-membered nitrogen containing heteroaryl; R$^1$ is selected from —C$_1$-C$_6$ alkyl-NR$^5$R$^6$ and —NR$^5$R$^6$; R$^2$ is selected from C$_1$-C$_6$ alkyl, C$_6$-C$_{10}$ aryloxy-C$_1$-C$_6$-alkyl, C$_6$-C$_{10}$ aryl-S—C$_1$-C$_6$-alkyl and C$_6$-C$_{10}$ aryl-C$_1$-C$_6$-alkyl, wherein any aryl may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_4$ alkoxy; R$^3$ is independently selected from C$_1$-C$_6$ alkyl, C$_6$-C$_{10}$ aryl, C$_6$-C$_{10}$ aryl-C$_1$-C$_6$-alkyl, and a 5-membered heteroaryl-C$_1$-C$_6$-alkyl, wherein any C$_6$-C$_{10}$ aryl and heteroaryl, may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_6$ alkoxy; R$^4$ is C$_1$-C$_6$ alkyl, optionally substituted with one or more substituents selected from the group consisting of OH, CN, —C(=O)OH, —C(=O)NR$^8$R$^9$; C$_6$-C$_{10}$ aryl, or a 5-membered nitrogen containing heteroaryl, wherein the aryl or heteroaryl may be optionally substituted with OH, =O, CN, halo, C$_1$-C$_4$ alkyl, C$_1$-C$_4$ alkoxy, halo-C$_1$-C$_4$ alkyl or halo-C$_1$-C$_4$ alkoxy; R$^5$, is selected from H, C$_1$-C$_6$ alkyl and halo C$_1$-C$_6$ alkyl; R$^6$ is selected from H, C$_1$-C$_6$ alkyl, halo C$_1$-C$_6$ alkyl and —C(=O)R$^7$; R$^7$ is selected from C$_1$-C$_6$ alkyl and C$_1$-C$_6$ alkoxy; R$^8$ is selected from H, C$_1$-C$_4$ alkyl, C$_1$-C$_4$ alkoxy, and halo-C$_1$-C$_4$-alkyl; and R$^9$ is selected from H, C$_1$-C$_4$ alkyl, C$_1$-C$_4$ alkoxy, and halo-C$_1$-C$_4$-alkyl.

In another embodiment, A is a 8- to 10-membered bicyclic heterocyclyl, wherein the bicyclic heterocyclyl contains at least two N atoms; X is selected from —C(=O)—NR$^5$—; and —C$_1$-C$_6$ alkyl-NR$^5$—C(=O)—; R$^1$ is selected from —C$_1$-C$_6$ alkyl-NR$^5$R$^6$ and —NR$^5$R$^6$; R$^2$ is selected from C$_1$-C$_6$ alkyl, C$_6$-C$_{10}$ aryloxy-C$_1$-C$_6$-alkyl, and C$_6$-C$_{10}$ aryl-C$_1$-C$_6$-alkyl, wherein any aryl may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_4$ alkoxy; R$^3$ is selected from C$_1$-C$_6$ alkyl, C$_6$-C$_{10}$ aryl and C$_6$-C$_{10}$ aryl-C$_1$-C$_6$-alkyl, wherein any C$_6$-C$_{10}$ aryl may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_6$ alkoxy; R$^4$ is C$_1$-C$_6$ alkyl, optionally substituted with one or more substituents selected from the group consisting of OH, CN, —C(=O)OH, —C(=O)NR$^8$R$^9$; or C$_6$-C$_{10}$ aryl, wherein the aryl may be optionally substituted with OH, CN, halo, C$_1$-C$_4$ alkyl, C$_1$-C$_4$ alkoxy, halo-C$_1$-C$_4$ alkyl or halo-C$_1$-C$_4$ alkoxy; R$^5$ is selected from H, C$_1$-C$_6$ alkyl and halo C$_1$-C$_6$ alkyl; R$^6$ is selected from H, C$_1$-C$_6$ alkyl, halo C$_1$-C$_6$ alkyl and —C(=O)R$^7$; R$^7$ is selected from C$_1$-C$_6$ alkyl and C$_1$-C$_6$ alkoxy; R$^8$ is selected from H, C$_1$-C$_4$ alkyl, C$_1$-C$_4$ alkoxy, and halo-C$_1$-C$_4$-alkyl; and R$^9$ is selected from H, C$_1$-C$_4$ alkyl, C$_1$-C$_4$ alkoxy, and halo-C$_1$-C$_4$-alkyl.

In yet another embodiment, A is

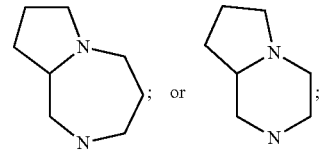 [SMILES: C1CNCC2CCCN2C1 ; C1CC2CNCCN2C1]

X is selected from —C(=O)—NR$^5$—; and —C$_1$-C$_6$ alkyl-NR$^5$—C(=O)—; R$^1$ is selected from —C$_1$-C$_6$ alkyl-NR$^5$R$_6$ and —NR$^5$R$^6$; R$^2$ is selected from C$_1$-C$_6$ alkyl and C$_6$-C$_{10}$ aryl-C$_1$-C$_6$-alkyl, wherein the aryl may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_4$ alkoxy; R$^3$ is selected from C$_1$-C$_6$ alkyl, C$_6$-C$_{10}$ aryl, and C$_6$-C$_{10}$ aryl-C$_1$-C$_6$-alkyl, wherein any C$_6$-C$_{10}$ aryl may be optionally substituted with one or more substituents selected from the group consisting of OH, CN, halo, C$_1$-C$_4$ alkyl, C$_1$-C$_4$ alkoxy, halo-C$_1$-C$_4$ alkyl and halo-C$_1$-C$_6$ alkoxy; R$^4$ is C$_1$-C$_6$ alkyl, optionally substituted with one or more substituents selected from the group consisting of OH, —C(=O)OH, —C(=O)NR$^8$R$^9$; and C$_6$-C$_{10}$ aryl, wherein the aryl may be optionally substituted with OH, CN, halo, C$_1$-C$_4$ alkyl, C$_1$-C$_4$ alkoxy, halo-C$_1$-C$_4$ alkyl or halo-C$_1$-C$_4$ alkoxy; R$^5$, is selected from H and C$_1$-C$_6$ alkyl; R$^6$ is selected from H, C$_1$-C$_6$ alkyl and —C(=O)R$^7$; R$^7$ is selected from C$_1$-C$_6$ alkyl and C$_1$-C$_6$ alkoxy; R$^8$ is selected from H, C$_1$-C$_4$ alkyl and halo-C$_1$-C$_4$-alkyl; and R$^9$ is selected from H, C$_1$-C$_4$ alkyl and halo-C$_1$-C$_4$-alkyl.

In yet another embodiment A is

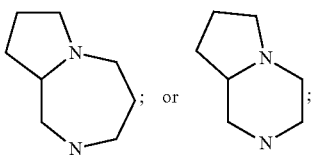 [SMILES: C1CNCC2CCCN2C1 ; C1CC2CNCCN2C1]

X is —C(=O)—NR$^5$—; R$^1$ is —NR$^5$R$^6$; R$^2$ is selected from C$_1$-C$_6$ alkyl and C$_6$-C$_{10}$ aryl-C$_1$-C$_6$-alkyl, wherein the aryl may be optionally substituted with one or more substituents selected from the group consisting of OH, CN, halo, C$_1$-C$_4$ alkyl and halo-C$_1$-C$_4$ alkyl; R$^3$ is selected from C$_1$-C$_6$ alkyl, C$_6$-C$_{10}$ aryl, and C$_6$-C$_{10}$ aryl-C$_1$-C$_6$-alkyl, wherein any C$_6$-C$_{10}$ aryl may be optionally substituted with one or more substituents selected from the group consisting of OH, CN, halo, C$_1$-C$_4$ alkyl and halo-C$_1$-C$_4$ alkyl; R$^4$ is C$_1$-C$_6$ alkyl, optionally substituted with one or more substituents selected from the group consisting of OH, —C(=O)OH, and C$_6$-C$_{10}$ aryl, wherein the aryl may be optionally substituted with OH, CN, halo, C$_1$-C$_4$ alkyl or halo-C$_1$-C$_4$ alkyl; R$^5$ is selected from H and C$_1$-C$_6$ alkyl; R$^6$ is selected from H, C$_1$-C$_6$ alkyl and —C(=O)R$^7$; and R$^7$ is independently selected from C$_1$-C$_6$ alkyl and C$_1$-C$_6$ alkoxy.

In various embodiments, the present invention provides compounds, stereoisomers, tautomers, salts, solvates or prodrugs thereof, wherein the compound is selected from compounds set forth in the examples.

The compounds, stereoisomers, tautomers, salts, solvates or prodrugs of the invention have IC$_{50}$ values in the TREX1 exonuclease assay (described hereinafter) of about 100 μM or less, preferably 50 μM or less, and more preferably 25 μM or less, even more preferably 10 μM or less. Activity data for compounds, stereoisomers, tautomers, salts, solvates or prodrugs of the present invention are presented in Table 28.

In some embodiments, the present invention provides a pharmaceutical composition, which includes a pharmaceutically acceptable carrier and a therapeutically effective amount of a compound of Formula I, preferably, a compound selected from one of the examples, or stereoisomers, tautomers, pharmaceutically acceptable salts, prodrug esters, or solvates thereof, alone or in combination with another therapeutic agent.

In some embodiments, the present invention provides a pharmaceutical composition which further includes another therapeutic agent(s). In a preferred embodiment, the present invention provides a pharmaceutical composition, wherein the additional therapeutic agent(s) are an anti-cancer agent, an anti-viral compound, an antigen, an adjuvant, a lipid, a liposome, a peptide, a cytotoxic agent, a chemotherapeutic agent, an immunomodulatory cell line, a checkpoint inhibitor (such as an anti-PD1 or an anti-PD-L1 agent), a biotherapeutic agent, an immunogenic agent, and cells transfected with genes encoding immune stimulating cytokines or a combination thereof. Preferably, the additional therapeutic agents are VEGF, VEGFR, EGFR, Her2/neu, other growth factor receptors, CD20, CD40, CD-40L, CTLA-4, OX-40, 4-1BB, ICOS, IL-2, IFNa2, GM-CSF, a STING agonist, another TREX1 inhibitor, a CTLA-4 pathway antagonist, a LAG-3 pathway antagonist, a PD-1 pathway antagonist, a PD-L1 antibody, a vascular endothelial growth factor (VEGF) receptor inhibitor, a topoisomerase II inhibitor, a smoothen inhibitor, an alkylating agent, an anti-tumor antibiotic, an anti-metabolite, a retinoid, Tim-3/gal9, CD73 inhibitors, adenosine A2A+/−A2B antagonists and an anti-cancer vaccine.

In one embodiment, the present invention provides a pharmaceutical composition which is utilized in combination with radiation therapy.

In some embodiments, the present invention provides a method for the treatment or prophylaxis of a disorder, disease, syndrome, or condition, wherein the disease, syndrome, or condition is affected by the inhibition of TREX1, which includes the step of administering to a subject (for example, a human) in need of such treatment or prophylaxis a therapeutically effective amount of at least one of the compounds of the present invention or stereoisomers, tautomers, pharmaceutically acceptable salts, solvates, or prodrug esters thereof.

In some embodiments, the present invention provides methods for the treatment of a disorder, disease, syndrome, or condition affected by the inhibition of TREX1, which includes the steps of administering to a patient (for example, a human) in need thereof a therapeutically effective amount of a compound of Formula I, preferably, a compound selected from one of the examples, more preferably, Examples 4, 15B, 16, 21, 22, 24, 27, 30, 31, 32, 75, 77, 88, 89, 92, 93, 101, 102, 104, 106, 116, 117, 118, 119, 120, 121, 122, 130, 133, 137, 138, 140, 142, 144, 146, or stereoisomers, tautomers, pharmaceutically acceptable salts, prodrug esters, or solvates thereof, wherein the disorder, disease, syndrome, or condition is selected cancer or a viral infection. In particular, the cancer may be melanoma, colon cancer, breast cancer, prostate cancer, lung cancer, bladder cancer or fibrosarcoma; and the viral infection may be HIV. In a particular embodiment, the cancer is non-muscle invasive bladder cancer with BCG resistance.

In some embodiments, the present invention provides a process for making a compound of formula 1 or a stereoisomer, tautomer, pharmaceutically acceptable salt, solvate or prodrug ester thereof.

In some embodiments, the present invention provides an intermediate for making a compound of formula 1.

In some embodiments, the present invention provides a compound of the present invention or stereoisomers, tautomers, pharmaceutically acceptable salts, solvates, or prodrug esters thereof, for use in therapy for the treatment or prophylaxis of a disorder, disease, syndrome, or condition affected by the inhibition of TREX1.

In some embodiments, the present invention also provides the use of a compound of the present invention or stereoisomers, tautomers, pharmaceutically acceptable salts, solvates, or prodrug esters thereof, for the manufacture of a medicament for the treatment or prophylaxis of a disorder, disease, syndrome, or condition affected by the inhibition of TREX1.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Chemistry

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. Preferably, diastereomers are resolved prior to any type of in vitro or in vivo testing. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

In the synthesis of the compounds in tables below wherein A is an 8-aminooctahydro-1H-pyrrolo[1,2-a][1,4]diazepin-1-one, the 7-membered ring is commonly formed via an intramolecular reductive amination reaction. This method consistently gives rise to a mixture of diastereomers which are epimeric at C(5) of the 7-ring (the position bearing the $R^2$ substituent):

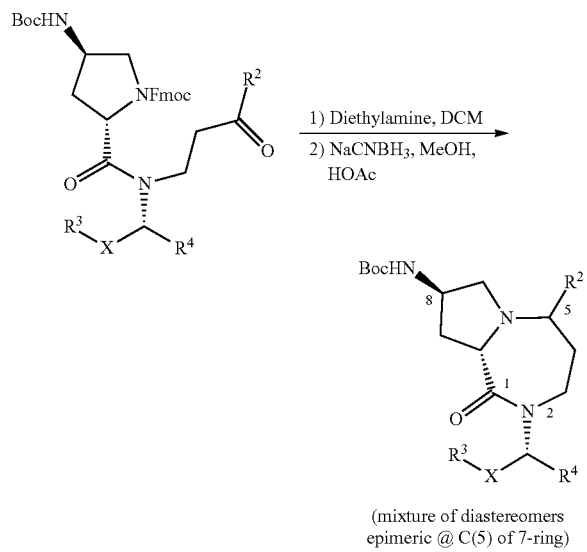

(mixture of diastereomers epimeric @ C(5) of 7-ring)

The diastereomers can normally be separated at this stage via column chromatography and it has been observed that the "major" diastereomer is commonly more potent. For that reason, in many cases only the "major" diastereomer has been isolated and carried forward. The absolute stereochemical configuration at C(5) of the 7-ring has not been definitively ascertained, and so the structures in the tables do not indicate the stereochemistry. Each compound whose activity is shown in the table is a single diastereomer with unknown configuration at C(5). In a small number of cases both the "major" and "minor" diastereomers were isolated and carried forward independently to final analogs. One such pair of compounds that are epimeric at C(5) with respect to one another are compounds 2-3A (minor diastereomer) and compound 2-3B (major diasteromer), which were each independently carried forward to prepare Example 2A and Example 2B respectively. Another pair of final examples that are epimeric at C(5) with respect to one another are Example 15A and Example 15B.

In some embodiments, the compounds of the invention will be isomers in which the carbon attached to X, $R^4$ and the $N^2$ nitrogen of the pyrrolo[1,2-a][1,4]diazepine is greater than 95% isomeric excess in one configuration. Similarly, the carbon at the ring junction of the pyrrolo[1,2-a][1,4]diazepine (9a), the carbon at C(8), and the carbon at C(5) may be greater than 95% isomeric excess in one configuration. In some embodiments one or more will be greater than 95% in the (R) configuration; in other embodiments one or more will be greater than 95% in the (S) configuration. The term "optically pure" may be used to describe compositions contain at least 90% by weight of one enantiomer and 10% by weight or less of the other. In a more preferred embodiment the term "substantially optically pure" means that the composition contains at least 99% by weight of one enantiomer, and 1% or less of the opposite enantiomer.

As used herein, the term "alkyl" or "alkylene", alone or as part of another group, is intended to include both branched and straight-chain saturated aliphatic hydrocarbon groups having from 1 to 10 carbons or the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl), as well as chain isomers thereof, and the like. Alkyl groups may carry substituents such as F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio as well as (=O), $OR^{18}$, $SR^{18}$, (=S), —$NR^{18}R^{19}$, —$N(alkyl)_3^+$, —NR"$SO_2$, —NR"$SO_2R^{20}$, —$SO_2R^{20}$, —$SO_2NR^{18}R^{19}$, —$SO_2NR^{18}C(=O)R^{19}$, $SO_3H$, —$PO(OH)_2$, —$C(=O)R^{18}$, —$CO_2R^{18}$, —$C(=O)NR^{18}R^{19}$, —$C(=O)(C_1$-$C_4$ alkylene)$NR^{18}R^{19}$, —$C(=O)NR^{18}(SO_2)R^{19}$, —$CO_2(C_1$-$C_4$ alkylene)$NR^{18}R^{19}$, —$NR^{18}C(=O)R^{19}$, —$NR^{18}CO_2R^{19}$, —$NR^{18}(C_1$-$C_4$ alkylene)$CO_2R^{19}$, =N—OH, =N—O-alkyl, wherein $R^{18}$ and $R^{19}$ are the same or different and are independently selected from hydrogen, alkyl, alkenyl, $CO_2H$, $CO_2$(alkyl), $C_3$-$C_7$cycloalkyl, phenyl, benzyl, phenylethyl, naphthyl, a 4- to 7-membered heterocyclo, or a 5- to 6-membered heteroaryl, or when attached to the same nitrogen atom may join to form a heterocyclo or heteroaryl, and $R^{20}$ is selected from same groups as $R^{18}$ and $R^{19}$ but is not hydrogen. Each group $R^{18}$ and $R^{19}$ when other than hydrogen, and each $R^{20}$ group optionally has up to three further substituents attached at any available carbon or nitrogen atom of $R^{18}$, $R^{19}$, and/or $R^{20}$, said substituent(s) being the same or different and are independently selected from the group consisting of ($C_1$-$C_6$)alkyl, ($C_2$-$C_6$)alkenyl, hydroxy, halogen, cyano, nitro, $CF_3$, $O(C_1$-$C_6$ alkyl), $OCF_3$, $C(=O)H$, $C(=O)(C_1$-$C_6$ alkyl), $CO_2H$, $CO_2(C_1$-$C_6$ alkyl), $NHCO_2(C_1$-$C_6$ alkyl), —$S(C_1$-$C_6$ alkyl), —$NH_2$, $NH(C_1$-$C_6$ alkyl), $N(C_1$-$C_6$ alkyl)$_2$, $N(CH_3)_3^+$, $SO_2(C_1$-$C_6$ alkyl), $C(=O)(C_1$-$C_4$ alkylene)$NH_2$, $C(=O)(C_1$-$C_4$ alkylene)NH(alkyl), $C(=O)(C_1$-$C_4$ alkylene)N($C_1$-$C_4$ alkyl)$_2$, $C_3$-$C_7$ cycloalkyl, phenyl, benzyl, phenylethyl, phenyloxy, benzyloxy, naphthyl, a 4- to 7-membered heterocyclo, or a 5- to 6-membered heteroaryl. When a substituted alkyl is substituted with an aryl, heterocyclo, cycloalkyl, or heteroaryl group, said ringed systems are as defined below and thus may have zero, one, two, or three substituents, also as defined below.

"Alkenyl" or "alkenylene", alone or as part of another group, is intended to include hydrocarbon chains of either straight or branched configuration and having one or more carbon-carbon double bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl. Alkenyl groups may be optionally substituted with 1 to 4 substituents such as halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, and/or alkylthio.

"Alkynyl" or "alkynylene", alone or as part of another group, is intended to include hydrocarbon chains of either straight or branched configuration and having one or more carbon-carbon triple bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl. Alkynyl groups may be substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio.

The term "alkoxy" or "alkyloxy", alone or as part of another group, refers to an —O-alkyl group, where alkyl is as defined above. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy", alone or as part of another group, represents an alkyl group or alkoxy group as defined above with the indicated number of carbon atoms attached through a sulphur bridge; for example methyl-S— and ethyl-S—.

"Halo" or "halogen", alone or as part of another group, includes fluoro, chloro, bromo, and iodo.

"Halo-$C_1$-$C_6$-alkyl" or "Haloalkyl" is intended to include both branched and straight-chain saturated aliphatic hydrocarbon groups having the specified number of carbon atoms, substituted with 1 to 7 halogens, preferably 1 to 4 halogens, preferably F and/or Cl. Examples of haloalkyl include, but are not limited to, fluoromethyl, difluoromethyl, trifluoromethyl, trichloromethyl, pentafluoroethyl, pentachloroethyl, 1,1-difluoroethyl, 1-fluoroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 to 7 fluorine atoms, preferably 1 to 4 fluorine atoms.

"Halo-$C_1$-$C_4$-alkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 10 carbons forming the ring ($C_3$-$C_{10}$ cycloalkyl), and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl, cyclobutenyl, norbornyl,

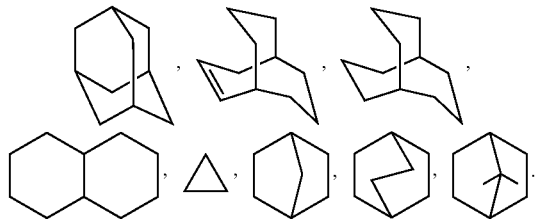

Cycloalkyl groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl, as well as such groups including 2 free bonds and thus are linking groups.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., Hawley's Condensed Chemical Dictionary, 13th Edition, John Wiley & Sons, Inc., New York (1997). "$C_{6-10}$ aryl" includes phenyl and naphthyl. Unless otherwise specified, "aryl", "$C_{6-10}$ aryl" or "aromatic residue" may be unsubstituted or substituted with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, $C(=O)CH_3$, $SCH_3$, $S(=O)CH_3$, $S(=O)_2CH_3$, $C_1$-$C_3$ alkyl, $CO_2H$, and $CO_2CH_3$.

As used herein, the term "heterocycle," "heterocyclo", "heterocyclyl" or "heterocyclic" group is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may optionally be substituted on carbon or on a nitrogen atom if the resulting compound is stable, with 1 to 3 groups selected from OH, OC$_1$-C$_3$ alkoxy, Cl, F, Br, I, CN, NO$_2$, NH$_2$, N(CH$_3$)H, N(CH$_3$)$_2$, CF$_3$, OCF$_3$, OCHF$_2$, =O, C(=O)CH$_3$, SCH$_3$, S(=O)CH$_3$, S(=O)$_2$CH$_3$, C$_1$-C$_3$ alkyl, CO$_2$H and CO$_2$CH$_3$. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Spiro and bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. When the term "heterocycle" or "heterocyclyl" is used, it implies an aliphatic heterocycle, not a heteroaryl.

Exemplary monocyclic heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include quinuclidinyl.

Preferred heterocyclo groups include:

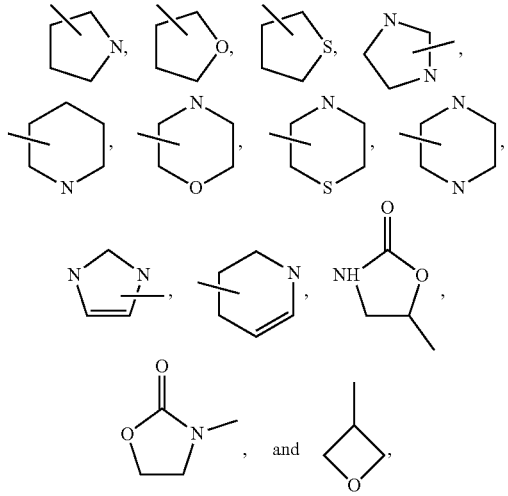

which optionally may be substituted.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are unsubstituted or substituted with 1 to 3 groups selected from OH, OC$_1$-C$_3$ alkoxy, Cl, F, Br, I, CN, NO$_2$, NH$_2$, N(CH$_3$)H, N(CH$_3$)$_2$, CF$_3$, OCF$_3$, OCHF$_2$, =O, C(=O)CH$_3$, SCH$_3$, S(=O)CH$_3$, S(=O)$_2$CH$_3$, C$_1$-C$_3$ alkyl, CO$_2$H and CO$_2$CH$_3$. The nitrogen atom is substituted or unsubstituted (i.e., N or NR wherein R is H or another substituent, if defined). For the purpose of this application, 2-oxopyridines, including those substituted on nitrogen, will be considered heteroaryl. The nitrogen and sulfur heteroatoms may optionally be oxidized (i.e., N→O and S(O)$_p$, wherein p is 0, 1 or 2). Preferred heteroaryl groups include:

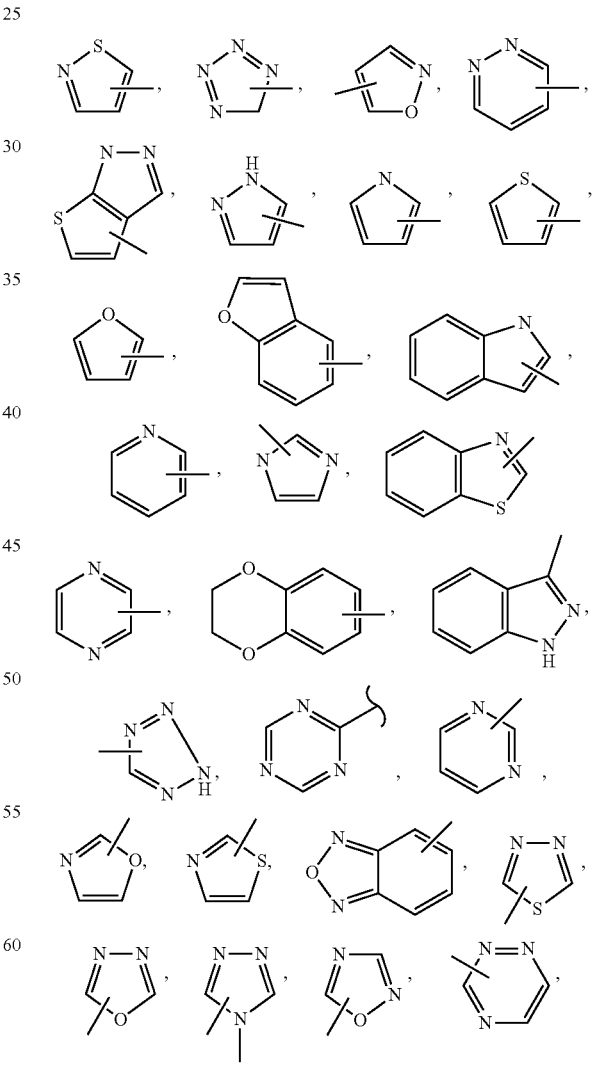

and the like.

The designation "〰" or

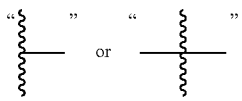

attached to a ring or other group refers to a free bond or linking group.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bonds.

When any variable occurs more than one time in any constituent or formula for a compound, its definition at each occurrence is independent of its definition at every other occurrence. Thus, for example, if a group is shown to be substituted with 0 to 3 $R^{10}$, then said group may optionally be substituted with up to three $R^{10}$ groups, and at each occurrence $R^{10}$ is selected independently from the definition of $R^{10}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington: *The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

Isotopically labeled compounds of the present invention, i.e., wherein one or more of the atoms described are replaced by an isotope of that atom (e.g., $^{12}C$ replaced by $^{13}C$ or by $^{14}C$; and isotopes of hydrogen including tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, methanolates, and isopropanolates. Methods of solvation are generally known in the art.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

During the chemical syntheses, various protecting groups may be employed and subsequently removed in order to generate the compounds of the present invention. Exemplary protecting groups and conditions for their removal are described in Greene's *Protecting Groups in Organic Synthesis* P. G. M. Wuts, T. W. Greene, Fourth Edition, Wiley, New York, 2006.

EXAMPLES

The following compounds of the invention have been prepared, isolated and characterized using the methods disclosed herein. They demonstrate a partial scope of the invention and are not meant to be limiting of the scope of the invention.

General Synthetic Schemes

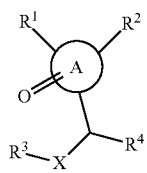

The compounds of the present invention were prepared by methods well known in the art of synthetic organic chemistry. During synthetic sequences it was sometimes necessary or desirable to protect sensitive or reactive groups on any of the molecules concerned. This was achieved by means of conventional protecting groups, such as those described in T. W. Greene and P. G. M. Wuts '*Greene's Protective Groups in Organic Synthesis*' Fourth edition, John Wiley and Sons, 2006. The protecting groups were removed at a convenient subsequent stage using methods well known in the art.

In general compounds of the present invention can be prepared by the methods illustrated in the general reaction schemes described below, or by modifications thereof, using readily available starting materials, reagents and conventional synthetic procedures. However, those skilled in the art will recognize that other methods may also be suitable. Also, in these reactions, it is possible to make use of variants that are in themselves known, but are not mentioned here. In the schemes below, the variables shown are defined as in Formula (I).

Compounds where $R^1$ is $-NH_2$,

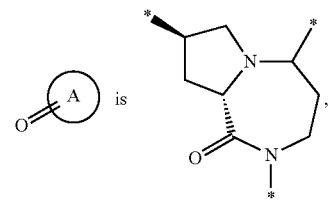

X is $-C(=O)-NR^5$ and $R^5$ is $-H$ (shown as 11 below) can be prepared by the general synthetic sequence shown in Scheme 1, Scheme 2, or Scheme 3.

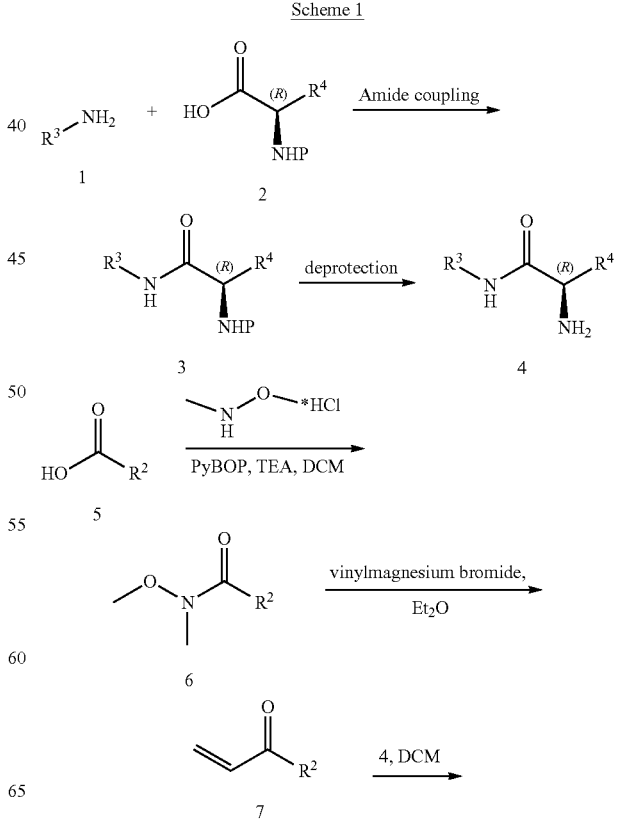

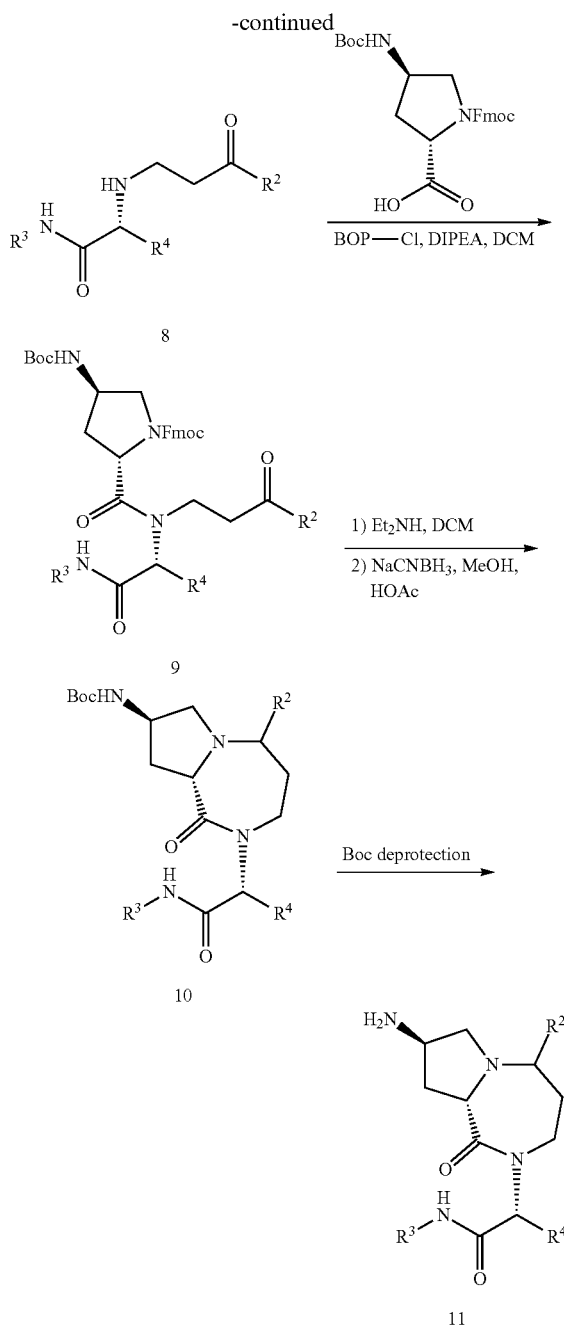

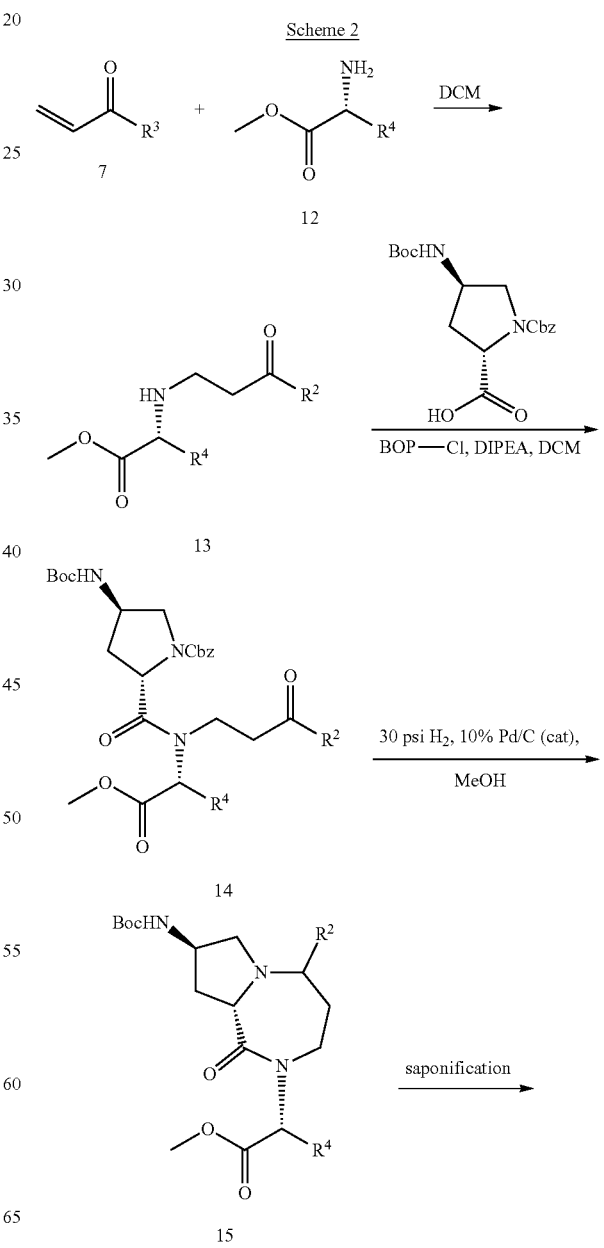

will provide the Michael addition adduct 8. Acylation of 8 with (2S,4R)-1-(((9H-fluoren-9-yl)methoxy)carbonyl)-4-((tert-butoxycarbonyl)amino)pyrrolidine-2-carboxylic acid, which is commercially available or otherwise can be prepared by procedures well known in the art, utilizing the coupling reagent BOP—Cl in the presence of a tertiary amine base such as DIPEA or TEA will give amide 9. Deprotection of the Fmoc protecting group in 9 with diethylamine in DCM, followed by an intramolecular reductive amination reaction using a suitable reducing agent such as sodium cyanoborohydride will provide 10. Deprotection of the Boc-protected amino group under conditions well known to those in the art (e.g. with acidic reagents such as TFA, HCl in MeOH, or formic acid) will then give compounds of formula 11.

First, an appropriately protected (i.e. P is a protecting group) amino acid 2 is converted to amide 3 by reaction with an amine 1 utilizing appropriate coupling reagents. One example would be to couple 1 and 2 utilizing EDAC and HOBt in a suitable solvent such as dichloromethane or DMF at ambient temperature. Any number of suitable protecting groups (P) can be utilized with Boc or Cbz being two such examples. The protecting group in 3 is then removed to give amine 4. Reaction of Carboxylic acid 5 with N,O-dimethylhydroxyl amine hydrochloride in the presence of a suitable base such as DIPEA and a suitable coupling reagent such as PyBOP will give Weinreb amide 6 which can then be reacted with vinyl magnesium bromide to afford enone 7. Reaction of amine 4 with enone 7 in a suitable solvent such as DCM 23
-continued

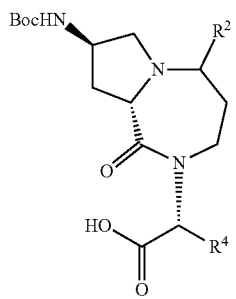

16

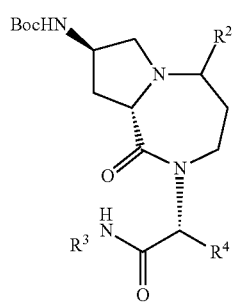

10

Alternatively compounds of general formula 11 can be prepared as shown in Scheme 2. Reaction of enone 7 with an amino acid methyl ester 12 in DCM will provide the Michael addition adduct 13. Acylation of 13 with (2S,4R)-1-((benzyloxy)carbonyl)-4-((tert-butoxycarbonyl)amino)pyrrolidine-2-carboxylic acid, which is commercially available or otherwise can be prepared by procedures well known in the art, utilizing the coupling reagent BOP—Cl in the presence of a tertiary amine base such as DIPEA or TEA will give amide 14. Reaction of 14 under an atmosphere of hydrogen gas at elevated pressure (e.g. 30-40 psi) in the presence of suitable catalyst such as 10% Pd/C will remove the Cbz protecting group, and after subsequent intramolecular reductive amination, provide 15. Saponification of the methyl ester with LiOH or NaOH, in a suitable solvent system such as aqueous methanol, a mixture of dioxane and water or a mixture of MeOH, THF and H$_2$O, for example, will provide carboxylic acid 16. Coupling of carboxylic acid 16 with an amine (R$^3$NH$_2$) in the presence of a suitable

24 coupling reagent such as HATU in a solvent such as DMF will give amide 10. Deprotection of the Boc-protected amino group under conditions well known to those in the art (e.g. with acidic reagents such as TFA, HCl in MeOH, or formic acid) will then give compounds of 11.

Scheme 3

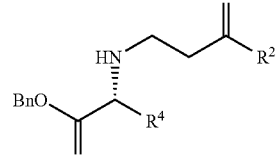

7                17

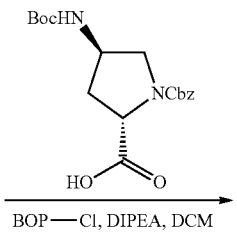

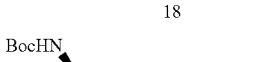

18

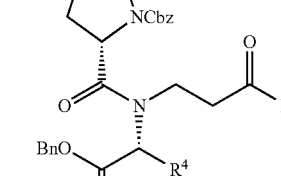

19

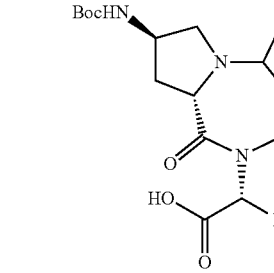

20

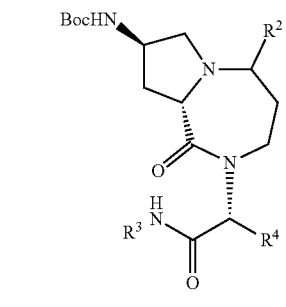

10

25
-continued

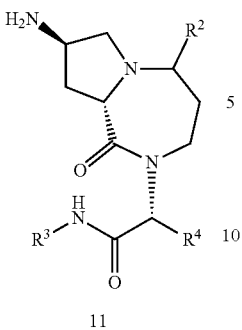
11

It will be appreciated by one skilled in the art that compounds of formula 11 may be prepared analogously to the methods described above for Scheme 2, but using an amino acid benzyl ester (i.e. 17) instead of the corresponding methyl ester. Consequently, reaction of intermediate 19 under an atmosphere of hydrogen gas at elevated pressure (e.g. 30-40 psi) in the presence of suitable catalyst such as 10% Pd/C will also remove the benzyl protecting group on the ester moiety to directly give carboxylic acid 20. This can then be converted to compounds of 11 as described for Scheme 2.

Scheme 4

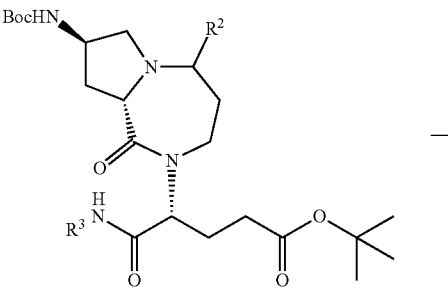
21

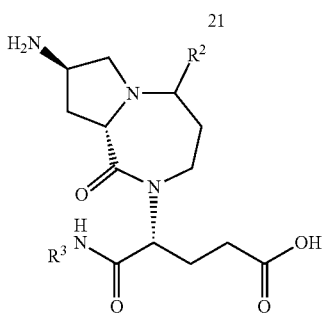
22

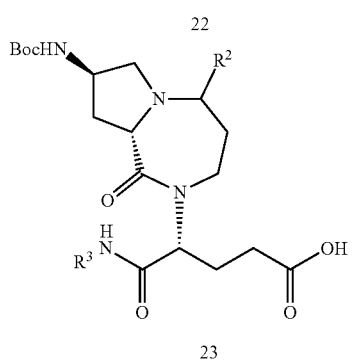
23

26
-continued

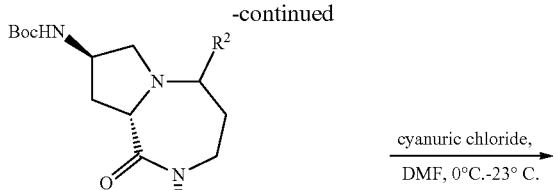

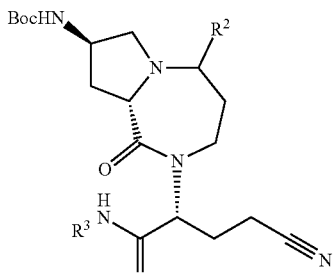
24

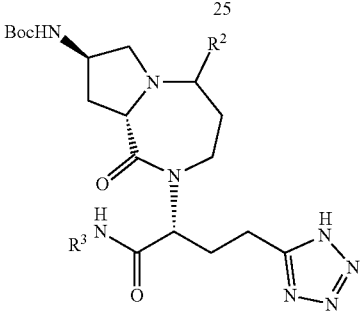
25

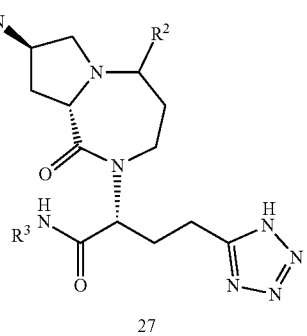
26

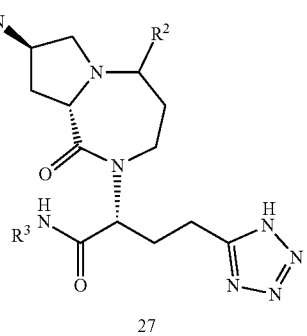
27

Furthermore, it shall be readily apparent to one skilled in the art that various synthetic transformations can be utilized at appropriate steps in the general schemes above to modify certain positions of the molecule such as at the $R^2$, $R^3$ and/or $R^4$ groups. For example, for compounds 10 where $R^4$ is —$(CH_2)_2COOt$-Bu (shown as 21), the t-Bu group can be removed simultaneously with the Boc protecting group upon treatment with a suitable acid (e.g. 50% TFA in DCM) to provide amino acid 22 (see Scheme 4). Re-protection of the primary amine with a Boc protecting group gives 23. Reaction of carboxylic acid 23 with ammonium chloride in the presence of DIPEA and the coupling reagent HATU in an appropriate solvent such as DMF provides primary amide 24. At this point, Boc deprotection of 24 will give compounds of formula 11 where $R^4$ is —$(CH_2)_2C(O)NH_2$.

Alternatively, the primary amide of compound 24 can be dehydrated with an appropriate dehydrating agent such as cyanuric chloride to provide nitrile 25. At this point Boc deprotection of 25 will give compounds of formula 11 where $R^2$ is —$(CH_2)_2CN$. Or, the nitrile can be converted to tetrazole 26 by reaction with sodium azide using reaction conditions well known to those skilled in the art. Boc deprotection of 26 will provide compounds of formula (I) where $R^4$ is

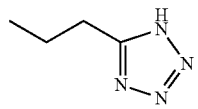

(shown as 27). One skilled in the art will appreciate that many more possibilities exist for structural variations within the $R^2$, $R^3$, and $R^4$ groups.

PREPARATIVE EXAMPLES

The compounds of the present invention were prepared using the experimental procedures described herein. Those skilled in the art will recognize that other procedures may also be suitable to prepare compounds of the present invention. Techniques, solvents and reagents may be referred to by the following abbreviations:

AcOH=acetic acid
Ala=alanine
Arg=arginine
Asn=asparagine
Atm=atmosphere
ACN=acetonitrile
Boc=t-butoxycarbonyl
BOP—Cl=bis(2-oxo-3-oxazolidinyl)phosphinic chloride
t-Bu=tert-butyl
Cbz=carboxybenzyl
d=day
DCC=N,N'-Dicyclohexylcarbodiimide
DCM=dichloromethane
DEAD=diethyl azodicarboxylate
DIEA=DIPEA=N,N-diisopropylethylamine
DMAP=4-Dimethylaminopyridine
DMSO=dimethylsulfoxide
EDAC=1-ethyl-3-(3-dimethylaminopropyl)carbodiimide hydrochloride
EtOAc=ethyl acetate
EtOH=ethanol
FCC=flash column chromatography
Fmoc=fluorenylmethyloxycarbonyl
Glu=glutamic acid
h=hour
HATU=1-[Bis(dimethylamino)methylene]-1H-1,2,3-triazolo[4,5-b]pyridinium 3-oxid hexafluorophosphate
HOBt=1-hydroxybenzotriazole
HPLC=high pressure liquid chromatography
IPA=isopropyl alcohol
i-Pr=isopropyl
LCMS=liquid chromatography-mass spectrometry
Leu=leucine
m-CPBA=meta-chloroperbenzoic acid
min=minute
MeOH=methanol
MPLC=medium pressure liquid chromatography
NMP=N-methylpyrrolidinone
NMR=nuclear magnetic resonance
Pd/C=palladium on carbon
Pmc=2,2,5,7,8-pentamethyl-chroman-6-sulfonyl chloride
PyBOP=benzotriazol-1-yloxy)tripyrrolidinophosphonium hexafluorophosphate
sat.=saturated
Ser=serine
$SiO_2$=silica gel
TBAF=tetrabutylammonium fluoride
TEA=triethylamine
TIPS=triisopropylsilane
TFA=trifluoroacetic acid
Tyr=tyrosine
Z=Cbz=carboxybenzyl LCMS Analysis Methods:

Compounds were analyzed using the methods set forth below on an Acquity Ultra Performance Liquid Chromatography system employing an Acquity UPLC BEH C18, 1.7 µm, 2.1×50 mm column. Detection was via an Acquity Ultra Performance LC PDA detector and either an Acquity SQD single quadrupole mass spectrometer or a Waters Micromass Quattro micro triple quadrupole mass spectrometer with API source, using $H_2O$+0.1% formic acid (A) and ACN+0.1% formic acid (B) as eluents.

Method A—Gradient: 0-0.1 min—Isocratic—10% B; 0.1-1.3 min—Linear gradient 10%-90% B; 1.3-1.8 min—Isocratic 90% B; 1.8-1.9 min—Linear gradient—90%-10% B; 1.9-2.0 min—Isocratic—B. Flow rate: 0.6 mL/min.

Method B—Gradient: 0-0.1 min—Isocratic—40% B; 0.1-1.3 min—Linear gradient—5%-95% B; 1.3-1.8 min—Isocratic—95% B; 1.8-1.9 min—Linear gradient—60%-40% B; 1.9-2.0 min—Isocratic—40% B. Flow rate: 0.6 mL/min.

Method C—Gradient: 0-0.1 min—Isocratic—40% B; 0.1-1.0 min—Linear gradient 40%-99% B; 1.0-1.8 min—Isocratic 99% B; 1.8-1.9 min—Linear gradient—99%-40% B; 1.9-2.0 min—Isocratic—40% B. Flow rate: 0.6 mL/min.

Method D—Gradient: 0-0.1 min—Isocratic—20% B; 0.1-1.3 min—Linear gradient 20%-95% B; 1.3-1.8 min—Isocratic 95% B; 1.8-1.9 min—Linear gradient—95%-20% B; 1.9-2.0 min—Isocratic—20% B. Flow rate: 0.6 mL/min.

Method E—Gradient: 0-0.1 min—Isocratic—25% B; 0.1-1.5 min—Linear gradient—25%-99% B; 1.5-1.8 min—Isocratic—99% B; 1.8-2.0 min—Linear gradient—99%-25% B; 2.0-2.2 min—Isocratic—25% B. Flow rate: 0.6 mL/min.

Method F—Gradient: 0-0.1 min—Isocratic—60% B; 0.1-1.5 min—Linear gradient 60%-99% B; 1.5-1.8 min—Isocratic 99% B; 1.8-2.0 min—Linear gradient—99%-60% B; 2.0-2.2 min—Isocratic—60% B. Flow rate: 0.6 mL/min."

Method G—Gradient: 0-0.1 min—Isocratic—2% B; 0.1-1.3 min—Linear gradient 2%-80% B; 1.3-1.8 min—Isocratic 80% B; 1.8-1.9 min—Linear gradient—80%-2% B; 1.9-2.0 min—Isocratic—2% B. Flow rate: 0.6 mL/min HPLC Analysis Method:

Compounds were analyzed on a Waters Alliance 2695 High-Performance Liquid Chromatography system employing a SunFire C18, 5 µm, 4.6×100 mm column. Detection was via a Waters 996 PDA detector using $H_2O$+0.1% trifluoroacetic acid (A) and ACN+0.1% trifluoroacetic acid (B) as eluents. Gradient: 0-7.0 min—Linear gradient 10%-100% B; 7.0-8.0 min—Isocratic 100% B; 8.0-8.3 min—Linear gradient—100%-10% B; 8.3-10.0 min—Isocratic—10% B. Flow rate: 1.5 mL/min.

$^1$H NMR Spectroscopy was performed on a Bruker 400 MHz Avance II FTNMR Spectrometer. All $^1$H NMR chemical shifts are reported in parts per million (ppm) and either referenced to the residual C—H signal from the deuterated solvent indicated or to tetramethylsilane.

Synthesis of Precursors and Intermediates According to the Invention (R)-3-(3,4-dichlorophenyl)morpholine

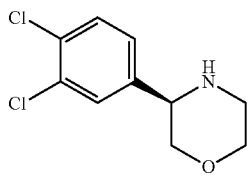 [SMILES: Clc1ccc([C@@H]2COCCN2)cc1Cl]

The title compound was prepared from (R)-2-amino-2-(3,4-dichlorophenyl)ethanol according to the same general method used for the preparation of (3R)-3-phenylmorpholine as described by Charrier et al. in *Compounds useful as inhibitors of ATR kinase*, PCT Int. Appl., (2013) WO2013/049719. (R)-2-amino-2-(3,4-dichlorophenyl)ethanol was prepared from 2-bromo-1-(3,4-dichlorophenyl)ethanone according to the synthetic procedure described by Wang, et al. (Wang, H. Y., et al. *Tetrahedron: Asymmetry*, 2016, 27, 91-100). $^1$H NMR (400 MHz, CD$_3$OD): δ 7.61 (d, 1H), 7.50 (d, 1H), 7.33 (dd, 1H), 3.91-3.80 (m, 3H), 3.64-3.57 (m, 1H), 3.35 (m, 1H), 3.04-2.96 (m, 2H) ppm; LCMS (Method A): t$_R$=0.69 min, m/z 232.2/234.2 (M+H)$^+$; [α]$_D^{20.2}$=−46.2 (c 0.84, MeOH).

(S)-2-(3,4-dichlorophenyl)piperidine

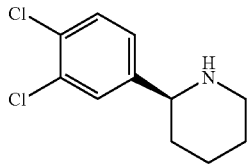 [SMILES: Clc1ccc([C@@H]2CCCCN2)cc1Cl]

The title compound was prepared from glutaric anhydride and (3,4-dichlorophenyl)magnesium bromide according to the synthetic procedure described by Guijjarro, et al. (Guijjarro, D., et al. *J. Org. Chem*, 2013, 78, 3647-3654). $^1$H NMR (400 MHz, CD$_3$OD): δ 7.56 (d, 1H), 7.47 (d, 1H), 7.29 (dd, 1H), 3.64-3.56 (m, 1H), 3.13 (m, 1H), 2.81-2.74 (m, 1H), 1.93-1.90 (m, 1H), 1.83-1.80 (m, 1H), 1.70-1.67 (m, 1H), 1.64-1.48 (m, 3H) ppm; [α]$_D^{20.2}$=−27.4 (c 0.68, CHCl$_3$).

(S)-2-(3,4-dichlorophenyl)pyrrolidine

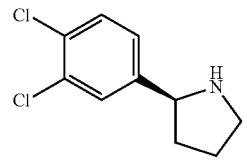 [SMILES: Clc1ccc([C@@H]2CCCN2)cc1Cl]

The title compound was prepared from succinic anhydride and (3,4-dichlorophenyl)magnesium bromide according to the synthetic procedure described by Guijjarro, et al. (Guijjarro, D., et al. *J. Org. Chem*, 2013, 78, 3647-3654). $^1$H NMR (400 MHz, CD$_3$OD): δ 7.49 (d, 1H), 7.37 (d, 1H), 7.20 (dd, 1H), 4.10 (t, 1H), 3.20-3.15 (m, 1H), 3.06-3.02 (m, 1H), 2.21-2.16 (m, 1H), 1.93-1.84 (m, 2H), 1.63-1.60 (m, 1H) ppm; [α]$_D^{20.2}$=−49.5 (c 0.60, CHCl$_3$).

Intermediate I.1: (R)-tert-butyl 4-amino-5-oxo-5-((4-(trifluoromethyl)benzyl)amino)pentanoate Step 1: (R)-tert-butyl 4-(((benzyloxy)carbonyl)amino)-5-oxo-5-((4-(trifluoromethyl)benzyl)amino)pentanoate

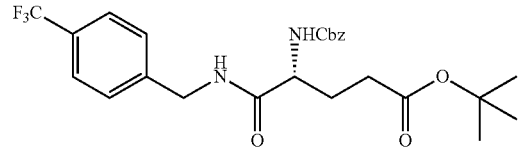 [SMILES: CC(C)(C)OC(=O)CC[C@@H](NC(=O)OCc1ccccc1)C(=O)NCc1ccc(C(F)(F)F)cc1]

To a mixture of Z-D-Glu-(Ot-Bu)-OH (1.00 g, 2.96 mmol) and 4-trifluoromethylbenzyl amine (0.42 mL, 3.0 mmol) in DCM (10 mL) was added EDAC (680 mg, 3.55 mmol) followed by HOBt.H$_2$O (480 mg, 3.55 mmol). The mixture was stirred at room temperature for 16 h. The mixture was then concentrated in vacuo and the crude residue was taken up in EtOAc (100 mL). This was washed successively with sat. NaHSO$_4$ (aq) (1×50 mL), sat. NaHCO$_3$ (aq) (1×50 mL) and brine (1×50 mL). The organic layer was then dried (Na$_2$SO$_4$), filtered and concentrated in vacuo to provide 1.39 g (95%) of (R)-tert-butyl 4-(((benzyloxy)carbonyl)amino)-5-oxo-5-((4-(trifluoromethyl)benzyl)amino)pentanoate which was used in the next step without further purification.

Step 2: (R)-tert-butyl 4-amino-5-oxo-5-((4-(trifluoromethyl)benzyl)amino)pentanoate (Intermediate I.1)

Intermediate I.1

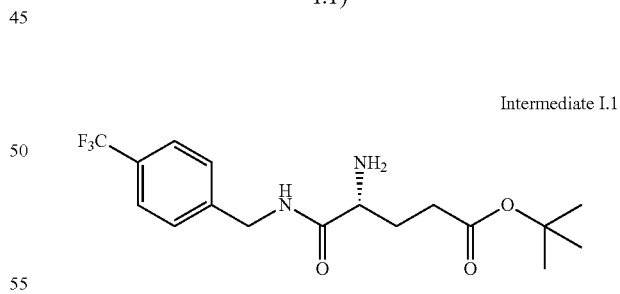

A mixture of the crude product obtained in step 1 above (1.39 g, 2.81 mmol) and 10% Pd/C (100 mg) in MeOH (20 mL) was stirred vigorously under 1 atm of H$_2$ (g) (balloon) for 2.5 h. The mixture was then filtered through a pad of Celite, rinsing with DCM, and the filtrate was concentrated in vacuo to provide 1.01 g (100%) of Intermediate I.1. $^1$H NMR (400 MHz, CDCl$_3$): δ 7.73 (br t, 1H, N—H), 7.59 (d, 2H), 7.40 (d, 2H), 4.51 (d, 2H), 3.46 (dd, 1H), 2.44-2.31 (m, 2H), 2.20-2.12 (m, 1H), 1.89-1.80 (m, 1H), 1.44 (s, 9H) ppm; LCMS (Method A): t$_R$=0.94 min, m/z 361.3 (M+H)$^+$, 305.2 (M+H—C$_4$H$_8$)$^+$, 721.4 (2M+H)$^+$.

Intermediate I.2: (R)-2-amino-N-(3,4-dichlorobenzyl)-4-methylpentanamide

Step 1: (R)-tert-butyl (1-((3,4-dichlorobenzyl)amino)-4-methyl-1-oxopentan-2-yl)carbamate

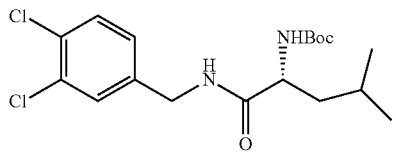 [SMILES: CC(C)C[C@@H](NC(=O)OC(C)(C)C)C(=O)NCc1ccc(Cl)c(Cl)c1]

Using the same general procedure as described in Step 1 for the preparation of Intermediate I.1, 3,4-dichlorobenzyl amine (1.14 g, 6.49 mmol) was reacted with Boc-D-Leu-OH (1.50 g, 6.49 mmol) to provide 1.94 g (77%) of (R)-tert-butyl (1-((3,4-dichlorobenzyl)amino)-4-methyl-1-oxopentan-2-yl)carbamate after purification by FCC (SiO$_2$, elution with 40% EtOAc/hexanes). $^1$H NMR (400 MHz, CDCl$_3$): δ 7.37 (d, 1H), 7.34 (d, 1H), 7.09 (dd, 1H), 6.70 (br t, 1H), 4.86 (br d, 1H), 4.38 (m, 2H), 4.11 (m, 1H), 1.74-1.66 (m, 2H), 1.52-1.47 (m, 1H), 1.42 (s, 9H), 0.95 (d, 3H), 0.93 (d, 3H) ppm; LCMS (Method A): $t_R$=1.41 min, m/z 389.3/391.3 (M+H)$^+$.

Step 2: (R)-2-amino-N-(3,4-dichlorobenzyl)-4-methylpentanamide (Intermediate I.2)

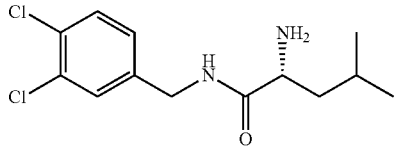

To a solution of the intermediate obtained in step 1 (1.94 g, 5.00 mmol) in DCM (15 mL) was added TFA (15 mL) dropwise. The mixture was stirred at room temperature for 2 h, then quenched with 2M NaOH to adjust the pH to ~9 and extracted with DCM (2×50 mL). The combined organic extracts were washed with sat. NaHCO$_3$ (aq) (1×50 mL) and brine (1×50 mL), dried (Na$_2$SO$_4$), filtered and concentrated in vacuo to provide 1.30 g (90%) of Intermediate I.2 after purification by FCC (SiO$_2$, elution with 0-10% MeOH/DCM). $^1$H NMR (400 MHz, CDCl$_3$): δ 7.79 (br t, 1H, N—H), 7.39 (d, 1H), 7.36 (d, 1H), 7.12 (dd, 1H), 4.39 (d, 2H), 3.45 (dd, 1H), 1.80-1.69 (m, 2H), 1.42-1.31 (m, 1H), 0.97 (d, 3H), 0.94 (d, 3H) ppm; LCMS (Method A): $t_R$=0.88 min, m/z 289.2/291.2 (M+H)$^+$.

Intermediate I.3: (R)-2-amino-3-(tert-butoxy)-N-(3,4-dichlorobenzyl)propanamide

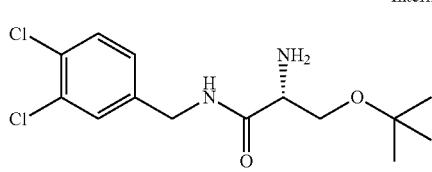

Step 1: (R)-(9H-fluoren-9-yl)methyl (3-(tert-butoxy)-1-((3,4-dichlorobenzyl)amino)-1-oxopropan-2-yl)carbamate

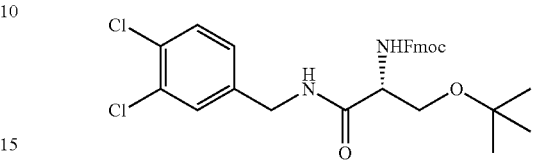

Using the same general procedure as described in Step 1 for the preparation of Intermediate I.1, 3,4-dichlorobenzyl amine (173 µL, 1.30 mmol) was reacted with Fmoc-D-Ser(t-Bu)OH (0.50 g, 1.3 mmol) to provide 0.64 g (91%) of (R)-(9H-fluoren-9-yl)methyl (3-(tert-butoxy)-1-((3,4-dichlorobenzyl)amino)-1-oxopropan-2-yl)carbamate after purification by FCC (SiO$_2$, elution with 0-100% EtOAc/hexanes). $^1$H NMR (400 MHz, d$_6$-DMSO): δ 8.55 (t, 1H), 7.89 (d, 2H), 7.74 (br d, 2H), 7.54 (d, 1H), 7.50 (d, 1H), 7.45-7.40 (m, 3H), 7.31 (td, 2H), 7.26 (dd, 1H), 4.37-4.20 (m, 5H), 4.12 (m, 1H), 3.50 (m, 2H), 1.11 (s, 9H) ppm; LCMS (Method B): $t_R$=1.36 min, m/z 541.3/543.4 (M+H)$^+$.

Step 2: (R)-2-amino-3-(tert-butoxy)-N-(3,4-dichlorobenzyl)propanamide (Intermediate I.3)

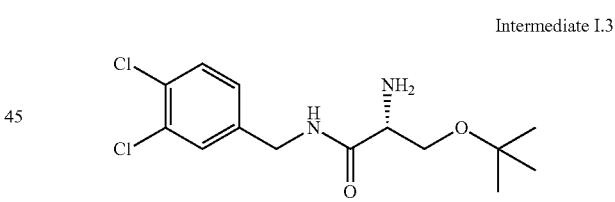

To a solution of (R)-(9H-fluoren-9-yl)methyl (3-(tert-butoxy)-1-((3,4-dichlorobenzyl)amino)-1-oxopropan-2-yl)carbamate (0.64 g, 1.18 mmol) in DCM (12 mL) was added diethylamine (2.50 mL, 23.7 mmol). The mixture was stirred at room temperature for 4 h. This was then concentrated in vacuo and the crude residue was purified by FCC (SiO$_2$, elution with 0-10% MeOH/DCM) to provide 0.38 g (99%) of Intermediate I.3. $^1$H NMR (400 MHz, d$_6$-DMSO): δ 8.46 (br t, 1H, N—H), 7.55 (d, 1H), 7.49 (d, 1H), 7.26 (dd, 1H), 4.28 (m, 2H), 3.39 (m, 2H), 3.27 (t, 1H), 1.81 (br s, 2H, NH$_2$), 1.11 (s, 9H) ppm; LCMS (Method A): $t_R$=0.92 min, m/z 319.3/321.3 (M+H)$^+$.

Following the methods described above for the preparation of Intermediates I.1-I.3, and substituting the corresponding reagents, the following intermediates were prepared as indicated in Table 1

TABLE 1

| Intermediate | Structure | Reagents | LCMS Method | $t_R$ (min) | $(M + H)^+$ observed |
|---|---|---|---|---|---|
| I.4 | 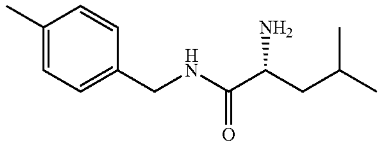 [SMILES: Cc1ccc(CNC(=O)[C@H](N)CC(C)C)cc1] | 4-methylbenzyl-amine and Boc-D-Leu-OH | A | 0.75 | 235.3 |
| I.5 | 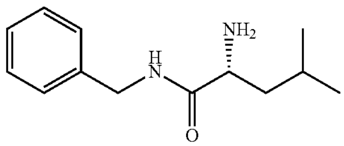 [SMILES: CC(C)C[C@@H](N)C(=O)NCc1ccccc1] | Benzylamine and Boc-D-Leu-OH | A | 0.70 | 221.3 |
| I.6 | 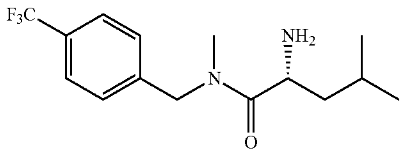 [SMILES: CC(C)C[C@@H](N)C(=O)N(C)Cc1ccc(C(F)(F)F)cc1] | N-methyl-4-trifluoromethyl-benzylamine and Boc-D-Leu-OH | A | 0.89 | 303.3 |
| I.7 | 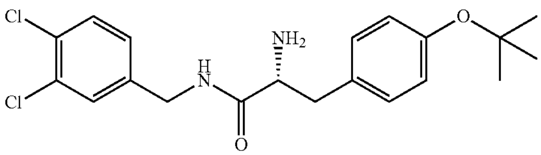 [SMILES: CC(C)(C)Oc1ccc(C[C@@H](N)C(=O)NCc2ccc(Cl)c(Cl)c2)cc1] | 3,4-dichlorobenzyl amine and Fmoc-D-Tyr(t-Bu)OH | A | 1.06 | 395.3/397.3 |
| I.8 | 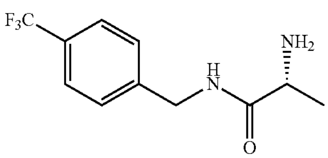 [SMILES: C[C@@H](N)C(=O)NCc1ccc(C(F)(F)F)cc1] | 4-(trifluoromethyl)-benzyl amine and Boc-D-Ala-OH | A | 0.74 | 247.3 |
| I.9 | 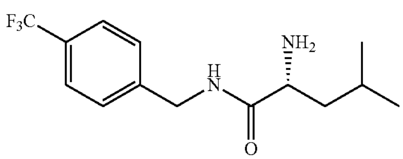 [SMILES: CC(C)C[C@@H](N)C(=O)NCc1ccc(C(F)(F)F)cc1] | 4-(trifluoromethyl)-benzyl amine and Boc-D-Leu-OH | A | 0.84 | 289.3 |
| I.10 | 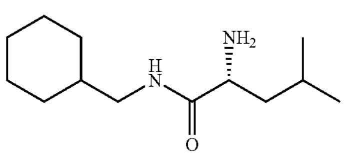 [SMILES: CC(C)C[C@@H](N)C(=O)NCC1CCCCC1] | Cyclohexylmethyl amine and Boc-D-Leu-OH | A | 0.80 | 227.3 |
| I.11 | 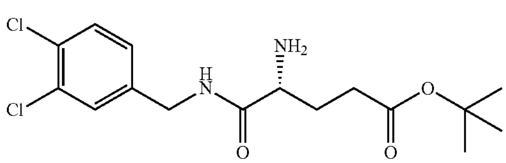 [SMILES: CC(C)(C)OC(=O)CC[C@@H](N)C(=O)NCc1ccc(Cl)c(Cl)c1] | 3,4-dichlorobenzyl amine and Fmoc-D-Glu-(Ot-Bu)-OH | A | 0.97 | 361.3/363.3 |
| I.12 | 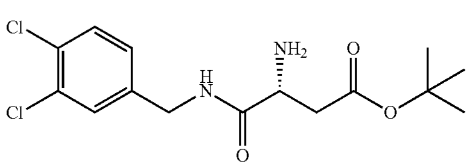 [SMILES: CC(C)(C)OC(=O)C[C@@H](N)C(=O)NCc1ccc(Cl)c(Cl)c1] | 3,4-dichlorobenzyl amine and Fmoc-D-Asp-(Ot-Bu)-OH | A | 0.92 | 347.2/349.2 |

TABLE 1-continued

| Intermediate | Structure | Reagents | LCMS Method | $t_R$ (min) | $(M + H)^+$ observed |
|---|---|---|---|---|---|
| I.13 | 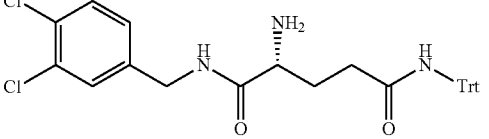 | 3,4-dichlorobenzyl amine and Fmoc-D-Glu-(Trt)-OH | A | 1.22 | 546.3/548.3 |
| I.14 | 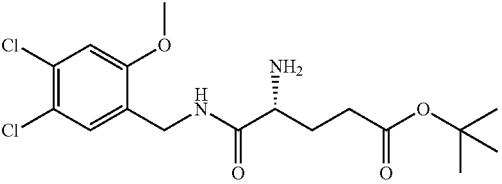 [SMILES: COc1cc(Cl)c(Cl)cc1CNC(=O)[C@H](N)CCC(=O)OC(C)(C)C] | 4,5-dichloro-2-methoxybenzyl amine and Fmoc-D-Glu-(Ot-Bu)-OH | D | 0.82 | 391.3/393.3 |
| I.15 | 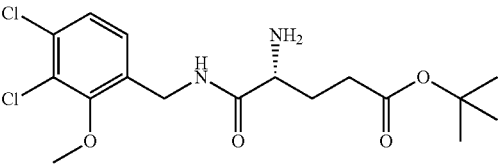 [SMILES: COc1c(CNC(=O)[C@H](N)CCC(=O)OC(C)(C)C)ccc(Cl)c1Cl] | 3,4-dichloro-2-methoxybenzyl amine and Fmoc-D-Glu-(Ot-Bu)-OH | D | 0.84 | 391.3/394.3 |
| I.16 | 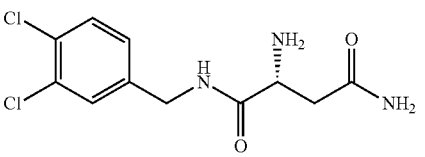 [SMILES: NC(=O)C[C@@H](N)C(=O)NCc1ccc(Cl)c(Cl)c1] | 3,4-dichlorobenzyl amine and Fmoc-D-Asp-OH | A | 0.70 | 290.1/292.1 |
| I.17 | 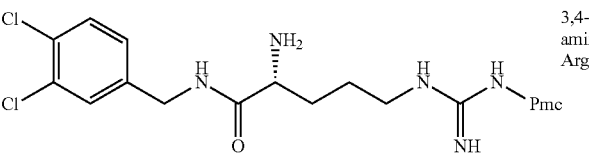 | 3,4-dichlorobenzyl amine and Fmoc-D-Arg(Pmc)-OH | A | 1.14 | 598.4/600.4 |
| I.18 | 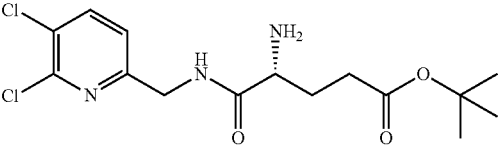 [SMILES: CC(C)(C)OC(=O)CC[C@@H](N)C(=O)NCc1ccc(Cl)c(Cl)n1] | (5,6-dichloropyridin-2-yl)methanamine and Fmoc-D-Glu-(Ot-Bu)-OH | A | 0.84 | 362.3/364.3 |
| I.19 | 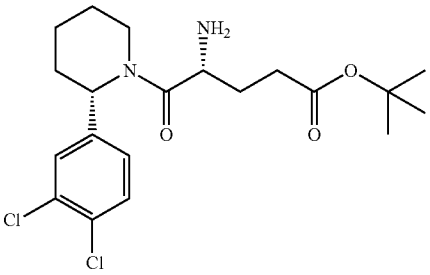 [SMILES: CC(C)(C)OC(=O)CC[C@@H](N)C(=O)N1CCCC[C@H]1c1ccc(Cl)c(Cl)c1] | (S)-2-(3,4-dichlorophenyl)piperidine and Fmoc-D-Glu-(Ot-Bu)-OH | A | 1.01 | 415.3/417.3 |
| I.20 | 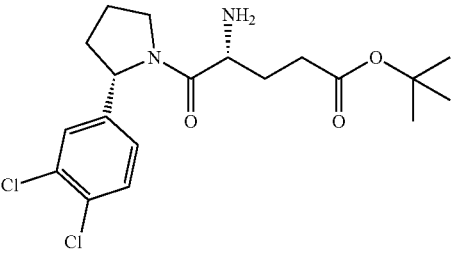 [SMILES: CC(C)(C)OC(=O)CC[C@@H](N)C(=O)N1CCC[C@H]1c1ccc(Cl)c(Cl)c1] | (S)-2-(3,4-dichlorophenyl)pyrrolidine and Fmoc-D-Glu-(Ot-Bu)-OH | A | 0.90 | 401.3/403.3 |

TABLE 1-continued

| Intermediate | Structure | Reagents | LCMS Method | $t_R$ (min) | $(M + H)^+$ observed |
|---|---|---|---|---|---|
| I.21 | 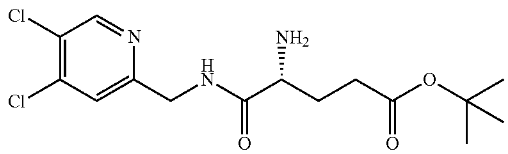 [SMILES: CC(C)(C)OC(=O)CC[C@@H](N)C(=O)NCc1cc(Cl)c(Cl)cn1] | (4,5-dichloropyridin-2-yl)methanamine and Fmoc-D-Glu-(Ot-Bu)-OH | A | 0.86 | 362.3/364.3 |
| I.22 | 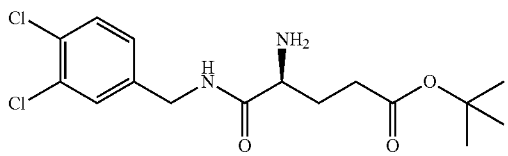 [SMILES: CC(C)(C)OC(=O)CC[C@H](N)C(=O)NCc1ccc(Cl)c(Cl)c1] | 3,4-dichlorobenzyl amine and Fmoc-Glu-(Ot-Bu)-OH | A | 0.99 | 361.2/363.2 |
| I.23 | 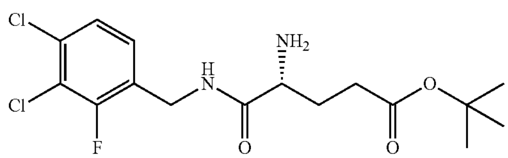 [SMILES: CC(C)(C)OC(=O)CC[C@@H](N)C(=O)NCc1ccc(Cl)c(Cl)c1F] | 3,4-dichloro-2-fluorobenzylamine and Fmoc-D-Glu-(Ot-Bu)-OH | A | 0.84 | 379.2/381.3 |
| I.24 | 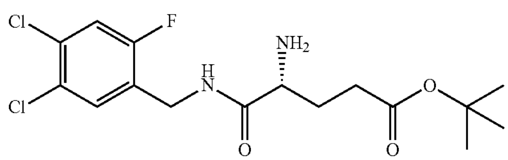 [SMILES: CC(C)(C)OC(=O)CC[C@@H](N)C(=O)NCc1cc(Cl)c(Cl)cc1F] | 4,5-dichloro-2-fluorobenzylamine and Fmoc-D-Glu-(Ot-Bu)-OH | A | 0.84 | 379.2/381.3 |
| I.25 | 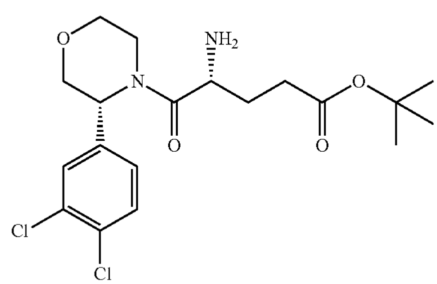 [SMILES: CC(C)(C)OC(=O)CC[C@@H](N)C(=O)N1CCOC[C@H]1c1ccc(Cl)c(Cl)c1] | (R)-3-(3,4-dichlorophenyl)morpholine and Fmoc-D-Glu-(Ot-Bu)-OH | A | 0.92 | 417.3/419.3 |
| I.26 | 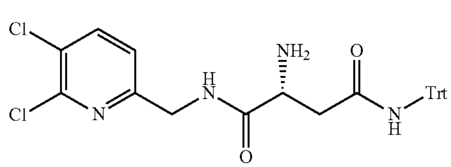 | (5,6-dichloropyridin-2-yl)methanamine and Fmoc-D-Asn(Trt)-OH | A | 1.14 | 533.3/535.3 |
| I.27 | 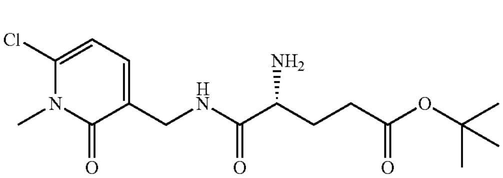 [SMILES: Cn1c(Cl)ccc(CNC(=O)[C@H](N)CCC(=O)OC(C)(C)C)c1=O] | 3-(aminomethyl)-6-chloro-1-methyl-pyridin-2(1H)-one and Fmoc-D-Glu-(Ot-Bu)-OH | A | 0.80 | 358.3/360.3 |

Intermediate I.28: (R)-methyl 2-amino-4-oxo-4-(tritylamino)butanoate

Step 1: (R)-methyl 2-((((9H-fluoren-9-yl)methoxy)carbonyl)amino)-4-oxo-4-(tritylamino)butanoate

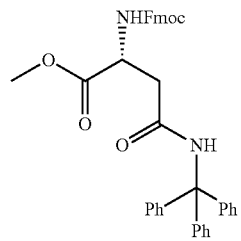

To a mixture of Fmoc-D-Asn(Trt)-OH (4.20 g, 7.04 mmol) and potassium carbonate (1.16 g, 8.45 mmol) in DMF (20 mL) at 0° C. was added a solution of methyl iodide (0.66 mL, 10.56 mmol) in DMF (20 mL). The mixture was warmed to room temperature and stirred for 2 h. The mixture was then quenched with 10% $Na_2S_2O_3$ solution (20 mL) and extracted with EtOAc. The organic layer was washed with $H_2O$ (2×50 mL) and brine (1×50 mL), dried ($Na_2SO_4$), filtered and concentrated in vacuo to provide 4.20 g (quantitative) of (R)-methyl 2-((((9H-fluoren-9-yl)methoxy)carbonyl)amino)-4-oxo-4-(tritylamino)butanoate as an off-white solid which was used without further purification in the next step. LCMS (Method A): $t_R$=1.61 min, m/z 611.5 (M+H)$^+$.

Step 2: (R)-methyl 2-amino-4-oxo-4-(tritylamino)butanoate (Intermediate I.28)

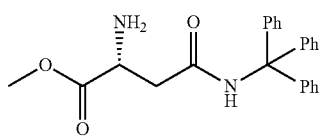

Intermediate I.28

To a solution of (R)-methyl 2-((((9H-fluoren-9-yl)methoxy)carbonyl)amino)-4-oxo-4-(tritylamino)butanoate (4.20 g, 6.89 mmol) in DCM (40 mL) was added diethylamine (15.0 mL, 137.8 mmol). The mixture was stirred at room temperature for 4 h. The mixture was then concentrated in vacuo and the crude residue was purified by FCC ($SiO_2$, elution with 0-10% MeOH/DCM) to provide 2.60 g (97%) of Intermediate I.28 as a yellow oil. $^1$H NMR (400 MHz, CDCl$_3$): δ 8.44 (s, 1H, N—H), 7.30-7.20 (m, partially obscured by solvent peak, 15H), 3.84 (dd, 1H), 3.72 (s, 3H), 2.70 (dd, 1H), 2.60 (dd, 1H) ppm.

Intermediate I.29: (R)-benzyl 2-amino-3-(tert-butoxy)propanoate

Step 1: (R)-benzyl 2-((((9H-fluoren-9-yl)methoxy)carbonyl)amino)-3-(tert-butoxy)propanoate

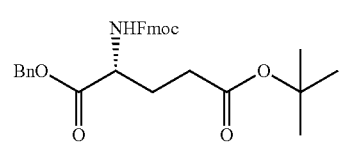

To a mixture of Fmoc-D-Glu(OtBu)-OH (1 g, 2.35 mmol), DCC (536 mg, 2.60 mmol), and DMAP (29 mg, 0.24 mmol) in DCM was added benzylalcohol (0.24 mL, 2.35 mmol) under nitrogen and stirred at room temperature for 16 h. The reaction mixture was filtered to remove dicyclohexylurea. The filtrate was diluted with DCM (50 mL) and washed successively with sat. NaHSO$_4$ (aq) (1×50 mL), sat. NaHCO$_3$ (aq) (1×50 mL) and brine (1×50 mL). The organic layer was dried (Na$_2$SO$_4$), filtered, concentrated in vacuo and purified by FCC (SiO$_2$, elution with 0-50% EtOAc/hexanes) to provide 1.07 g (88%) of (R)-benzyl 2-((((9H-fluoren-9-yl)methoxy)carbonyl)amino)-3-(tert-butoxy)propanoate as a white solid. $^1$H NMR (400 MHz, CDCl$_3$): δ 7.76 (d, 2H), 7.59 (d, 2H), 7.40-7.35 (m, 3H), 7.35-7.29 (m, 6H), 5.50 (br d, 1H), 5.19 (s, 2H), 4.70 (d, 1H), 4.46-4.40 (m, 2H), 4.37-4.33 (m, 1H), 4.21 (t, 1H), 2.36-2.26 (m, 1H), 2.22-2.15 (m, 1H), 2.00-1.95 (m, 1H), 1.43 (s, 9H) ppm.

Step 2: (R)-benzyl 2-amino-3-(tert-butoxy)propanoate (Intermediate I.29)

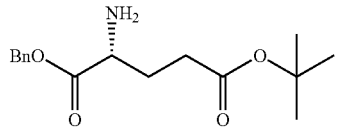

Intermediate I.29

To a solution of (R)-benzyl 2-((((9H-fluoren-9-yl)methoxy)carbonyl)amino)-3-(tert-butoxy)propanoate (1.07 g, 2.07 mmol) in DCM (10 mL) was added diethylamine (4.20 mL, 41.5 mmol) and the reaction mixture was stirred at room temperature for 4 h. This was then concentrated in vacuo and the crude residue was purified by FCC (SiO$_2$, elution with 0-10% MeOH/DCM) to provide 0.59 g (97%) of Intermediate I.29 as a white solid. $^1$H NMR (400 MHz, CDCl$_3$): δ 7.36 (m, 5H), 5.16 (s, 2H), 3.51 (m, 1H), 2.35 (t, 2H), 2.08-2.03 (m, 1H), 1.86-1.79 (m, 1H), 1.43 (s, 9H) ppm.

Intermediate I.30: (S)-2-amino-N-(3,4-dichlorobenzyl)-3-((2-hydroxyphenyl)thio)propanamide Step 1: (R)-(9H-fluoren-9-yl)methyl (3-(tert-butoxy)-1-((3,4-dichlorobenzyl)amino)-1-oxopropan-2-yl)carbamate

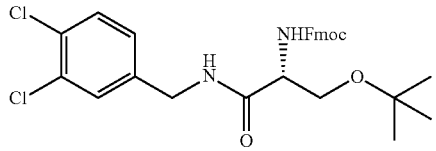

Using the same general procedure as described in Step 1 for the preparation of Intermediate I.1, 3,4-dichlorobenzyl amine (173 µL, 1.30 mmol) was reacted with Fmoc-D-Ser (t-Bu)OH (0.50 g, 1.3 mmol) to provide 0.64 g (91%) of (R)-(9H-fluoren-9-yl)methyl (3-(tert-butoxy)-1-((3,4-dichlorobenzyl)amino)-1-oxopropan-2-yl)carbamate after purification by FCC (SiO$_2$, elution with 0-100% EtOAc/hexanes). $^1$H NMR (400 MHz, d$_6$-DMSO): δ 8.55 (t, 1H), 7.89 (d, 2H), 7.74 (br d, 2H), 7.54 (d, 1H), 7.50 (d, 1H), 7.45-7.40 (m, 3H), 7.31 (td, 2H), 7.26 (dd, 1H), 4.37-4.20 (m, 5H), 4.12 (m, 1H), 3.50 (m, 2H), 1.11 (s, 9H) ppm; LCMS (Method B): t$_R$=1.36 min, m/z 541.3/543.4 (M+H)$^+$.

Step 2: (R)-(9H-fluoren-9-yl)methyl (1-((3,4-dichlorobenzyl)amino)-3-hydroxy-1-oxopropan-2-yl)carbamate

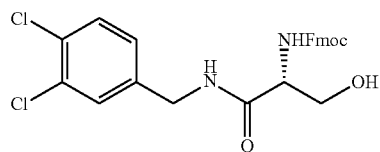

(R)-(9H-fluoren-9-yl)methyl (3-(tert-butoxy)-1-((3,4-dichlorobenzyl)amino)-1-oxopropan-2-yl)carbamate (0.5 g, 0.926 mmol) was stirred in TFA (10 mL) at room temperature for 30 min then concentrated in vacuo. The residue was partitioned between EtOAc and sat. (aq) NaHCO$_3$ and the aqueous phase was extracted with EtOAc (2×). The combined organic extracts were dried (MgSO$_4$), filtered and concentrated in vacuo. The crude residue was purified by FCC (SiO$_2$, elution with 0-10% MeOH/DCM) to give 413 mg (92%) of (R)-(9H-fluoren-9-yl)methyl (1-((3,4-dichlorobenzyl)amino)-3-hydroxy-1-oxopropan-2-yl)carbamate. $^1$H NMR (400 MHz, d$_6$-DMSO): δ 8.51 (m, 1H), 7.89 (d, 2H), 7.74 (m, 2H), 7.53 (m, 2H), 7.42 (m, 3H), 7.34 (m, 2H), 7.26 (m, 1H), 4.95 (t, 1H), 4.30-4.28 (m, 4H), 4.23 (m, 1H), 4.07 (m, 1H), 3.62 (m, 2H) ppm; LCMS (Method B): t$_R$=1.02 min, m/z 485.1/487.2 (M+H)$^+$.

Step 3: (S)-(9H-fluoren-9-yl)methyl (1-((3,4-dichlorobenzyl)amino)-3-((2-hydroxyphenyl)thio)-1-oxopropan-2-yl)carbamate

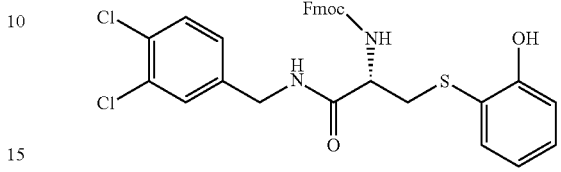

To a solution of (R)-(9H-fluoren-9-yl)methyl (1-((3,4-dichlorobenzyl)amino)-3-hydroxy-1-oxopropan-2-yl)carbamate (0.104 g, 0.215 mmol) in THF (2 mL) was added 2-mercaptophenol (0.028 mL, 0.28 mmol) followed by triphenylphosphine (0.101 g, 0.386 mmol). The mixture was cooled to −10° C. and DEAD solution (40% in toluene, 147 µL, 0.322 mmol) was added very slowly over 30 minutes. The reaction was warmed to room temperature and stirred for 16 h. The mixture was then concentrated in vacuo and the crude residue was directly purified by FCC (SiO$_2$, elution with 0-5% MeOH/DCM) to provide 167 mg of semipure (S)-(9H-fluoren-9-yl)methyl (1-((3,4-dichlorobenzyl)amino)-3-((2-hydroxyphenyl)thio)-1-oxopropan-2-yl)carbamate as white solid. LCMS (Method D): t$_R$=1.43 min, m/z 593.1/595.2 (M+H)$^+$.

Step 4: (S)-2-amino-N-(3,4-dichlorobenzyl)-3-((2-hydroxyphenyl)thio)propanamide (Intermediate I.30)

Intermediate I.30

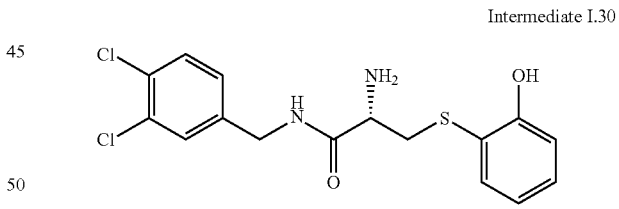

Using the same general procedure as described in Step 2 for the preparation of Intermediate I.3, diethylamine (0.44 mL, 4.3 mmol) was reacted with (S)-(9H-fluoren-9-yl)methyl (1-((3,4-dichlorobenzyl)amino)-3-((2-hydroxyphenyl)thio)-1-oxopropan-2-yl)carbamate (127 mg, 0.214 mmol) in DCM (2 mL) to afford 60 mg (76%) of (S)-2-amino-N-(3,4-dichlorobenzyl)-3-((2-hydroxyphenyl)thio)propanamide after purification by FCC (SiO$_2$, elution with 0-5% MeOH/DCM). $^1$H NMR (400 MHz, CDCl$_3$): δ 7.48 (m, 2H), 7.40 (m, 2H), 7.30 (m, 1H), 7.12 (m, 1H), 7.00 (d, 1H), 6.84 (t, 1H), 6.39 (m, 1H), 4.38 (m, 2H), 3.47 (m, 1H), 3.21 (m, 1H), 2.91 (m, 1H) ppm; LCMS (Method D): t$_R$=0.78 min, m/z 371.1/373.1 (M+H)$^+$.

Intermediate I.31: (S)-methyl 2-amino-3-((2-(benzyloxy)phenyl)thio)propanoate

Step 1: (S)-methyl 2-((tert-butoxycarbonyl)amino)-3-hydroxypropanoate

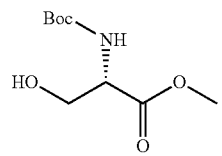

To a mixture of Boc-D-Serine (5.0 g, 24.4 mmol) and K₂CO₃ (4.0 g, 29.2 mmol) in DMF (100 mL) at 0° C. was added iodomethane (2.30 mL. 36.6 mmol). The reaction mixture was warmed to room temperature and stirred for 2 h. The mixture was then quenched with 10% Na₂S₂O₃ (aq) and extracted with EtOAc. The organic phase was washed with H₂O (3×) and brine (1×), dried (MgSO₄), filtered, and concentrated in vacuo. The crude residue was purified by FCC (SiO₂, elution with 0-100% EtOAc/hexane) to afford 3.0 g (56%) of (S)-methyl 2-((tert-butoxycarbonyl)amino)-3-hydroxypropanoate as a clear oil. ¹H NMR (400 MHz, CDCl₃): δ 5.44 (m, 1H), 4.40 (m, 1H), 3.96 (m, 2H), 3.80 (s, 3H), 2.23 (m, 1H), 1.45 (s, 9H) ppm.

Step 2: (S)-methyl 2-((tert-butoxycarbonyl)amino)-3-((2-hydroxyphenyl)thio)propanoate

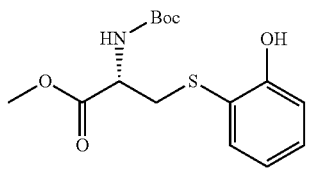 [SMILES: COC(=O)[C@@H](CSc1ccccc1O)NC(=O)OC(C)(C)C]

Using the same general procedure as described in Step 3 for the preparation of Intermediate I.30, (S)-methyl 2-((tert-butoxycarbonyl)amino)-3-hydroxypropanoate (3.7 g, 16.9 mmol) was reacted with 2-mercaptophenol (2.2 mL, 21.9 mmol) to provide 3.50 g (63%) of (S)-methyl 2-((tert-butoxycarbonyl)amino)-3-((2-hydroxyphenyl)thio)propanoate as a clear oil after purification by FCC (SiO₂, elution with 0-100% EtOAc/hexanes). ¹H NMR (400 MHz, CDCl₃): δ 7.47 (dd, 1H), 6.98 (m, 2H), 6.87 (m, 1H), 5.36 (m, 1H), 4.52 (m, 1H), 3.63 (s, 3H), 3.22 (m, 1H), 3.10 (m, 1H), 1.51 (s, 1H), 1.42 (s, 9H) ppm; LCMS (Method A): $t_R$=1.20 min, m/z 228.2 (M+H-Boc)⁺.

Step 3: (S)-methyl 3-((2-(benzyloxy)phenyl)thio)-2-((tert-butoxycarbonyl)amino)propanoate

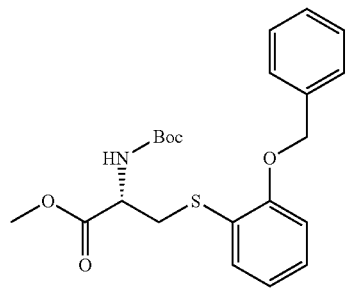 [SMILES: COC(=O)[C@@H](CSc1ccccc1OCc1ccccc1)NC(=O)OC(C)(C)C]

To a solution of (S)-methyl 2-((tert-butoxycarbonyl)amino)-3-((2-hydroxyphenyl)thio)propanoate (1.90 g, 5.80 mmol) in acetone (10 mL) was added benzyl bromide (0.76 mL, 6.4 mmol) followed by K₂CO₃ (1.20 g, 8.71 mmol). The mixture was stirred at room temperature for 16 h. The mixture was diluted with EtOAc and then quenched with 1N HCl (aq). The layers were partitioned and the aqueous layer was extracted with EtOAc (3×). The combined organic extracts were washed H₂O (1×) and brine (1×), dried (MgSO₄), filtered and concentrated in vacuo. The crude residue was purified by FCC (SiO₂, elution with 0-50% EtOAc/hexanes to afford 1.72 g (71%) (S)-methyl 3-((2-(benzyloxy)phenyl)thio)-2-((tert-butoxycarbonyl)amino) propanoate as a yellow oil. ¹H NMR (400 MHz, CDCl₃): δ 7.48 (m, 2H), 7.41 (m, 3H), 7.35 (m, 1H), 7.21 (m, 1H), 6.90 (m, 2H), 5.47 (m, 1H), 5.17 (s, 2H), 4.52 (m, 1H), 3.45 (m, 4H), 3.28 (m, 1H), 1.16 (s, 9H) ppm; LCMS (Method A): $t_R$=1.50 min, m/z 318.3 (M+H-Boc)⁺.

Step 4: (S)-methyl 2-amino-3-((2-(benzyloxy)phenyl)thio)propanoate (Intermediate I.31)

Intermediate I.31

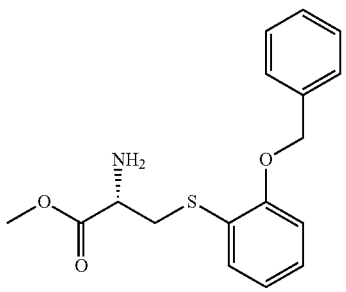

(S)-methyl 3-((2-(benzyloxy)phenyl)thio)-2-((tert-butoxycarbonyl)amino)propanoate (2.40 g, 5.75 mmol) was taken up in 20% TFA in DCM (60 mL) and stirred at room temperature for 2 h. The mixture was concentrated in vacuo and the crude residue was diluted with DCM, washed with sat. NaHCO₃ (aq) (3×), dried (Na₂SO₄), filtered and concentrated in vacuo to give 1.70 g (93%) of (S)-methyl 2-amino-3-((2-(benzyloxy)phenyl)thio)propanoate. ¹H NMR (400 MHz, CDCl₃): δ 7.48 (m, 2H), 7.40 (m, 3H), 7.34 (m, 1H), 7.20 (m, 1H), 6.93 (m, 2H), 5.18 (s, 2H), 3.61 (m, 1H), 3.57 (s, 3H), 3.33 (m, 1H), 3.11 (m, 1H) ppm; LCMS (Method A): $t_R$=0.89 min, m/z 318.3/319.3 (M+H)⁺.

Intermediate I.32: (S)-3-amino-1-(3,4-dichlorobenzyl)pyrrolidin-2-one.HCl

Step 1: (S)-tert-butyl (1-(3,4-dichlorobenzyl)-2-oxopyrrolidin-3-yl)carbamate

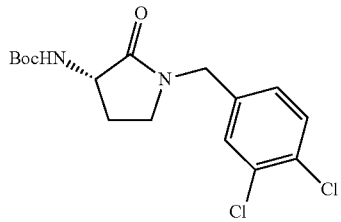 [SMILES: CC(C)(C)OC(=O)N[C@H]1CCN(Cc2ccc(Cl)c(Cl)c2)C1=O]

To a suspension of (2-oxopyrrolidin-3-(S)-yl)carbamic acid tert-butyl ester (243 mg, 1.21 mmol) in THF (4.5 mL) and DMF (0.5 mL) at 0° C. was added NaH (60% suspension in mineral oil, 58 mg, 1.5 mmol). After stirring for 20 min at 0° C., 3,4-dichlorobenzylchloride (0.20 mL, 1.5 mmol) was added and the reaction mixture was warmed to room temperature and stirred for 16 h. The mixture was then quenched with sat. NH$_4$Cl (aq) (20 mL) and extracted with EtOAc (3×20 mL). The organic phases were combined, dried (Na$_2$SO$_4$), filtered and concentrated in vacuo. The residue was purified by FCC (SiO$_2$, elution with 0-100% EtOAc/hexanes) to give 374 mg (86%) of the title compound as a white solid. $^1$H NMR (400 MHz, CDCl$_3$): δ 7.41 (d, 1H), 7.33 (d, 1H), 7.08 (dd, 1H), 5.13 (br s, 1H, N—H), 4.42 (ABq, 2H), 4.20 (m, 1H), 3.24-3.20 (m, 2H), 2.63 (m, 1H), 1.88 (m, 1H), 1.45 (s, 9H) ppm; LCMS (Method A): $t_R$=1.30 min, m/z 303.1/305.1 (M+H)$^+$.

Step 2: (S)-3-amino-1-(3,4-dichlorobenzyl)pyrrolidin-2-one.HCl (Intermediate I.32)

Intermediate I.32

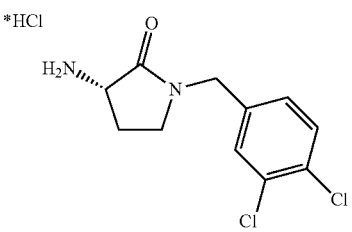

A solution of (S)-tert-butyl (1-(3,4-dichlorobenzyl)-2-oxopyrrolidin-3-yl)carbamate (374 mg, 1.04 mmol) in 3N HCl in MeOH (4 mL) was stirred at room temperature for 16 h. The reaction mixture was then concentrated in vacuo and the residue was triturated with Et$_2$O to provide 321 mg (quantitative) of the title compound, Intermediate I.32, as an off-white solid. $^1$H NMR (400 MHz, CD$_3$OD): δ 7.53 (d, 1H), 7.50 (d, 1H), 7.25 (dd, 1H), 4.50 (ABq, 2H), 4.13 (app t, 1H), 3.46-3.37 (m, 2H), 2.56 (m, 1H), 1.98 (m, 1H) ppm; LCMS (Method A): $t_R$=0.77 min, m/z 259.1/261.1 (M+H)$^+$.

Intermediate I.33 (S)-3-amino-1-(3,4-dichlorobenzyl)piperidin-2-one.HCl

Intermediate I.33

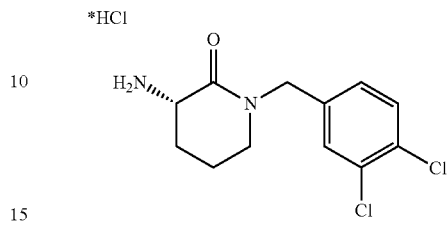

Intermediate I.33 was prepared from (2-oxopiperidin-3-yl)carbamic acid tert-butyl ester using the same general method described for the preparation of Intermediate I.32. $^1$H NMR (400 MHz, CD$_3$OD): δ 7.51-7.49 (m, 2H), 7.26 (dd, 1H), 4.59 (ABq, 2H), 4.00 (dd, 1H), 3.38-3.34 (m, 2H), 2.31 (m, 1H), 2.08-1.92 (m, 2H), 1.85 (m, 1H) ppm; LCMS (Method A): $t_R$=0.79 min, m/z 273.2/275.2 (M+H)$^+$.

Intermediate I.34: (R)-3-amino-1-(3,4-dichlorobenzyl)piperidin-2-one.HCl

Intermediate I.34

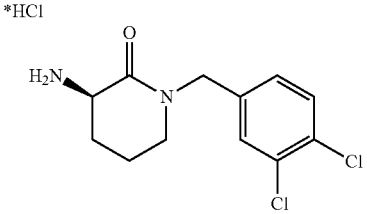

Intermediate I.34 was prepared from (2-oxopiperidin-3-(R)-yl)carbamic acid tert-butyl ester using the same general method described for the preparation of Intermediate I.32. $^1$H NMR (400 MHz, CD$_3$OD): δ 7.52-7.50 (m, 2H), 7.26 (dd, 1H), 4.59 (ABq, 2H), 4.00 (dd, 1H), 3.38-3.34 (m, 2H), 2.30 (m, 1H), 2.08-1.92 (m, 2H), 1.84 (m, 1H) ppm; LCMS (Method A): $t_R$=0.78 min, m/z 273.2/275.2 (M+H)$^+$.

Intermediate I.35: 3-amino-1-(3,4-dichlorobenzyl)pyridin-2(1H)-one

Intermediate I.35

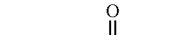

Intermediate I.35 was prepared from 2-hydroxy-3-nitropyridine and 3,4-dichlorobenzylchloride according to the same general method used for the preparation of 3-amino-1-(4-methoxybenzyl)-2-pyridone as described by Proudfoot et al. (Proudfoot, J. R., et al. *J. Med. Chem.*, 2001, 44, 2421-2431). However, PtO₂ was used in place of Pd/C as the catalyst for the nitro reduction (with H₂ gas) in the second step of the synthesis in order to avoid possible dechlorination of the dichlorophenyl moiety. $^1$H NMR (400 MHz, CD₃OD): δ 7.40 (d, 1H), 7.38 (d, 1H), 7.15 (dd, 1H), 6.71 (dd, 1H), 6.53 (dd, 1H), 6.10 (app t, 1H), 5.10 (s, 2H), 4.24 (br s, 2H, NH₂) ppm.

Intermediate I.36

Step 1: (R)-(9H-fluoren-9-yl)methyl tert-butyl (4-((3,4-dichlorobenzyl)amino)-4-oxobutane-1,3-diyl)dicarbamate

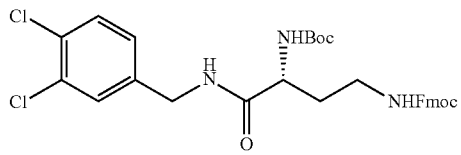

To a mixture of Boc-D-Dab(Fmoc)-OH (500 mg, 1.14 mmol) and 3,4-dichlorobenzyl amine (300 mg, 1.703 mmol) in ACN (10 mL) was added HATU (647 mg, 1.703 mmol) followed by DIEA (293 mg, 2.27 mmol). The mixture was stirred at room temperature for 2 h. The solids were filtered and dried. The filtered crude solids were purified by FCC (SiO₂, elution with 0.5-5% MeOH/DCM) to provide 433 mg (64%) of (R)-(9H-fluoren-9-yl)methyl tert-butyl (4-((3,4-dichlorobenzyl)amino)-4-oxobutane-1,3-diyl)dicarbamate. $^1$H NMR (400 MHz, d₆-DMSO): δ 8.39 (s, 1H), 7.89 (d, 2H), 7.68 (d, 2H), 7.54 (d, 1H), 7.51 (d, 1H), 7.41 (t, 2H), 7.32 (t, 2H), 7.27-7.22 (m, 2H), 7.07 (d, 1H), 4.29-4.21 (m, 5H), 3.97-3.90 (m, 1H), 3.05-2.97 (m, 2H), 1.84-1.73 (m, 1H), 1.70-1.59 (m, 1H), 1.39 (s, 9H) ppm.

Step 2: (R)-(9H-fluoren-9-yl)methyl (3-amino-4-((3,4-dichlorobenzyl)amino)-4-oxobutyl)carbamate.
HCl (Intermediate I.36)

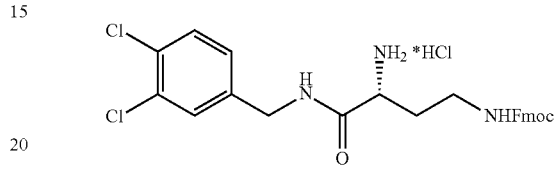

Intermediate I.36

(R)-(9H-fluoren-9-yl)methyl tert-butyl (4-((3,4-dichlorobenzyl)amino)-4-oxobutane-1,3-diyl)dicarbamate (370 mg, 0.62 mmol) was stirred in 4M HCl in Dioxane (1 mL) at room temperature for 30 minutes. This was then concentrated in vacuo to provide 319 mg (97%) of intermediate I.36. $^1$H NMR (400 MHz, CD₃OD): δ 8.90 (s, 1H), 7.81 (d, 2H), 7.64 (d, 2H), 7.51-7.48 (d, 2H), 7.41-7.38 (m, 2H), 7.33-7.24 (m, 3H), 4.48-4.45 (m, 3H), 4.38-4.31 (m, 1H), 4.22 (m, 1H), 3.78 (m, 1H), 3.24 (m, 2H), 2.08-1.89 (m, 2H); LCMS (Method A): $t_R$=1.12 min, m/z 498.4/500.4 (M+H)⁺.

Following the methods described above for the preparation of Intermediates I.1-I.3, and substituting the corresponding reagents, the following intermediates were prepared as indicated in Table 2.

TABLE 2

| Intermediate | Structure | Reagents | LCMS Method | $t_R$ (min) | (M + H)⁺ observed |
|---|---|---|---|---|---|
| I.37 | ![structure] | 4,5-dichloro-2-ethoxybenzyl amine and Fmoc-D-Glu-(Ot-Bu)-OH | A | 1.10 | 405.3/407.3 |
| I.38 | ![structure] | 4,5-dichloro-2-isopropoxybenzyl amine and Fmoc-D-Glu-(Ot-Bu)-OH | A | 1.16 | 419.3/421.3 |

Intermediate II.1: 5-phenylpent-1-en-3-one

Step 1: N-methoxy-N-methyl-3-phenylpropanamide

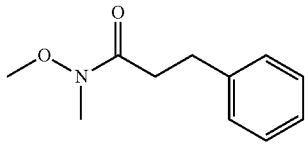

To a solution of 3-phenylpropionic acid (1.00 g, 6.66 mmol) in DCM (20 mL) was added PyBOP (3.47 g, 6.66 mmol) followed by TEA (1.1 mL, 7.6 mmol). The mixture was stirred at room temperature for 30 min. This was then cooled to 0° C. and N,O-dimethylhydroxyl amine.HCl (0.72 g, 7.33 mmol) was added followed by additional TEA (1.1 mL, 7.6 mmol). The reaction mixture was warmed to room temperature and stirred for 16 h. The mixture was then concentrated in vacuo and the crude residue was purified by FCC (SiO$_2$, elution with 0-100% EtOAc/hexanes) to provide 1.21 g (94%) of N-methoxy-N-methyl-3-phenylpropanamide. $^1$H NMR (400 MHz, CDCl$_3$): δ 7.32-7.18 (m, 5H), 3.61 (s, 3H), 3.18 (s, 3H), 2.97 (t, 2H), 2.75 (t, 2H) ppm; LCMS (Method A): t$_R$=1.04 min, m/z 194.4 (M+H)$^+$.

Step 2: 5-phenylpent-1-en-3-one (Intermediate II.1)

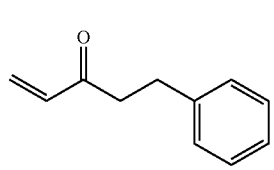

Intermediate II.1

To a solution of the Weinreb amide obtained in step 1 above (0.20 g, 1.04 mmol) in anhydrous Et$_2$O (5 mL) at 0° C. was added vinylmagnesium bromide (1.0 M in THF, 1.25 mL, 1.25 mmol). The mixture was stirred at 0° C. for 30 min, then allowed to warm to room temperature and stirred for an additional 2.5 h. The mixture was then cooled to 0° C. and additional vinylmagnesium bromide (1.0 M in THF, 0.40 mL, 0.40 mmol) was added. The resultant mixture was warmed to room temperature and stirred an additional 1 h. The mixture was then quenched with 2 N HCl (aq) and extracted with EtOAc (3×). The combined organic extracts were dried (Na$_2$SO$_4$), filtered and concentrated in vacuo. The crude residue was taken up in DCM and filtered through a 1 gram cartridge of SiO$_2$, eluting with additional DCM. The filtrate was concentrated in vacuo to provide 0.13 g (78%) of Intermediate II.1. $^1$H NMR (400 MHz, CDCl$_3$): δ 7.31-7.19 (m, 5H), 6.37 (dd, 1H), 6.22 (dd, 1H), 5.84 (dd, 1H), 2.99-2.89 (m, 4H) ppm.

Using the synthetic method described above for the preparation of Intermediate II.1 the following intermediates were prepared from the corresponding reagent as indicated in Table 3.

TABLE 3

| Intermediate | Structure | Reagent | $^1$H NMR |
|---|---|---|---|
| II.2 | 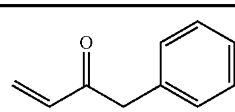 | Phenylacetic acid | (400 MHz, CDCl$_3$): δ 7.36-7.21 (m, 5H), 6.42 (dd, 1H), 6.32 (dd, 1H), 6.84 (dd, 1H), 3.89 (s, 2H) ppm |
| II.3 | 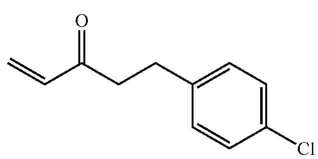 | 4-Chloro-phenyl-propionic acid | (400 MHz, CDCl$_3$): δ 7.25 (d, 2H), 7.13 (d, 2H), 6.35 (dd, 1H), 6.21 (dd, 1H), 5.84 (dd, 1H), 2.95-2.87 (m, 4H) ppm |
| II.4 | 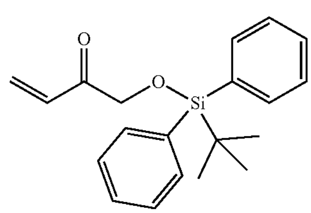 [SMILES: C=CC(=O)CO[Si](c1ccccc1)(c1ccccc1)C(C)(C)C] | 2-((tert-butyldiphenylsilyl)oxy)-acetic acid | (400 MHz, CDCl$_3$): δ 7.66 (m, 4H), 7.42 (m, 6H), 6.70 (dd, 1H), 6.32 (dd, 1H), 5.77 (dd, 1H), 4.37 (s, 2H), 1.10 (s, 9H) ppm |

Synthesis of Examples According to the Invention

Example 1: (2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-4-methylpentanamide.HCl Step 1: (R)—N-(3,4-dichlorobenzyl)-4-methyl-2-((3-oxo-5-phenylpentyl)amino)pentanamide (Compound 1-1)

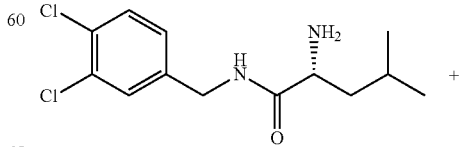

Intermediate I.2

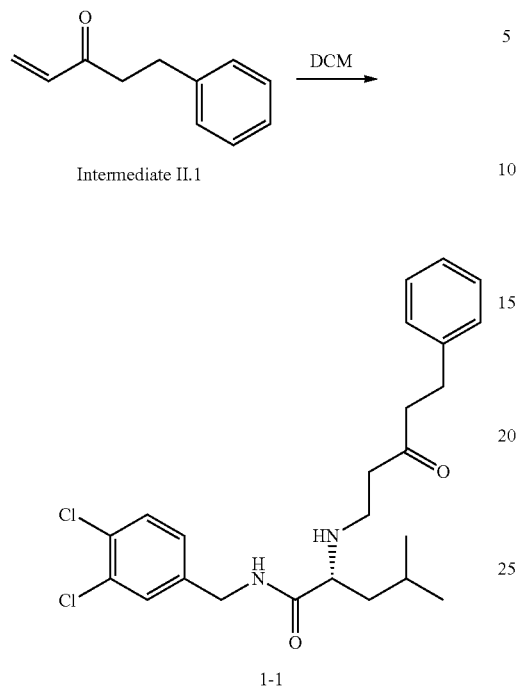

A mixture of Intermediate I.2 (218 mg, 0.755 mmol) and Intermediate II.1 (121 mg, 0.755 mmol) in DCM (5 mL) was stirred at room temperature for 16 h. The mixture was then concentrated in vacuo and the crude residue was purified by FCC (SiO$_2$, elution with 0-10% MeOH/DCM) to provide 297 mg (88%) of Compound 1-1 as a clear oil. $^1$H NMR (400 MHz, CDCl$_3$): δ 7.88 (br t, 1H, amide N—H), 7.40 (d, 1H), 7.38 (d, 1H), 7.29-7.25 (m partially obscured by solvent peak, 2H), 7.21-7.43 (m, 4H), 4.40 (m, 2H), 3.10 (dd, 1H), 2.89 (app t, 2H), 2.81-2.67 (m, 4H), 2.53 (m, 2H), 1.71-1.24 (m, 4H including amine N—H), 0.95 (d, 3H), 0.93 (d, 3H) ppm.

Step 2: (2S,4R)-(9H-fluoren-9-yl)methyl 4-((tert-butoxycarbonyl)amino)-2-(((R)-1-((3,4-dichlorobenzyl)amino)-4-methyl-1-oxopentan-2-yl)(3-oxo-5-phenylpentyl)carbamoyl)pyrrolidine-1-carboxylate (Compound 1-2)

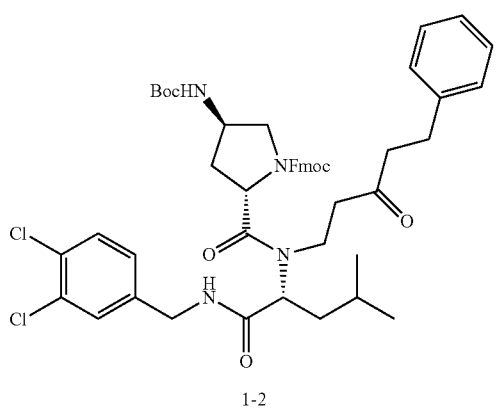

To a solution of (2S,4R)-Boc-4-amino-Fmoc proline (330 mg, 0.729 mmol) in DCM (2 mL) was added DIPEA (0.35 mL, 2.0 mmol). This mixture was then added via pipette to a reaction vial containing Compound 1-1 (297 mg, 0.662 mmol). The vessel originally containing the proline reagent and DIPEA mixture was rinsed with DCM (1 mL) and this was also added via pipette to the reaction vial. BOP—Cl (253 mg, 0.99 mmol) was then added, and the reaction mixture was stirred at room temperature for 3 d. The reaction mixture was quenched with sat. NaHCO$_3$ (aq) and extracted with DCM (3×). The combined organic extracts were dried (Na$_2$SO$_4$), filtered and concentrated in vacuo. The crude residue was purified by FCC (SiO$_2$, elution with 0-50% EtOAc/hexanes) to provide 449 mg (77%) of Compound 1-2 as an off-white solid. LCMS (Method A): t$_R$=1.83 min, m/z 883.6/885.6 (M+H)$^+$.

Steps 3 and 4: tert-butyl ((8R,9aS)-2-((R)-1-((3,4-dichlorobenzyl)amino)-4-methyl-1-oxopentan-2-yl)-1-oxo-5-phenethyloctahydro-1H-pyrrolo[1,2-a][1,4]diazepin-8-yl)carbamate (Compound 1-3)

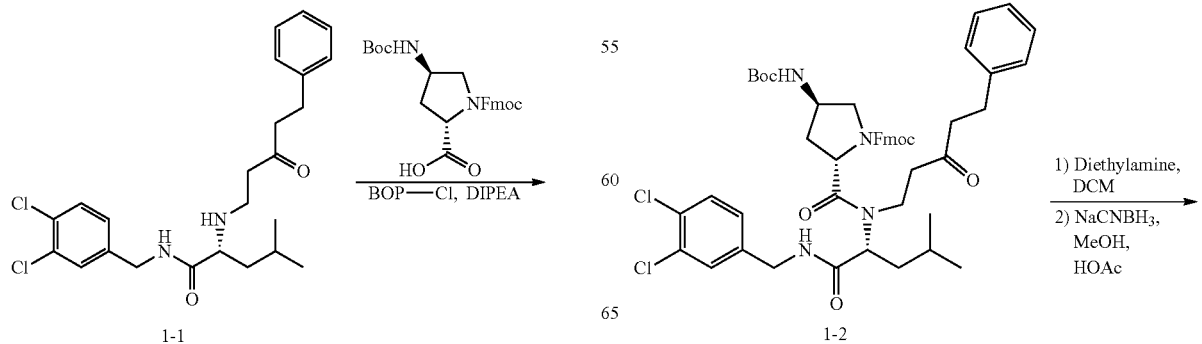

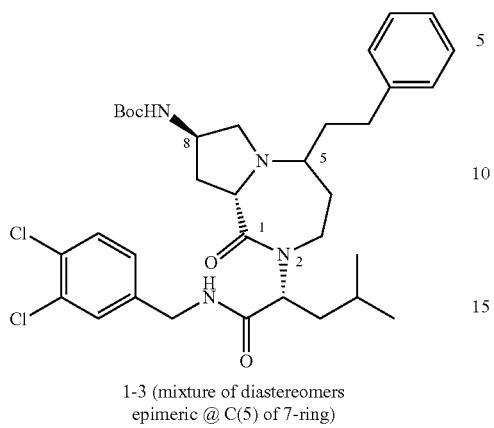

1-3 (mixture of diastereomers epimeric @ C(5) of 7-ring)

To a solution of Compound 1-2 (445 mg; 0.503 mmol) in DCM (5 mL) was added diethylamine (1.00 mL, 10.1 mmol) and the mixture was stirred for 3 h at room temperature. The mixture was then concentrated in vacuo and the crude residue was taken up in MeOH (5 mL). To this was added AcOH (0.10 mL) followed by NaCNBH$_3$ (1 M in THF, 0.65 mL, 0.65 mmol). The reaction mixture was stirred at room temperature for 45 min. The mixture was then quenched with sat. NaHCO$_3$ (aq) and extracted with DCM (3×). The combined organic extracts were dried (Na$_2$SO$_4$), filtered and concentrated in vacuo. The crude residue was purified by FCC (SiO$_2$, elution with 0-50% EtOAc/hexanes) to provide 255 mg (78%) of Compound 1-3 as a white solid. Analysis by LCMS indicated 1-3 to be a mixture of two diastereomers in a ratio of 88:12. This mixture of diastereomers was carried directly into the next step. LCMS (Method A): t$_R$=1.38 min (major diastereomer, 88%) and 1.45 min (minor diastereomer, 12%), m/z 645.5/647.5 (M+H)$^+$.

Step 5: (2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-4-methylpentanamide-.HCl (Example 1)

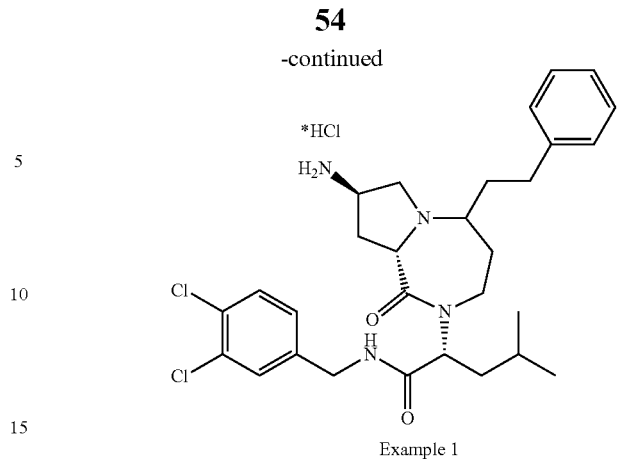

Example 1

Compound 1-3 (255 mg, 0.395 mmol) was taken up in 3N HCl in MeOH (2 mL) and stirred in a tightly capped reaction vial at 40° C. for 2 h. The reaction temperature was increased to 50° C. and stirring was continued for 30 min. The reaction mixture was then cooled, concentrated in vacuo and the crude residue was purified directly by mass-directed preparative reversed-phase HPLC (C18 column, elution with 5-95% ACN/H$_2$O containing 0.25% formic acid). The desired fractions containing mainly the desired first eluting (major) diastereomer and a small amount of second eluting (minor) diastereomer were combined and concentrated in vacuo. To the residue was added 3N HCl in MeOH (~10 mL) and the volatiles were removed in vacuo. This treatment with 3N HCl in MeOH was repeated to ensure formation of the hydrochloride salt. The mixture was then concentrated in vacuo and the residue was taken up in H$_2$O and a small amount of ACN was added to provide a clear solution which was then lyophilized to provide 96 mg (42%) of Example 1 as an off-white solid. Analysis by HPLC indicated Example 1 to be a mixture of diastereomers in a ratio of 96:4. $^1$H NMR (400 MHz, CD$_3$OD): δ 7.52 (d, 1H), 7.47 (d, 1H), 7.32-7.19 (m, 6H), 5.22 (dd, 1H), 5.04 (m, 1H), 4.35 (AB q, 2H), 4.15 (m, 1H), 3.96 (m, 1H), 3.85-3.62 (m, 3H), 3.37 (m, 1H), 3.20 (m, 1H), 2.77 (m, 1H), 2.59 (m, 1H), 2.38-2.26 (m, 2H), 2.16 (m, 1H), 1.98-1.66 (m, 4H), 1.50 (m, 1H), 0.98 (d, 3H), 0.92 (d, 3H) ppm; LCMS (Method A): t$_R$=1.17 min, m/z 545.4/547.4 (M+H)$^+$; HPLC: t$_R$=4.866 min (96%, major diastereomer) and 5.207 min (4%, minor diastereomer).

Example 2: (4R)-4-((8R,9aS)-8-amino-1-oxo-5-phenethylhexahydro-1H-pyrrolo[1,2-a][1,4]diazepin-2(3H)-yl)-5-oxo-5-((4-(trifluoromethyl)benzyl)amino)-pentanoic Acid Steps 1-4: (4R)-tert-butyl 4-((8R,9aS)-8-((tert-butoxycarbonyl)amino)-1-oxo-5-phenethylhexahydro-1H-pyrrolo[1,2-a][1,4]diazepin-2(3H)-yl)-5-oxo-5-((4-(trifluoromethyl)benzyl)amino)pentanoate (Compound 2-3)

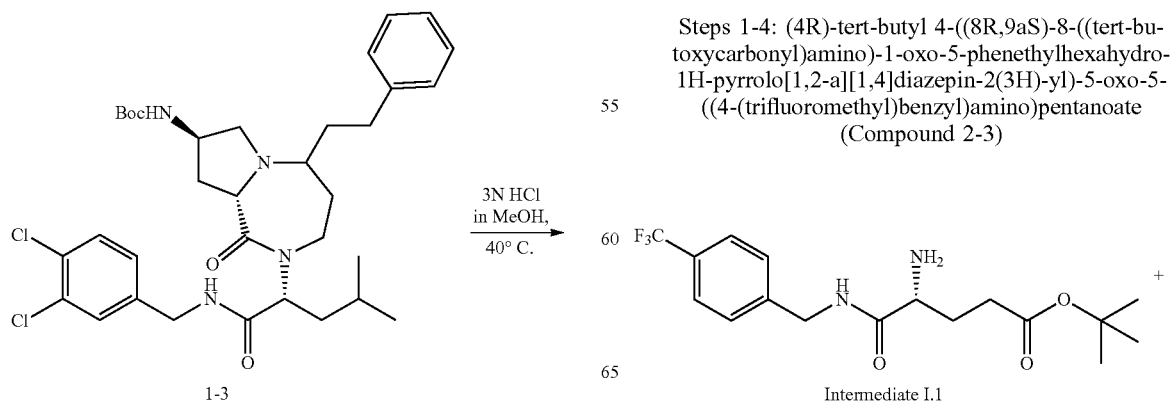

Intermediate I.1

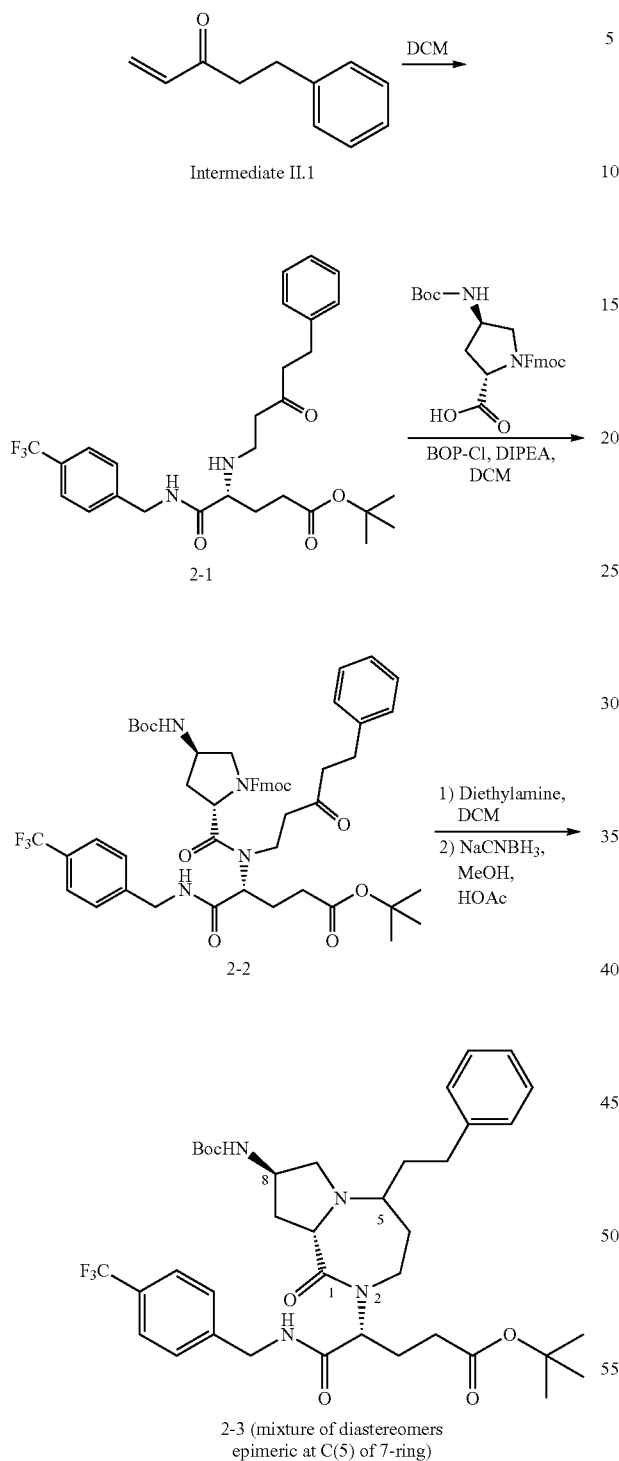

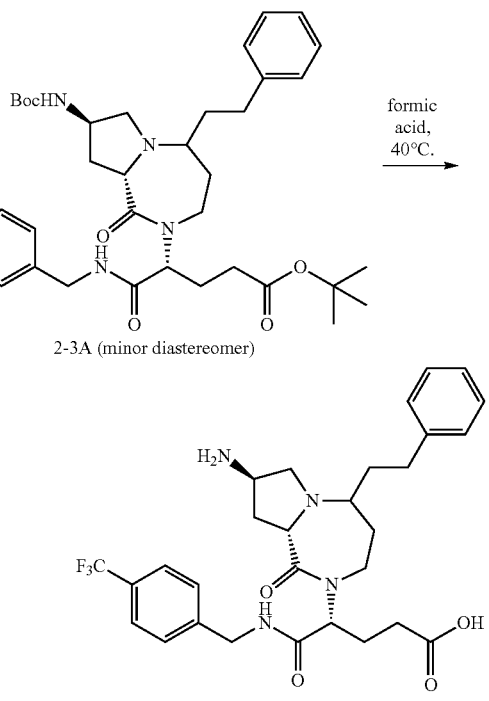

Compound 2-3 was prepared from Intermediate I.1 (254 mg, 0.705 mmol) and Intermediate II.1 (113 mg, 0.705 mmol) using the same general method described for the preparation of compound 1-3 in steps 1-4 in Example 1. After work-up the crude product was purified by FCC (SiO$_2$, elution with 0-100% EtOAc/hexanes) to provide 56 mg of a first eluting, minor diastereomer (Compound 2-3A) and 124 mg of a second eluting, major diastereomer (Compound 2-3B). The pure minor diastereomer 2-3A and pure major diastereomer 2-3B were carried independently into the next step. Data for Compound 2-3A (minor diastereomer): LCMS (Method A): $t_R$=1.41 min, m/z 717.6 (M+H)$^+$. Data for Compound 2-3B (major diastereomer): $^1$H NMR (400 MHz, CD$_3$OD): δ 7.61 (d, 2H), 7.51 (d, 2H), 7.25 (m, 2H), 7.15 (m, 3H), 5.13 (dd, 1H), 4.46 (ABq, 2H), 4.00 (m, 1H), 3.71 (dd, 1H), 3.56 (dd, 1H), 3.46-3.40 (m, 2H), 2.81 (m, 1H), 2.63-2.53 (m, 2H), 2.42 (m, 1H), 2.29-2.13 (m, 5H), 1.96-1.82 (m, 3H), 1.71 (m, 1H), 1.55 (m partially obscured by singlet, 1H), 1.44 (s superimposed on multiplet, 18H), ppm; LCMS (Method A): $t_R$=1.33 min, m/z 717.6 (M+H)$^+$.

Step 5A: (4R)-4-((8R,9aS)-8-amino-1-oxo-5-phenethylhexahydro-1H-pyrrolo[1,2-a][1,4]diazepin-2(3H)-yl)-5-oxo-5-((4(trifluoromethyl)benzyl)amino)pentanoic Acid (Example 2A)

A solution of Compound 2-3A (55 mg, 0.077 mmol) in formic acid (2 mL) was heated to 40° C. for 2 h. The reaction mixture was then concentrated in vacuo and the crude residue was taken up in 1:1 ACN/H$_2$O (2 mL) and then purified directly by mass-directed preparative reversed-phase HPLC (C-18, elution with 5-95% ACN/H$_2$O containing 0.25% formic acid). The desired fractions containing purified product were combined, diluted with H$_2$O, and lyophilized to provide 36 mg (84%) of Example 2A as a white solid. $^1$H NMR (400 MHz, CD$_3$OD): δ 7.62 (d, 2H), 7.47 (d, 2H), 7.27-7.13 (m, 5H), 5.14 (dd, 1H), 4.46 (s, 2H), 3.81-3.73 (m, 2H), 3.67 (dd, 1H), 3.51 (dd, 1H), 3.34 (m partially obscured by solvent peak, 1H), 2.78-2.57 (m, 5H), 2.42-2.27 (m, 4H), 2.07-1.88 (m, 3H), 1.82-1.71 (m, 2H), ppm; LCMS (Method A): $t_R$=1.00 min, m/z 561.5 (M+H)$^+$.

Step 5B: (4R)-4-((8R,9aS)-8-amino-1-oxo-5-phenethylhexahydro-1H-pyrrolo[1,2-a][1,4]diazepin-2(3H)-yl)-5-oxo-5-((4-(trifluoromethyl)benzyl)amino)-pentanoic Acid (Example 2B)

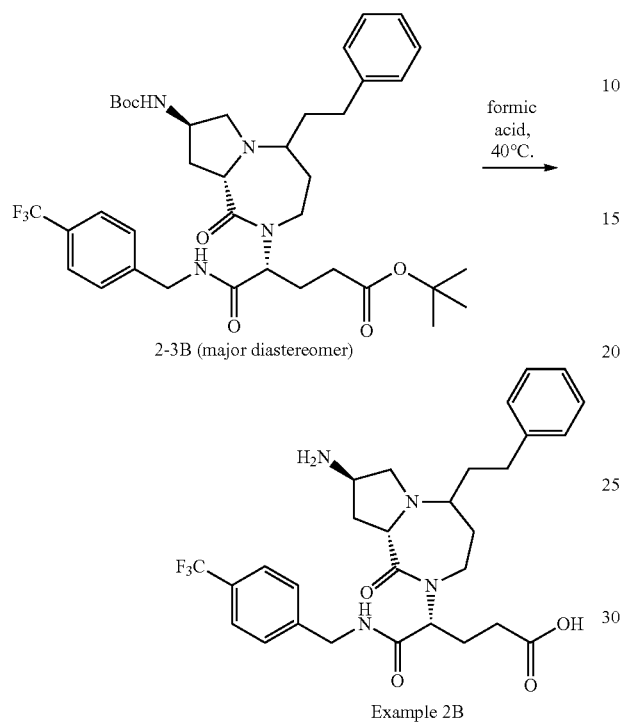

A solution of Compound 2-3B (124 mg, 0.173 mmol) in formic acid (2 mL) was heated to 40° C. for 2 h. The reaction mixture was then concentrated in vacuo and the crude residue was taken up in 1:1 ACN/H$_2$O (2 mL) and then purified directly by mass-directed preparative reversed-phase HPLC (C-18, elution with 5-95% ACN/H$_2$O containing 0.25% formic acid). The desired fractions containing purified product were combined, diluted with H$_2$O, and lyophilized to provide 74 mg (76%) of Example 2B as a white solid. $^1$H NMR (400 MHz, CD$_3$OD): δ 7.60 (d, 2H), 7.50 (d, 2H), 7.25 (m, 2H), 7.17-7.14 (m, 3H), 5.09 (m, 1H), 4.46 (ABq, 2H), 3.82 (dd, 1H), 3.67-3.52 (m, 4H), 2.97 (m, 1H), 2.68-2.60 (m, 2H), 2.50 (m, 1H), 2.40 (app t, 1H), 2.20-2.03 (m, 4H), 1.97-1.82 (m, 3H), 1.67-1.55 (m, 2H) ppm; LCMS (Method A): t$_R$=0.95 min, m/z 561.5 (M+H)$^+$.

Example 3: (2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-3-hydroxypropanamide.HC Steps 1-4: tert-butyl ((8R,9aS)-2-((R)-3-(tert-butoxy)-1-((3,4-dichlorobenzyl)amino)-1-oxopropan-2-yl)-1-oxo-5-phenethyloctahydro-1H-pyrrolo[1,2-a][1,4]diazepin-8-yl)carbamate (Compound 3-3)

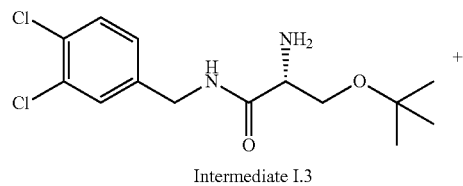

Intermediate I.3

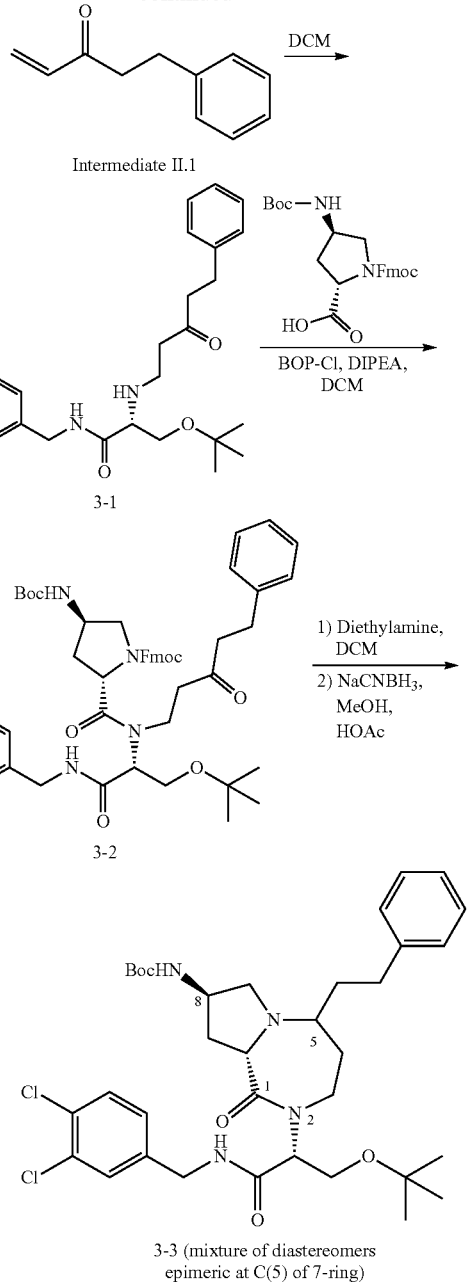

Compound 3-3 was prepared from Intermediate I.3 (99 mg, 0.31 mmol) and Intermediate II.1 (50 mg, 0.31 mmol) using the same general method described for the preparation of compound 1-3 in steps 1-4 in Example 1. After work-up the crude product was purified by FCC (SiO$_2$, elution with 0-100% EtOAc/hexanes) to provide 17 mg of a first eluting, minor diastereomer (Compound 3-3A) and 91 mg of a second eluting, major diastereomer (Compound 3-3B). The pure major diastereomer 3-3B was carried into the next step. Data for Compound 3-3A (minor diastereomer): LCMS (Method A): t$_R$=0.90 min, m/z 675.4/677.3 (M+H)$^+$. Data for Compound 3-3B (major diastereomer): $^1$H NMR (400 MHz, CDCl$_3$): δ 7.39-7.36 (m, 2H), 7.28 (m partially obscured by solvent peak, 2H), 7.20-7.08 (m, 6H), 4.95 (app t, 1H), 4.49-4.29 (m, 3H), 4.09 (m, 1H), 3.82 (dd, 1H), 3.67-3.62 (m, 2H), 3.51-3.44 (m, 3H), 2.91-2.51 (m, 4H), 2.45 (m, 1H), 2.23 (m, 1H), 1.91-1.82 (m, 2H), 1.67 (m partially obscured by H₂O peak, 1H), 1.44 (s, 9H), 1.17 (s, 9H) ppm; LCMS (Method C): $t_R$=0.87 min, m/z 675.4/677.3 (M+H)⁺.

Step 5: (2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-3-hydroxypropanamide.HCl (Example 3)

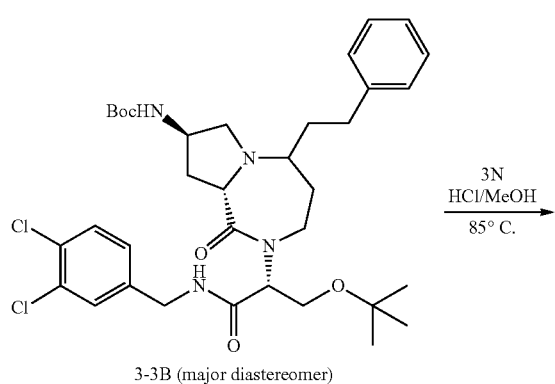

Compound 3-3B (85 mg, 0.13 mmol) was treated with 3N HCl in MeOH (2 mL) and the resultant reaction mixture was heated to 85° C. in a tightly capped reaction vial for 2 h. The reaction mixture was then cooled and concentrated in vacuo. The crude residue was taken up in DMSO (1.5 mL) and was then purified directly by mass-directed preparative reversed-phase HPLC (elution with 5-95% ACN/H₂O containing 0.25% formic acid). The desired fractions were combined and concentrated in vacuo. To the residue was added 3N HCl (~10 mL) and the volatiles were removed in vacuo. This treatment with 3N HCl was repeated to ensure formation of the hydrochloride salt. The mixture was then concentrated in vacuo and the residue was taken up in H₂O and a small amount of ACN was added to provide a clear solution which was lyophilized to provide 26 mg (38%) of Example 3 as yellow solid. ¹H NMR (400 MHz, CD₃OD): δ 7.53 (d, 1H), 7.46 (d, 1H), 7.32-7.19 (m, 6H), 5.07 (dd, 1H), 4.97 (m partially obscured by H₂O peak, 1H), 4.38 (ABq, 2H), 4.12 (m, 1H), 4.03-3.88 (m, 3H), 3.85-3.79 (m, 2H), 3.65 (m, 1H), 3.34 (m partially obscured by solvent peak, 1H), 3.20 (m, 1H), 2.77 (m, 1H), 2.60 (m, 1H), 2.36-2.25 (m, 2H), 2.17 (m, 1H), 2.05 (m, 1H), 1.87 (m, 1H) ppm; LCMS (Method A): $t_R$=0.97 min, m/z 519.4/521.4 (M+H)⁺.

Example 4: (2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-3-hydroxypropanamide.HCl Steps 1-4: tert-butyl ((8R,9aS)-2-((R)-1-((3,4-dichlorobenzyl)amino)-1,5-dioxo-5-(tritylamino)pentan-2-yl)-1-oxo-5-phenethyloctahydro-1H-pyrrolo[1,2-a][1,4]diazepin-8-yl)carbamate (Compound 4-3)

61
-continued

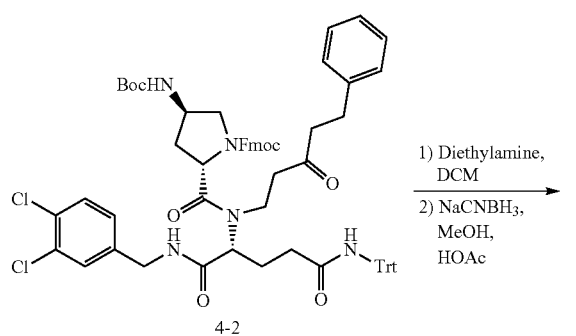

4-2

1) Diethylamine, DCM
2) NaCNBH₃, MeOH, HOAc
→

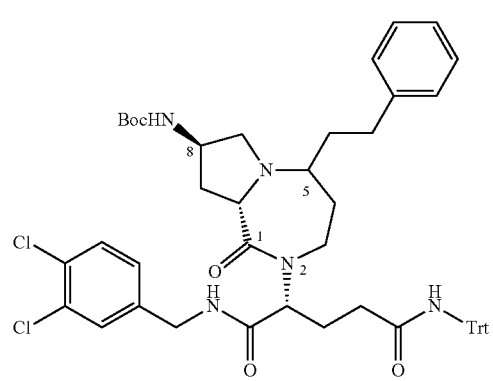

4-3 (mixture of diastereomers epimeric at C(5) of 7-ring)

Compound 4-3 was prepared from Intermediate I.13 (186 mg, 0.340 mmol) and Intermediate II.1 (55 mg, 0.34 mmol) using the same general procedures described for the preparation of compound 1-3 in steps 1-4 in Example 1. After work-up the crude product was purified by FCC (SiO₂, elution with 0-100% EtOAc/hexanes) to provide 105 mg of a second eluting, major diasteromer 4-3B (the first eluting, minor diastereomer 4-3A was not isolated). The pure major diasteromer 4-3B was carried forward into the next step. Data for Compound 4-3B (major diastereomer): ¹H NMR (400 MHz, CD₃OD): δ 7.50 (d, 1H), 7.44 (d, 1H), 7.28-7.14 (m, 21H), 5.07 (dd, 1H), 4.34 (ABq, 2H), 3.99 (m, 1H), 3.65 (dd, 1H), 3.49-3.34 (m, 3H), 2.83 (m, 1H), 2.60 (m, 1H), 2.51 (m, 1H), 2.43-2.28 (m, 2H), 2.22-2.08 (m, 3H), 1.96-1.84 (m, 2H), 1.79 (m, 1H), 1.69 (m, 1H), 1.57-1.28 (m partially obscured by singlet, 2H), 1.44 (s, superimposed on multiplet, 9H) ppm; LCMS (SQD-nonpolar): $t_R$=1.40 min, m/z 902.4/904.4 (M+H)⁺.

62

Step 5: (2R)-2-((8R,9aS)-8-amino-1-oxo-5-phenethylhexahydro-1H-pyrrolo[1,2-a][1,4]diazepin-2(3H)-yl)-N1-(3,4-dichlorobenzyl)pentanediamide.HCl (Example 4)

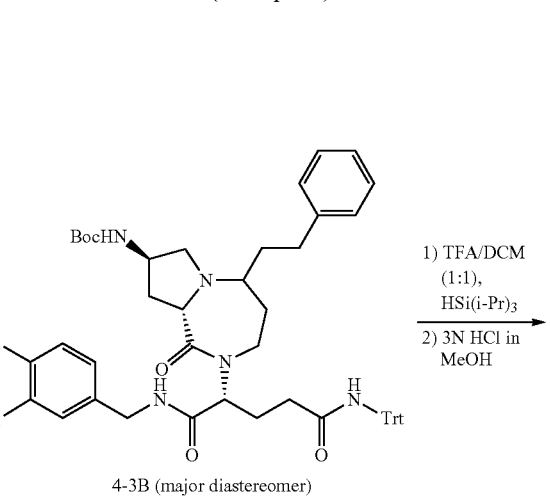

4-3B (major diastereomer)

1) TFA/DCM (1:1), HSi(i-Pr)₃
2) 3N HCl in MeOH
→

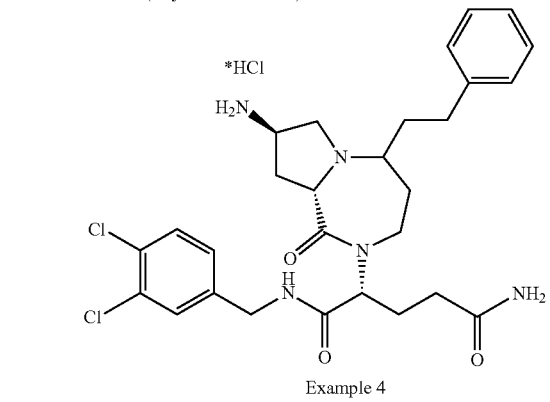

Example 4

Compound 4-3B (105 mg, 0.120 mmol) was dissolved in DCM (1 mL) and TFA (1 mL) was added, followed by triisopropylsilane (0.2 mL). The mixture was stirred at room temperature for 2 h. The mixture was concentrated in vacuo and the crude residue was purified directly by mass-directed preparative reversed-phase HPLC (C-18, elution with 5-95% ACN/H₂O containing 0.25% formic acid). The desired fractions were combined and concentrated in vacuo. To the residue was added 3N HCl (~10 mL) and the volatiles were removed in vacuo. This treatment with 3N HCl was repeated to ensure formation of the hydrochloride salt. The mixture was then concentrated in vacuo and the residue was taken up in H₂O and a small amount of ACN was added to provide a clear solution which was lyophilized to provide 26 mg (61%) of Example 4 as an HCl salt. ¹H NMR (400 MHz, CD₃OD): δ 7.55 (d, 1H), 7.47 (d, 1H), 7.33-7.20 (m, 6H), 5.16 (m, 2H), 4.37 (ABq, 2H), 4.21 (dd, 1H), 4.00 (m, 1H), 3.82-3.65 (m, 3H), 3.49 (m, 1H), 3.24 (m, 1H), 2.77 (m, 1H), 2.58 (m, 1H), 2.42-2.15 (m, 6H), 2.12-1.83 (m, 3H) ppm; LCMS (Method A): $t_R$=0.99 min, m/z 560.4/562.3 (M+H)⁺.

Following the methods described above for Examples 1-4, and using the corresponding intermediates and reagents in step 1, the examples set forth in Table 3 were prepared. Unless indicated otherwise, the examples in Table 4 were prepared from the major diastereomer obtained in step 4 (intramolecular reductive amination) of the synthesis.

TABLE 4

| Example | Structure | Intermediates and reagents | LCMS Method | $t_R$ (min) | $(M + H)^+$ observed |
|---------|-----------|---------------------------|-------------|-------------|----------------------|
| 5 | 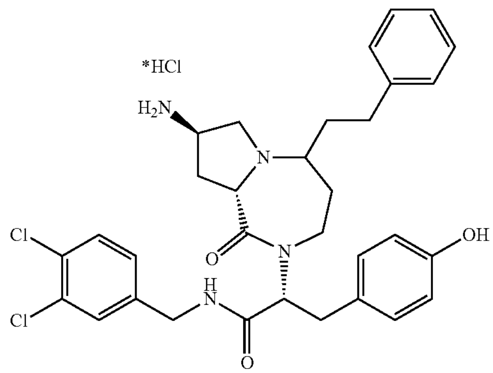 | I.7 and II.1 | A | 1.08 | 595.5/597.4 |
| 6 | 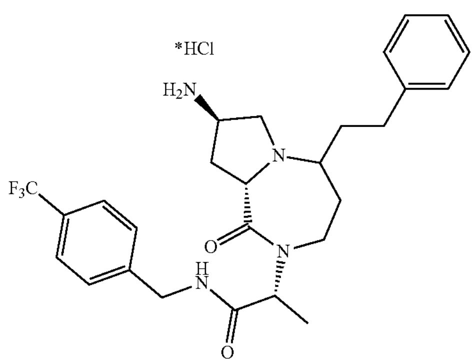 | I.8 and II.1 | A | 1.00 | 503.5 |
| 7 | 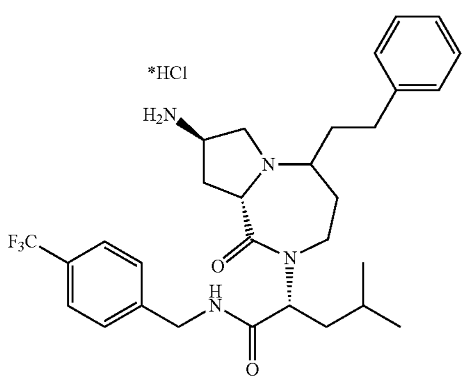 | I.9 and II.1 | A | 1.07 | 545.5 |
| 8 | 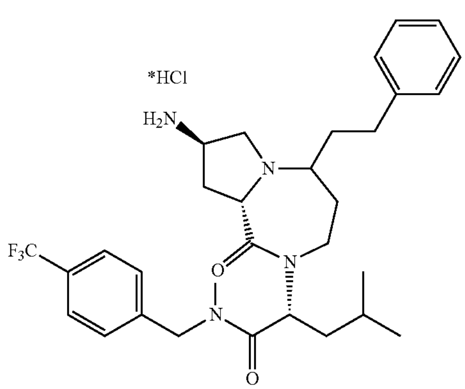 | I.6 and II.1 | A | 1.12 | 559.5 |

TABLE 4-continued
| Example | Structure | Intermediates and reagents | LCMS Method | $t_R$ (min) | $(M + H)^+$ observed |
|---|---|---|---|---|---|
| 9 | 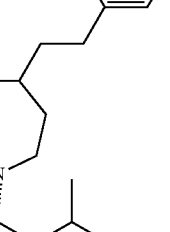 | I.5 and II.1 | A | 0.98 | 477.5 |
| 10 | 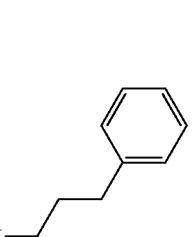 | I.4 and II.1 | A | 1.00 | 491.5 |
| 11 | 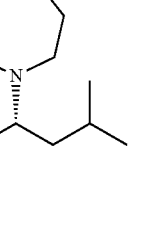 | I.2 and II.2 | A | 1.14 | 531.5/533.5 |
| 12 | 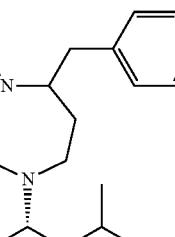 | I.2 and II.3 | A | 1.27 | 579.5/581.4 |

TABLE 4-continued
| Example | Structure | Intermediates and reagents | LCMS Method | $t_R$ (min) | $(M + H)^+$ observed |
|---|---|---|---|---|---|
| 13 | 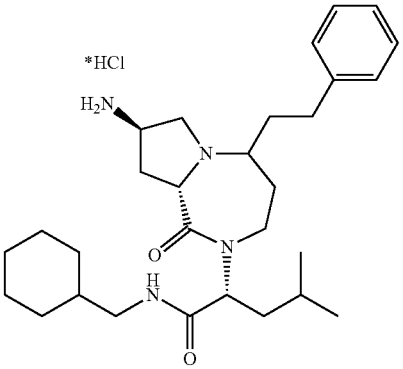 | I.10 and II.1 | A | 1.07 | 483.6 |
| 14 | 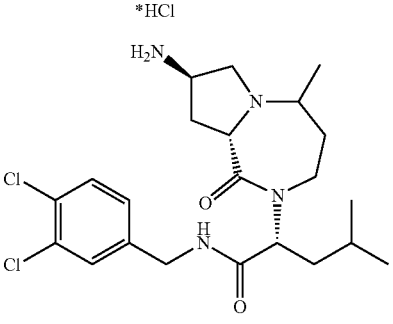 | I.2 and 3-buten-2-one | A | 0.96 | 455.4/457.4 |
| 15A | 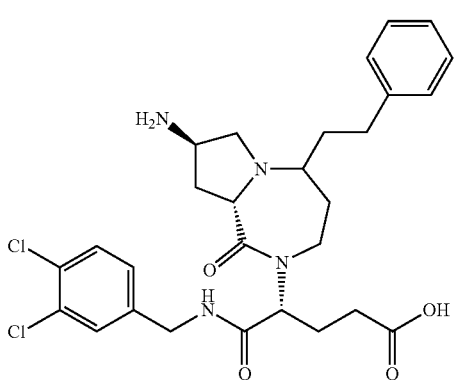<br>(minor diastereomer; diastereomer of 15B, epimeric @ C(5)) | I.11 and II.1 | A | 1.08 | 561.4/563.4 |
| 15B | 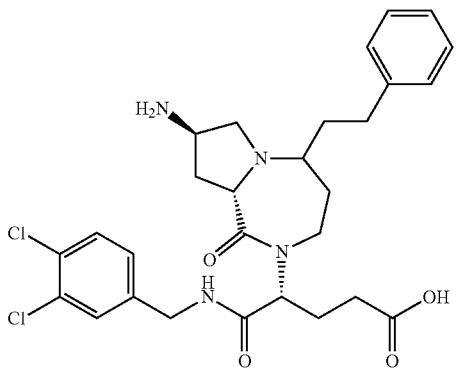<br>(major diastereomer; diastereomer of 15A, epimeric @ C(5)) | I.11 and II.1 | A | 0.94 | 561.3/563.3 |

TABLE 4-continued
| Example | Structure | Intermediates and reagents | LCMS Method | $t_R$ (min) | $(M + H)^+$ observed |
|---|---|---|---|---|---|
| 16 | 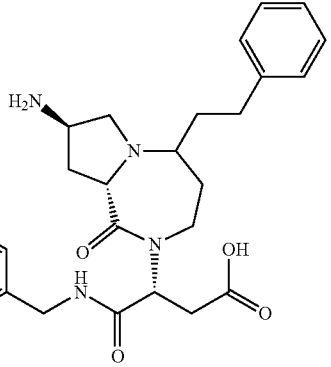 | I.12 and II.1 | A | 1.02 | 547.3/549.3 |
| 17 | 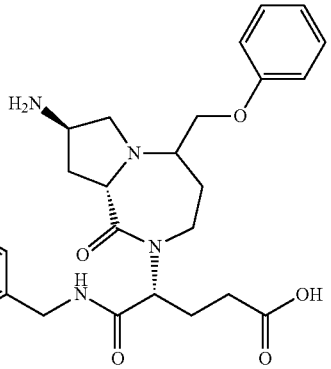 | I.11 and phenoxymethyl vinyl ketone | A | 0.96 | 563.5/565.5 |
| 18 | 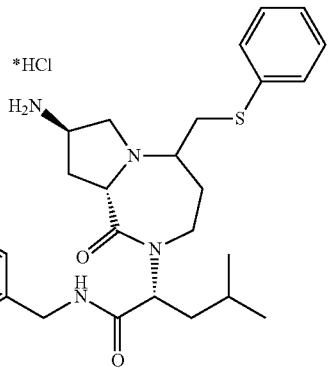 | I.2 and (phenylsulfanyl)methyl vinyl ketone | A | 1.15 | 563.5/565.5 |
| 19 | 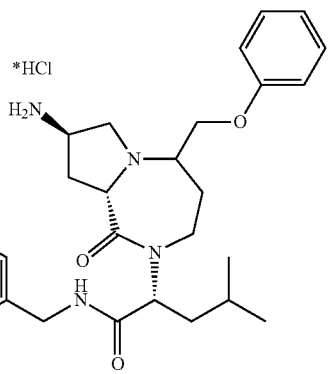 | I.2 and II.4 | A | 1.11 | 547.4/549.4 |

TABLE 4-continued
| Example | Structure | Intermediates and reagents | LCMS Method | $t_R$ (min) | $(M + H)^+$ observed |
|---|---|---|---|---|---|
| 20 | 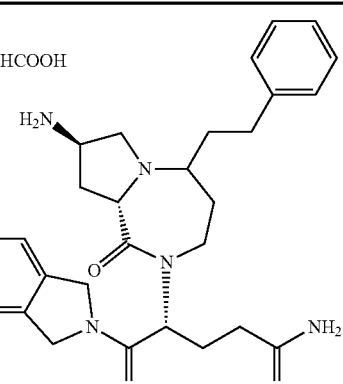 *HCOOH | I.13 and II.1 | A | 0.94 | 572.3/574.3 |
| 21 | 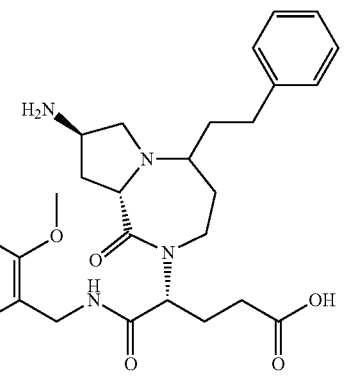 | I.14 and II.1 | A | 1.01 | 591.4/593.4 |
| 22 | 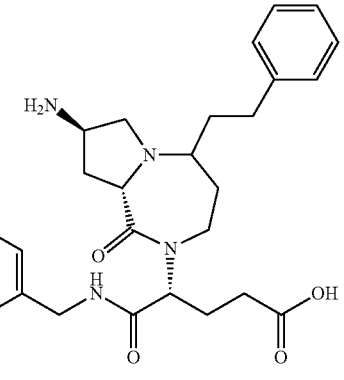 | I.15 and II.1 | A | 0.99 | 591.4/593.4 |
| 23 | 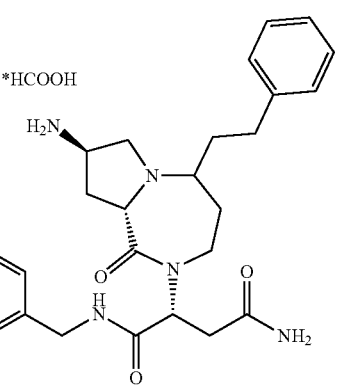 *HCOOH | I.16 and II.1 | A | 0.90 | 546.3/548.3 |

TABLE 4-continued
| Example | Structure | Intermediates and reagents | LCMS Method | $t_R$ (min) | $(M + H)^+$ observed |
|---|---|---|---|---|---|
| 24 | 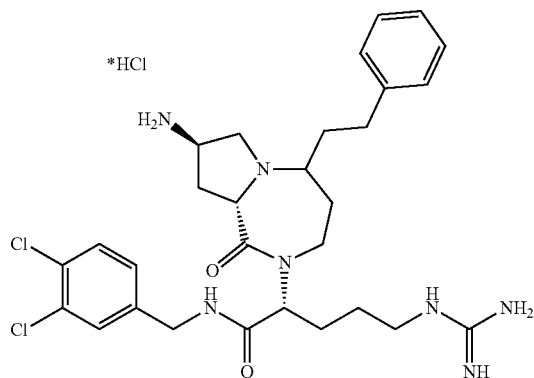 | I.17 and II.1 | A | 0.89 | 588.3/590.3 |
| 25 | 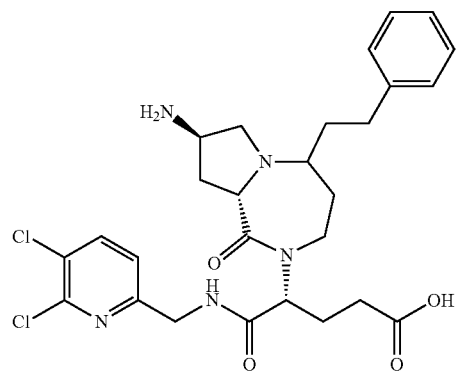 | I.18 and II.1 | A | 0.91 | 562.5/564.5 |
| 26 | 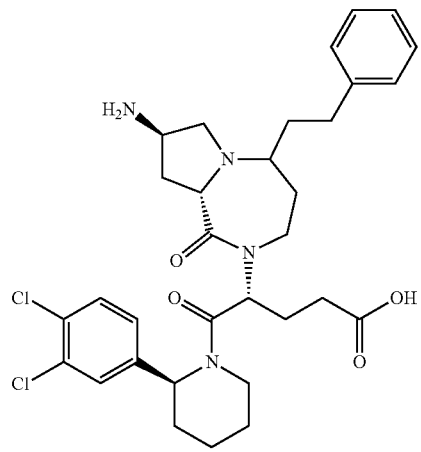 | I.19 and II.1 | A | 1.13 | 615.3/617.3 |

TABLE 4-continued

| Example | Structure | Intermediates and reagents | LCMS Method | $t_R$ (min) | $(M + H)^+$ observed |
|---|---|---|---|---|---|
| 27 | 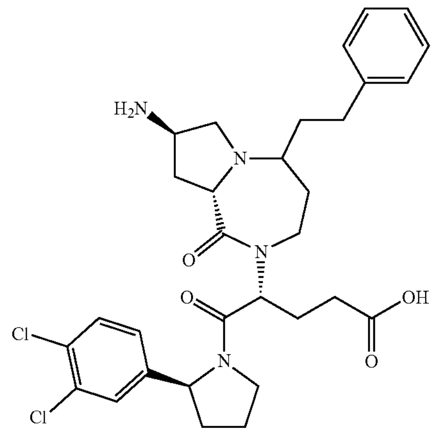 | I.20 and II.1 | A | 1.00 | 601.4/603.4 |
| 28 | 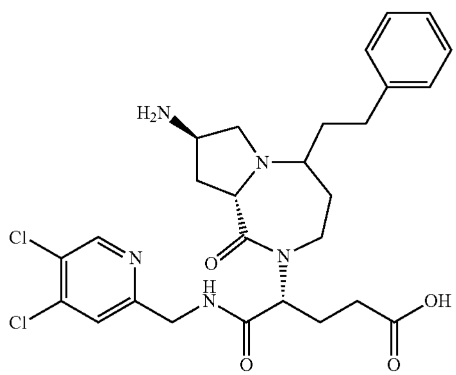 | I.21 and II.1 | A | 0.96 | 562.2/564.2 |
| 29 | 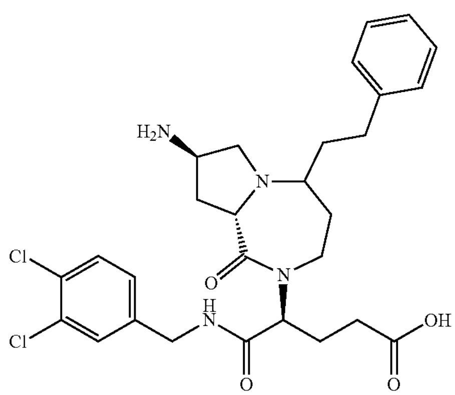 | I.22 and II.1 | A | 0.95 | 562.3/564.3 |
| 30 | 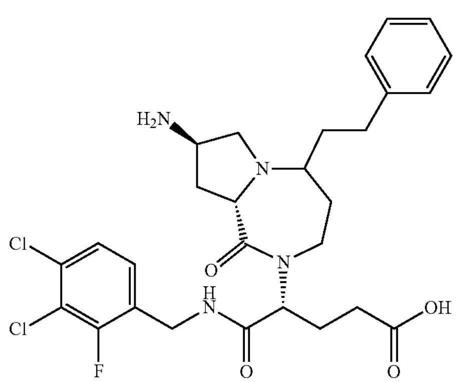 | I.23 and II.1 | A | 1.00 | 579.3/581.3 |

TABLE 4-continued
| Example | Structure | Intermediates and reagents | LCMS Method | $t_R$ (min) | $(M + H)^+$ observed |
|---------|-----------|---------------------------|-------------|-------------|----------------------|
| 31 | 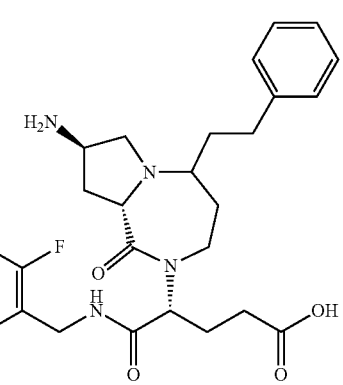 | I.24 and II.1 | A | 1.01 | 579.3/581.3 |
| 32 | 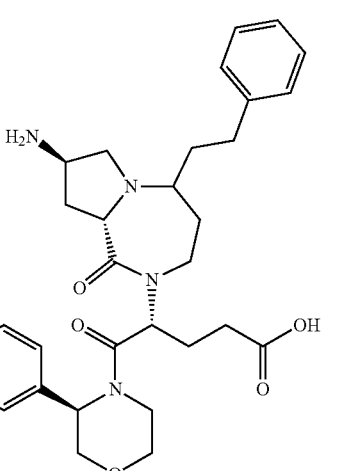 | I.25 and II.1 | A | 1.03 | 617.4/619.4 |
| 33 | *HCOOH<br>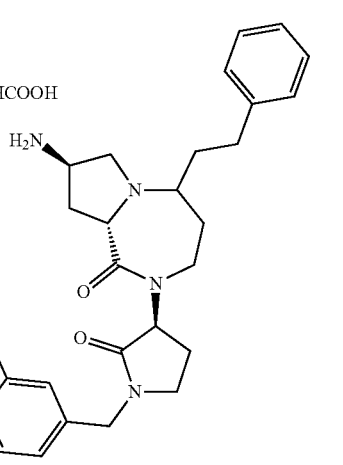 | I.32 and II.1 | A | 0.99 | 515.4/517.3 |

TABLE 4-continued

| Example | Structure | Intermediates and reagents | LCMS Method | $t_R$ (min) | $(M + H)^+$ observed |
|---|---|---|---|---|---|
| 34 | *HCOOH | I.33 and II.1 | A | 1.02 | 529.4/531.4 |
| 35 | *HCOOH | I.34 and II.1 | A | 1.01 | 529.5/531.5 |
| 36 | 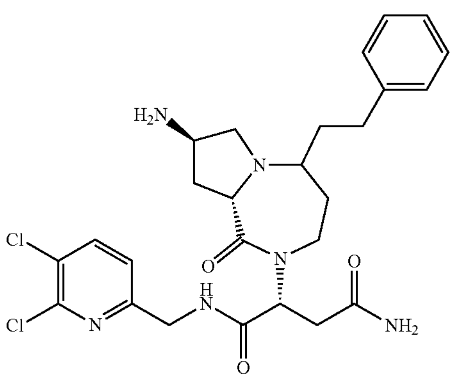 | I.26 and II.1 | A | 0.86 | 547.3/549.3 |
| 37 | 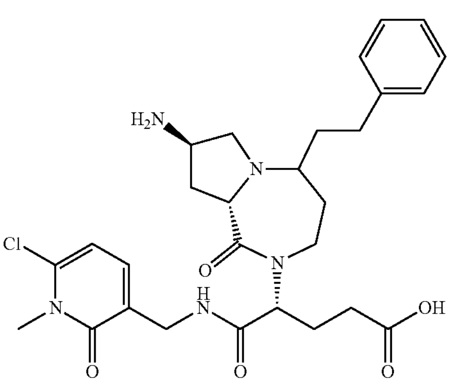 | I.27 and II.1 | A | 0.82 | 558.4/560.4 |

| Example | Structure | Intermediates and reagents | LCMS Method | $t_R$ (min) | $(M + H)^+$ observed |
|---|---|---|---|---|---|
| 38 | 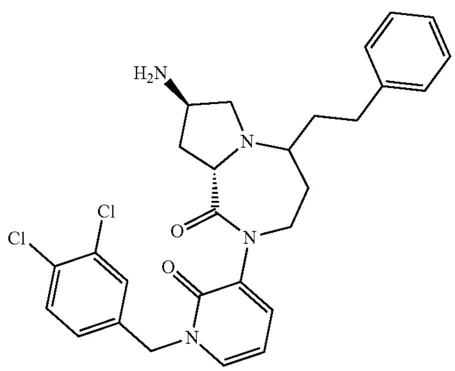 | I.35 and II.1 | A | 0.99 | 525.5/527.5 |

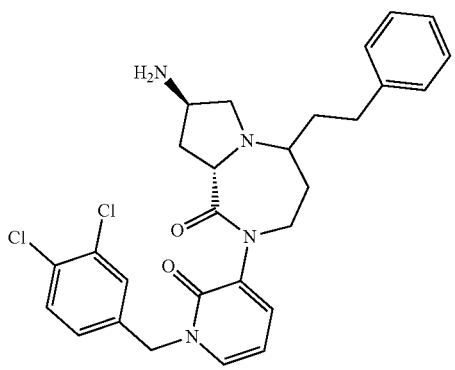

Example 39: (2R)-2-((8R,9aS)-8-amino-1-oxo-5-phenethylhexahydro-1H-pyrrolo[1,2-a][1,4]diazepin-2(3H)-yl)-N-(4-chlorobenzyl)-4-methylpentanamide Step 1: (R)-methyl 4-methyl-2-((3-oxo-5-phenylpentyl)amino)pentanoate (Compound 39-1)

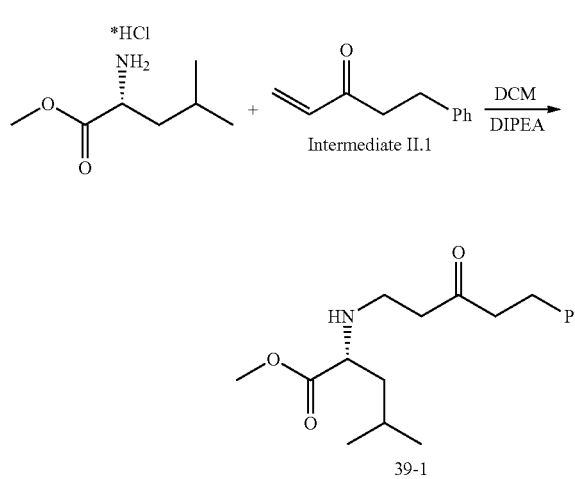

To mixture of D-leucine methyl ester hydrochloride (737 mg, 4.06 mmol) and Intermediate II.1 (650 mg, 4.06 mmol) in DCM (10 mL) was added DIPEA (1 mL, 6.09 mmol) and the reaction mixture was then stirred at room temperature for 16 h. The mixture was concentrated in vacuo and the crude residue was purified by FCC (SiO$_2$, elution with 0-5% MeOH/DCM) to provide 900 mg (73%) of Compound 39-1 as a yellow oil. $^1$H NMR (400 MHz, CDCl$_3$): δ 7.29-7.25 (m partially obscured by solvent peak, 2H), 7.20-7.16 (m, 3H), 3.71 (s, 3H), 3.24 (t, 1H), 2.91-2.86 (m, 2H), 2.83 (app t, 1H), 2.77-2.73 (m, 2H), 2.70-2.64 (m, 1H), 2.56 (m, 2H), 1.66 (m, 1H), 1.45 (m, 2H), 0.91 (d, 3H), 0.88 (d, 3H) ppm.

Step 2: (2S,4R)-benzyl 4-((tert-butoxycarbonyl)amino)-2-(((R)-1-methoxy-4-methyl-1-oxopentan-2-yl)(3-oxo-5-phenylpentyl)carbamoyl)pyrrolidine-1-carboxylate (Compound 39-2)

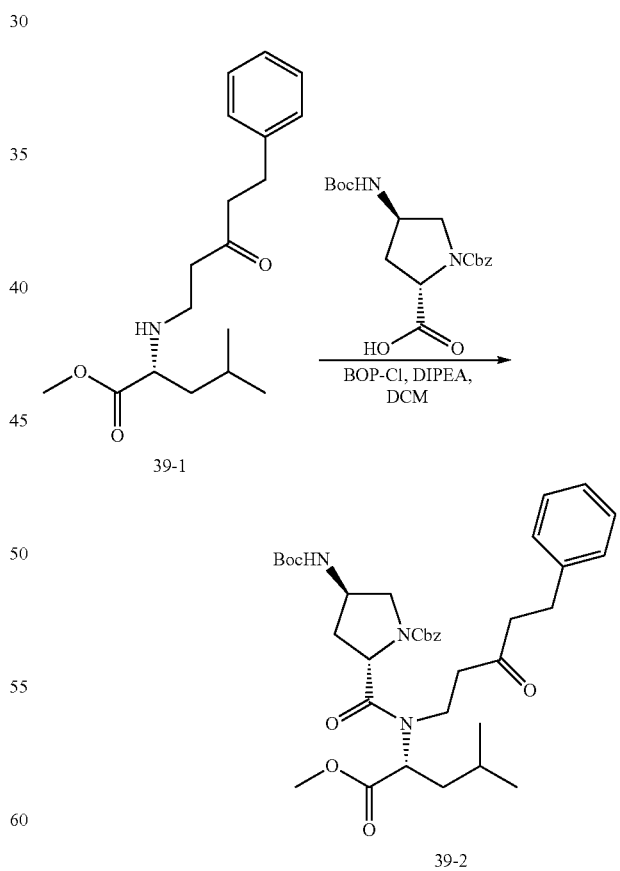

To a solution of (2S,4R)-Boc-4-amino-Cbz proline (900 mg, 2.47 mmol) in DCM (8 mL) was added DIPEA (1.1 mL, 6.72 mmol). This mixture was then added via pipette to a reaction vial containing Compound 39-1 (686 mg, 2.24 mmol). The vessel originally containing the proline reagent and DIPEA mixture was rinsed with DCM (2 mL) and this was also added via pipette to the reaction vial. BOP—Cl (857 mg, 3.36 mmol) was added and the resultant reaction mixture was stirred at room temperature for 3 d. The reaction mixture was quenched with sat. NaHCO₃ (aq) and extracted with DCM (3×). The combined organic extracts were dried (Na₂SO₄), filtered and concentrated in vacuo. The crude residue was purified by FCC (SiO₂, elution with 0-50% EtOAc/hexanes) to provide 1.06 g (73%) of Compound 39-2 as an off-white solid. LCMS (Method A): $t_R$=1.52 min, m/z 652.6 (M+H)⁺.

Steps 3: (2R)-methyl 2-((8R,9aS)-8-((tert-butoxycarbonyl)amino)-1-oxo-5-phenethylhexahydro-1H-pyrrolo[1,2-a][1,4]diazepin-2(3H)-yl)-4-methylpentanoate (Compound 39-3)

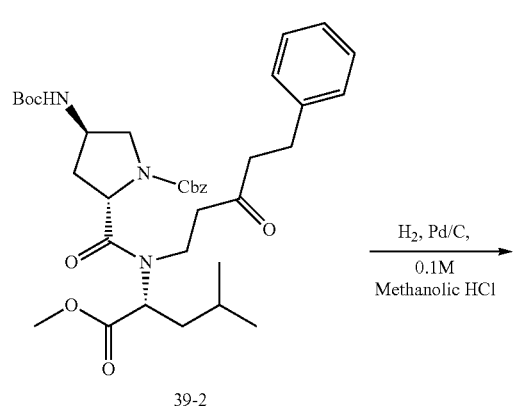

39-2

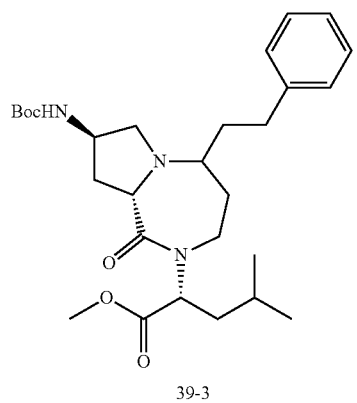

39-3

To solution of Compound 39-2 (661 mg, 1.02 mmol) in 0.1M methanolic HCl (5 mL) was added 10% Pd/C (108 mg, 1.02 mmol) and the mixture was then shaken under 30 psi of H₂ (g) in a parr reactor for 16 h. After the completion of the reaction, the catalyst was removed by filtration through a pad of celite rinsing with 20% MeOH/DCM (3×). The filtrate was concentrated in vacuo to provide 466 mg (92%) of Compound 39-3 as a white solid. ¹H NMR (400 MHz, CD₃OD): δ 7.27-7.15 (m, 5H), 5.81 (dd, 1H), 3.99 (m, 1H), 3.71 (s, 3H), 3.69 (m, 1H), 3.55-3.46 (m, 3H), 2.78-2.68 (m, 2H), 2.61-2.57 (m, 2H), 2.24 (t, 1H), 1.97-1.84 (m, 3H), 1.77-1.64 (m, 4H), 1.44 (m partially obscured by a singlet, 10H), 0.94 (d, 3H), 0.89 (d, 3H) ppm.

Step 4: (2R)-2-((8R,9aS)-8-((tert-butoxycarbonyl)amino)-1-oxo-5-phenethylhexahydro-1H-pyrrolo[1,2-a][1,4]diazepin-2(3H)-yl)-4-methylpentanoic Acid (Compound 39-4)

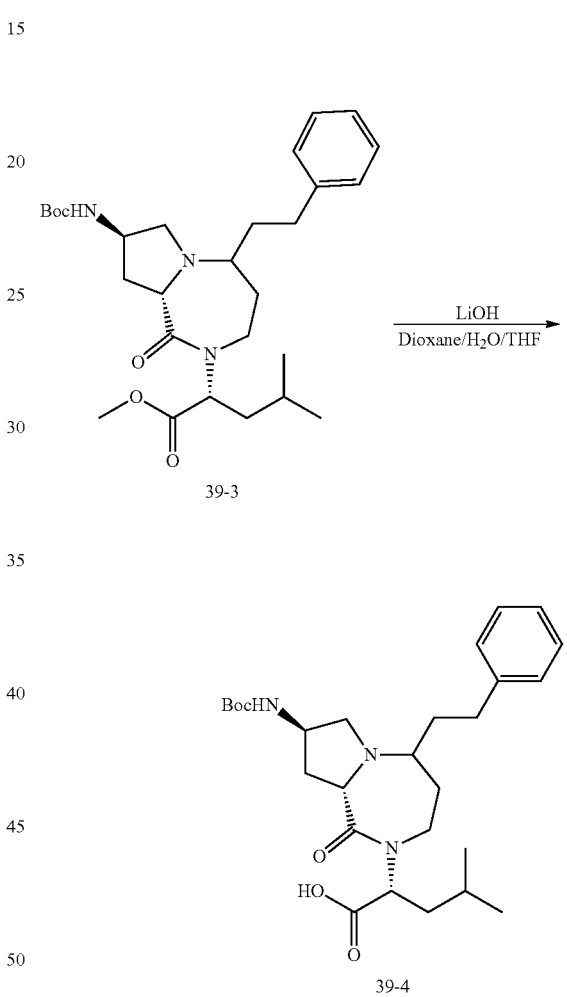

To a solution of Compound 39-3 (150 mg, 0.299 mmol) in THF (1 mL), dioxane (1 mL) and H₂O (1 mL) was added LiOH (28.7 mg, 1.197 mmol). The mixture was stirred at ambient temperature for 4 h. The reaction mixture was concentrated in vacuo, diluted with H₂O (5 mL), and then acidified with formic acid to pH 4. The aqueous layer was extracted with DCM (3×). The combined organic extracts were dried (Na₂SO₄), filtered and concentrated in vacuo to provide 122 mg (84%) of Compound 39-4 as an off-white solid. ¹H NMR (400 MHz, CD₃OD): δ 7.29-7.16 (m, 5H), 5.17 (t, 1H), 4.05-4.01 (m, 1H), 3.91-3.88 (m, 1H), 3.61-3.52 (m, 3H), 2.84-2.70 (m, 3H), 2.63-2.55 (m, 1H), 2.41 (m, 1H), 2.07-1.95 (m, 3H), 1.77 (m, 4H), 1.45 (m partially obscured by a singlet, 10H), 0.95 (d, 3H), 0.89 (d, 3H) ppm;

Step 5 and step 6: (2R)-2-((8R,9aS)-8-amino-1-oxo-5-phenethylhexahydro-1H-pyrrolo[1,2-a][1,4]diazepin-2(3H)-yl)-N-(4-chlorobenzyl)-4-methyl-pentanamide.HCl (Example 39)

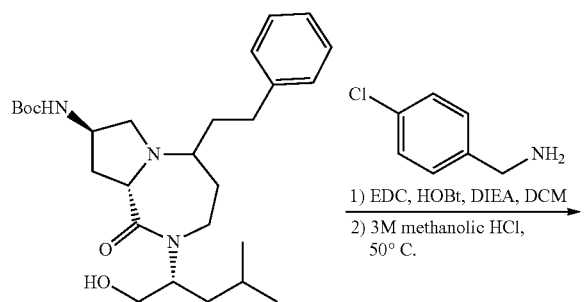

39-4

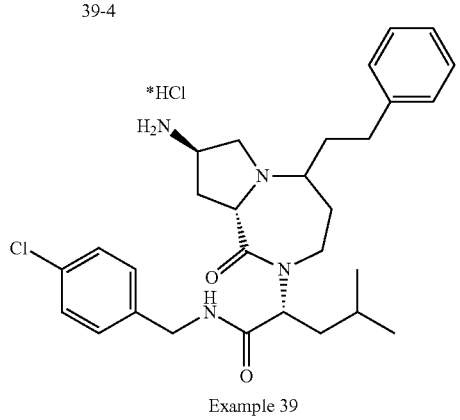

Example 39

To a mixture of Compound 39-4 (15 mg, 0.031 mmol) and 4-chlorobenzyl amine (4.3 mg, 0.031 mmol) in DCM (1 mL) was added EDAC (6.0 mg, 0.037 mmol) followed by HOBt.H$_2$O (5 mg, 0.037 mmol). The reaction mixture was stirred at room temperature for 16 h. The mixture was then quenched with sat. NaHCO$_3$ (aq) (50 mL) and extracted with DCM (3×). The combined organic extracts were dried (Na$_2$SO$_4$), filtered and concentrated in vacuo. The residue was taken as is in 3N HCl in MeOH (2 mL) and stirred at 50° C. in a tightly capped reaction vial for 3 h. The mixture was then cooled, concentrated in vacuo and the residue was purified directly by mass-directed, preparative reversed-phase HPLC (C18 column, elution with 5-95% ACN/H$_2$O containing 0.25% formic acid). The desired fractions containing the desired product were combined and partially concentrated in vacuo. To this was added 3N HCl (~5 mL) and the volatiles were removed in vacuo. This treatment with 3N HCl was repeated to ensure formation of the hydrochloride salt. The mixture was then concentrated in vacuo and the residue was taken up in H$_2$O and a small amount of ACN was added to provide a clear solution which was lyophilized to provide 13 mg (81% over two steps) of Example 39 as a white solid. $^1$H NMR (400 MHz, CD$_3$OD): δ7.33 (d, 3H), 7.30 (d, 2H), 7.25-7.21 (m, 3H), 5.21 (dd, 1H), 4.99 (m, 1H), 4.36 (ABq, 2H), 4.13 (m, 1H), 3.95 (m, 1H), 3.77-3.66 (m, 3H), 3.37 (m, 1H), 3.19 (m, 1H), 2.74 (m, 1H), 2.58 (m, 1H), 2.30 (m, 2H), 2.14 (m, 1H), 1.90-1.82 (m, 2H), 1.71 (t, 2H), 1.49 (m, 1H), 1.33 (m, 1H), 0.97 (d, 3H), 0.91 (d, 3H) ppm; LCMS (Method A): t$_R$=1.10 min, m/z 511.5/513.5 (M+H)$^+$; HPLC: t$_R$=4.611 min (100%).

Following the method described above for the preparation of Example 39, and utilizing the corresponding amine reagent in step 5, the following examples set forth in Table 5 were prepared.

TABLE 5

| Example | Structure | Amine reagent | LCMS Method | t$_R$ (min) | (M + H)$^+$ observed |
|---------|-----------|---------------|-------------|-------------|----------------------|
| 40      | 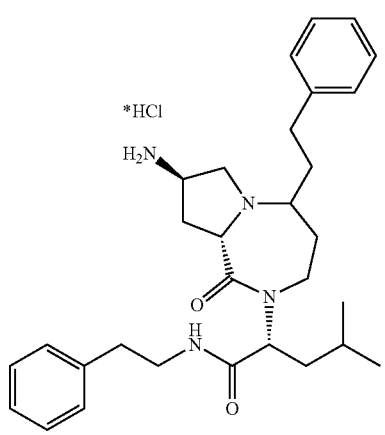 | phenethylamine | A | 1.04 | 491.5 |

TABLE 5-continued

| Example | Structure | Amine reagent | LCMS Method | $t_R$ (min) | $(M + H)^+$ observed |
| --- | --- | --- | --- | --- | --- |
| 41 | 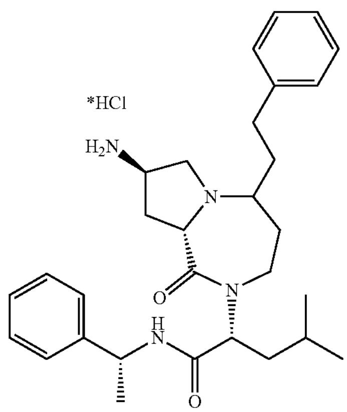 | (R)-1-phenylethanamine | A | 1.06 | 491.5 |
| 42 | 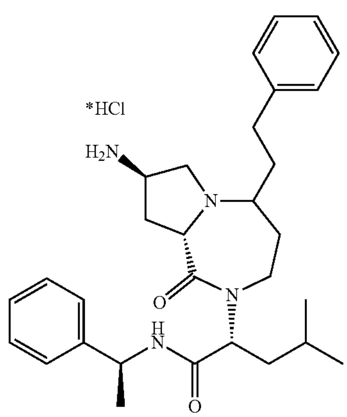 | (S)-1-phenylethanamine | A | 1.02 | 491.5 |
| 43 | 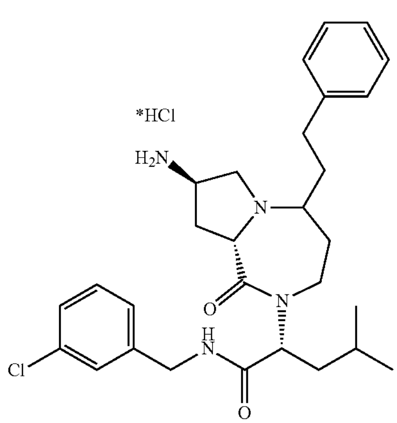 | 3-chlorobenzylamine | A | 1.08 | 511.5/513.5 |

TABLE 5-continued
| Example | Structure | Amine reagent | LCMS Method | $t_R$ (min) | $(M + H)^+$ observed |
|---|---|---|---|---|---|
| 44 | 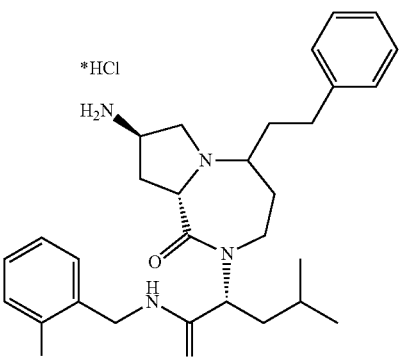 | 2-chlorobenzylamine | A | 1.05 | 511.5/513.5 |
| 45 | 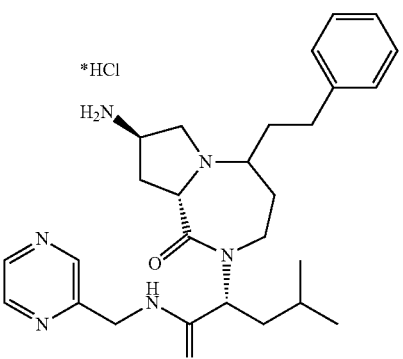 | pyrazin-2-ylmethanamine | A | 0.79 | 479.5 |
| 46 | 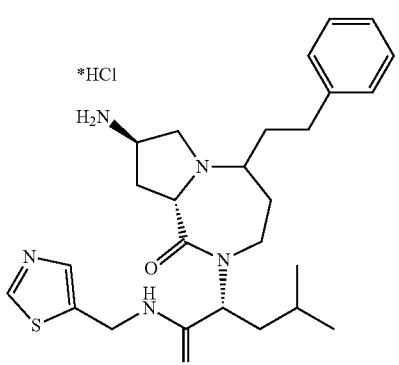 | thiazol-5-ylmethanamine | A | 0.86 | 484.5 |
| 47 | 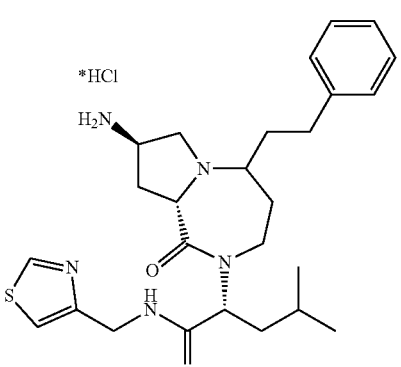 | thiazol-4-ylmethanamine | A | 0.85 | 484.5 |

TABLE 5-continued
| Example | Structure | Amine reagent | LCMS Method | $t_R$ (min) | $(M + H)^+$ observed |
|---|---|---|---|---|---|
| 48 | 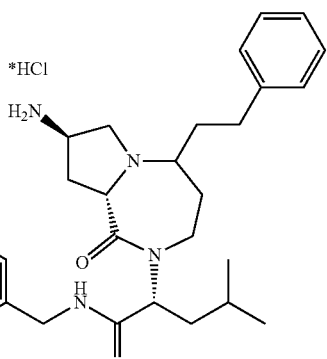 | 2,4-dichlorobenzylamine | A | 1.12 | 545.5 |
| 49 | 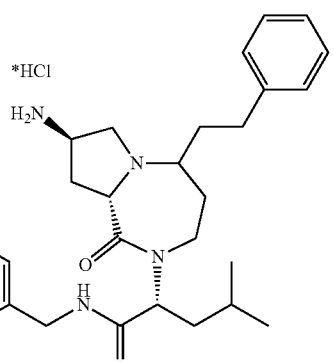 | 4-cyanobenzylamine | A | 0.96 | 502.5 |
| 50 | 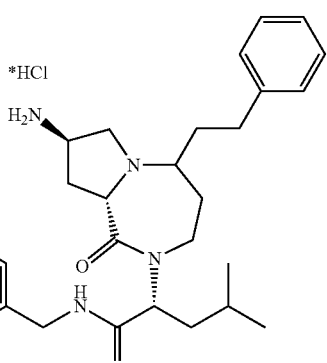 | 3,5-dichlorobenzylamine | A | 1.17 | 545.4/547.4 |
| 51 | 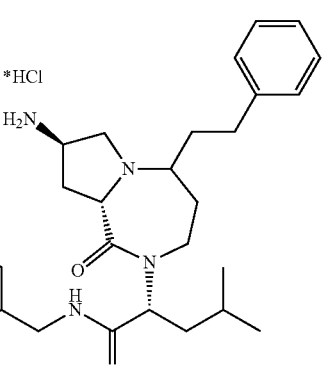 | 4-fluorobenzylamine | A | 0.98 | 495.2 |

TABLE 5-continued
| Example | Structure | Amine reagent | LCMS Method | $t_R$ (min) | $(M + H)^+$ observed |
|---|---|---|---|---|---|
| 52 | 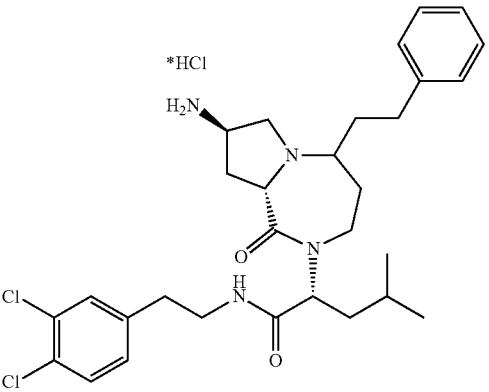 | 3,4-dichlorophethylamine | A | 1.16 | 560.4/562.4 |
| 53 | 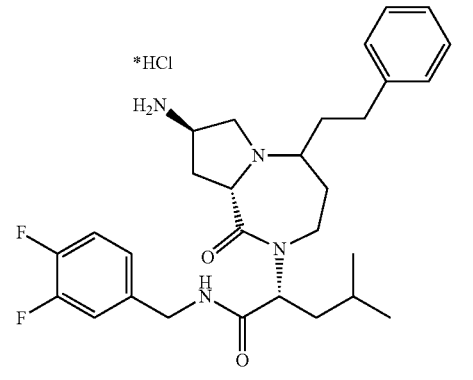 | 3,4-difluorobenzylamine | A | 1.08 | 513.4 |
| 54 | 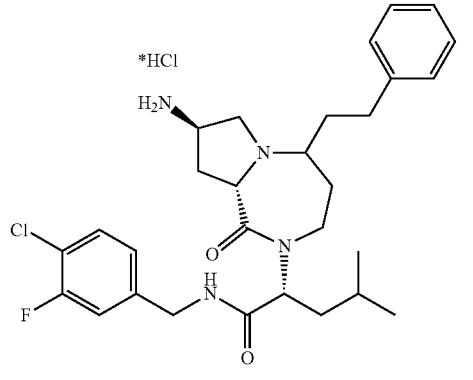 | 4-chloro-3-fluorobenzylamine | A | 1.14 | 529.3/531.3 |
| 55 | 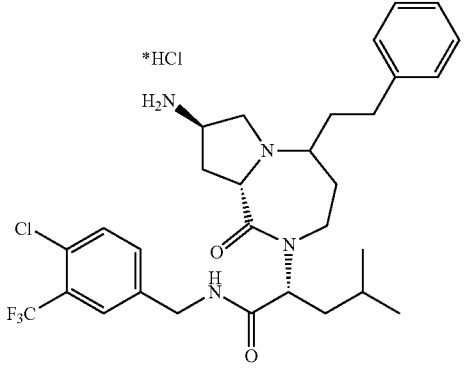 | 4-chloro-3-trifluoromethylbenzylamine | A | 1.12 | 579.3/581.4 |

TABLE 5-continued
| Example | Structure | Amine reagent | LCMS Method | $t_R$ (min) | $(M + H)^+$ observed |
|---|---|---|---|---|---|
| 56 | 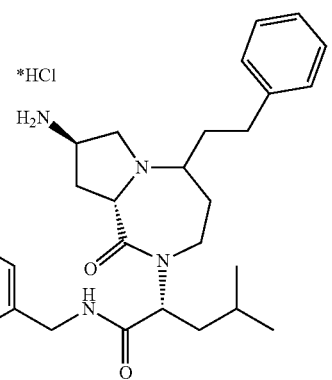 | 3-fluoro-4-trifluoromethylbenzylamine | A | 1.12 | 563.4 |
| 57 | 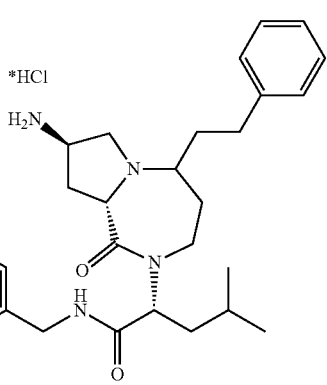 | 3-chloro-4-methylbenzylamine | A | 1.08 | 525.4/527.4 |
| 58 | 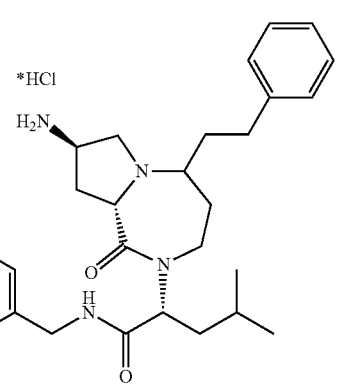 | 3-chloro-4-methoxybenzylamine | A | 1.04 | 541.4/543.4 |
| 59 | 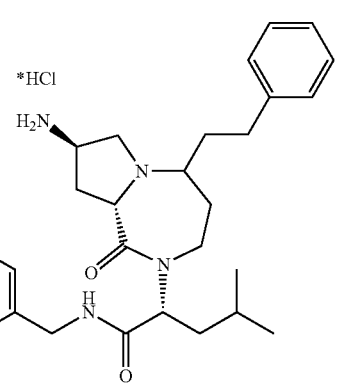 | 4-methoxybenzylamine | A | 0.97 | 507.4 |

TABLE 5-continued

| Example | Structure | Amine reagent | LCMS Method | $t_R$ (min) | $(M + H)^+$ observed |
|---|---|---|---|---|---|
| 60 | 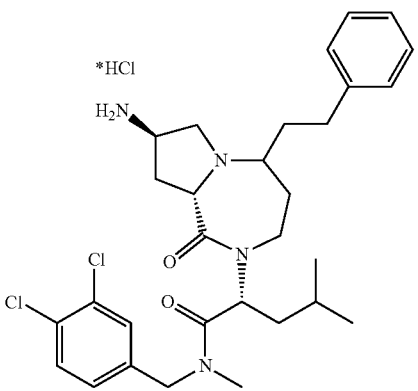 | 1-(3,4-dichlorophenyl)-N-methylmethanamine | A | 1.15 | 559.4/561.4 |

Following the method described above for the preparation of Example 39, and coupling the carboxylic acid 39-4 with the corresponding sulfonamide reagent in step 5—utilizing the coupling reagent HATU—the following examples set forth in Table 6 were prepared.

TABLE 6

| Example | Structure | Sulfonamide reagent | LCMS Method | $t_R$ (min) | $(M + H)^+$ observed |
|---|---|---|---|---|---|
| 61 | 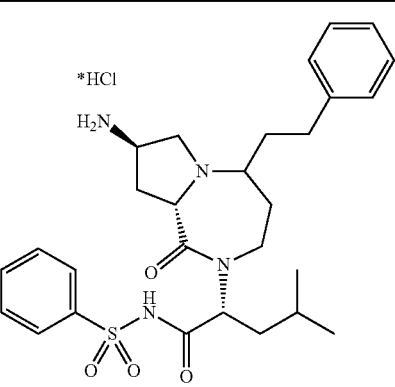 | benzenesulfonamide | A | 1.02 | 527.4 |
| 62 | 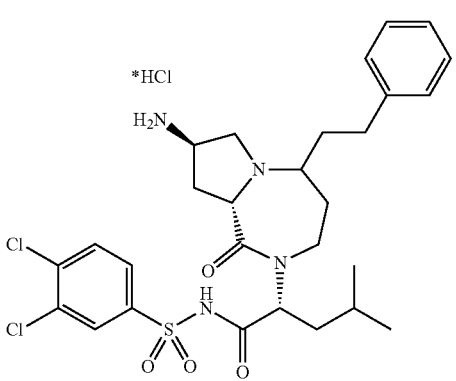 | 3,4-dichlorobenzene-sulfonamide | A | 1.15 | 595.3/597.3 |

Example 63: (2R)-2-((8R,9aS)-8-amino-1-oxo-5-phenethylhexahydro-1H-pyrrolo[1,2-a][1,4]diazepin-2(3H)-yl)-N-((5-chloropyridin-2-yl)methyl)-3-cyanopropanamide Step 1: (R)-methyl 4-oxo-2-((3-oxo-5-phenylpentyl)amino)-4-(tritylamino)butanoate (Compound 63-1)

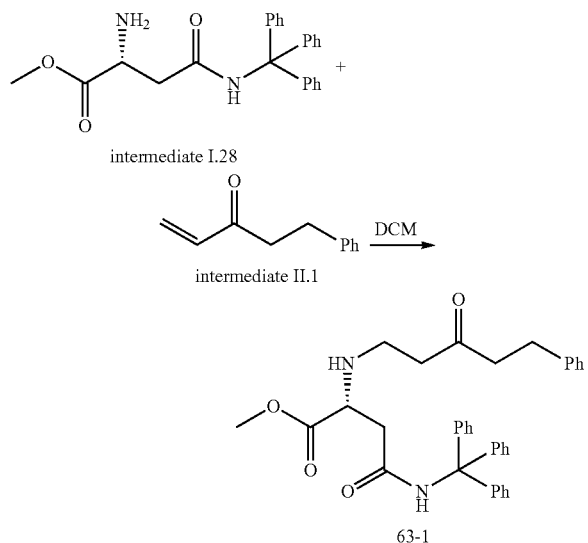

A mixture of intermediate I.28 (2.6 g, 6.70 mmol) and Intermediate II.1 (1.6 g, 10.05 mmol) in DCM (25 mL) was stirred at room temperature for 16 h. The mixture was concentrated in vacuo and the crude residue was purified by FCC (SiO$_2$, elution with 0-5% EtOAc/Hexanes) to provide 3.1 g (84%) of Compound 63-1 as a yellow solid. $^1$H NMR (400 MHz, CDCl$_3$): δ 9.17 (s, 1H, N—H), 7.28-7.26 (m, 3H), 7.26-7.14 (m partially obscured by solvent peak, 17H), 3.74 (s, 3H), 3.55 (dd, 1H), 2.94-2.88 (m, 1H), 2.83 (t, 2H), 2.65-2.47 (m, 5H), 2.42-2.28 (m, 2H) ppm.

Step 2: (2S,4R)-benzyl 4-((tert-butoxycarbonyl)amino)-2-(((R)-1-methoxy-1,4-dioxo-4-(tritylamino)butan-2-yl)(3-oxo-5-phenylpentyl)carbamoyl)pyrrolidine-1-carboxylate (Compound 63-2)

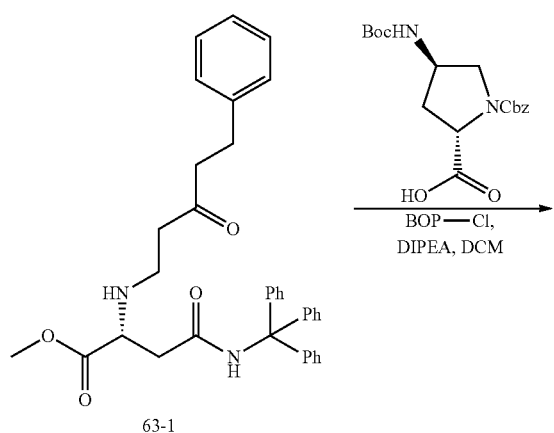

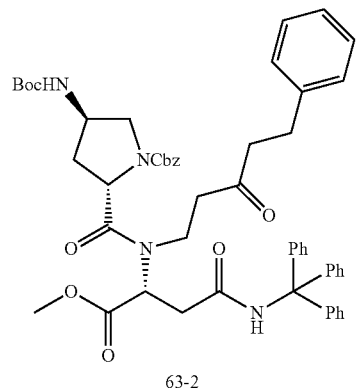

To a solution of (2S,4R)-Boc-4-amino-Cbz proline (2.3 g, 6.22 mmol) in DCM (25 mL) was added DIPEA (3.0 mL, 17.0 mmol). This mixture was then added via pipette to a reaction vial containing Compound 63-1 (3.1 g, 5.65 mmol). The vessel originally containing the proline reagent and DIPEA mixture was rinsed with DCM (5 mL) and this was also added via pipette to the reaction vial. BOP—Cl (2.2 g, 8.48 mmol) was then added and the resultant mixture was stirred at room temperature for 3 d. The reaction mixture was quenched with sat. NaHCO$_3$ (aq) and extracted with DCM (3×). The combined organic extracts were dried (Na$_2$SO$_4$), filtered and concentrated in vacuo. The crude residue was purified by FCC (SiO$_2$, elution with 0-60% EtOAc/hexanes) to provide 3.10 g (62%) of Compound 63-2 as an off-white solid. LCMS (Method A): t$_R$=1.68 min, m/z 895.7 (M+H)$^+$.

Steps 3: (2R)-methyl 2-((8R,9aS)-8-((tert-butoxycarbonyl)amino)-1-oxo-5-phenethylhexahydro-1H-pyrrolo[1,2-a][1,4]diazepin-2(3H)-yl)-4-oxo-4-(tritylamino)butanoate (Compound 63-3)

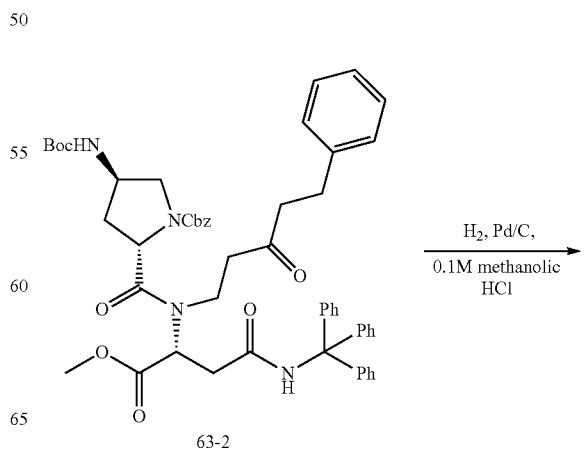

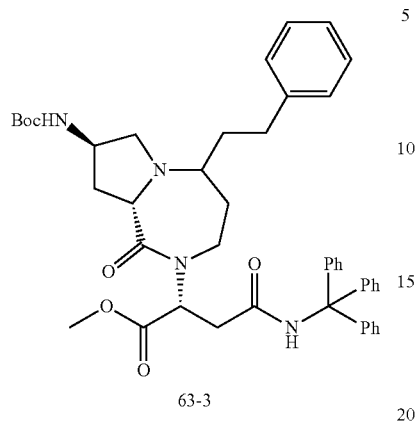

63-3

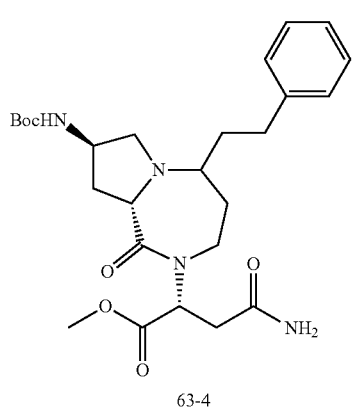

63-4

To a solution of Compound 63-2 (3.0 g, 3.35 mmol) in 0.1M methanolic HCl (50 mL) was added 10% Pd/C (714 mg, 6.71 mmol) and the mixture was then shaken under 30 psi of $H_2$ (g) in a parr reactor for 16 h. After the completion of the reaction, the catalyst was removed by filtration through a pad of celite rinsing with 20% MeOH/DCM (3×). The filtrate was concentrated in vacuo to provide 2.1 g (80%) of Compound 63-3 as a white solid. $^1$H NMR (400 MHz, CD$_3$OD): δ 8.82 (s, 1H, N—H), 7.32-7.20 (m partially obscured by solvent peak, 20H), 5.16 (dd, 1H), 4.55 (m, 1H), 4.44-4.20 (m, 1H), 4.12 (m, 1H), 4.00 (m, 1H), 3.73 (s, 3H), 3.70-3.40 (m, 3H), 3.28-3.22 (m, 1H), 3.11 (m, 1H), 2.89-2.80 (m, 1H), 2.77-2.74 (m, 1H), 2.66-2.60 (m, 1H), 2.37 (m, 1H), 2.26 (m, 1H), 2.19 (m, 1H), 2.06-1.93 (m, 1H), 1.84-1.81 (m, 1H), 1.46 (s, 9H) ppm.

Step 4 and step 5: (2R)-methyl 4-amino-2-((8R,9aS)-8-((tert-butoxycarbonyl)amino)-1-oxo-5-phenethylhexahydro-1H-pyrrolo[1,2-a][1,4]diazepin-2(3H)-yl)-4-oxobutanoate (63-4)

To a solution of Compound 63-3 (2.1 g, 2.8 mmol) in DCM (40 mL) was added dropwise TFA (10 mL) and TIPS (4 mL). The mixture was stirred at room temperature for 10 min. Additional TFA (10 mL) was added and the mixture was stirred at room temperature for an additional 1 hr. The reaction mixture was concentrated in vacuo to dryness. To the residue was added sat NaHCO$_3$ (aq) and the aqueous layer was extracted with 3:1 CHCl$_3$/IPA (3×). The combined organic extracts were washed with brine (50 mL), dried (Na$_2$SO$_4$), filtered and concentrated in vacuo. The residue was dissolved in DCM (15 mL) and TEA (0.3 mL) was added, followed by portionwise addition of (Boc)$_2$O (500 mg, 2.24 mmol). The mixture was stirred at room temperature for 1 h. The mixture was then concentrated in vacuo and the residue was purified by FCC (SiO$_2$, elution with 0-10% MeOH/DCM) to provide 0.89 g (64% for 2 steps) of Compound 63-4 as white solid. LCMS (Method A): t$_R$=0.88 min, m/z 503.4. (M+H)$^+$.

Step 6: (2R)-methyl 2-((8R,9aS)-8-((tert-butoxycarbonyl)amino)-1-oxo-5-phenethylhexahydro-1H-pyrrolo[1,2-a][1,4]diazepin-2(3H)-yl)-3-cyanopropanoate (Compound 63-5)

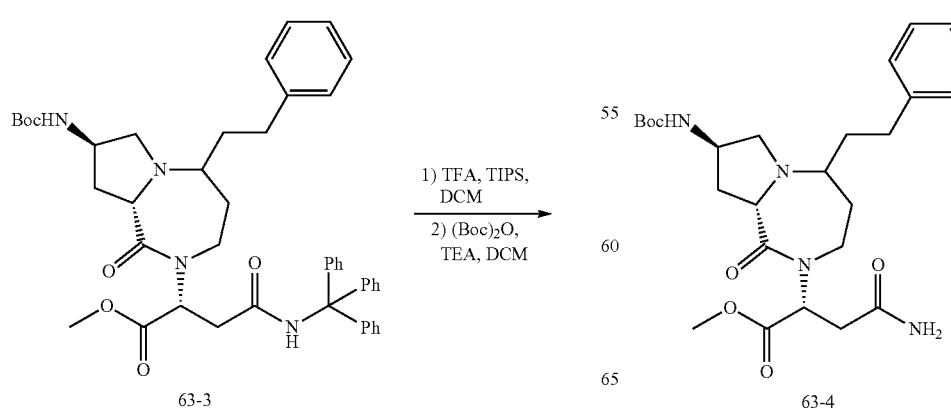

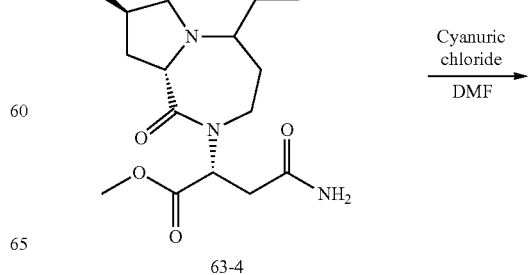

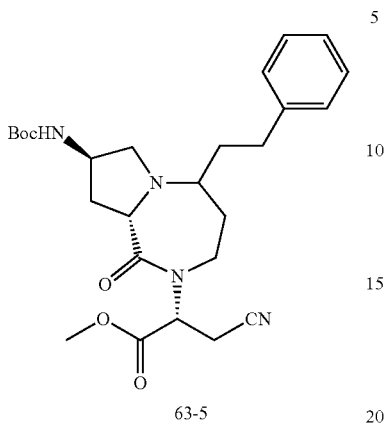

63-5

To a solution of Compound 63-4 (894 mg, 1.78 mmol) in DMF (6 mL) at 0° C. was added cyanuric chloride (0.41 g, 3.0 mmol) portionwise over 30 minutes. After the completion of the addition, the reaction mixture was slowly warmed to room temperature and stirred for an additional 1 h. The reaction mixture was quenched with 0.5N NaOH (aq) and extracted with EtOAc (3×). The combined organic layers were washed with brine, dried (Na$_2$SO$_4$), filtered and concentrated in vacuo. The crude residue was purified by FCC (SiO$_2$, elution with 0-10% MeOH/DCM) to provide 800 mg (92%) of Compound 63-5 as a yellow solid. LCMS (Method A): t$_R$=1.01 min, m/z 485.5. (M+H)$^+$.

Step 7: (2R)-2-((8R,9aS)-8-((tert-butoxycarbonyl)amino)-1-oxo-5-phenethylhexahydro-1H-pyrrolo[1,2-a][1,4]diazepin-2(3H)-yl)-3-cyanopropanoic Acid (Compound 63-6)

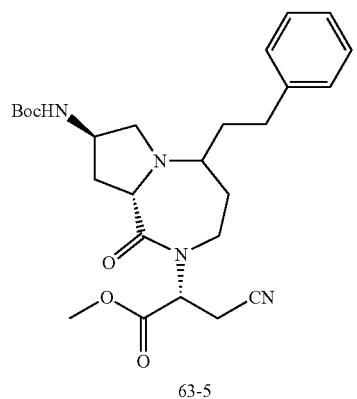

63-5

LiOH, Dioxane/H$_2$O →

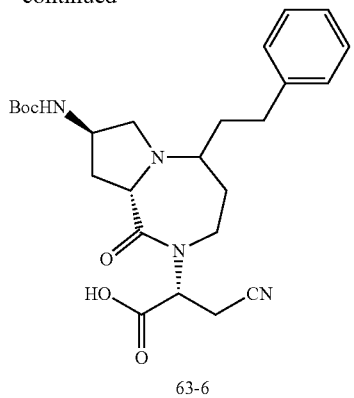

63-6

To a solution of Compound 63-5 (800 mg, 1.64 mmol) in dioxane (5 mL) and H$_2$O (5 mL) was added LiOH (119 mg, 4.96 mmol). The mixture was stirred at room temperature for 4 h. The mixture was concentrated in vacuo and to the residue was added H$_2$O (10 mL) and the pH was adjusted to 4 by addition of 2N HCl. The aqueous layer was extracted with 3:1 CHCl$_3$/IPA (3×). The combined organic extracts were dried (Na$_2$SO$_4$), filtered and concentrated in vacuo to provide 540 mg (69%) of Compound 63-6 as an off-white solid. $^1$H NMR (400 MHz, CD$_3$OD): δ 7.31-7.17 (m, 5H), 5.12 (dd, 1H), 4.39 (m, 1H), 4.14-4.08 (m, 1H), 3.92-3.85 (m, 2H), 3.57 (m, 1H), 3.33-3.34 (m, 1H), 3.15-3.08 (m, 2H), 2.90-2.74 (m, 3H), 2.68-2.63 (m, 1H), 2.27-2.12 (m, 3H), 2.02-1.83 (m, 2H), 1.46 (s, 9H) ppm.

Step 8: tert-butyl ((8R,9aS)-2-((R)-1-(((5-chloropyridin-2-yl)methyl)amino)-3-cyano-1-oxopropan-2-yl)-1-oxo-5-phenethyloctahydro-1H-pyrrolo[1,2-a][1,4]diazepin-8-yl)carbamate (Compound 63-7)

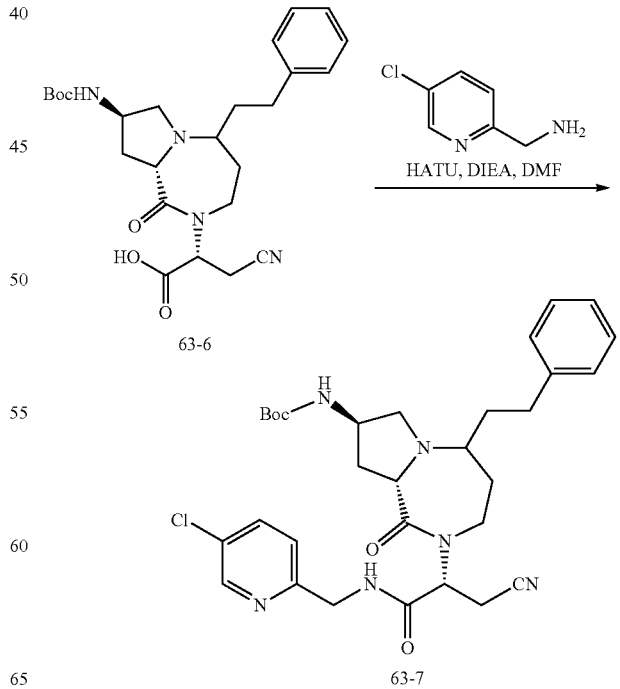

To a solution of Compound 63-6 (40 mg, 0.085 mmol) in DMF (2 mL) was added DIEA (60 µL, 0.340 mmol) followed by HATU (39 mg, 0.102 mmol) and (5-chloropyridin-2-yl)methanamine (18 mg, 0.128 mmol). The mixture was stirred at room temperature for 16 h.

The mixture was then quenched with water (5 mL) and extracted with EtOAc (3×). The combined organic extracts were washed with brine (1×), dried ($Na_2SO_4$), filtered and concentrated in vacuo. The crude residue was purified directly by mass-directed, preparative reversed-phase HPLC (C18 column, elution with 5-95% ACN/$H_2O$ containing 0.25% formic acid). The desired fractions were combined and concentrated in vacuo to provide 32 mg (64%) of Compound 63-7 as a white solid. LCMS (Method A): $t_R$=1.08 min, m/z 595.6/597.6. $(M+H)^+$.

Step 9: (2R)-2-((8R,9aS)-8-amino-1-oxo-5-phenethylhexahydro-1H-pyrrolo[1,2-a][1,4]diazepin-2(3H)-yl)-N-((5-chloropyridin-2-yl)methyl)-3-cyanopropanamide.HCOOH (Example 63)

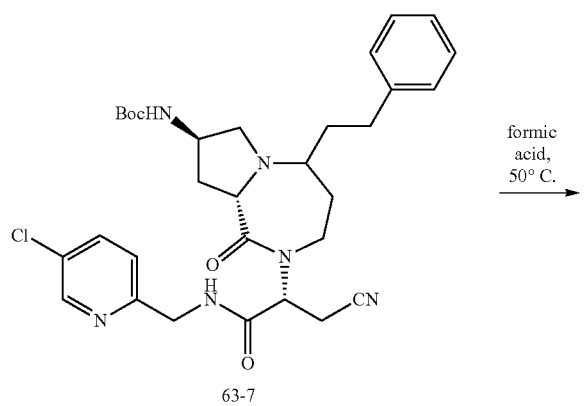

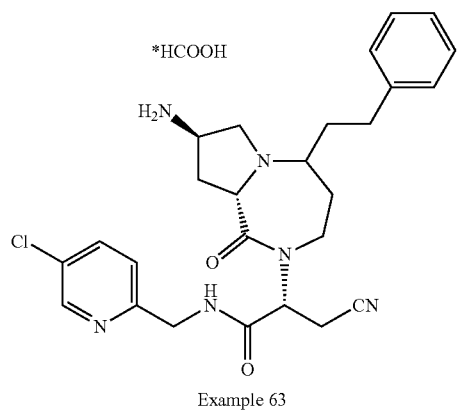

Example 63

A solution of Compound 63-7 (31 mg, 0.0.053 mmol) in formic acid (1 mL) was heated to 50° C. for 2 h. The reaction mixture was then concentrated in vacuo and the crude residue was taken up in 1:1 ACN/$H_2O$ (2 mL) and then purified directly by mass-directed preparative reversed-phase HPLC (C-18, elution with 5-95% ACN/$H_2O$ containing 0.25% formic acid). The desired fractions containing purified product were combined, diluted with $H_2O$, and lyophilized to provide 19 mg (81%) of Example 63 as a white solid. $^1H$ NMR (400 MHz, $CD_3OD$): δ 8.37 (d, 1H), 7.69 (dd, 1H), 7.31 (d, 1H), 7.17 (t, 2H), 7.08 (d, 3H), 5.13 (dd, 1H), 4.40 (ABq, 2H), 3.76 (dd, 1H), 3.68 (dd, 1H), 3.48-3.40 (m, 3H), 2.98-2.96 (m, 2H), 2.86 (m, 1H), 2.61-2.56 (m, 2H), 2.43-2.41 (m, 1H), 2.34 (t, 1H), 1.87-1.84 (m, 2H), 1.76 (m, 1H), 1.59 (m, 2H) ppm; LCMS (Method A): $t_R$=0.84 min, m/z 495.5/497.5 $(M+H)^+$; HPLC: $t_R$=4.098 min (100%).

Following the methods described above for the preparation of Example 63, and substituting the corresponding amine reagent in step 8, the following examples set forth in Table 7 were prepared.

TABLE 7

| Example | Structure | Amine reagent | LCMS Method | $t_R$ (min) | $(M+H)^+$ observed |
|---|---|---|---|---|---|
| 64 | 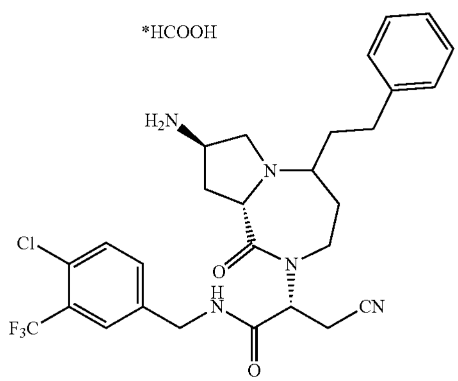 | 4-chloro-3-trifluoromethylbenzylamine | A | 1.02 | 562.4/564.4 |

107
108
TABLE 7-continued
| Example | Structure | Amine reagent | LCMS Method | $t_R$ (min) | $(M + H)^+$ observed |
|---|---|---|---|---|---|
| 65 | 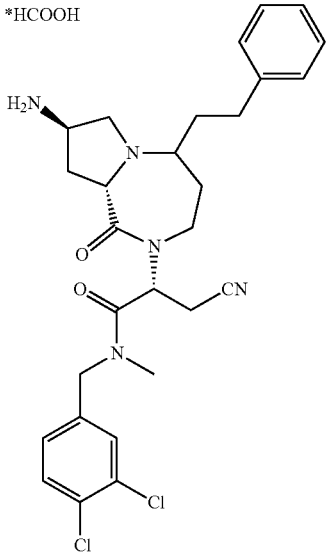 | 1-(3,4-dichlorophenyl)-N-methylmethanamine | A | 1.02 | 542.4/544.4 |
| 66 | 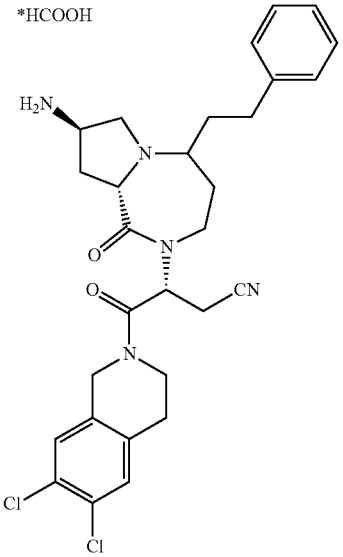 | 6,7-dichloro-1,2,3,4-tetrahydroisoquinoline | A | 1.00 | 554.4/556.4 |

TABLE 7-continued

| Example | Structure | Amine reagent | LCMS Method | $t_R$ (min) | $(M + H)^+$ observed |
|---|---|---|---|---|---|
| 67 | *HCOOH | 5,6-dichloro-1,2,3,4-tetrahydroisoquinoline | A | 1.00 | 554.4/556.4 |
| 68 | *HCOOH | (S)-3-phenylmorpholine | A | 0.99 | 516.5 |
| 69 | *HCOOH | (R)-3-phenylmorpholine | A | 1.00 | 516.6 |

Example 70: (4R)-4-((8R,9aS)-8-amino-1-oxo-5-phenethylhexahydro-1H-pyrrolo[1,2-a][1,4]diazepin-2(3H)-yl)-5-(((5-chloropyridin-2-yl)methyl)amino)-5-oxopentanoic Acid

Step 1: (R)-1-benzyl 5-tert-butyl 2-((3-oxo-5-phenylpentyl)amino)pentanedioate (Compound 70-1)

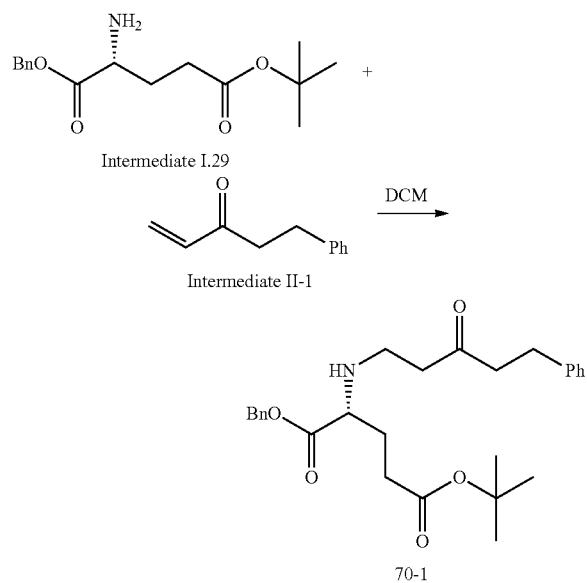

A mixture of Intermediate I.29 (932 mg, 3.18 mmol) and Intermediate II.1 (509 mg, 3.18 mmol) in DCM (20 mL) was stirred at room temperature for 16 h. The mixture was then concentrated in vacuo and the residue purified by FCC (SiO$_2$, elution with 0-5% MeOH/DCM) to provide 830 mg (58%) of Compound 70-1 as a yellow solid. $^1$H NMR (400 MHz, CDCl$_3$): δ 7.37-7.32 (m, 5H), 7.29-7.26 (m partially obscured by solvent peak, 2H), 7.18 (m, 3H), 5.16 (s, 2H), 3.25 (m, 1H), 2.89 (m, 3H), 2.74 (m, 2H), 2.69-2.63 (m, 1H), 2.70-2.53 (m, 2H), 2.30 (t, 2H), 1.95-1.90 (m, 1H), 1.84-1.77 (m, 1H), 1.42 (s, 9H) ppm.

Step 2: (R)-1-benzyl 5-tert-butyl 2-((2S,4R)-1-((benzyloxy)carbonyl)-4-((tert-butoxycarbonyl)amino)-N-(3-oxo-5-phenylpentyl)pyrrolidine-2-carboxamido)pentanedioate (70-2)

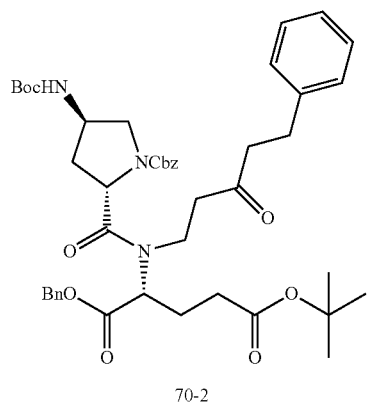

To a solution of (2S,4R)-Boc-4-amino-Cbz proline (735 mg, 2.01 mmol) in DCM (16 mL) was added DIPEA (1.0 mL, 5.49 mmol). This mixture was then added via pipette to a reaction vial containing Compound 70-1 (830 mg, 1.83 mmol). The vessel originally containing the proline reagent and DIPEA mixture was rinsed with DCM (4 mL) and this was also added via pipette to the reaction vial. BOP—Cl (699 mg, 2.75 mmol) was then added and the resultant reaction mixture was stirred at room temperature for 3 d. The reaction mixture was quenched with sat. NaHCO$_3$ (aq) and extracted with DCM (3×). The combined organic extracts were dried (Na$_2$SO$_4$), filtered and concentrated in vacuo. The residue was purified by FCC (SiO$_2$, elution with 0-60% EtOAc/hexanes) to provide 890 mg (61%) of Compound 70-2 as an off-white solid. LCMS (Method A): t$_R$=1.64 min, m/z 800.8 (M+H)$^+$.

Steps 3: (2R)-5-(tert-butoxy)-2-((8R,9aS)-8-((tert-butoxycarbonyl)amino)-1-oxo-5-phenethylhexahydro-1H-pyrrolo[1,2-a][1,4]diazepin-2(3H)-yl)-5-oxopentanoic Acid (Compound 70-3)

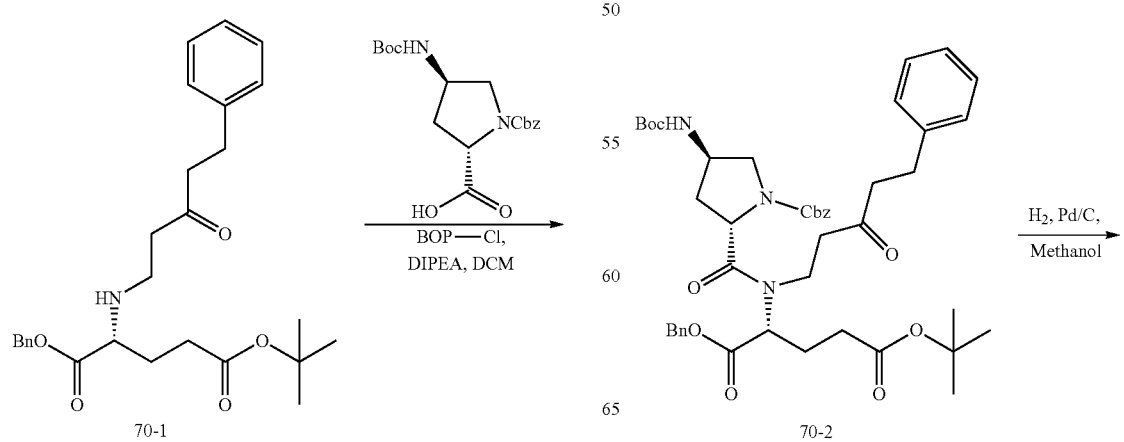

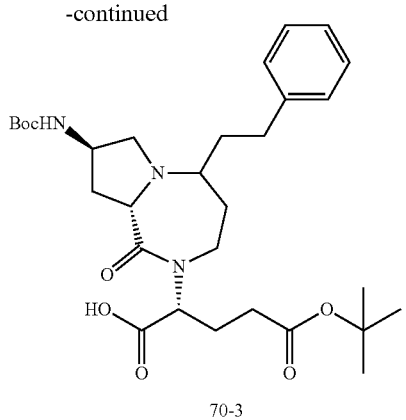

70-3

To a solution of Compound 70-2 (861 mg, 1.08 mmol) in methanol (20 mL) was added 10% Pd/C (229 mg, 2.15 mmol) and the mixture was shaken under 30 psi of H$_2$ (g) in a Parr shaker for 16 h. The mixture was filtered through a pad of celite rinsing with 20% MeOH/DCM (3×). The filtrate was concentrated in vacuo to provide 534 mg (91%) of Compound 70-3 as white solid. $^1$H NMR (400 MHz, CD$_3$OD): δ 7.29-7.15 (m, 5H), 5.00 (dd, 1H), 4.04-3.96 (m, 2H), 3.68-3.61 (m, 2H), 3.47-3.41 (m, 1H), 2.85-2.76 (m, 2H), 2.74-2.70 (m, 1H), 2.63-2.56 (m, 1H), 2.45 (m, 1H), 2.25 (m, 3H), 2.05-1.94 (m, 4H), 1.84-1.74 (m, 2H), 1.45 (s, 18H) ppm.

Step 4: (4R)-tert-butyl 4-((8R,9aS)-8-((tert-butoxycarbonyl)amino)-1-oxo-5-phenethylhexahydro-1H-pyrrolo[1,2-a][1,4]diazepin-2(3H)-yl)-5-(((5-chloropyridin-2-yl)methyl)amino)-5-oxopentanoate (Compound 70-4)

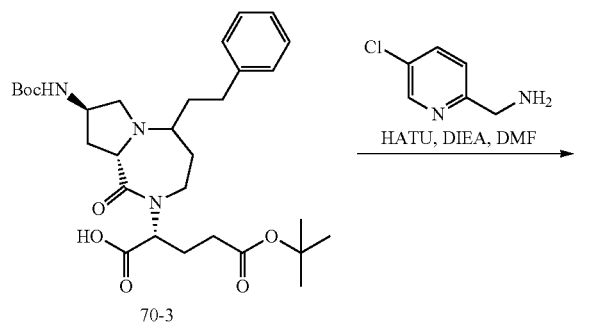

To a mixture of Compound 70-3 (40 mg, 0.072 mmol) in DMF (2 mL) was added DIEA (50 µL, 0.288 mmol) followed by HATU (33 mg, 0.086 mmol) and (5-chloropyridin-2-yl)methanamine (16 mg, 0.107 mmol). The reaction mixture was stirred at room temperature for 16 h. The mixture was quenched with water (5 mL) and extracted with EtOAc (3×). The combined organic extracts were washed with brine, dried (Na$_2$SO$_4$), filtered and concentrated in vacuo. The residue was purified directly by mass-directed, preparative reversed-phase HPLC (C18 column, elution with 5-95% ACN/H$_2$O containing 0.25% formic acid). The desired fractions were combined and concentrated in vacuo. to provide 27 mg (50%) of the major diasteromer 70-4 as a white solid. LCMS (Method A): t$_R$=1.17 min, m/z 684.7/686.7. (M+H)$^+$.

Step 5: (4R)-4-((8R,9aS)-8-amino-1-oxo-5-phenethylhexahydro-1H-pyrrolo[1,2-a][1,4]diazepin-2(3H)-yl)-5-(((5-chloropyridin-2-yl)methyl)amino)-5-oxopentanoic Acid (Example 70)

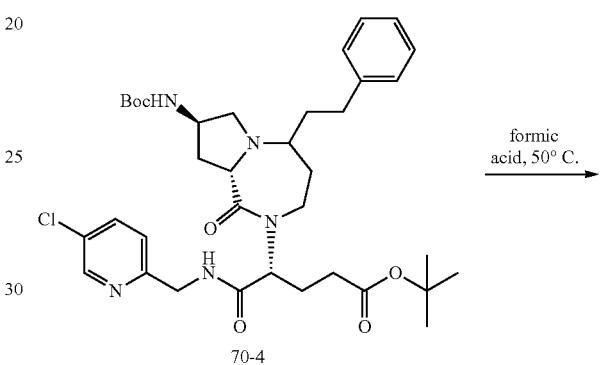

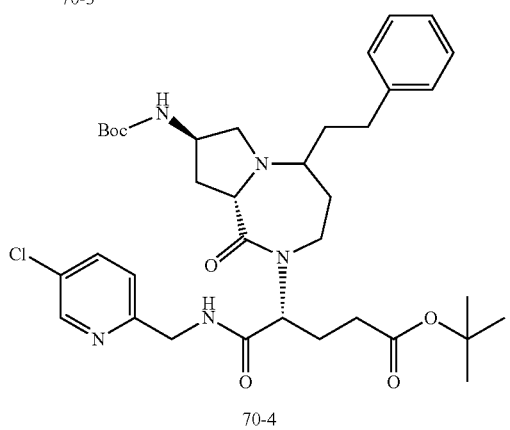

Example 70

A solution of Compound 70-4 (10 mg, 0.015 mmol) in formic acid (0.5 mL) was heated to 50° C. for 2 h. The reaction mixture was then concentrated in vacuo and the residue was taken up in 1:1 ACN/H$_2$O (2 mL) and then purified directly by mass-directed preparative reversed-phase HPLC (C-18, elution with 5-95% ACN/H$_2$O containing 0.25% formic acid). The desired fractions containing purified product were combined, diluted with H$_2$O, and lyophilized to provide 6.2 mg (81%) of Example 70 as a white solid. $^1$H NMR (400 MHz, CD$_3$OD): δ 8.36 (d, 1H), 7.68 (dd, 1H), 7.29 (d, 1H), 7.16 (m, 2H), 7.04 (m, 3H), 5.02 (dd, 1H), 4.39 (ABq, 2H), 3.74 (dd, 1H), 3.56-3.43 (m, 4H), 2.88 (m, 1H), 2.57-2.49 (m, 2H), 2.43-2.39 (m, 1H), 2.33 (m, 1H), 2.11-2.07 (m, 2H), 2.07-2.02 (m, 1H), 2.00-1.93 (m, 1H), 1.85-1.74 (m, 3H), 1.59-1.50 (m, 2H) ppm; LCMS (Method A): t$_R$=0.79 min, m/z 528.5/530.5 (M+H)$^+$; HPLC: t$_R$=3.871 min (96%).

Example 71: (4R)-4-((8R,9aS)-8-amino-1-oxo-5-(2-phenoxyethyl)hexahydro-1H-pyrrolo[1,2-a][1,4]diazepin-2(3H)-yl)-5-((3,4-dichlorobenzyl)amino)-5-oxopentanoic Acid
Steps 1-4: (4R)-tert-butyl 4-((8R,9aS)-8-((tert-butoxycarbonyl)amino)-5-(2-((tert-butyldiphenylsilyl)oxy)ethyl)-1-oxohexahydro-1H-pyrrolo[1,2-a][1,4]diazepin-2(3H)-yl)-5-((3,4-dichlorobenzyl)amino)-5-oxopentanoate (Compound 71-3)
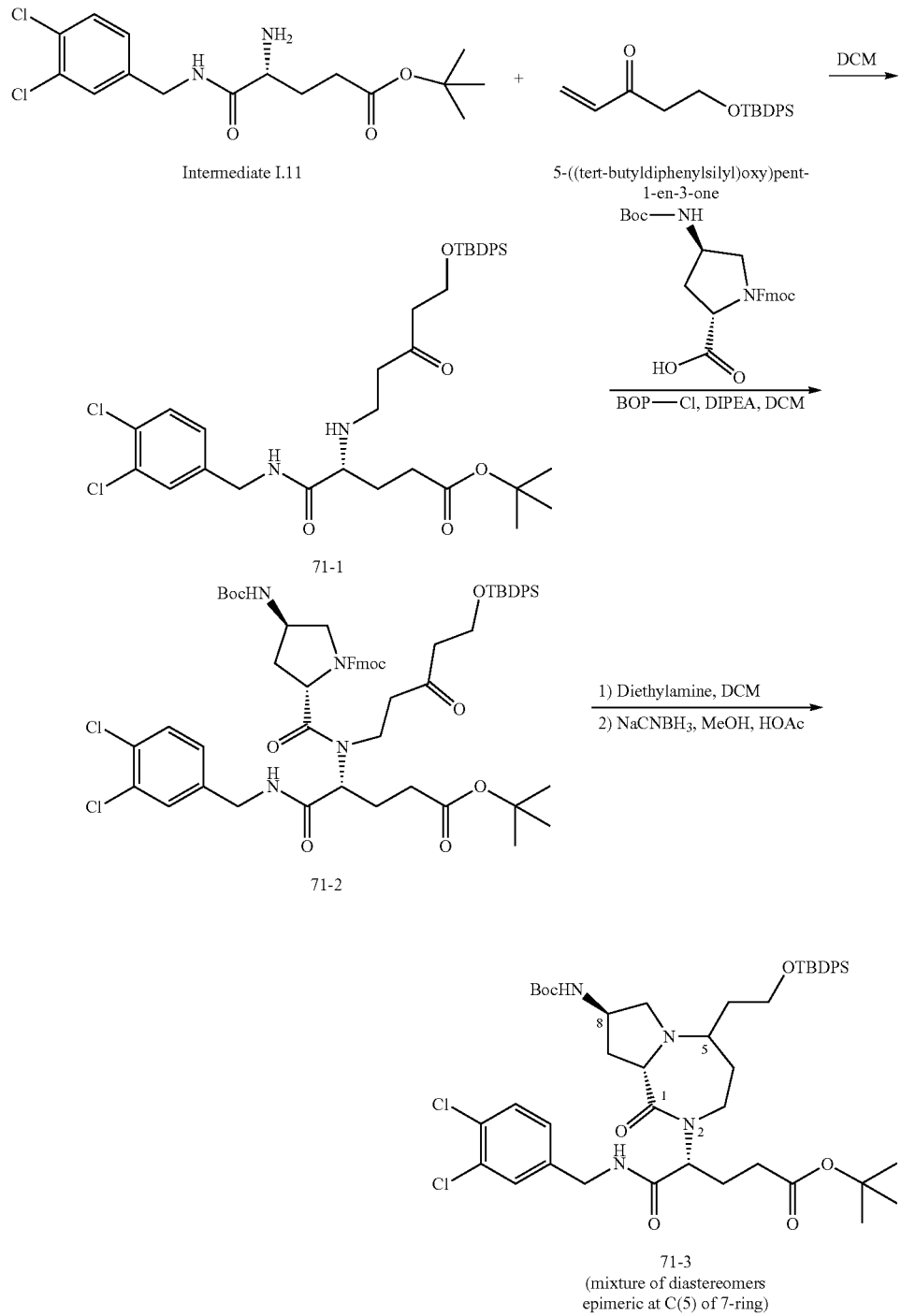

Compound 71-3 was prepared from Intermediate I.11 (399 mg, 1.11 mmol) and 5-((tert-butyldiphenylsilyl)oxy)pent-1-en-3-one (375 mg, 1.11 mmol) using the same general procedures described for the preparation of compound 1-3 in steps 1-4 in Example 1.

After work-up the crude product was purified by FCC (SiO$_2$, elution with 0-100% EtOAc/hexanes) to provide 101 mg of semi-pure material as a mixture of diastereomers. This was used without further purification in the next step. LCMS (Method C): m/z 895.1/897.2 (M+H)$^+$.

Step 5: (4R)-tert-butyl 4-((8R,9aS)-8-((tert-butoxy-carbonyl)amino)-5-(2-hydroxyethyl)-1-oxohexahydro-1H-pyrrolo[1,2-a][1,4]diazepin-2(3H)-yl)-5-((3,4-dichlorobenzyl)amino)-5-oxopentanoate (Compound 71-4)

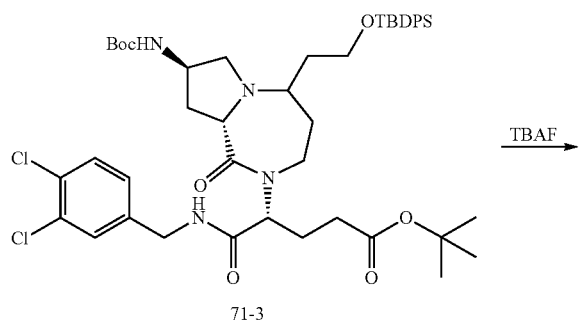

To Compound 71-3 (98 mg, 0.11 mmol) was slowly added dropwise 1.0 M TBAF in THF (1 mL) and the resultant solution was stirred at room temperature for 45 min. The reaction mixture was then quenched with sat. NH$_4$Cl (aq) (5 mL) and extracted with EtOAc (3×). The combined organic extracts were dried (MgSO$_4$) and concentrated in vacuo. The residue was purified by mass-directed, preparative reversed-phase HPLC (C18 column, elution with 5-95% ACN/H$_2$O containing 0.25% formic acid). The desired fractions containing mainly the first eluting, major diastereomer and a small amount of second eluting, minor diasteromer were lyophilized to provide 13 mg (18%) of Compound 71-4 as a white solid. LCMS (SQD, Method D): t$_R$=1.07 min, m/z 657.4/659.3 (M+H).

Step 6: (4R)-tert-butyl 4-((8R,9aS)-8-((tert-butoxycarbonyl)amino)-1-oxo-5-(2-phenoxyethyl)hexahydro-1H-pyrrolo[1,2-a][1,4]diazepin-2(3H)-yl)-5-((3,4-dichlorobenzyl)amino)-5-oxopentanoate (Compound 71-5)

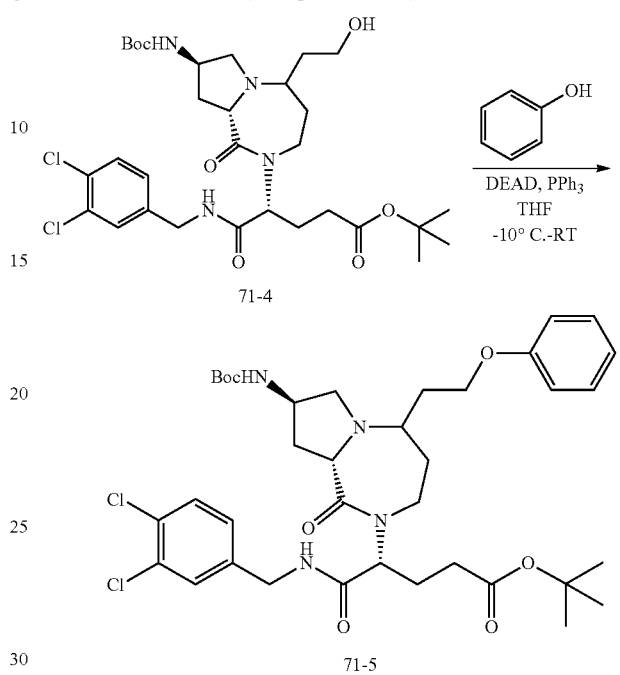

A 20 mL reaction vial was charged with Compound 71-4 (23 mg, 0.035 mmol) and this was azeotroped with toluene (3×) to remove adventitious water. This was further dried in a vacuum oven and then the vial was purged with N2 (g) for 20 min. Phenol (4 mg, 0.046 mmol) and PPh$_3$ (17 mg, 0.063 mmol) were added to the reaction vial followed by THF (1 mL). The mixture was cooled to −10° C. in an ice/acetone bath and DEAD (40% soln. in toluene, 23 μL, 0.053 mmol) was added dropwise over 15 min. The reaction mixture was slowly warmed to RT and stirred for 16 h. The mixture was then concentrated in vacuo and purified by FCC (SiO$_2$, elution with a step gradient of 0-10%, 10-40%, 40-100% EtOAc/hexanes) to provide 31 mg of a mixture of Compound 71-5 and a significant amount of triphenylphosphine oxide as determined by HPLC analysis. LCMS (Method C): t$_R$=1.07 min, m/z 733.3/735.2 (M+H)$^+$; HPLC: t$_R$=6.395 min (71-5) and 5.825 min (triphenylphosphine oxide).

Step 7: (4R)-4-((8R,9aS)-8-amino-1-oxo-5-(2-phenoxyethyl)hexahydro-1H-pyrrolo[1,2-a][1,4]diazepin-2(3H)-yl)-5-((3,4-dichlorobenzyl)amino)-5-oxopentanoic Acid (Example 71)

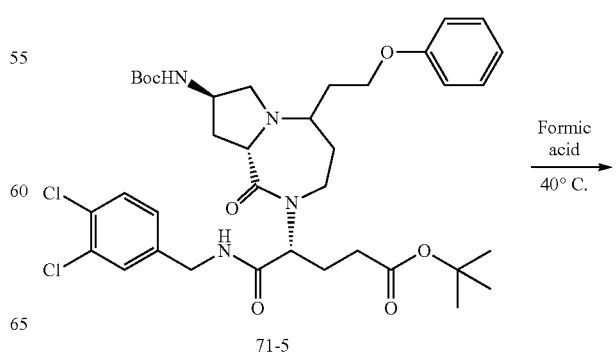

-continued

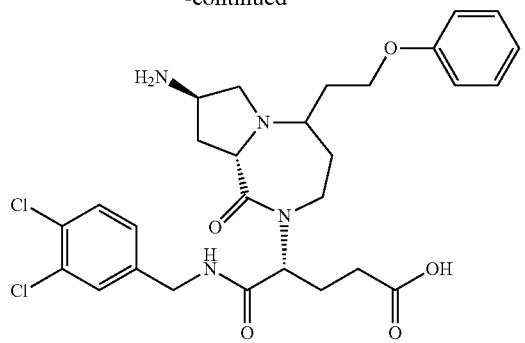

Example 71

A solution of Compound 71-5 in 1 mL formic acid was heated to 40° C. for 2 h. The reaction mixture was then concentrated in vacuo and the crude residue was purified by reversed-phase FCC (C18, elution with 5-100% ACN/H2O, 0.25% formic acid). The desired fractions were combined and lyophilized to provide 6 mg (24%) of Example 71 as a white solid. $^1$H NMR (400 MHz, DMSO-$d_6$): δ 8.48 (t, 1H, N—H), 7.53 (d, 1H), 7.49 (d, 1H), 7.28-7.22 (m, 3H), 6.93-6.86 (m, 3H), 4.86 (dd, 1H), 4.30 (dd, 1H), 4.14, (dd, 1H), 3.97-3.84 (m, 2H), 3.68 (dd, 1H), 3.52-3.22 (m, 7H, partial overlap with broad H$_2$O peak), 2.69-2.62 (m, 2H), 2.19 (t, 1H), 2.11-1.53 (m, 8H), 1.32 (m, 1H) ppm; LCMS (Method A) $t_R$=1.11 min, m/z 577.3/579.3 (M+H)$^+$.

Example 72: (4R)-4-((8R,9aS)-8-amino-5-((4-methoxyphenoxy)methyl)-1-oxohexahydro-1H-pyrrolo[1,2-a][1,4]diazepin-2(3H)-yl)-5-((3,4-dichlorobenzyl)amino)-5-oxopentanoic Acid Steps 1-4: (4R)-tert-butyl 4-((8R,9aS)-8-((tert-butoxycarbonyl)amino)-5-(((tert-butyldiphenylsilyl)oxy)methyl)-1-oxohexahydro-1H-pyrrolo[1,2-a][1,4]diazepin-2(3H)-yl)-5-((3,4-dichlorobenzyl)amino)-5-oxopentanoate (Compound 72-3)

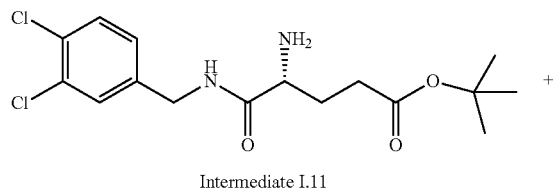

Intermediate I.11

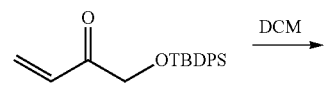

Intermediate II.4

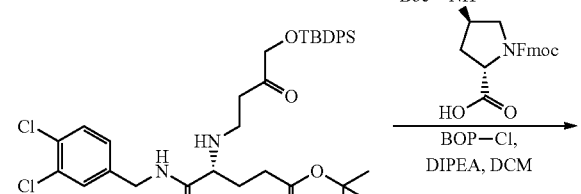

72-1

-continued

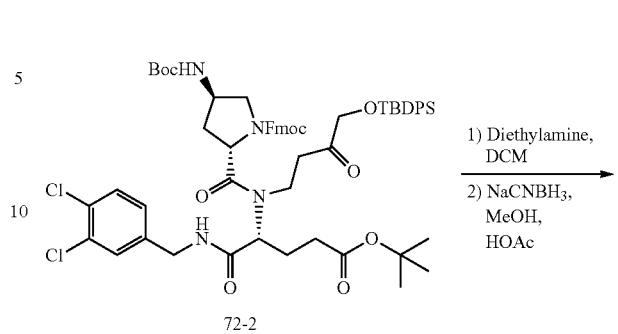

72-2

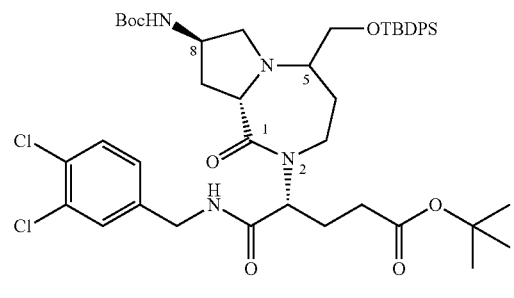

72-3 (mixture of diastereomers epimeric at C(5) of 7-ring)

Compound 72-3 was prepared from Intermediate I.11 and Intermediate II.4 using the same general method described for the preparation of compound 1-3 in steps 1-4 in Example 1. After work-up following the intramolecular reductive amination (step 4), the crude product—comprising a mixture of diastereomers epimeric at C(5)—was purified by FCC (SiO$_2$, elution with 0-50% EtOAc/hexanes). This provided the second eluting, major diastereomer 72-3B (the first eluting, minor diasteromer 72-3A was not isolated) which was carried into the next step. Data for Compound 72-3B: LCMS (Method C): $t_R$=1.35 min, m/z 881.2/883.2 (M+H)$^+$.

Step 5: (4R)-tert-butyl 4-((8R,9aS)-8-((tert-butoxycarbonyl)amino)-5-(hydroxymethyl)-1-oxohexahydro-1H-pyrrolo[1,2-a][1,4]diazepin-2(3H)-yl)-5-((3,4-dichlorobenzyl)amino)-5-oxopentanoate (72-4)

72-3B

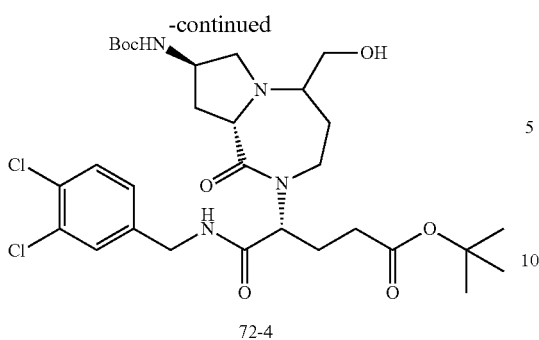

72-4

To a solution of Compound 72-3B (232 mg, 0.263 mmol) in THF (2.5 mL) was added TBAF (1M solution in THF, 0.32 mL, 0.32 mmol) and the mixture was stirred at room temperature for 2 h. The mixture was then concentrated in vacuo and the residue was purified by FCC (SiO$_2$, elution with 0-5% MeOH/DCM) to provide 160 mg (95%) of Compound 72-4. $^1$H NMR (400 MHz, CD$_3$OD): δ 7.48 (d, 1H), 7.46 (d, 1H), 7.24 (dd, 1H), 5.10 (dd, 1H), 4.34 (ABq, 2H), 4.02 (m, 1H), 3.74 (dd, 1H), 3.61-3.54 (m, 2H), 3.45-3.41 (m, 2H), 2.80 (m, 1H), 2.59 (m, 1H), 2.33 (t, 1H), 2.25-2.09 (m, 4H), 1.90 (m, 1H), 1.80 (m, 1H), 1.70 (m, 1H), 1.50 (m partially obscured by singlet, 1H), 1.44 (s superimposed on multiplet, 18H) ppm; LCMS (Method A) t$_R$=1.15 min, m/z 643.3/645.3 (M+H)$^+$.

Step 6: (4R)-tert-butyl 4-((8R,9aS)-8-(((tert-butoxycarbonyl)amino)-5-((4-methoxyphenoxy)methyl)-1-oxohexahydro-1H-pyrrolo[1,2-a][1,4]diazepin-2(3H)-yl)-5-((3,4-dichlorobenzyl)amino)-5-oxopentanoate (Compound 72-5)

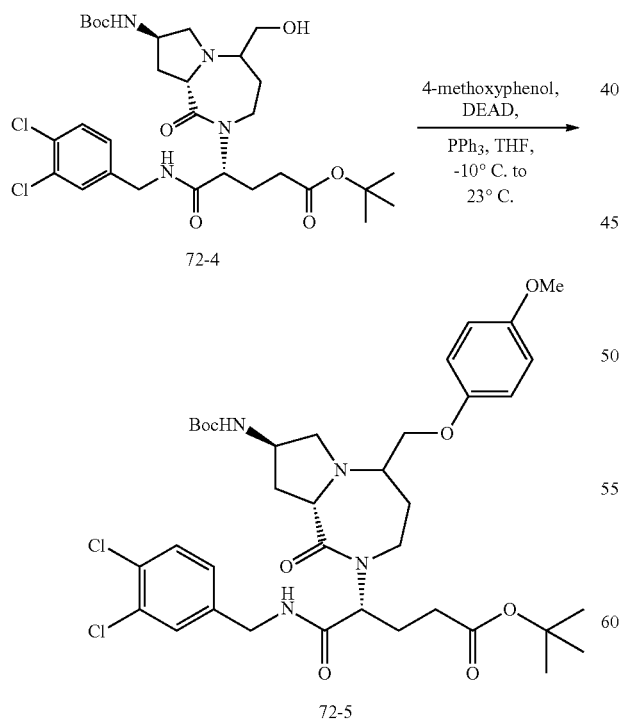

A mixture of Compound 72-4 (40 mg, 0.062 mmol), 4-methoxyphenol (10 mg, 0.081 mmol) and triphenylphosphine (29 mg, 0.11 mmol) in THF (1 mL) was degassed by bubbling N2 (g) through for ~10 min. The mixture was then cooled to −10° C. and DEAD (43 μL, 0.093 mmol) was added dropwise over 60 min. The reaction mixture was warmed to room temperature and stirred for 16 h. The mixture was then concentrated in vacuo and the residue was purified directly by FCC (SiO$_2$, elution with 0-100% EtOAc/hexanes) to provide 26 mg (57%) of Compound 72-5. LCMS (Method A) t$_R$=1.43 min, m/z 749.3/751.3 (M+H)$^+$.

Step 7: (4R)-4-((8R,9aS)-8-amino-5-((4-methoxyphenoxy)methyl)-1-oxohexahydro-1H-pyrrolo[1,2-a][1,4]diazepin-2(3H)-yl)-5-((3,4-dichlorobenzyl)amino)-5-oxopentanoic Acid (Example 72)

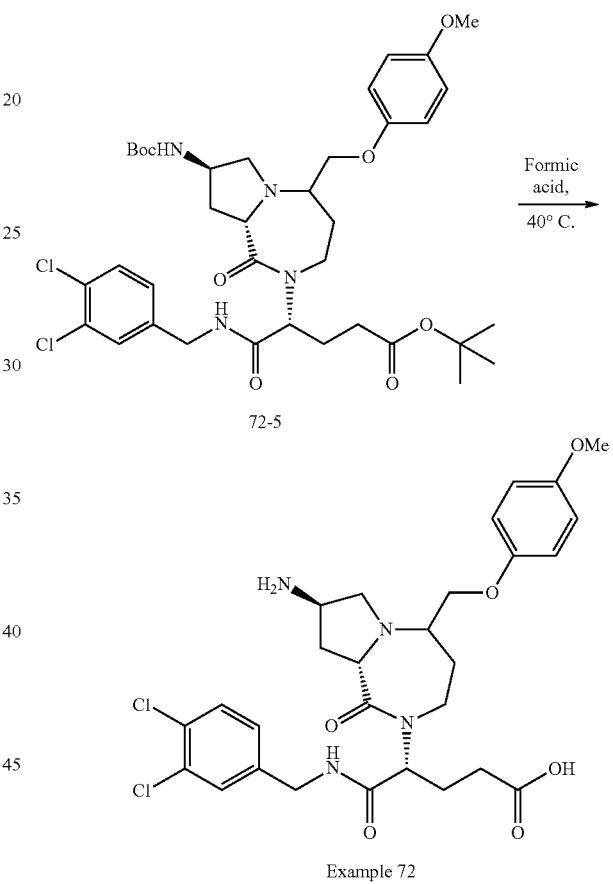

A solution of Compound 72-5 (30 mg, 0.040 mmol) in formic acid (1 mL) was heated to 40° C. for 1 h. This was then concentrated in vacuo and the residue was purified directly by mass-directed preparative reversed-phase HPLC (C18, elution with 5-100% ACN/H$_2$O, 0.25% formic acid). The desired fractions were combined and lyophilized to provide 5 mg (20%) of Example 72 as a white solid. $^1$H NMR (400 MHz, CD$_3$OD): δ 7.47 (d, 1H), 7.41 (d, 1H), 7.23 (dd, 1H), 6.85-6.80 (m, 4H), 5.09 (dd, 1H), 4.33 (ABq, 2H), 3.92-3.82 (m, 3H), 3.68-3.56 (m, 3H), 3.49 (dd, 1H), 2.98 (m, 2H), 2.68 (t, 1H), 2.20-2.00 (m, 4H), 1.93-1.83 (m, 2H), 1.63 (m, 1H) ppm; LCMS (Method A) t$_R$=0.97 min, m/z 593.3/595.3 (M+H)$^+$.

Following the methods described above for Example 72, and substituting the corresponding aryl alcohol reagent in step 6, the following examples set forth in Table 8 were prepared.

TABLE 8
| Example | Structure | Aryl alcohol reagent | LCMS Method | $t_R$ (min) | $(M + H)^+$ observed |
|---|---|---|---|---|---|
| 73 | 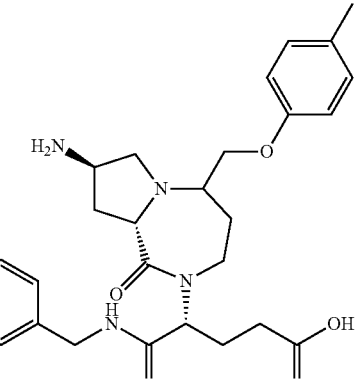 | 4-methylphenol | A | 1.05 | 577.3/579.3 |
| 74 | 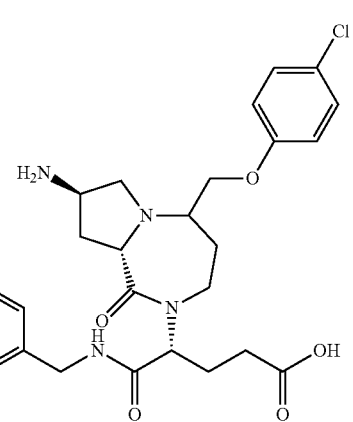 | 4-chlorophenol | A | 1.00 | 597.2/599.2 |
| 75 | 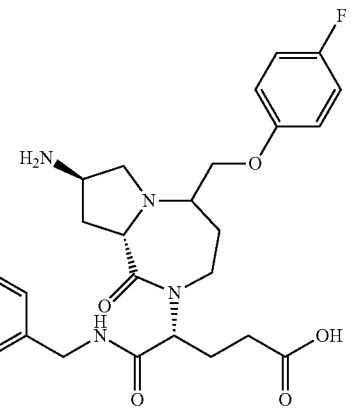 | 4-fluorophenol | A | 0.95 | 581.3/583.3 |
| 76 | 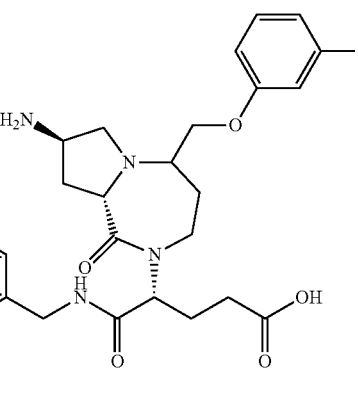 | 3-chlorophenol | A | 0.99 | 597.2/599.2 |

TABLE 8-continued

| Example | Structure | Aryl alcohol reagent | LCMS Method | $t_R$ (min) | $(M + H)^+$ observed |
|---|---|---|---|---|---|
| 77 | 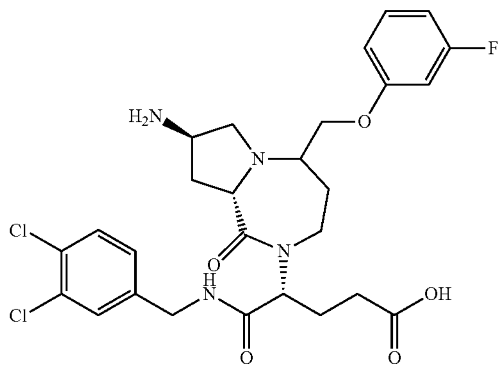 | 3-fluorophenol | A | 0.96 | 580.3/582.3 |
| 78 | 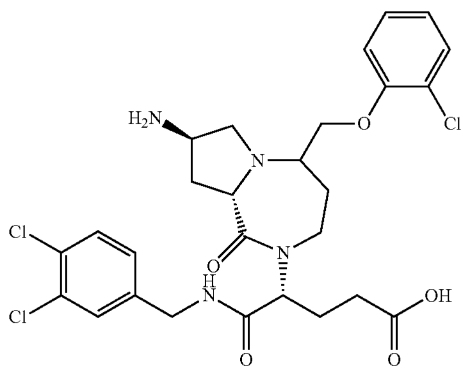 | 2-chlorophenol | A | 0.98 | 597.2/599.3 |
| 79 | 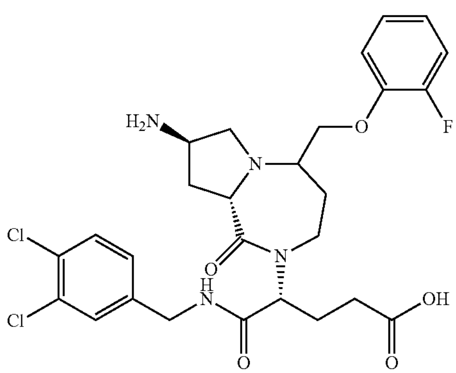 | 2-fluorophenol | A | 0.95 | 582.4/584.4 |
| 80 | 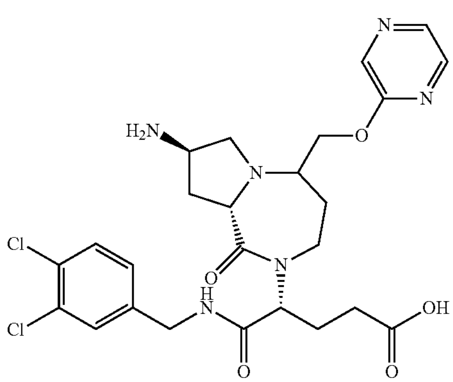 | 2-hydroxypyrazine | A | 0.81 | 565.4/567.3 |

Example 81: N-((2R)-2-((8R,9aS)-8-amino-1-oxo-5-phenethylhexahydro-1H-pyrrolo[1,2-a][1,4]diazepin-2(3H)-yl)-4-methylpentyl)-3,4-dichlorobenzene-sulfonamide.HCl

Step 1: tert-butyl ((8R,9aS)-2-((R)-1-amino-4-methyl-1-oxopentan-2-yl)-1-oxo-5-phenethyloctahydro-1H-pyrrolo[1,2-a][1,4]diazepin-8-yl)carbamate (Compound 81-1)

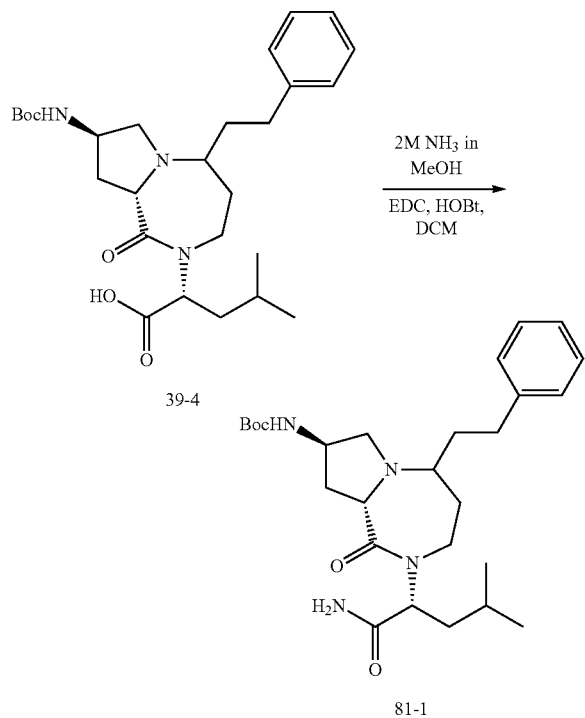

To a solution of Compound 39-4 (135 mg, 0.277 mmol) in DMF (1 mL) were added DIPEA (200 μL, 1.15 mmol), EDC (52 mg, 0.332 mmol), HOBt (45 mg, 0.332 mmol) and 2M NH$_3$ in methanol (210 μL, 0.416 mmol). The reaction mixture was stirred at room temperature for 16 h. The mixture was then quenched with sat. NaHCO$_3$ (aq) and extracted with EtOAc (3×). The combined organic layers were washed with brine, dried (Na$_2$SO$_4$), filtered and concentrated in vacuo. The residue was purified by FCC (SiO$_2$, elution with 0-10% MeOH/DCM) to give 101 mg (73%) of Compound 81-1. LCMS (Method A): t$_R$=1.01 min, m/z 487.4 (M+H)$^+$.

Step 2: tert-butyl ((8R,9aS)-2-((R)-1-cyano-3-methylbutyl)-1-oxo-5-phenethyloctahydro-1H-pyrrolo[1,2-a][1,4]diazepin-8-yl)carbamate (Compound 81-2)

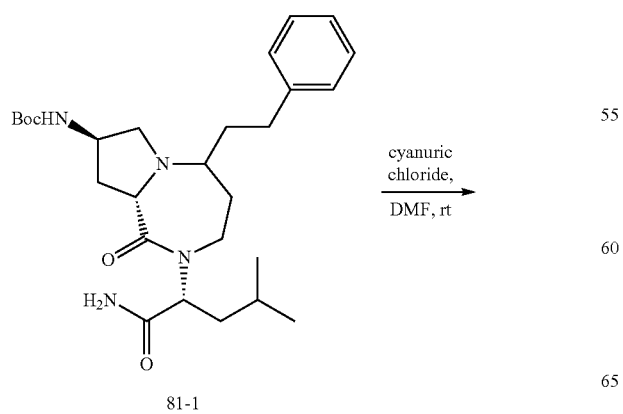

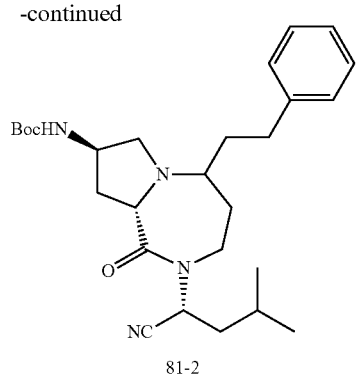

To a solution of Compound 81-1 (100 mg, 0.206 mmol) in DMF (1 mL) at 0° C. was added cyanuric chloride (57 mg, 0.309 mmol). The reaction mixture was warmed to room temperature and stirred for 1.5 h. The mixture was then cooled to 0° C. and quenched with 0.5 N NaOH (aq) (5 mL). The aqueous layer was extracted with EtOAc (3×5 mL) and the organic extracts were filtered through an Isolute® HM-N cartridge (3 mL capacity) which was prewetted with 2 mL of brine. The eluent was collected (gravity filtration) and concentrated in vacuo. The residue was purified by FCC (SiO$_2$, elution with 0-10% MeOH/DCM) to provide 70 mg (73%) of Compound 81-2 as white solid. Data for 81-2: $^1$H NMR (400 MHz, CDCl$_3$): δ 7.28 (m, 2H), 7.18-7.16 (m, 3H), 5.65 (m, 1H), 4.44 (m, 1H), 4.07 (m, 1H), 3.52 (m, 4H), 2.96-2.89 (m, 1H), 2.73 (m, 1H), 2.56 (m, 2H), 2.26 (m, 1H), 2.02-1.60 (m, 6H), 1.44 (m, 9H), 1.26 (m, 1H), 0.97 (d, 6H) ppm.

Step 3: tert-butyl ((8R,9aS)-2-((R)-1-amino-4-methylpentan-2-yl)-1-oxo-5-phenethyloctahydro-1H-pyrrolo[1,2-a][1,4]diazepin-8-yl)carbamate (Compound 81-3)

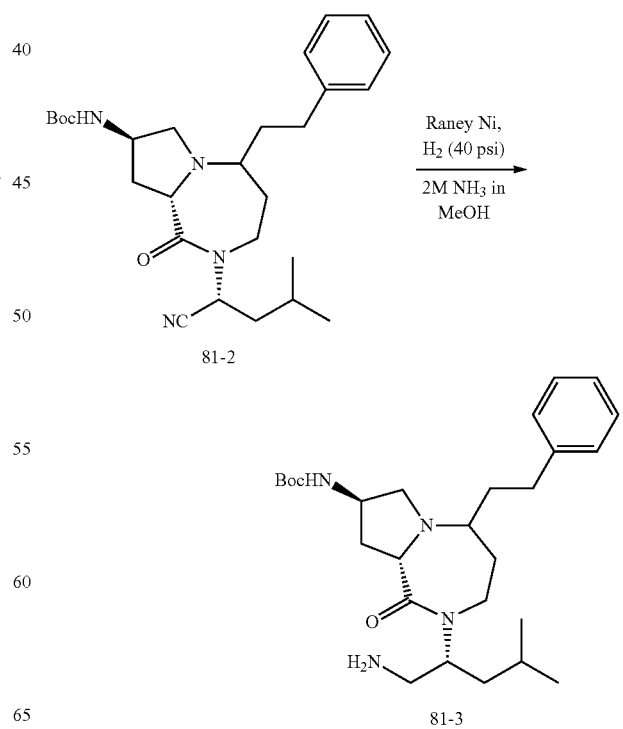

To a solution of Compound 81-2 (63 mg, 0.135 mmol) in methanol (7 mL) was added 2M NH$_3$ in methanol (3 mL) followed by Raney Ni (~1 mL of slurry in H$_2$O). The mixture was shaken under 40 psi of H$_2$ (g) in a Parr shaker for 4 h. The mixture was then filtered through a pad of Celite rinsing with 20% MeOH/DCM (3×). The filtrate was concentrated in vacuo to provide 63 mg (quantitative) of Compound 81-3 as white solid. $^1$H NMR (400 MHz, CD$_3$OD): δ 7.30-7.16 (m, 5H), 4.03 (m, 1H), 3.82 (dd, 1H), 3.53 (m, 3H), 2.98 (m, 2H), 2.87-2.55 (m, 4H), 2.30-2.03 (m, 3H), 1.81-1.57 (m, 3H), 1.53 (m, 1H), 1.45 (s, 9H), 1.29 (m, 3H), 0.95 (s, 3H), 0.89 (s, 3H) ppm.

Step 4: tert-butyl ((8R,9aS)-2-((R)-1-(3,4-dichlorophenylsulfonamido)-4-methylpentan-2-yl)-1-oxo-5-phenethyloctahydro-1H-pyrrolo[1,2-a][1,4]diazepin-8-yl)carbamate (Compound 81-4)

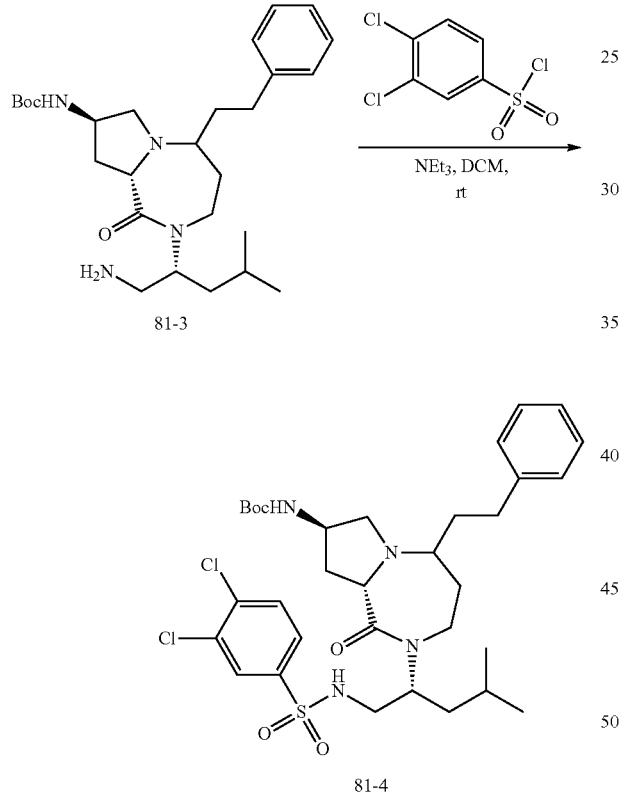

To a solution of Compound 81-3 (20 mg, 0.042 mmol) in DCM (1 mL) was added TEA (20 μL, 0.143 mmol) followed by 3,4-dichlorobenzenesulfonyl chloride (13.4 mg, 0.055 mmol). The mixture was stirred at room temperature for 2 h. The mixture was then quenched with sat. NaHCO$_3$ (aq) and extracted with EtOAc (3×). The combined organic extracts were washed with brine, dried (Na$_2$SO$_4$), filtered and concentrated in vacuo. The residue was purified by FCC (SiO$_2$, elution with 0-60% EtOAc/Hexanes) to give 20 mg (71%) of Compound 81-4. $^1$H NMR (400 MHz, CD$_3$OD): δ 7.96 (d, 1H), 7.70 (dd, 1H), 7.59 (d, 1H), 7.29 (m, 2H), 7.21-7.16 (m, 3H), 5.48 (m, 1H), 4.53 (m, 2H), 4.10 (m, 1H), 3.59-3.49 (m, 2H), 3.35 (m, 1H), 3.21 (m, 1H), 3.10 (m, 1H), 2.90 (m, 2H), 2.70 (m, 1H), 2.56 (m, 1H), 2.28 (m, 1H), 1.89 (m, 2H), 1.61 (m, 2H), 1.45 (s, 9H), 1.37 (m, 2H), 1.17 (m, 1H), 0.85 (d, 3H), 0.81 (d, 3H) ppm; LCMS (Method A): t$_R$=1.33 min, m/z 681.3/683.3 (M+H)$^+$.

Step 5: N-((2R)-2-((8R,9aS)-8-amino-1-oxo-5-phenethylhexahydro-1H-pyrrolo[1,2-a][1,4]diazepin-2(3H)-yl)-4-methylpentyl)-3,4-dichlorobenzenesulfonamide.HCl (Example 81)

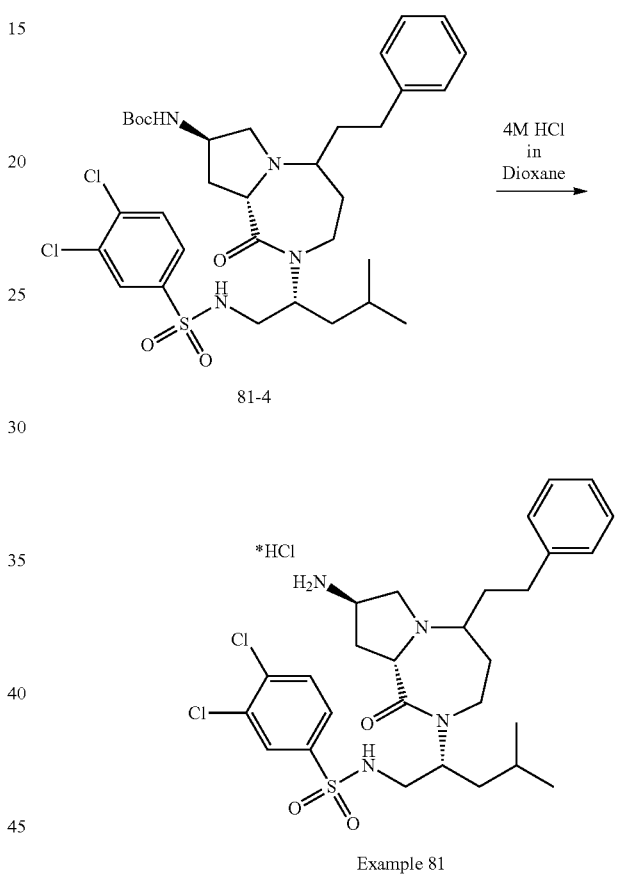

A solution of Compound 81-4 (20 mg, 0.029 mmol) in 4M HCl in Dioxane (1 mL) was stirred at room temperature for 2 h. The reaction mixture was then concentrated in vacuo and the residue was taken up in 1:1 ACN/H$_2$O (2 mL) and then purified directly by mass-directed preparative reversed-phase HPLC (C-18, elution with 5-95% ACN/H$_2$O containing 0.25% formic acid). The desired fractions were combined and concentrated in vacuo. To the residue was added 3N HCl in MeOH (5 mL) and then this was concentrated in vacuo. This treatment with HCl was repeated twice more to ensure formation of the HCl addition salt which was dissolved in H$_2$O (10 mL) and lyophilized to provide 16.2 mg (89%) of Example 81 as a white solid. $^1$H NMR (400 MHz, CD$_3$OD): δ 8.05 (s, 1H), 7.83-7.76 (m, 2H), 7.31-7.21 (m, 5H), 4.62 (m, 1H), 4.02 (m, 2H), 3.68-3.59 (m, 4H), 3.21-3.16 (m, 2H), 2.90-2.63 (m, 3H), 2.46-2.11 (m, 3H), 1.93 (m, 2H), 1.53 (m, 1H), 1.42 (m, 1H), 1.25 (m, 2H), 0.90 (d, 3H), 0.83 (d, 3H) ppm; LCMS (Method A): t$_R$=1.17 min, m/z 581.3/583.3 (M+H)$^+$.

Example 82: N-((2R)-2-((8R,9aS)-8-amino-1-oxo-5-phenethylhexahydro-1H-pyrrolo[1,2-a][1,4]diazepin-2(3H)-yl)-4-methylpentyl)-3,4-dichlorobenzamide.HCl

Step 1: tert-butyl ((8R,9aS)-2-((R)-1-(3,4-dichlorobenzamido)-4-methylpentan-2-yl)-1-oxo-5-phenethyloctahydro-1H-pyrrolo[1,2-a][1,4]diazepin-8-yl)carbamate (Compound 82-1)

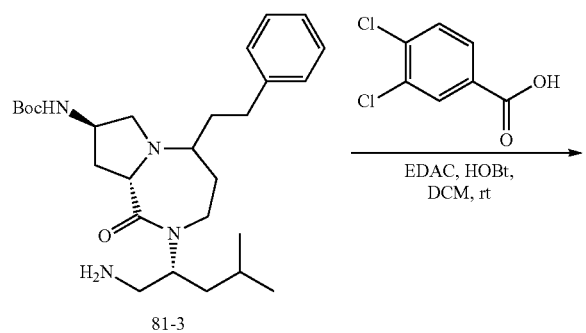

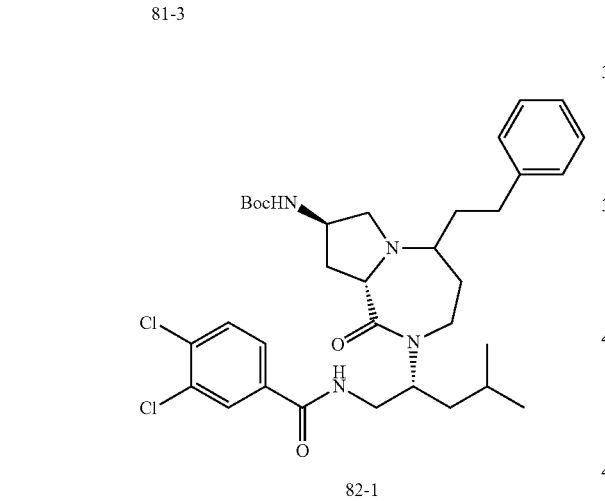

82-1

To a mixture of Compound 81-3 (40 mg, 0.085 mmol) and 3,4-dichlorobenzoic acid (19 mg, 0.102 mmol) in DCM (1 mL) was added EDAC (20 mg, 0.128 mmol) followed by HOBt.H$_2$O (18 mg, 1.5 mmol). The reaction mixture was stirred at room temperature for 16 h. The mixture was then concentrated in vacuo and the residue was taken up in EtOAc (5 mL). This was washed with sat. NaHCO$_3$ (aq) (5 mL) and brine (5 mL). The organic layer was dried (Na$_2$SO$_4$), filtered and concentrated in vacuo. The residue was purified by FCC (SiO$_2$, elution with 0-100% EtOAc/Hexanes) to give 30 mg (56%) of Compound 82-1. $^1$H NMR (400 MHz, CD$_3$OD): δ 7.92 (s, 1H), 7.59 (d, 2H), 7.22-7.14 (m, 3H), 6.94 (d, 2H), 5.01 (m, 1H), 4.31 (ABq, 2H), 3.66-3.26 (m, 5H), 2.92 (m, 1H), 2.58 (m, 1H), 2.26-2.14 (m, 3H), 1.90-1.58 (m, 5H), 1.52-1.47 (m, 3H), 1.49 (s, 9H), 0.94 (d, 3H), 0.89 (d, 3H) ppm; LCMS (Method A): t$_R$=1.34 min, m/z 645.3/647.3 (M+H)$^+$.

Step 2: N-((2R)-2-((8R,9aS)-8-amino-1-oxo-5-phenethylhexahydro-1H-pyrrolo[1,2-][1,4]diazepin-2(3H)-yl)-4-methylpentyl)-3,4-dichlorobenzamide.HCl (Example 82)

A solution of Compound 82-1 (22 mg, 0.050 mmol) in 4M HCl in Dioxane (1 mL) was stirred at room temperature for 2 h. The reaction mixture was then concentrated in vacuo and the crude residue was taken up in 1:1 ACN/H$_2$O (2 mL) and purified by mass-directed preparative reversed-phase HPLC (C-18, elution with 5-95% ACN/H$_2$O containing 0.25% formic acid). The desired fractions were combined and concentrated in vacuo. To the residue was added 3N HCl in MeOH (5 mL) and then this was concentrated in vacuo. This treatment with HCl was repeated twice more to ensure formation of the HCl addition salt which was dissolved in H$_2$O (10 mL) and lyophilized to provide 19.6 mg (98%) of Example 82 as a white solid. $^1$H NMR (400 MHz, CD$_3$OD): δ 8.01 (s, 1H), 7.78 (dd, 1H), 7.62 (d, 1H), 7.29 (m, 2H), 7.21-7.20 (m, 3H), 4.03 (m, 1H), 3.89 (m, 1H), 3.76-3.74 (m, 1H), 3.69-3.58 (m, 4H), 3.45-3.41 (dd, 1H), 3.13 (m, 2H), 2.75-2.56 (m, 2H), 2.40 (m, 1H), 2.23 (m, 1H), 2.16-2.05 (m, 1H), 1.89 (m, 2H), 1.69 (m, 1H), 1.53 (m, 1H), 1.43-1.38 (m, 2H), 0.98 (d, 3H), 0.92 (d, 3H) ppm; HPLC: t$_R$=4.823 min (100%).

Example 83: (8R,9aS)-8-amino-2-((R)-1-((3,4-dichlorophenyl)sulfonyl)piperidin-3-yl)-5-phenethyl-octahydro-1H-pyrrolo[1,2-a][1,4]diazepin-1-one.HCOOH

Steps 1-3: tert-butyl ((8R,9aS)-1-oxo-5-phenethyl-2-((R)-piperidin-3-yl)octahydro-1H-pyrrolo[1,2-a][1,4]diazepin-8-yl)carbamate (Compound 83-3)

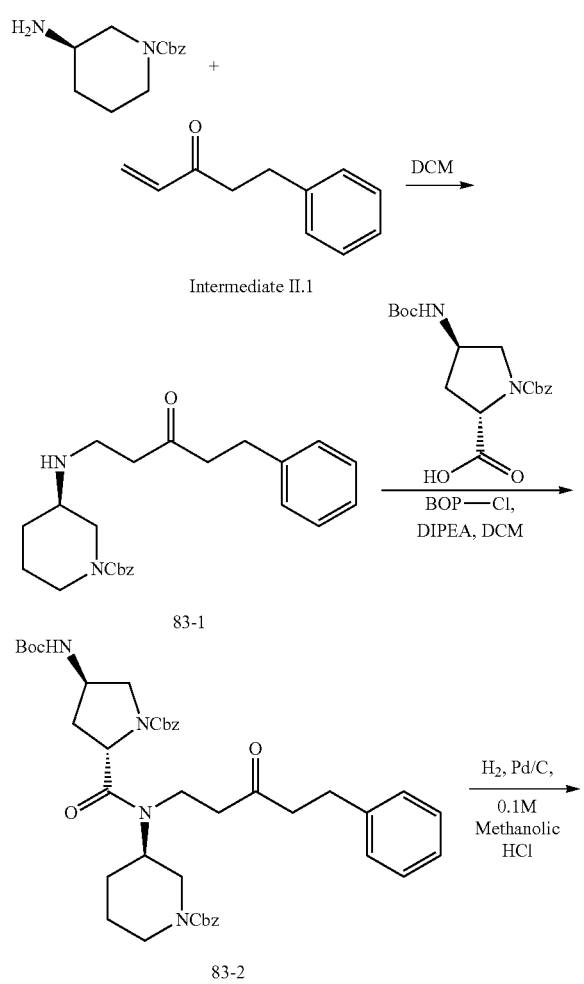

The title compound, 83-3, was prepared from (R)-3-amino-1-N-Cbz-piperidine and Intermediate II.1 using the same general method used in steps 1-3 for the preparation of Example 39. LCMS (Method G): $t_R$=0.89 min, m/z 457.6 (M+H)$^+$

Steps 4 and 5: (8R,9aS)-8-amino-2-((R)-1-((3,4-dichlorophenyl)sulfonyl)piperidin-3-yl)-5-phenethyl-octahydro-1H-pyrrolo[1,2-a][1,4]diazepin-1-one.HCOOH (Example 83)

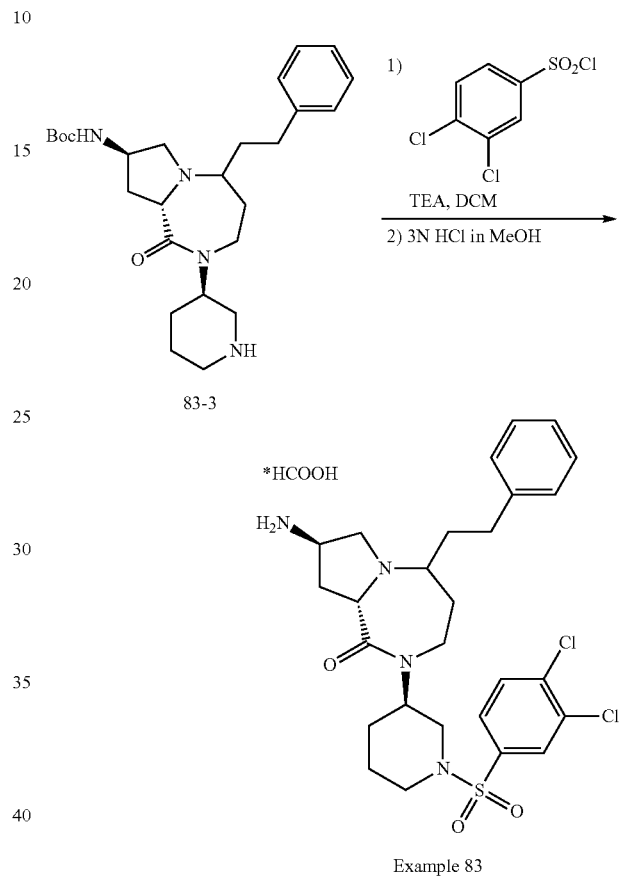

To a solution of Compound 83-3 (14 mg, 0.031 mmol) in DCM (1 mL) was added TEA (20 µL, 0.14 mmol) followed by 3,4-dichlorobenzene-1-sulfonyl chloride (10 µL, 0.064 mmol). The reaction mixture was stirred at room temperature for 30 min. The mixture was then quenched with sat. NaHCO$_3$ (aq) (5 mL) and extracted with DCM (3×5 mL). The combined organic extracts were dried by gravity filtration through an Isolute® HM-N cartridge (3 mL capacity). The filtrate was concentrated in vacuo and the residue was dissolved in 3N HCl in MeOH (2 mL). The resultant solution was heated to 40° C. for 2 h. The mixture was then cooled to room temperature and concentrated in vacuo. The residue was purified by mass-directed, preparative reversed-phase HPLC (C18 column, elution with 5-95% ACN/H$_2$O containing 0.25% formic acid). The desired fractions were combined and lyophilized to provide 13 mg (68% for 2 steps) of Example 83 as a fluffy white solid. $^1$H NMR (400 MHz, CD$_3$OD): δ 8.55 (s, 1H, HCOOH), 7.97 (d, 1H), 7.81 (d, 1H), 7.74 (dd, 1H), 7.29-7.26 (m, 2H), 7.22-7.15 (m, 3H), 4.47 (m, 1H), 3.81-3.72 (m, 3H), 3.57-3.41 (m, 4H), 2.87 (m, 1H), 2.76-2.53 (m, 3H), 2.45 (app t, 1H), 2.40-2.30 (m, 2H), 2.04-1.94 (m, 2H), 1.85 (m, 1H), 1.77-1.58 (m, 5H), 1.33 (m, 1H) ppm; LCMS (Method A): $t_R$=1.07 min, m/z 565.5/567.5 (M+H)$^+$.

Following the method described above for the preparation of Example 83, and utilizing the corresponding acylating or sulfonylating reagent in step 4, the following examples set forth in Table 9 were prepared.

TABLE 8

| Example | Structure | Acylating/sulfonylating reagent | LCMS Method | $t_R$ (min) | $(M + H)^+$ observed |
| --- | --- | --- | --- | --- | --- |
| 84 | *HCOOH | benzenesulfonyl chloride | A | 0.92 | 497.5 |
| 85 | *HCOOH | 3,4-dichlorobenzoyl chloride | A | 0.98 | 529.5/531.5 |

Following the method described above for the preparation of Example 83, and substituting (R)-3-amino-1-N-Cbz-piperidine with (S)-3-amino-1-N-Cbz-piperidine in step 1 and utilizing the corresponding acylating or sulfonylating reagent in step 4, the following examples set forth in Table 10 were prepared.

TABLE 10

| Example | Structure | Acylating/sulfonylating reagent | LCMS Method | $t_R$ (min) | $(M + H)^+$ observed |
| --- | --- | --- | --- | --- | --- |
| 86 | *HCOOH | 3,4-dichlorobenzene-1-sulfonyl chloride | A | 1.04 | 565.4/567.4 |

| Example | Structure | Acylating/sulfonylating reagent | LCMS Method | $t_R$ (min) | $(M + H)^+$ observed |
|---|---|---|---|---|---|
| 87 | *HCOOH [structure] | 3,4-dichlorobenzoyl chloride | A | 0.99 | 529.5/531.5 |

Example 88: (4R)-2-(diethylamino)-2-oxoethyl 4-((8R,9aS)-8-amino-1-oxo-5-phenethylhexahydro-1H-pyrrolo[1,2-a][1,4]diazepin-2(3H)-yl)-5-((3,4-dichlorobenzyl)amino)-5-oxopentanoate Step 1: (4R)-4-((8R,9aS)-8-((tert-butoxycarbonyl)amino)-1-oxo-5-phenethylhexahydro-1H-pyrrolo[1,2-a][1,4]diazepin-2(3H)-yl)-5-((3,4-dichlorobenzyl)amino)-5-oxopentanoic Acid (Compound 88-1)

To a solution of Example 15B (375 mg, 0.67 mmol) and Boc$_2$O (161 mg, 0.74 mmol) in DCM (5 mL) was added TEA (0.28 mL, 2.0 mmol). The mixture was stirred at room temperature for 16 h. The mixture was then concentrated in vacuo. The residue was purified by reversed-phase FCC (C18, elution with 0-100% ACN/H$_2$O) to provide 324 mg (73%) of Compound 88-1. $^1$H NMR (400 MHz, CD$_3$OD): δ 7.52 (d, 1H), 7.47 (d, 1H), 7.27 (t, 3H), 7.17 (t, 3H), 5.15 (dd, 1H), 4.50 (d, 1H), 4.22 (d, 1H), 4.01 (br, 1H), 3.73 (dd, 1H), 3.58-3.40 (m, 3H), 2.84-2.78 (m, 1H), 2.65-2.58 (m, 2H), 2.44-2.37 (m, 1H), 2.31-2.14 (m, 4H), 2.04-1.93 (m, 2H), 1.85 (d, 1H), 1.72 (q, 1H), 1.60-1.50 (m, 1H), 1.45 (s, 9H), 1.40-1.32 (m, 1H) ppm; LCMS (Method A): $t_R$=1.20 min, m/z 661.5/663.5 (M+H)$^+$.

Step 2: (4R)-2-(diethylamino)-2-oxoethyl 4-((8R,9aS)-8-((tert-butoxycarbonyl)amino)-1-oxo-5-phenethylhexahydro-1H-pyrrolo[1,2-a][1,4]diazepin-2(3H)-yl)-5-((3,4-dichlorobenzyl)amino)-5-oxopentanoate (Compound 88-2)

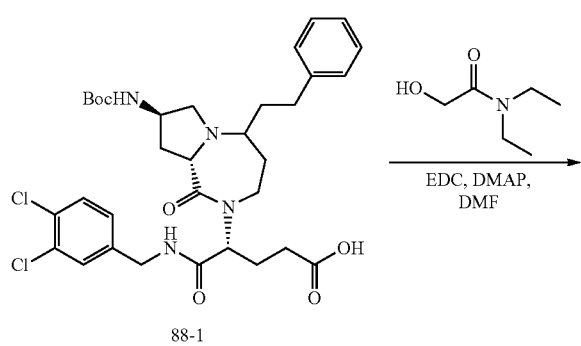

88-1

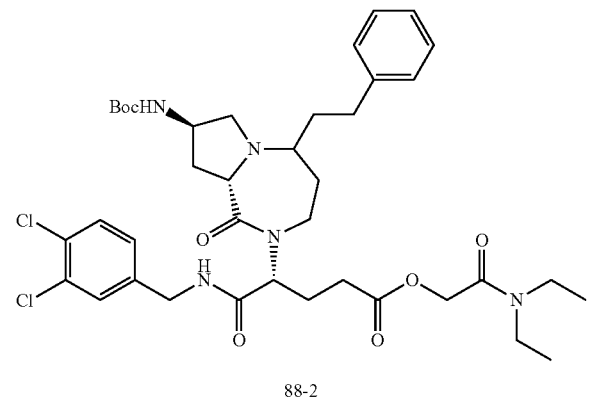

88-2

To a mixture of Compound 88-1 (40 mg, 0.06 mmol), EDC (23 mg, 0.12 mmol) and DMAP (18 mg, 0.15 mmol) in DMF (1 mL) was added N,N-diethyl-2-hydroxyacetamide (16 mg, 0.12 mmol). The mixture was stirred at room temperature for 16 h. The mixture was then diluted with DCM (50 mL) and washed with H$_2$O (5×). The organic layer was dried (Na$_2$SO$_4$), filtered and concentrated in vacuo. The residue was purified by reversed-phase FCC (C18, elution with 0-100% ACN/H$_2$O) to provide 33 mg (72%) of compound 88-2. $^1$H NMR (400 MHz, CDCl$_3$): δ 7.39 (d, 1H), 7.36 (d, 1H), 7.30-7.25 (m, 4H), 7.18 (d, 1H), 7.16-7.11 (m, 3H), 5.18 (t, 1H), 4.83 (d, 1H), 4.61 (d, 1H), 4.48 (br, 1H), 4.40-4.30 (m, 2H), 4.11 (br, 1H), 3.59 (q, 2H), 3.51 (t, 1H), 3.46-3.27 (m, 3H), 3.23 (q, 2H), 2.87 (br, 1H), 2.65-2.58 (m, 1H), 2.53-2.32 (m, 4H), 2.31-2.15 (m, 2H), 1.90-1.83 (m, 2H), 1.70-1.62 (m, 2H), 1.58 (br, 1H), 1.44 (s, 9H), 1.22 (t, 3H), 1.10 (t, 3H) ppm; LCMS (Method A): $t_R$=1.23 min, m/z 774.7/776.7 (M+H)$^+$.

Step 3: (4R)-2-(diethylamino)-2-oxoethyl 4-((8R,9aS)-8-amino-1-oxo-5-phenethylhexahydro-1H-pyrrolo[1,2-a][1,4]diazepin-2(3H)-yl)-5-((3,4-dichlorobenzyl)amino)-5-oxopentanoate (Example 88)

Example 89: (4R)-ethyl 4-((8R,9aS)-8-amino-1-oxo-5-phenethylhexahydro-1H-pyrrolo[1,2-a][1,4]diazepin-2(3H)-yl)-5-((3,4-dichlorobenzyl)amino)-5-oxopentanoate

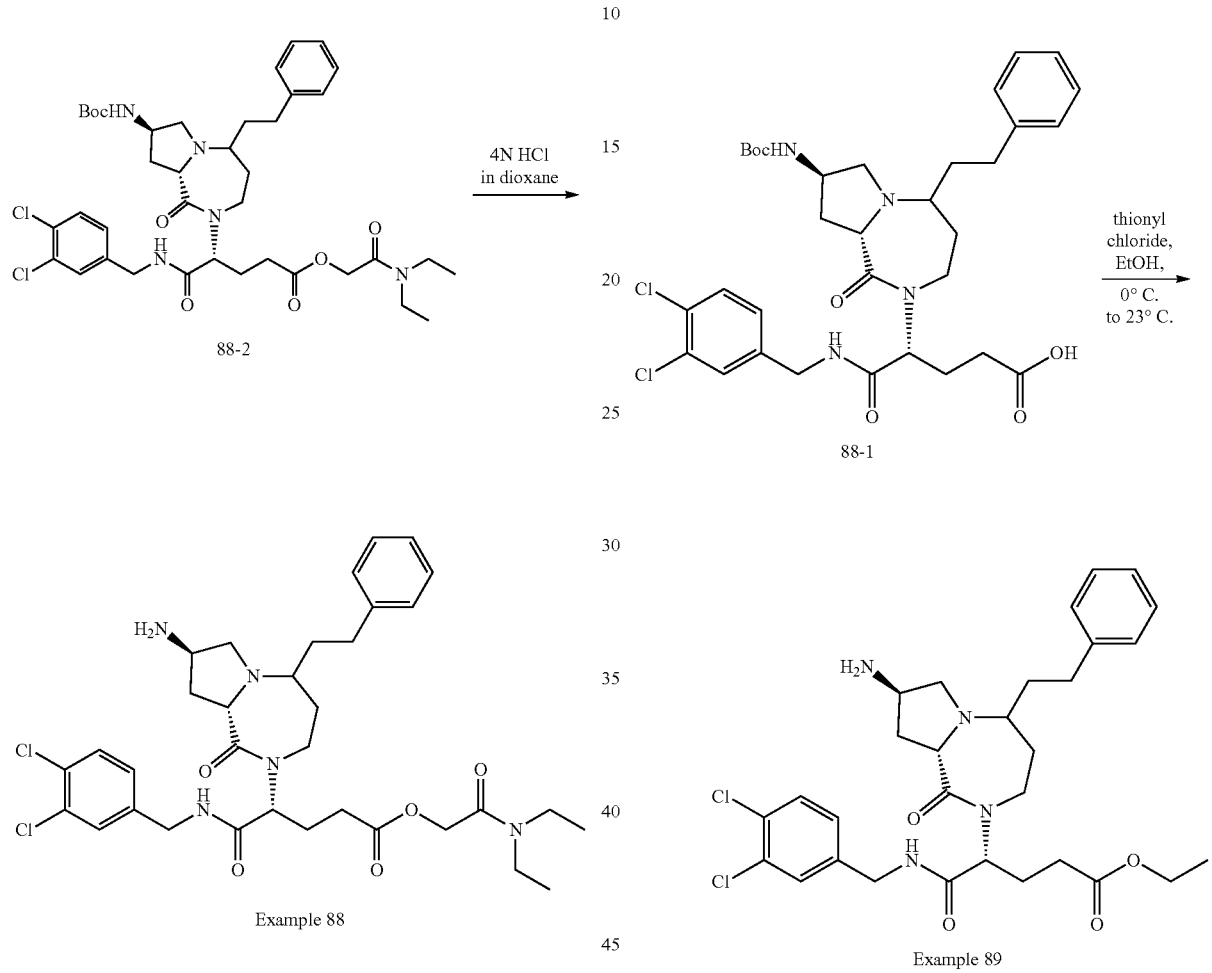

Compound 88-2 (29 mg, 0.038 mmol) was taken up in 4M HCl in Dioxane (1 mL) and stirred at room temperature in a tightly capped reaction vial for 2 h. The mixture was then concentrated in vacuo and the residue was purified by reversed-phase FCC (C18, elution with 0-100% ACN/H$_2$O) to provide 12 mg (44%) of Example 88. $^1$H NMR (400 MHz, CD$_3$OD): δ 7.44 (dd, 1H), 7.36 (dd, 1H), 7.21-7.16 (m, 3H), 7.14-7.06 (m, 3H), 5.08 (q, 1H), 4.77 (d, 1H), 4.65 (d, 1H), 4.41 (d, 1H), 4.14 (d, 1H), 3.68 (dd, 1H), 3.57-3.47 (m, 1H), 3.39-3.17 (m, 7H), 2.75-2.67 (m, 1H), 2.57-2.47 (m, 2H), 2.37-2.30 (m, 3H), 2.21-2.10 (m, 2H), 2.00-1.75 (m, 3H), 1.58-1.43 (m, 2H), 1.31 (q, 1H), 1.15 (t, 3H), 1.04 (t, 3H) ppm; LCMS (Method A): $t_R$=1.06 min, m/z 674.6/676.6 (M+H)$^+$.

To a solution of Compound 88-1 (20 mg, 0.03 mmol) in EtOH (1 mL) at 0° C. was added thionyl chloride (22 uL, 0.30 mmol). The mixture was warmed to room temperature and stirred for 16 h. The mixture was then concentrated in vacuo and the residue was purified by reverse-phase FCC (C18, elution with 0-100% ACN/H$_2$O) to provide 6.8 mg (39%) of Example 89. $^1$H NMR (400 MHz, CD$_3$OD): δ 7.40 (d, 1H), 7.34 (d, 1H), 7.16 (td, 3H), 7.06 (td, 3H), 4.95 (q, 1H), 4.41 (d, 1H), 4.09 (d, 1H), 4.01 (qd, 2H), 3.74 (dd, 1H), 3.55-3.41 (m, 4H), 2.91-2.87 (m, 1H), 2.57-2.47 (m, 2H), 2.37-2.29 (m, 2H), 2.22-2.18 (td, 2H), 2.11-2.04 (m, 1H), 1.96-1.88 (m, 1H), 1.83-1.75 (m, 3H), 1.50-1.46 (m, 1H), 1.32-1.23 (m, 1H), 1.14 (t, 3H) ppm; LCMS (Method A): $t_R$=1.09 min, m/z 589.5/591.5 (M+H)$^+$.

Following the general method described above, using the corresponding starting material and alcoholic solvent, the following examples set forth in Table 11 were prepared.

TABLE 11
| Example | Structure | Starting material | Solvent | LCMS Method | $t_R$ (min) | $(M + H)^+$ observed |
|---|---|---|---|---|---|---|
| 90 | 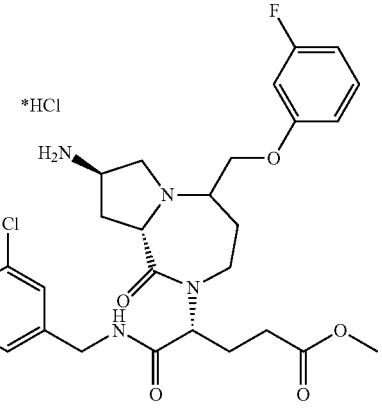 | Example 77 | MeOH | A | 1.03 | 596.4/598.4 |
| 91 | 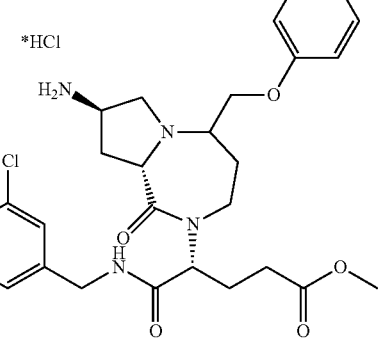 | Example 75 | MeOH | A | 1.02 | 596.5/598.5 |
| 92 | 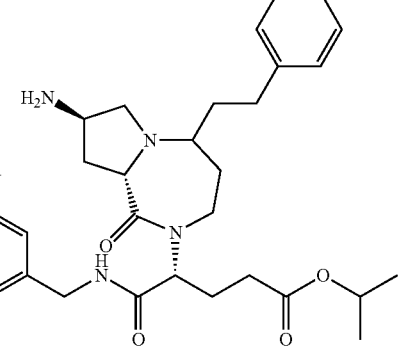 | 88-1 | i-PrOH | A | 1.12 | 603.5/605.5 |
| 93 | 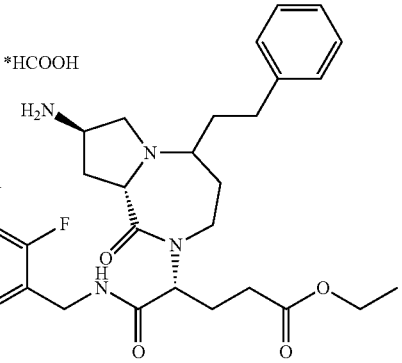 | Example 30 | EtOH | A | 1.16 | 608.2/610.2 |

US 11,583,538 B2

TABLE 11-continued

| Example | Structure | Starting material | Solvent | LCMS Method | $t_R$ (min) | $(M + H)^+$ observed |
|---|---|---|---|---|---|---|
| 94 | 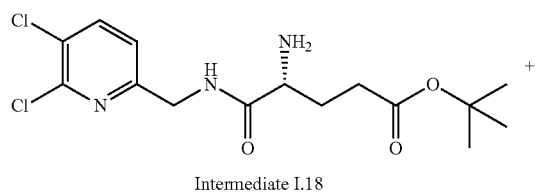 | Example 31 | EtOH | D | 0.98 | 607.4/609.4 |

Example 95: (4R)-Ethyl 4-((8R,9aS)-8-amino-1-oxo-5-phenethylhexahydro-1H-pyrrolo[1,2-a][1,4]diazepin-2(3H)-yl)-5-(((5,6-dichloropyridin-2-yl)methyl)amino)-5-oxopentanoate·HCl Steps 1-4: (4R)-tert-butyl 4-((8R,9aS)-8-((tert-butoxycarbonyl)amino)-1-oxo-5-phenethylhexahydro-1H-pyrrolo[1,2-a][1,4]diazepin-2(3H)-yl)-5-(((5,6-dichloropyridin-2-yl)methyl)amino)-5-oxopentanoate (Compound 95-3)

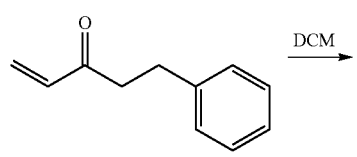

Intermediate I.18

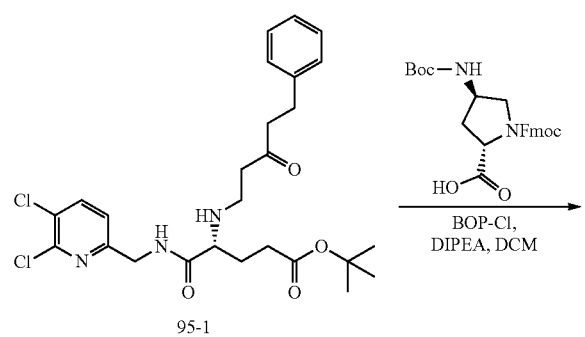

Intermediate II.1

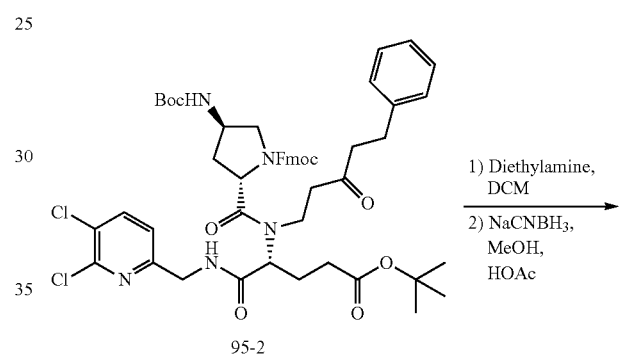

95-2

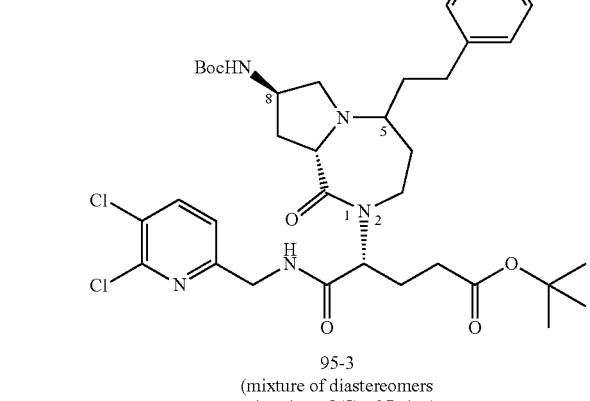

95-3
(mixture of diastereomers epimeric at C(5) of 7-ring)

Compound 95-3 was prepared from Intermediate I.18 (110 mg, 0.31 mmol) and Intermediate II.1 (49 mg, 0.31 mmol) using the same general method described for the preparation of compound 1-3 in steps 1-4 in Example 1. After work-up the crude product was purified by FCC (SiO$_2$, elution with 0-100% EtOAc/hexanes). This provided 50 mg (22% for 4 steps) of second eluting, major diastereomer (95-3B) (the minor diastereomer was not isolated). Data for Compound 95-3B (major diastereomer): $^1$H NMR (400 MHz, CD$_3$OD): δ 7.74 (m, 1H), 7.29 (m, 2H), 7.20 (d, 2H), 7.12-7.10 (m, 2H), 7.05 (br s, —N—H, 1H), 5.08 (dd, 1H), 4.57 (dd, 1H), 4.45 (ABq, 2H), 4.13 (m, 1H), 3.64 (m, 1H), 3.51-3.44 (m, 3H), 2.89 (m, 1H), 2.61-2.57 (m, 2H), 2.48-2.38 (m, 1H), 2.28-2.16 (m, 4H), 1.94-1.87 (m, 3H), 1.62 (m, partially obscured by solvent peak, 2H), 1.49 (s, 9H), 1.43 (s, 9H) ppm; LCMS (Method A): $t_R$=1.30 min, m/z 718.6/720.6 (M+H)$^+$.

Step 5: (4R)-Ethyl 4-((8R,9aS)-8-amino-1-oxo-5-phenethylhexahydro-1H-pyrrolo[1,2-a][1,4]diazepin-2(3H)-yl)-5-(((5,6-dichloropyridin-2-yl)methyl)amino)-5-oxopentanoate.HCl (Example 95)

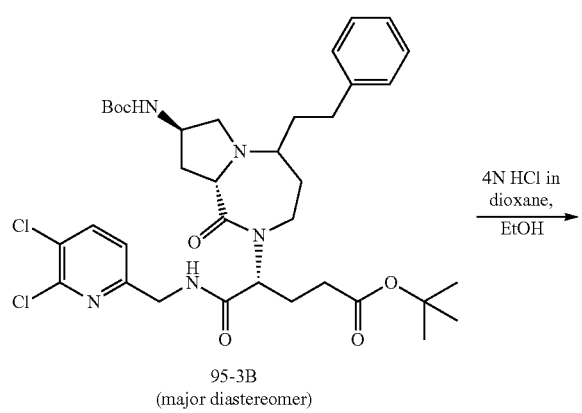

95-3B
(major diastereomer)

4N HCl in dioxane, EtOH

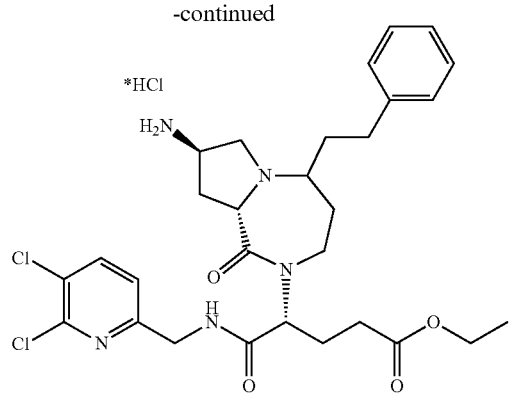

Example 95

To a solution of Compound 95-3B (16 mg, 0.023 mmol) in EtOH (1 mL) was added 4M HCl in Dioxane (0.5 mL) and the mixture was stirred at 80° C. in a tightly capped reaction vial for 1 h. The mixture was then cooled and concentrated in vacuo. The residue was purified by mass-directed, preparative reversed-phase HPLC (C18 column, elution with 5-95% ACN/H$_2$O containing 0.25% formic acid). The desired fractions were concentrated in vacuo and to the residue was added 3N HCl in MeOH (5 mL) and then this was concentrated in vacuo. This treatment with HCl was repeated twice more to ensure formation of the HCl addition salt which was then dissolved in H$_2$O (10 mL) and lyophilized to provide 13 mg (100%) of Example 95 as a white solid. $^1$H NMR (400 MHz, CD$_3$OD): δ 7.94 (d, 1H), 7.39 (d, 1H), 7.33-7.29 (m, 2H), 7.26-7.21 (m, 3H), 5.25 (m, 1H), 4.48 (s, 2H), 4.18-4.11 (m, 3H), 3.97 (m, 1H), 3.80-3.74 (m, 3H), 3.69-3.59 (m, 2H), 3.43 (m, 1H), 3.33-3.31 (m, 1H), 2.80 (m, 1H), 2.63 (m, 1H), 2.43-2.34 (m, 2H), 2.36-2.14 (m, 2H), 2.11-1.86 (m, 3H), 1.30 (m, 1H), 1.26 (t, 3H) ppm; LCMS (Method A): $t_R$=0.98 min, m/z 590.5/592.5 (M+H)$^+$; HPLC: $t_R$=4.280 min (100%).

Following the general method described above for Example 95, and using the corresponding intermediates in step 1, the examples set forth in Table 12 were prepared.

TABLE 11

| Example | Structure | Intermediates | LCMS Method | $t_R$ (min) | (M + H)$^+$ observed |
|---|---|---|---|---|---|
| 96 | 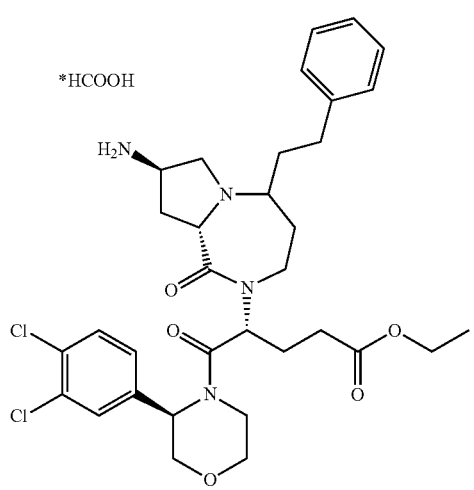 | I.25 and II.1 | D | 0.98 | 645.4/647.4 |

TABLE 11-continued
| Example | Structure | Intermediates | LCMS Method | $t_R$ (min) | $(M + H)^+$ observed |
|---|---|---|---|---|---|
| 97 | 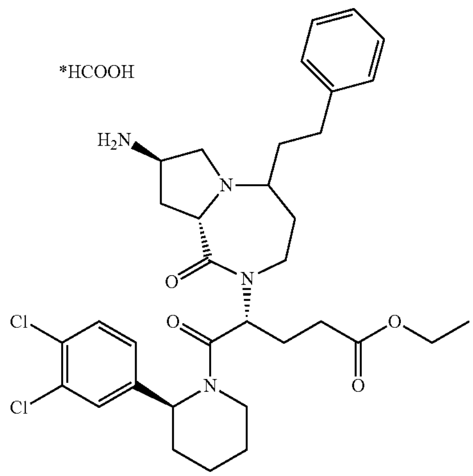 | I.19 and II.1 | A | 1.19 | 643.4/645.4 |
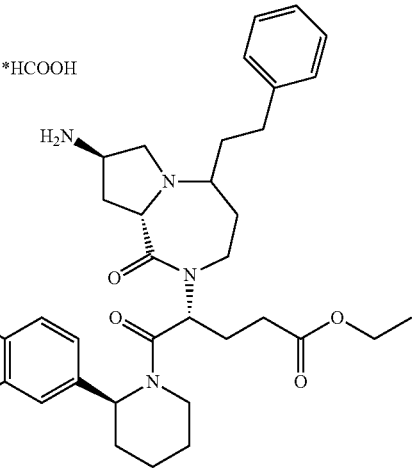
| 98 | | I.20 and II.1 | A | 1.08 | 629.5/631.5 |
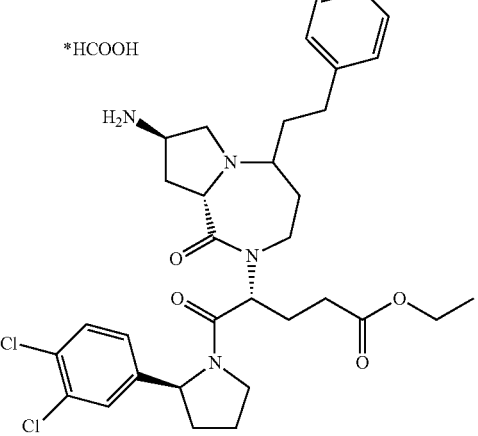
| 99 | | I.21 and II.1 | A | 1.07 | 590.2/592.2 |
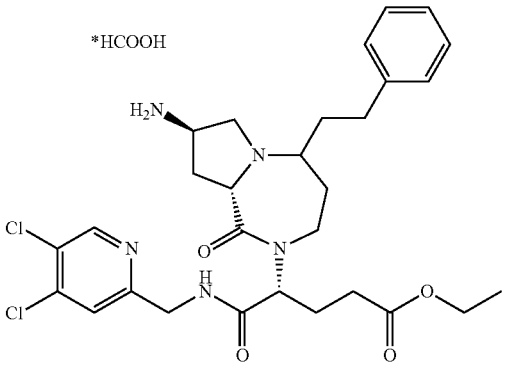

Following the method described above in step 5 for the preparation of Example 95, and substituting Compound 95-3B with Compound 70-4 and ethanol with methanol, the example set forth in Table 13 was prepared.

TABLE 13

| Example | Structure | LCMS Method | $t_R$ (min) | $(M + H)^+$ observed |
|---|---|---|---|---|
| 100 | 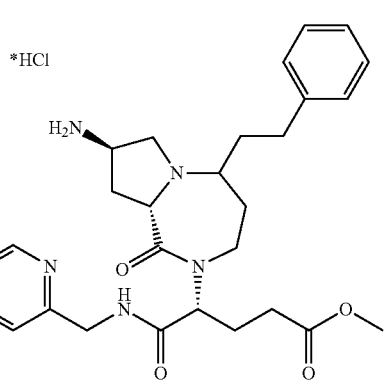 | A | 0.86 | 542.5/544.5 |

Following the method described above in step 5 for the preparation of Example 95, and substituting Compound 95-3B with (4R)-tert-butyl 4-((8R,9aS)-8-((tert-butoxycarbonyl)amino)-1-oxo-5-phenethylhexahydro-1H-pyrrolo[1,2-a][1,4]diazepin-2(3H)-yl)-5-(3,4-dichlorophenylsulfonamido)-5-oxopentanoate—obtained by substituting 5-chloropyridin-2-yl) methanamine with 3,4-dichlorobenzenesulfonamide in step 4 of the preparation of Example 70—and ethanol with methanol, the example set forth in Table 14 was prepared.

TABLE 14

| Example | Structure | LCMS Method | $t_R$ (min) | $(M + H)^+$ observed |
|---|---|---|---|---|
| 101 | 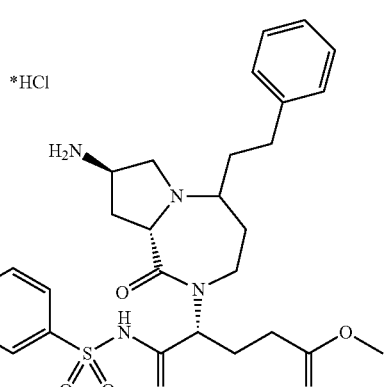 | A | 1.00 | 625.4/627.4 |

Following the method described above in step 5 for the preparation of Example 95, and substituting Compound 95-3B with the corresponding starting material (i.e. the major diasteromer obtained via the method described in steps 1-4 for the preparation of Example 21 or Example 22)—the examples set forth in Table 15 were prepared.

TABLE 15

| Example | Structure | Starting Material | LCMS Method | $t_R$ (min) | $(M + H)^+$ observed |
|---|---|---|---|---|---|
| 102 | *HCOOH (structure) | N-Boc-t-Bu ester intermediate analogous to 2-3B towards preparation of Example 22 | A | 1.10 | 619.5/621.5 |
| 103 | *HCOOH (structure) | N-Boc-t-Bu ester intermediate analogous to 2-3B towards preparation of Example 21 | A | 1.11 | 619.4/621.4 |

Example 104: (4R)-methyl 4-((8R,9aS)-8-amino-1-oxo-5-phenethylhexahydro-1H-pyrrolo[1,2-a][1,4]diazepin-2(3H)-yl)-5-(((3,4-dichlorobenzyl)amino)-5-oxopentanoate

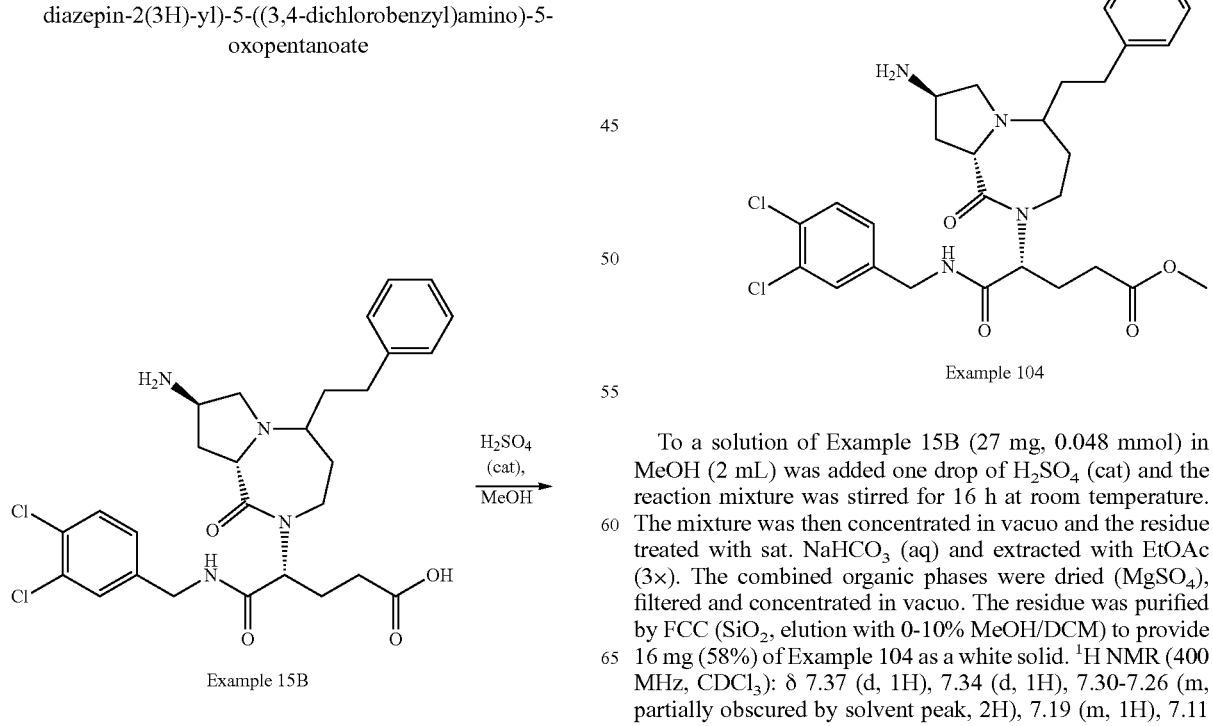

To a solution of Example 15B (27 mg, 0.048 mmol) in MeOH (2 mL) was added one drop of $H_2SO_4$ (cat) and the reaction mixture was stirred for 16 h at room temperature. The mixture was then concentrated in vacuo and the residue treated with sat. $NaHCO_3$ (aq) and extracted with EtOAc (3×). The combined organic phases were dried ($MgSO_4$), filtered and concentrated in vacuo. The residue was purified by FCC ($SiO_2$, elution with 0-10% MeOH/DCM) to provide 16 mg (58%) of Example 104 as a white solid. $^1$H NMR (400 MHz, $CDCl_3$): δ 7.37 (d, 1H), 7.34 (d, 1H), 7.30-7.26 (m, partially obscured by solvent peak, 2H), 7.19 (m, 1H), 7.11

(dd, 1H), 6.84 (br t, 1H, N—H), 5.04 (dd, 1H), 4.45 (dd, 1H), 4.26 (dd, 1H), 3.66 (s, 3H), 3.62 (dd, 1H), 3.53 (m, 1H), 3.47-3.44 (m, 2H), 3.39 (dd, 1H), 2.78 (m, 1H), 2.63-2.50 (m, 2H), 2.42-2.22 (m, 4H), 2.16 (t, 1H), 2.06-1.80 (m, 3H), 1.65-1.52 (m partially obscured by H$_2$O peak, 2H), 1.28 (m, 1H) ppm; LCMS (Method D): t$_R$=1.14 min, m/z 575.4/577.4 (M+H)$^+$.

Example 105: (2R)-2-((8R,9aS)-8-amino-1-oxo-5-phenethylhexahydro-1H-pyrrolo[1,2-a][1,4]diazepin-2(3H)-yl)-4-cyano-N-(3,4-dichlorobenzyl)butanamide.HCOOH Step 1: (4R)-4-((8R,9aS)-8-((tert-butoxycarbonyl)amino)-1-oxo-5-phenethylhexahydro-1H-pyrrolo[1,2-a][1,4]diazepin-2(3H)-yl)-5-((3,4-dichlorobenzyl)amino)-5-oxopentanoic Acid (Compound 105-1)

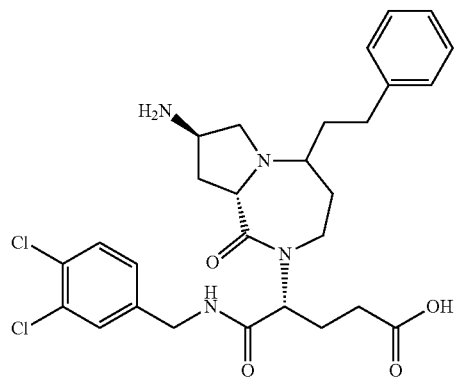

Example 15B

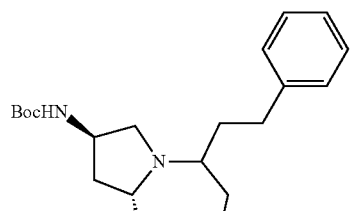

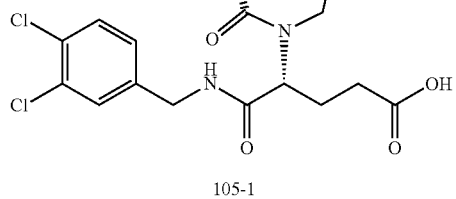

105-1

To a 20 mL capacity reaction vial containing Example 15B (153 mg, 0.272 mmol) was added 1 N NaOH (aq) (0.3 mL, 0.3 mmol) and the resultant solution was cooled to 0° C. To this was added a solution of Boc$_2$O (71 mg, 0.33 mmol) in dioxane (2 mL) and the reaction mixture was slowly warmed to room temperature and stirred for 16 h. The mixture was then quenched with 0.5 N citric acid (aq) and extracted with EtOAc (3×). The combined organic extracts were washed with brine, dried (Na$_2$SO$_4$), filtered and concentrated in vacuo. The crude product was purified by FCC (SiO$_2$, elution with 0-10% MeOH/DCM) to provide 148 mg (82%) of Compound 105-1 as a white solid. LCMS (Method A): t$_R$=1.11 min, m/z 661.5/663.5 (M+H)$^+$.

Step 2: tert-butyl ((8R,9aS)-2-((R)-5-amino-1-((3,4-dichlorobenzyl)amino)-1,5-dioxopentan-2-yl)-1-oxo-5-phenethyloctahydro-1H-pyrrolo[1,2-a][1,4]diazepin-8-yl)carbamate (Compound 105-2)

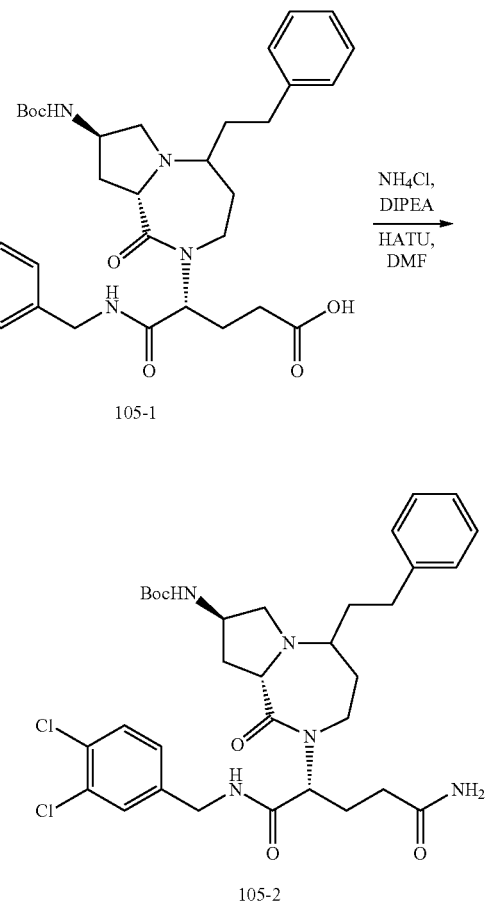

To a solution of Compound 105-1 (148 mg, 0.224 mmol) in DMF (2 mL) were added DIPEA (80 μL, 0.45 mmol), HATU (170 mg, 0.448 mmol) and NH$_4$Cl (60 mg, 1.1 mmol). The reaction mixture was stirred at room temperature for 16 h. The mixture was then quenched with sat. NaHCO$_3$ (aq) and extracted with EtOAc (3×). The combined organic extracts were washed with brine, dried (Na$_2$SO$_4$), filtered and concentrated in vacuo. The residue was purified by FCC (SiO$_2$, elution with 0-10% MeOH/DCM) to give 107 mg (72%) of Compound 105-2. $^1$H NMR (400 MHz, CDCl$_3$): δ 7.39-7.37 (m, 2H), 7.30-7.26 (m partially obscured by solvent peak, 2H), 7.20 (app t, 1H), 7.14-7.11 (m, 3H), 6.88 (br t, 1H, N—H), 5.62 (br s, 1H), 5.33 (br s, 1H), 5.05 (t, 1H), 4.44 (dd, 2H), 4.27 (dd, 2H), 4.11 (m, 1H), 3.57 (dd, 1H), 3.51-3.38 (m, 2H), 2.85 (m, 1H), 2.60 (m, 1H), 2.50 (m, 1H), 2.38 (m, 1H), 2.31-2.10 (m, 4H), 2.03 (m, 1H), 1.91-1.79 (m, 2H), 1.68-1.51 (m partially obscured by H$_2$O peak, 2H), 1.45 (s, 9H), 1.29 (m, 1H) ppm; LCMS (Method A): t$_R$=1.06 min, m/z 660.6/662.6 (M+H)$^+$.

Step 3: tert-butyl ((8R,9aS)-2-((R)-4-cyano-1-((3,4-dichlorobenzyl)amino)-1-oxobutan-2-yl)-1-oxo-5-phenethyloctahydro-1H-pyrrolo[1,2-a][1,4]diazepin-8-yl)carbamate (Compound 105-3)

Step 4: (2R)-2-((8R,9aS)-8-amino-1-oxo-5-phenethylhexahydro-1H-pyrrolo[1,2-a][1,4]diazepin-2(3H)-yl)-4-cyano-N-(3,4-dichlorobenzyl)butanamide·HCOOH (Example 105)

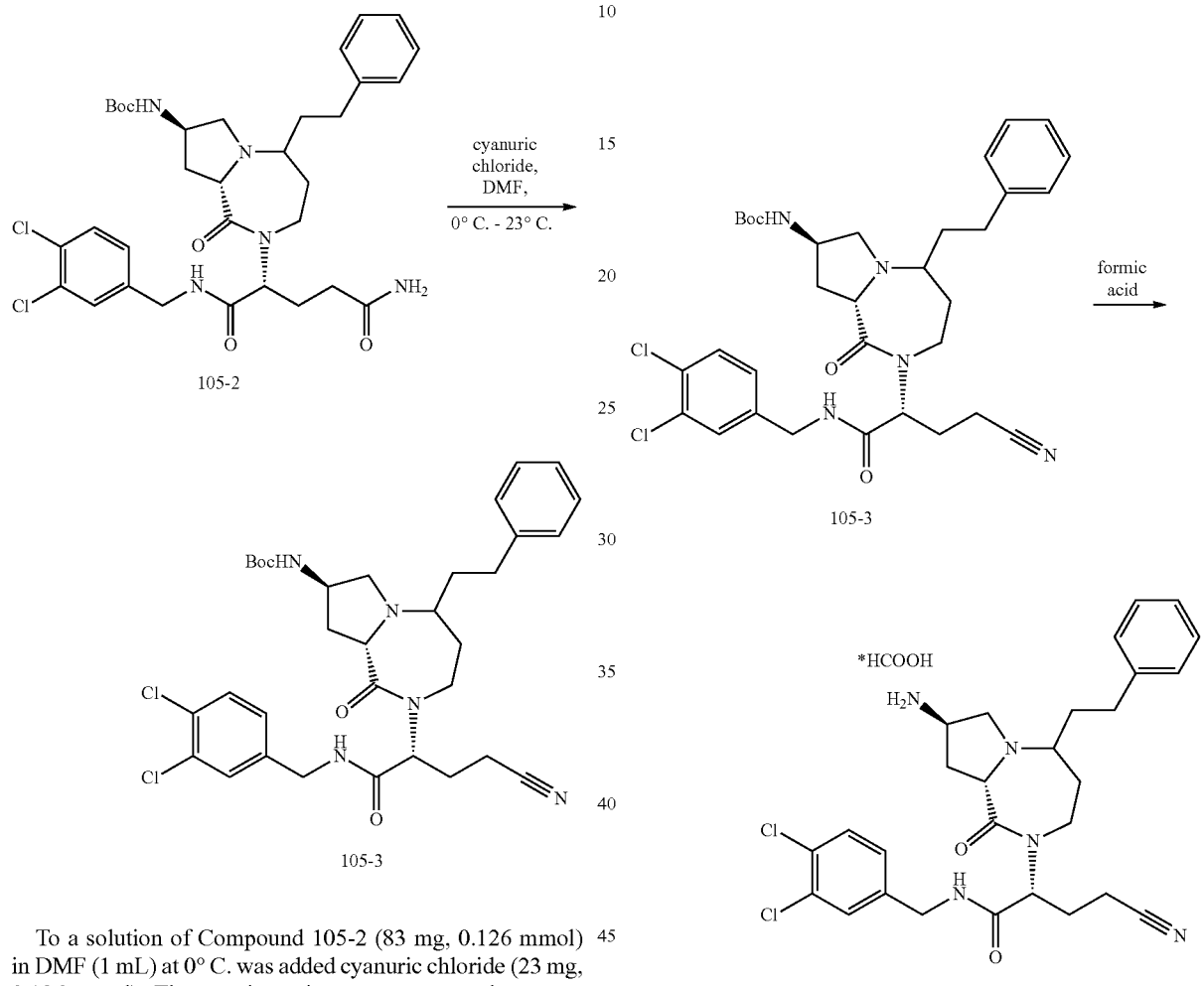

To a solution of Compound 105-2 (83 mg, 0.126 mmol) in DMF (1 mL) at 0° C. was added cyanuric chloride (23 mg, 0.126 mmol). The reaction mixture was warmed to room temperature and stirred for 1.5 h. Analysis by LC/MS indicated incomplete reaction so the mixture was cooled to 0° C. and more cyanuric chloride (23 mg, 0.126 mmol) was added. The mixture was warmed to room temperature and stirred for an additional 1 h. The mixture was then cooled to 0° C., quenched with 0.5 N NaOH (aq) (5 mL) and extracted with EtOAc (3×5 mL). The organic extracts were filtered through an Isolute® HM-N cartridge (3 mL capacity) which was prewetted with 2 mL of brine. The eluent was collected by gravity filtration and concentrated in vacuo. The residue was purified by FCC (SiO$_2$, elution with 0-10% MeOH/DCM) to provide 62 mg (77%) of Compound 105-3 as a white solid. $^1$H NMR (400 MHz, CDCl$_3$): δ 7.40-7.38 (m, 2H), 7.30-7.26 (m partially obscured by solvent peak, 2H), 7.19 (m, 1H), 7.13-7.10 (m, 3H), 6.75 (br t, 1H, N—H), 5.15 (dd, 1H), 4.46 (dd, 1H), 4.26 (dd, 1H), 4.12 (m, 1H), 3.60 (dd, 1H), 3.52 (dd, 2H), 3.36 (m, 1H), 2.87 (m, 1H), 2.63-2.24 (m, 6H), 2.18 (m, 1H), 2.05 (m, 1H), 1.92-1.80 (m, 2H), 1.68-1.45 (m partially obscured by singlet and H$_2$O peak, 3H), 1.45 (s superimposed on multiplet, 9H), 1.24 (m, 1H) ppm; LCMS (Method A): t$_R$=1.29 min, m/z 642.5/644.5 (M+H)$^+$.

Compound 105-3 (29 mg, 0.045 mmol) was treated with formic acid (1 mL) and the resultant solution was stirred at room temperature for 5.5 h. The mixture was then concentrated in vacuo and the residue was purified by mass-directed preparative reversed-phase HPLC (C-18, elution with 5-95% ACN/H$_2$O containing 0.25% formic acid). The desired fractions were combined and lyophilized to provide 20 mg (83%) of Example 105 as a white solid. $^1$H NMR (400 MHz, CD$_3$OD): δ 8.53 (s, 1H, HCOOH), 7.50 (d, 1H), 7.44 (d, 1H), 7.27-7.24 (m, 3H), 7.18-7.14 (m, 3H), 5.17 (dd, 1H), 4.36 (ABq, 2H), 3.80 (dd, 1H), 3.63-3.43 (m, 4H), 2.96 (m, 1H), 2.59 (m, 2H), 2.53-2.34 (m, 4H), 2.18 (m, 1H), 2.06 (m, 1H), 1.96-1.75 (m, 3H), 1.55 (m, 1H), 1.33 (m, 1H) ppm; LCMS (Method D): t$_R$=0.90 min, m/z 542.3/544.3 (M+H)$^+$.

Following steps 1 and 2 and then step 4 (i.e. skip step 3) in the method described above for the preparation of Example 105, the following examples set forth in Table 16 were prepared from the corresponding starting material.

TABLE 16

| Example | Structure | Starting Material | LCMS Method | $t_R$ (min) | $(M + H)^+$ observed |
|---|---|---|---|---|---|
| 106 | 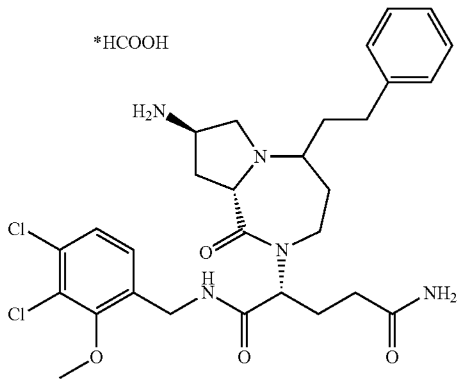 | Example 22 | A | 0.93 | 590.3/592.3 |
| 107 | 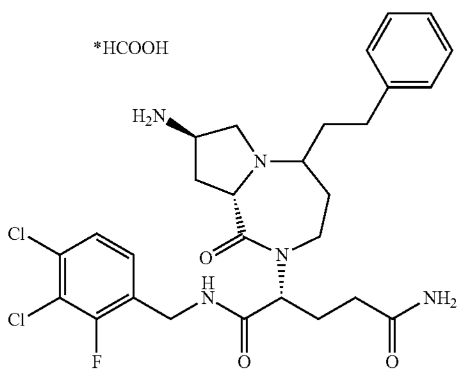 | Example 30 | A | 0.97 | 578.3/580.2 |

Following steps 1-4 in the method described above for the preparation of Example 105, the following examples set forth in Table 17 were prepared from the corresponding starting materials.

TABLE 17

| Example | Structure | Starting material | LCMS Method | $t_R$ (min) | $(M + H)^+$ observed |
|---|---|---|---|---|---|
| 108 | 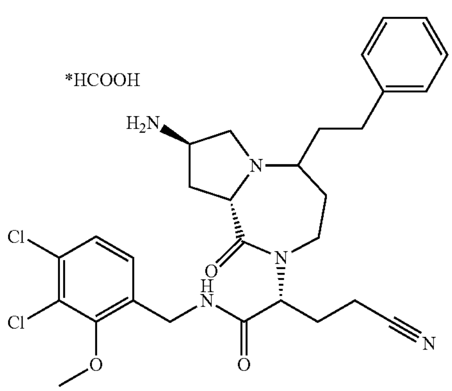 | Example 22 | A | 1.03 | 572.3/574.3 |

TABLE 17-continued

| Example | Structure | Starting material | LCMS Method | $t_R$ (min) | $(M + H)^+$ observed |
|---|---|---|---|---|---|
| 109 | 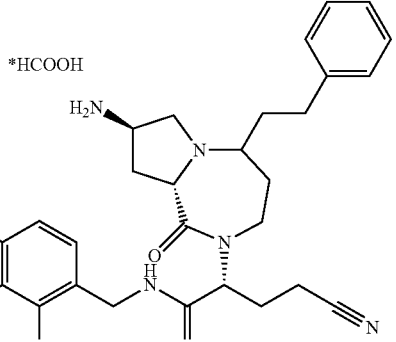 | Example 30 | D | 0.87 | 560.4/562.4 |

Following steps 1-4 in the method described above for the preparation of Example 105, the following examples set forth in Table 18 were prepared from the corresponding starting materials.

TABLE 18

| Example | Structure | Starting material | LCMS Method | $t_R$ (min) | $(M + H)^+$ observed |
|---|---|---|---|---|---|
| 110 | 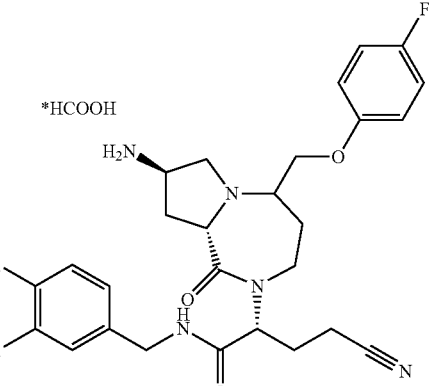 | Example 75 | A | 0.96 | 562.5/564.5 |
| 111 | 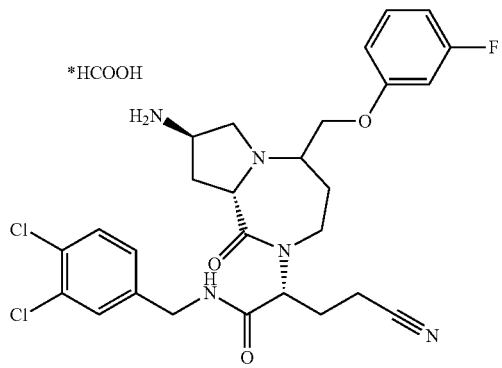 | Example 77 | A | 0.97 | 562.5/564.5 |

Following step 1 and then steps 3 and 4 (i.e. skip step 2) in the method described above for the preparation of Example 105, the following examples set forth in Table 19 were prepared from the corresponding starting materials.

TABLE 19

| Example | Structure | Starting material | LCMS Method | $t_R$ (min) | $(M + H)^+$ observed |
|---|---|---|---|---|---|
| 112 | 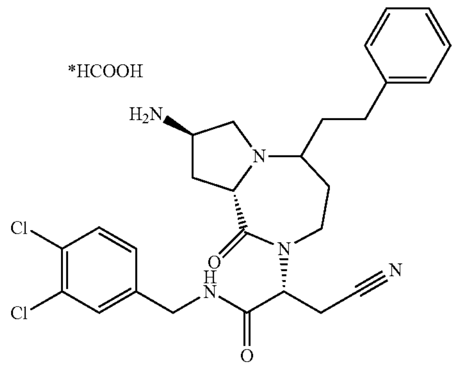 | Example 23 | A | 0.99 | 528.3/530.3 |
| 113 | 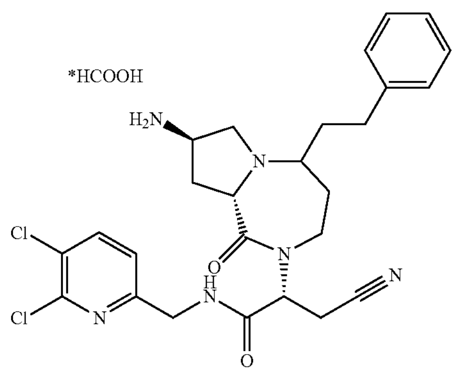 | Example 36 | A | 0.96 | 529.4/531.4 |

Example 114: (2R)-2-((8R,9aS)-8-amino-5-((3-fluorophenoxy)methyl)-1-oxohexahydro-1H-pyrrolo[1,2-a][1,4]diazepin-2(3H)-yl)-N1-(3,4-dichlorobenzyl)-N5-hydroxypentanediamide.HCOOH Step 1: (4R)-4-((8R,9aS)-8-(((tert-butoxycarbonyl)amino)-5-((3-fluorophenoxy)methyl)-1-oxohexahydro-1H-pyrrolo[1,2-a][1,4]diazepin-2(3H)-yl)-5-((3,4-dichlorobenzyl)amino)-5-oxopentanoic Acid (Compound 114-1)

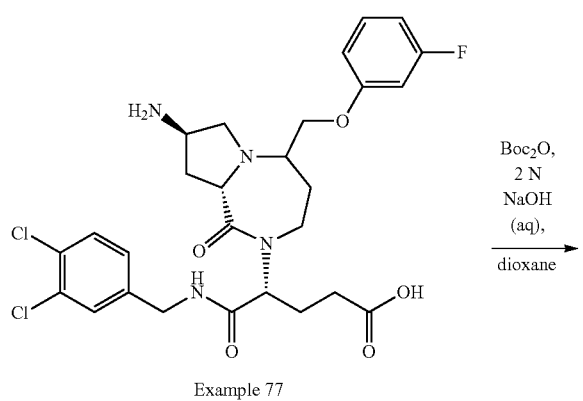

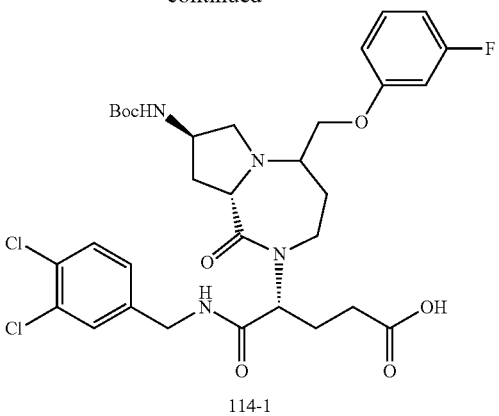

To a solution of Example 77 (51 mg, 0.088 mmol) in dioxane (0.5 mL) was added 2 N NaOH (aq) (0.090 mL, 0.18 mmol) followed by a solution of Boc$_2$O (29 mg, 0.13 mmol) in dioxane (0.5 mL). The reaction mixture was stirred at room temperature until analysis by LC/MS indicated complete reaction. The mixture was then quenched with 1 M citric acid (aq) (2 mL) and extracted with EtOAc (3×5 mL). The combined organic extracts were dried (Na$_2$SO$_4$), filtered and concentrated in vacuo to give 75 mg of crude Compound 114-1 which was used without further purification in the next step.

Step 2: tert-butyl ((8R,9aS)-2-((R)-1-((3,4-dichlorobenzyl)amino)-5-(hydroxyamino)-1,5-dioxopentan-2-yl)-5-((3-fluorophenoxy)methyl)-1-oxooctahydro-1H-pyrrolo[1,2-a][1,4]diazepin-8-yl)carbamate (Compound 114-2)

Step 3: (2R)-2-((8R,9aS)-8-amino-5-((3-fluorophenoxy)methyl)-1-oxohexahydro-1H-pyrrolo[1,2-a][1,4]diazepin-2(3H)-yl)-N1-(3,4-dichlorobenzyl)-N5-hydroxypentanediamide.HCOOH (Example 114)

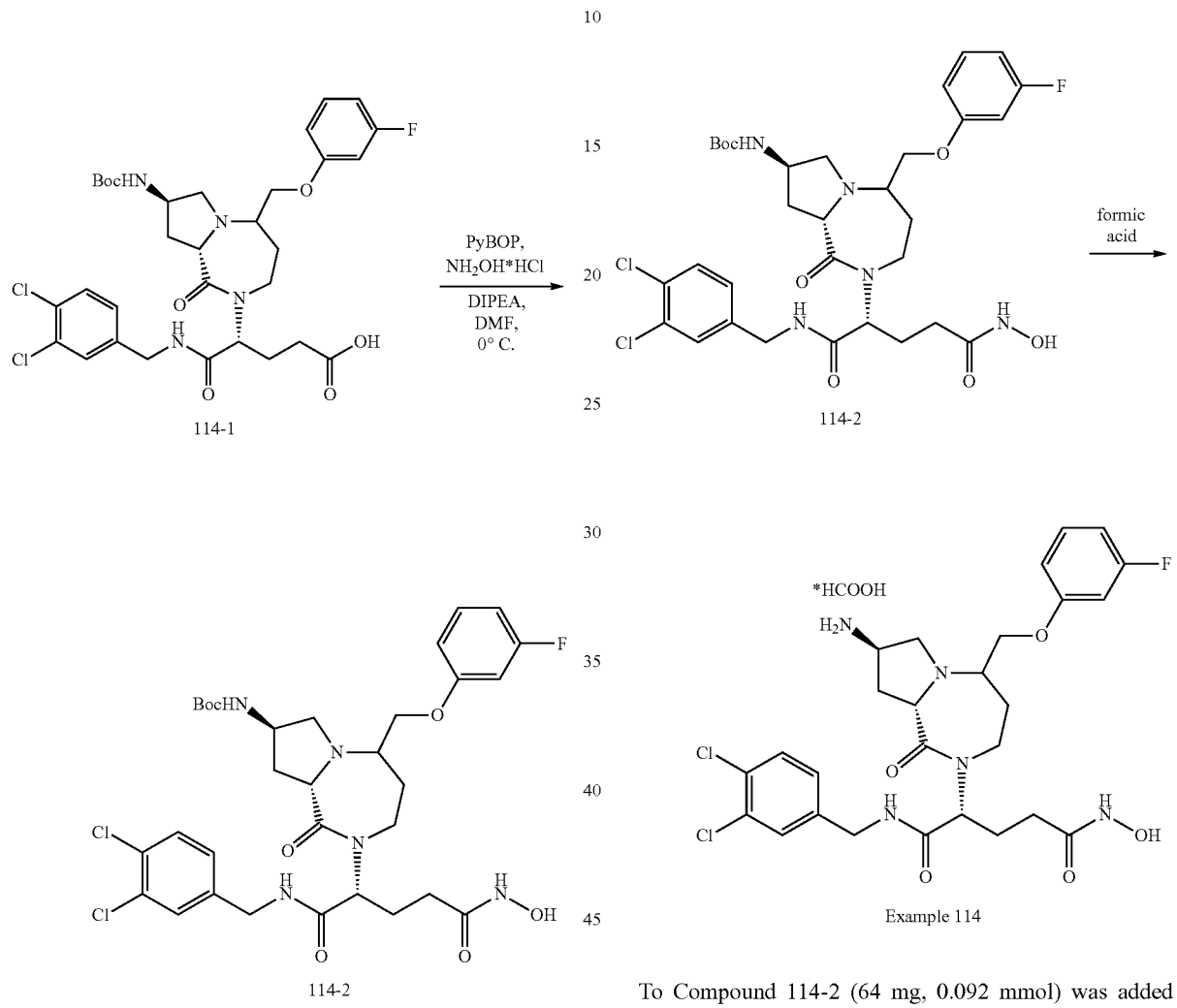

To a solution of Compound 114-1 (75 mg, 0.11 mmol) in DMF (1 mL) at 0° C. was added PyBOP (63 mg, 0.12 mmol) and NH$_2$OH.HCl (16 mg, 0.22 mmol) followed by DIPEA (0.12 mL, 0.66 mmol). The reaction mixture was warmed to room temperature and stirred for 16 h. The mixture was then quenched with saturated NaHCO$_3$ (aq) (15 mL) and extracted with EtOAc (3×5 mL). The combined organic extracts were dried (Na$_2$SO$_4$), filtered and concentrated in vacuo. The crude residue was purified by FCC (SiO$_2$, elution with 0-10% MeOH/DCM) to provide 64 mg of semi pure Compound 114-2 which was used without further purification in the next step. Data for Compound 114-2. LCMS (Method A): t$_R$=1.23 min, m/z 696.5/698.5 (M+H)$^+$.

To Compound 114-2 (64 mg, 0.092 mmol) was added formic acid (1 mL) and the resultant solution was stirred at room temperature for 5 h. The mixture was then concentrated in vacuo and the residue was purified directly by mass-directed preparative reverse-phase HPLC (C-18, elution with 5-95% ACN/H$_2$O containing 0.25% formic acid). The desired fractions were combined and lyophilized to provide 44 mg of Example 114 as a white solid. $^1$H NMR (400 MHz, CDCl$_3$): δ 8.54 (s, 1H, HCOOH), 7.48 (d, 1H), 7.40 (d, 1H), 7.30-7.23 (m, 2H), 6.72-6.63 (m, 3H), 5.09 (dd, 1H), 4.34 (ABq, 2H), 3.95-3.86 (m, 3H), 3.66-3.49 (m, 3H), 3.41 (dd, 1H), 3.03-2.90 (m, 2H), 2.59 (app t, 1H), 2.16-2.01 (m, 4H), 1.87-1.78 (m, 2H), 1.55 (m, 1H) ppm; LCMS (Method A): t$_R$=1.00 min, m/z 596.4/598.5 (M+H)$^+$.

Following the general method described above for the preparation of Example 114, and substituting the indicated starting material, the following examples set forth in Table 20 were prepared.

TABLE 20

| Example | Structure | Starting material | LCMS Method | $t_R$ (min) | $(M + H)^+$ observed |
|---------|-----------|-------------------|-------------|-------------|----------------------|
| 115 | 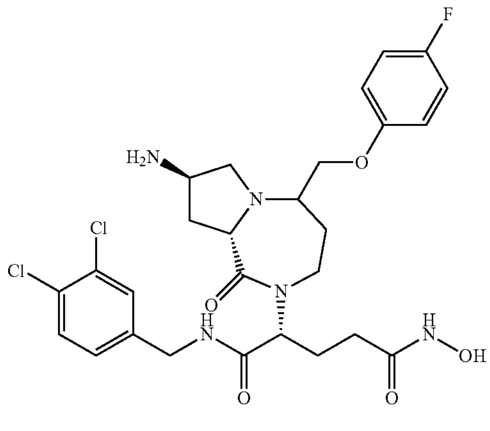 | Example 75 | A | 0.97 | 596.5/598.5 |
| 116 | 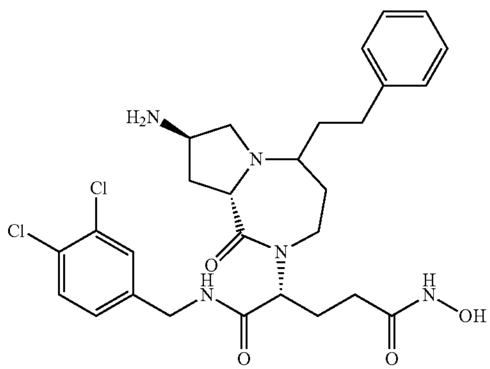 | Example 15B | A | 0.91 | 576.3/578.2 |

Following the general method described above for the preparation of Example 114 and substituting Example 15B as the starting material and using NH₂OMe.HCl instead of NH₂OH.HCl in step 2 the following example set forth in Table 21 was prepared.

TABLE 21

| Example | Structure | LCMS Method | $t_R$ (min) | $(M + H)^+$ observed |
|---------|-----------|-------------|-------------|----------------------|
| 117 | 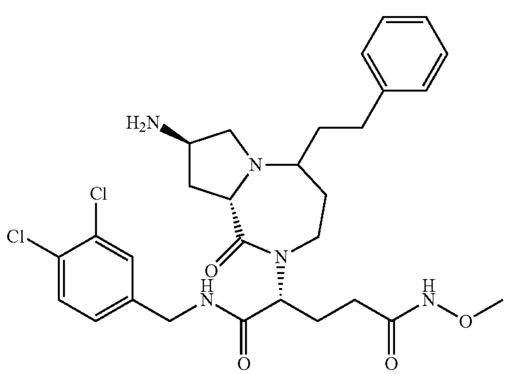 | A | 0.94 | 590.2/592.2 |

Example 118: (2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-4-(1H-tetrazol-5-yl)butanamide Step 1: tert-butyl ((8R,9aS)-2-((R)-1-((3,4-dichlorobenzyl)amino)-1-oxo-4-(1H-tetrazol-5-yl)butan-2-yl)-1-oxo-5-phenethyloctahydro-1H-pyrrolo[1,2-a][1,4]diazepin-8-yl)carbamate (Compound 118-1)

Step 2: (2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-4-(1H-tetrazol-5-yl)butanamide (Example 118)

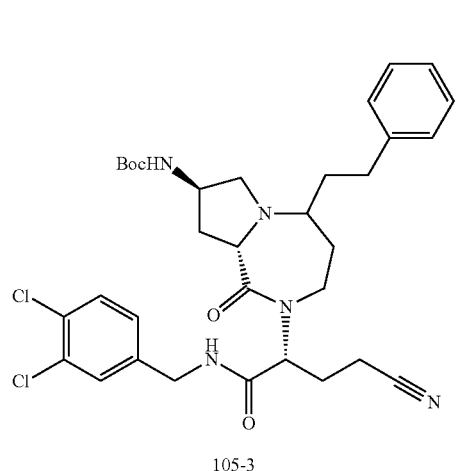

105-3

NaN₃, NH₄Cl, DMF

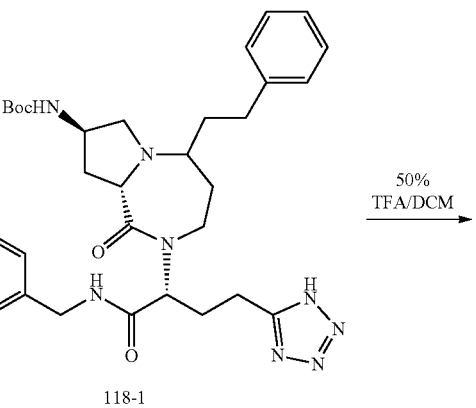

118-1

50% TFA/DCM

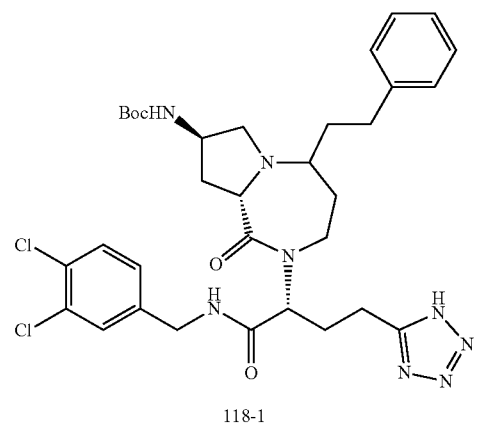

118-1

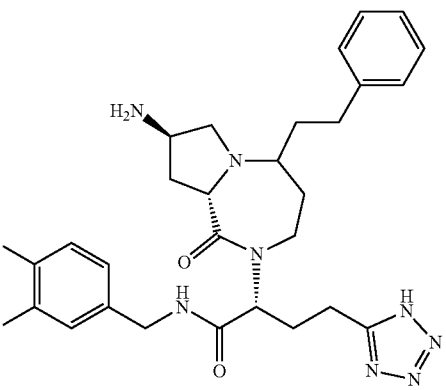

Example 118

To a solution of Compound 105-3 (47 mg, 0.073 mmol) in DMF (1 mL) was added sodium azide (48 mg, 0.73 mmol) followed by ammonium chloride (39 mg, 0.73 mmol). The reaction mixture was heated to 110° C. in a tightly capped reaction vial for 16 h. The mixture was then cooled to room temperature, concentrated in vacuo and the residue was purified by FCC (SiO₂, elution with 0-10% MeOH/DCM) to give 20 mg of semi pure Compound 118-1 which was used without further purification in the next step. LCMS (Method A): $t_R$=1.23 min, m/z 685.4/687.4 (M+H)⁺.

To Compound 118-1 was added DCM (1 mL) followed by TFA (1 mL) and the reaction mixture was stirred at room temperature for 1 h. The mixture was then concentrated in vacuo. The residue was treated with 3N HCl in MeOH (5 mL) and the volatiles were removed in vacuo. This treatment with HCl was repeated once more to remove residual TFA, and then the residue was purified directly by mass-directed preparative reversed-phase HPLC (C-18, elution with 5-95% ACN/H₂O containing 0.25% formic acid). The desired fractions were combined and lyophilized to provide 7 mg (41%) of Example 118 as a fluffy white solid. ¹H NMR (400 MHz, CD₃OD): δ 8.53 (s, 1H, HCOOH), 7.48 (d, 1H), 7.43 (d, 1H), 7.27-7.23 (m, 3H), 7.17-7.13 (m, 3H), 5.08 (dd, 1H), 4.34 (ABq, 2H), 3.63-3.50 (m, 4H), 3.23 (dd, 1H), 2.97-2.79 (m, 3H), 2.64-2.19 (m, 6H), 1.91-1.81 (m, 3H), 1.56 (m, 1H), 1.40 (m, 1H) ppm; LCMS (Method A): $t_R$=1.06 min, m/z 585.4/587.4 (M+H)⁺.

Following the method described above for the preparation of Example 118 utilizing the corresponding starting material, the compounds set forth in Table 22 were prepared.

TABLE 22

| Example | Structure | Starting material | LCMS Method | $t_R$ (min) | $(M + H)^+$ observed |
|---|---|---|---|---|---|
| 119 | 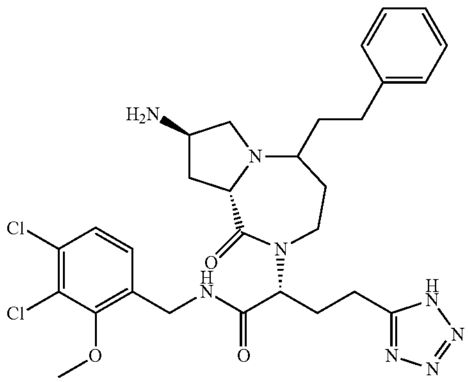 | Example 108 | A | 1.04 | 615.3/617.3 |
| 120 | 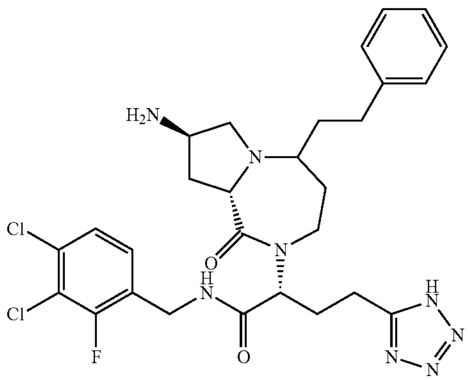 | Example 109 | A | 1.07 | 603.3/605.3 |

Example 121: (2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-4-(5-methyl-4H-1,2,4-triazol-3-yl)butanamide.HCl Step 1: tert-butyl ((8R,9aS)-2-((R)-5-amino-1-((3,4-dichlorobenzyl)amino)-1-oxo-5-thioxopentan-2-yl)-1-oxo-5-phenethyloctahydro-1H-pyrrolo[1,2-a][1,4]diazepin-8-yl)carbamate (Compound 121-1)

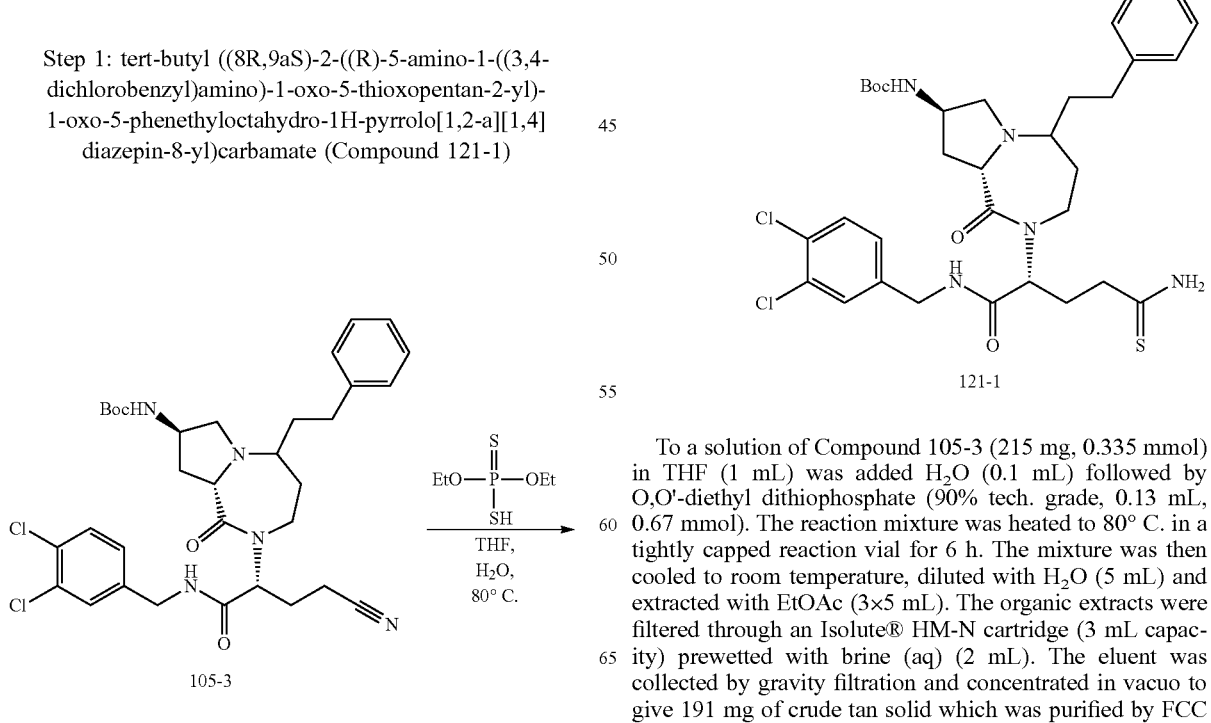

To a solution of Compound 105-3 (215 mg, 0.335 mmol) in THF (1 mL) was added H₂O (0.1 mL) followed by O,O'-diethyl dithiophosphate (90% tech. grade, 0.13 mL, 0.67 mmol). The reaction mixture was heated to 80° C. in a tightly capped reaction vial for 6 h. The mixture was then cooled to room temperature, diluted with H₂O (5 mL) and extracted with EtOAc (3×5 mL). The organic extracts were filtered through an Isolute® HM-N cartridge (3 mL capacity) prewetted with brine (aq) (2 mL). The eluent was collected by gravity filtration and concentrated in vacuo to give 191 mg of crude tan solid which was purified by FCC (SiO₂, elution with 0-8% MeOH/DCM) to give 74 mg (33%) of Compound 121-1. LCMS (Method D): $t_R$=1.12 min, m/z 676.3/678.3 (M+H)⁺.

Step 2: (4R)-methyl 4-((8R,9aS)-8-((tert-butoxycarbonyl)amino)-1-oxo-5-phenethylhexahydro-1H-pyrrolo[1,2-a][1,4]diazepin-2(3H)-yl)-5-((3,4-dichlorobenzyl)amino)-5-oxopentanimidothioate.HI (Compound 121-2)

Step 3: tert-butyl ((8R,9aS)-2-((R)-1-((3,4-dichlorobenzyl)amino)-4-(5-methyl-4H-1,2,4-triazol-3-yl)-1-oxobutan-2-yl)-1-oxo-5-phenethyloctahydro-1H-pyrrolo[1,2-a][1,4]diazepin-8-yl)carbamate (Compound 121-3)

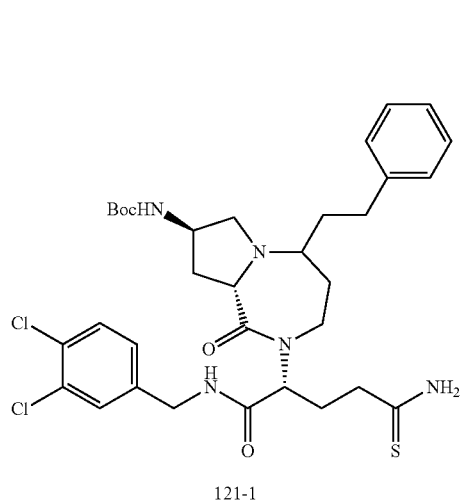

121-1

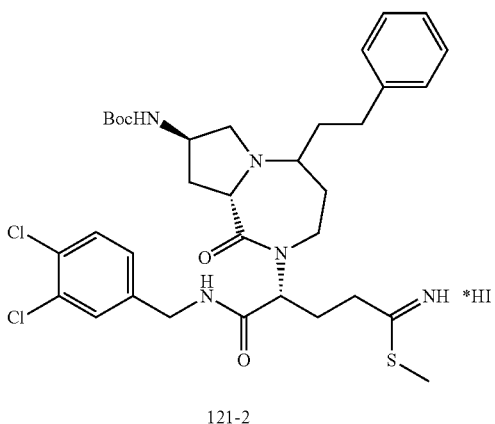

121-2

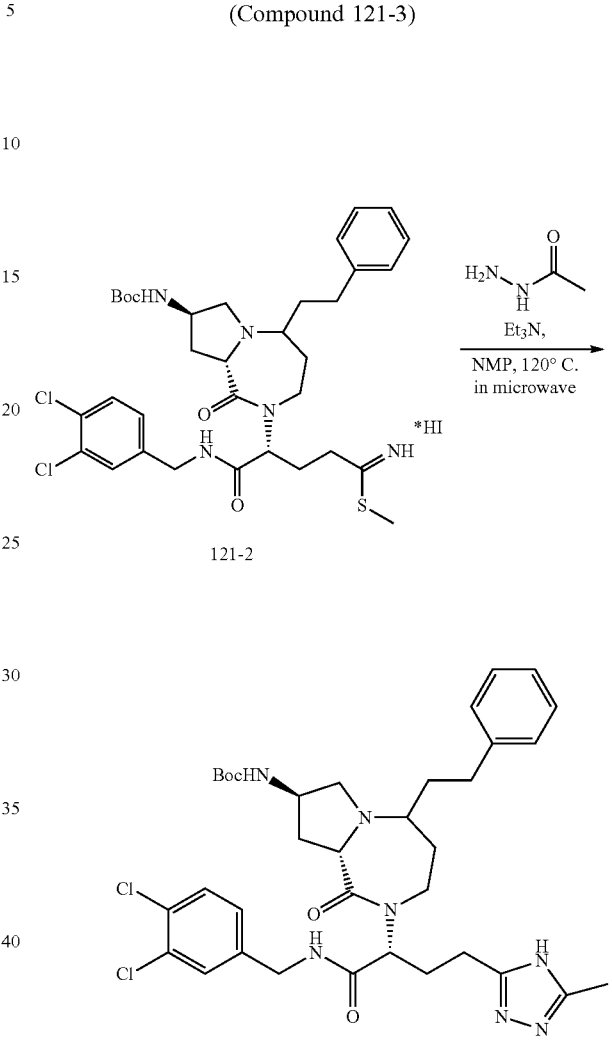

To a solution of Compound 121-1 (74 mg, 0.11 mmol) in THF (1 mL) was added iodomethane as a solution in THF (1M, 0.13 mL, 0.13 mmol). The reaction mixture was stirred at room temperature for 2 h. More iodomethane was added as a solution in THF (1M, 0.13 mL, 0.13 mmol) and the reaction mixture was stirred for an additional 16 h. The mixture was then concentrated in vacuo to provide 90 mg (100%) of crude Compound 121-2 which was used directly in the next step without further purification. LCMS (Method D): $t_R$=1.26 min, m/z 691.3/693.3 (M+H)⁺.

A microwave reaction vial (0.5-2 mL capacity) was charged with Compound 121-2 (44 mg, 0.054 mmol) and acetylhydrazide (6 mg, 0.081 mmol) and then tightly sealed (crimp top w/septum) and flushed with N₂ (g) for 5 min. To this was added NMP (0.5 mL) followed by TEA (15 µL, 0.11 mmol). The reaction mixture was heated to 120° C. in a microwave reactor for 1 h. The mixture was cooled to room temperature, more TEA was added (15 and then the reaction mixture was heated to 120° C. in a microwave reactor for an additional 1 h. The mixture was cooled to room temperature, diluted with EtOAc (~6 mL) and filtered through an Isolute® HM-N cartridge prewetted with H₂O (2 mL). The eluent was collected by gravity filtration. The cartridge was rinsed with additional EtOAc (~10 mL). The combined eluent was concentrated in vacuo and the residue was purified by FCC (SiO₂, elution with 0-10% MeOH/DCM) to provide 10 mg (26%) of Compound 121-3 as white solid. LCMS (Method D): $t_R$=0.97 min, m/z 698.4/700.3 (M+H)⁺.

Step 4: (2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-4-(5-methyl-4H-1,2,4-triazol-3-yl)butanamide.HCl (Example 121)

Example 122: (2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-4-(5-oxo-4,5-dihydro-1,2,4-thiadiazol-3-yl)butanamide

Step 1: tert-butyl ((8R,9aS)-2-((R)-1-((3,4-dichlorobenzyl)amino)-5-(hydroxyamino)-5-imino-1-oxopentan-2-yl)-1-oxo-5-phenethyloctahydro-1H-pyrrolo[1,2-a][1,4]diazepin-8-yl)carbamate (Compound 122-1)

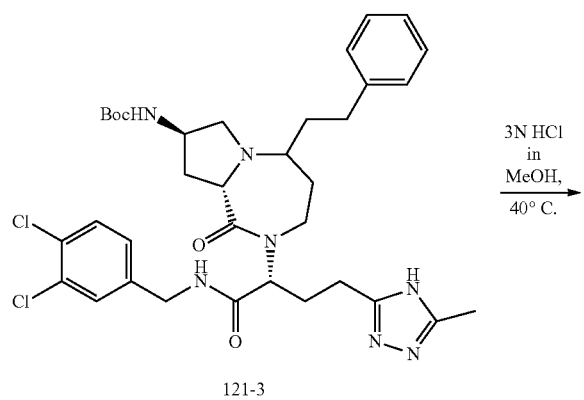

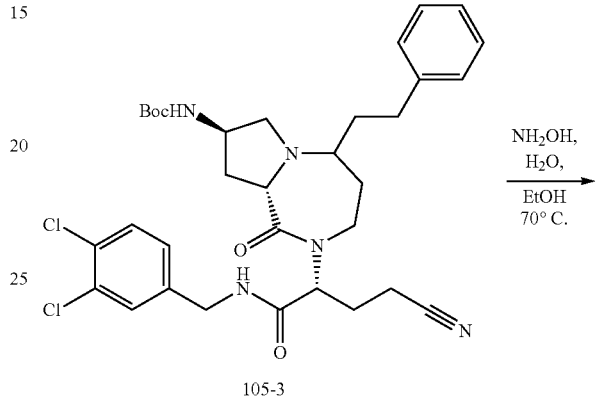

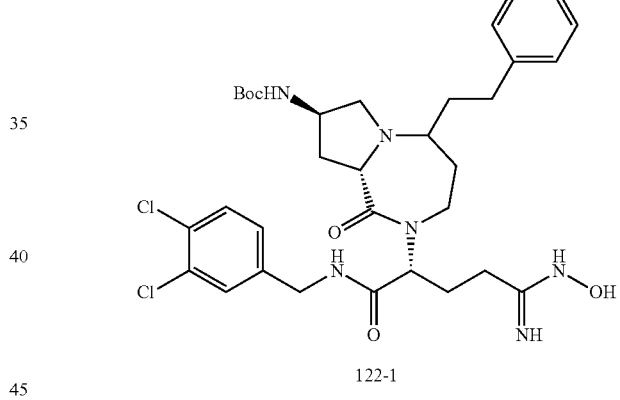

A solution of Compound 121-3 (10 mg, 0.014 mmol) in 3N HCl in MeOH (2 mL) was heated to 40° C. in a tightly capped reaction vial for 2 h. The reaction mixture was cooled to room temperature concentrated in vacuo and the crude residue was purified directly by mass-directed preparative reversed-phase HPLC (C-18, elution with 5-95% ACN/H$_2$O containing 0.25% formic acid). The desired fractions were combined and lyophilized to provide 8.4 mg (92%) of Example 121 as fluffy light yellow solid. $^1$H NMR (400 MHz, CD$_3$OD): δ 7.59 (s, 1H), 7.47 (d, 1H), 7.36-7.19 (m, 6H), 5.16 (m, 1H), 4.38 (ABq, 2H), 4.13 (m, 1H), 3.98 (m, 1H), 3.85 (m, 1H), 3.73 (m, 1H), 3.60 (m, 1H), 3.44-3.19 (m partially obscured by solvent peak, 3H), 2.97 (m, 2H), 2.72 (m, 1H), 2.64 (s, 3H), 2.56-2.11 (m, 6H), 1.88 (m, 2H) ppm; LCMS (Method A): t$_R$=1.03 min, m/z 598.3/600.3 (M+H)$^+$.

To a solution of Compound 105-3 (54 mg, 0.084 mmol) in EtOH (0.5 mL), in a microwave reaction vial (0.5-2 mL capacity), was added hydroxylamine solution (50 wt. % in H$_2$O, 10 μL, 0.17 mmol). The vial was tightly capped (crimp top) and the mixture heated to 75° C. for 5 h in a microwave reactor. After cooling to room temperature, more hydroxylamine solution (50 wt. % in H$_2$O, 10 μL, 0.17 mmol) was added and the vial was heated in a thermal heating block to 75° C. for 19 h. The mixture was then cooled to room temperature and concentrated in vacuo. The crude product 122-1 was used directly in the next step without further purification. $^1$H NMR (400 MHz, CD$_3$OD): δ 7.51 (d, 1H), 7.45 (d, 1H), 7.28-7.24 (m, 3H), 7.18-7.13 (m, 2H), 5.12 (dd, 1H), 4.35 (ABq, 2H), 4.00 (m, 1H), 3.70 (dd. 1H), 3.55 (m, 1H), 3.44 (m, 1H), 2.80 (m, 1H), 2.64-2.51 (m, 2H), 2.40 (m, 1H), 2.24-2.11 (m, 2H), 2.08-1.79 (m, 5H), 1.71 (m, 1H), 1.58-1.29 (m partially obscured by singlet, 3H), 1.44 (s superimposed on multiplet, 9H) ppm.

Steps 2 and 3: tert-butyl ((8R,9aS)-2-((R)-1-((3,4-dichlorobenzyl)amino)-1-oxo-4-(5-oxo-4,5-dihydro-1,2,4-thiadiazol-3-yl)butan-2-yl)-1-oxo-5-phenethyl-octahydro-1H-pyrrolo[1,2-a][1,4]diazepin-8-yl) carbamate (Compound 122-2)

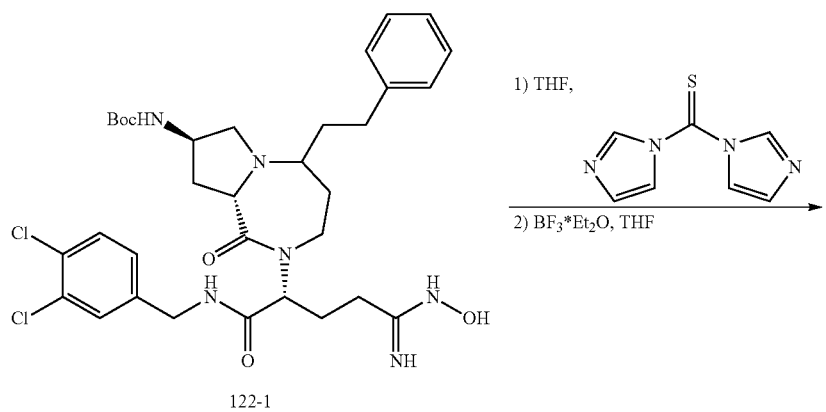

122-1

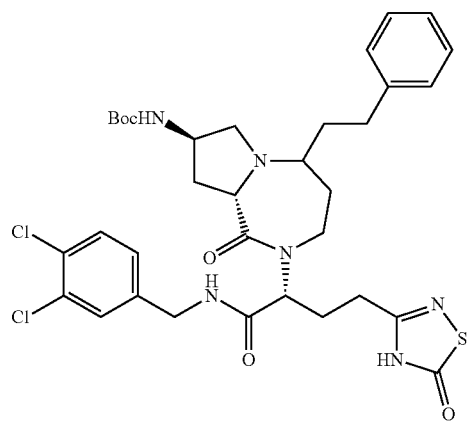

122-2

To a suspension of Compound 122-1 (0.084 mmol) in THF (1 mL) was added 1,1'-thiocarbonyl diimidazole (22 mg, 0.13 mmol). The reaction mixture was stirred at room temperature for 1 h. The mixture was then quenched with H$_2$O (5 mL) and extracted with DCM (3×5 mL). The organic extracts were filtered through an Isolute® HM-N cartridge (3 mL capacity) to dry, collecting the eluent by gravity filtration. The filtrate was concentrated in vacuo. The residue was then taken up in THF (1 mL) and to this was added BF$_3$.Et$_2$O (31 μL, 0.25 mmol). The reaction mixture was stirred for 3 h. The mixture was then quenched with H$_2$O (5 mL) and extracted with DCM (3×5 mL). The organic extracts were filtered through an Isolute® HM-N cartridge (3 mL capacity) to dry, collecting the eluent by gravity filtration. The filtrate was concentrated in vacuo. The crude product, 122-2, was used in the next step without further purification. LCMS (Method A): t$_R$=1.26 min, m/z 717.4/719.3 (M+H)$^+$.

Step 4: (2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-4-(5-oxo-4,5-dihydro-1,2,4-thiadiazol-3-yl)butanamide (Example 122)

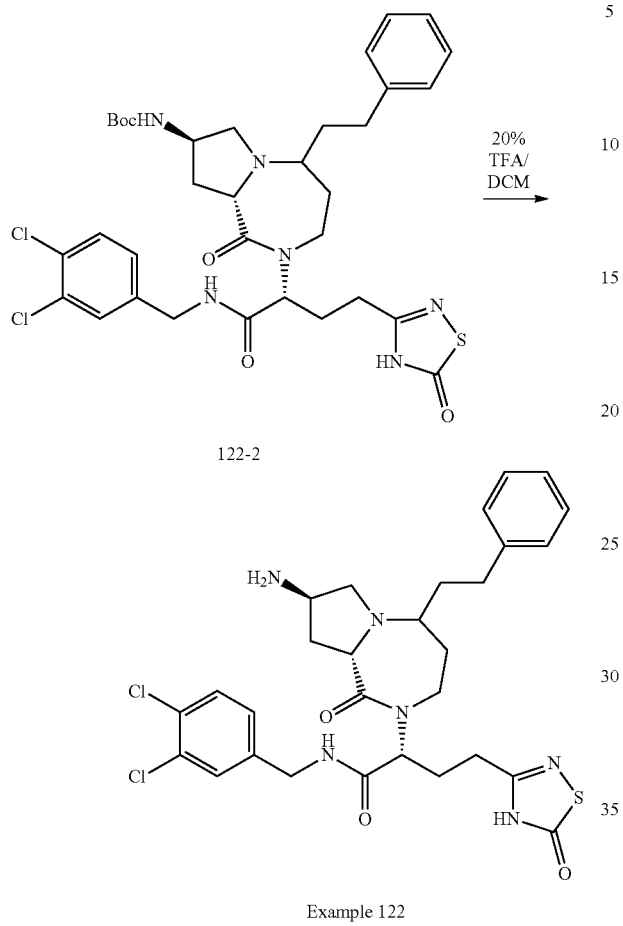

The crude product from the previous step, 122-2, was treated with 20% TFA in DCM (1 mL) and allowed to stand for 1 h at room temperature. The mixture was concentrated in vacuo and DCM (2 mL) was added followed by 4 N HCl in dioxane (2 mL). After standing for a couple minutes, the mixture was concentrated in vacuo. This treatment with HCl was repeated once more to remove residual TFA and form the HCl salt. The crude product was purified by mass-directed preparative reverse-phase HPLC (C-18, elution with 5-95% ACN/H$_2$O containing 0.25% formic acid). The desired fractions were combined and lyophilized to provide 14 mg (27% for 4 steps) of Example 122 as a fluffy white solid. $^1$H NMR (400 MHz, CD$_3$OD): δ 8.53 (br t, 1H, N—H), 7.50-7.43 (m, 2H), 7.28-7.14 (m, 6H), 5.09 (m, 1H), 4.53 (m, 1H), 4.18 (m, 1H), 3.78 (dd, 1H), 3.65-3.48 (m, 4H), 3.00 (m, 1H), 2.64-2.54 (m, 4H), 2.49-2.36 (m, 2H), 2.32-2.07 (m, 2H), 1.94-1.82 (m, 3H), 1.56 (m, 1H), 1.33 (m, 1H); LCMS (Method A): t$_R$=1.15 min, m/z 617.3/619.3 (M+H)$^+$.

Example 123: (2S)-2-((8R,9aS)-8-amino-1-oxo-5-phenethylhexahydro-1H-pyrrolo[1,2-a][1,4]diazepin-2(3H)-yl)-N-(3,4-dichlorobenzyl)-3-((2-hydroxyphenyl)thio)propanamide.HCOOH Steps 1-4: tert-butyl ((8R,9aS)-2-((S)-1-((3,4-dichlorobenzyl)amino)-3-((2-hydroxyphenyl)thio)-1-oxopropan-2-yl)-1-oxo-5-phenethyloctahydro-1H-pyrrolo[1,2-a][1,4]diazepin-8-yl)carbamate (Compound 123-3)

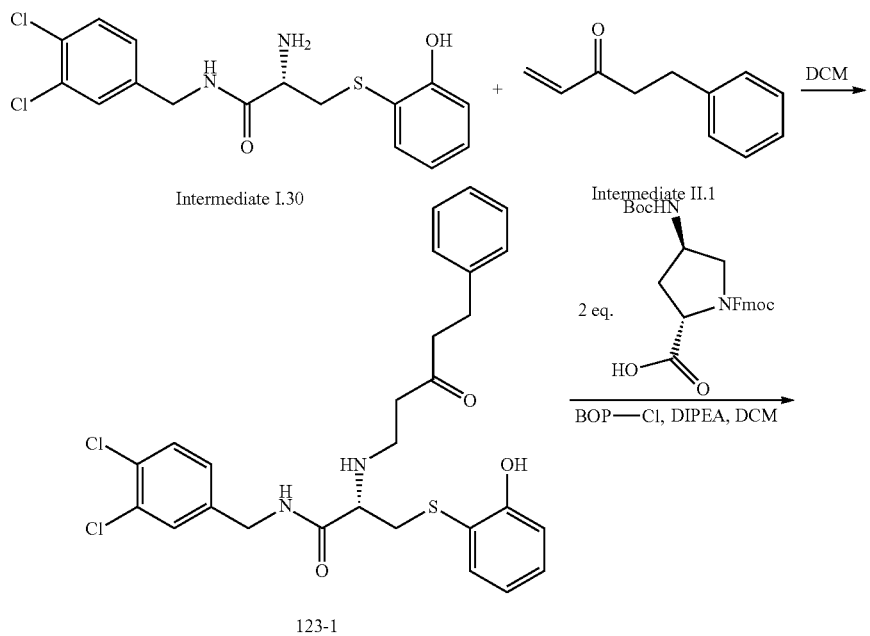

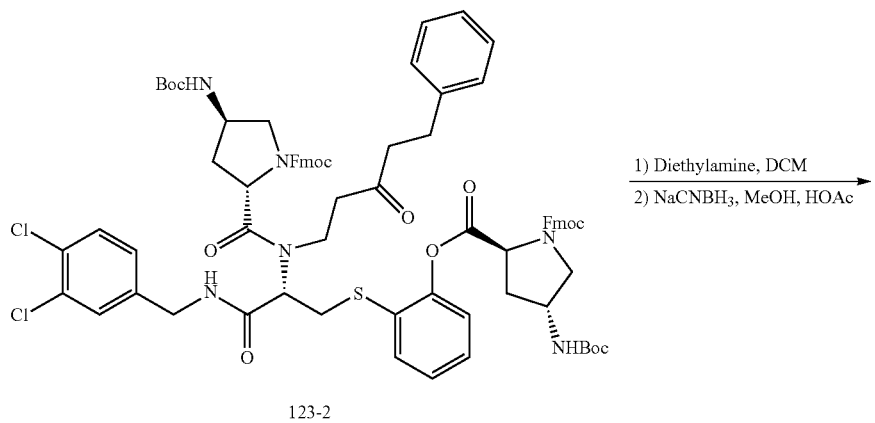

123-2

1) Diethylamine, DCM
2) NaCNBH₃, MeOH, HOAc

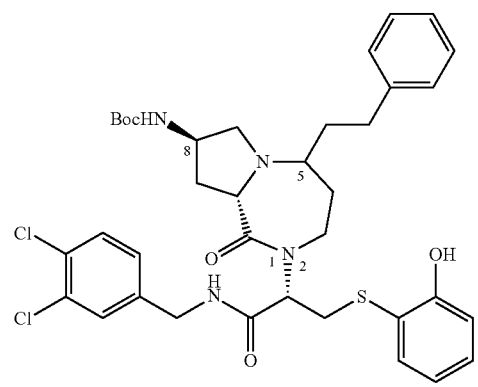

123-3 (mixture of diastereomers epimeric at C(5) of 7-ring)

Compound 123-3 was prepared from Intermediate I.30 and Intermediate II.1 using the same general methods for the preparation of compound 1-3 described in steps 1-4 of Example 1 (note: to compensate for competing phenol acylation in step 2, two equivalents of the carboxylic acid-based reactant and three equivalents of BOP—Cl were utilized). The phenolic ester was cleaved, to unmask the phenol, during the course of the Fmoc deprotection in step 3). After work-up the crude product was purified by FCC (SiO₂, elution with 0-100% EtOAc/hexanes). The second eluting, major diasteromer 123-3B was isolated and carried into the next step (the first eluting, minor diastereomer 123-3A was not isolated). Data for Compound 123-3B (major diastereomer): LCMS (Method B): $t_R$=0.98 min, m/z 727.3/730.3 (M+H)⁺.

Step 5: (2S)-2-((8R,9aS)-8-amino-1-oxo-5-phenethylhexahydro-1H-pyrrolo[1,2-a][1,4]diazepin-2(3H)-yl)-N-(3,4-dichlorobenzyl)-3-((2-hydroxyphenyl)thio)propanamide (Example 123)

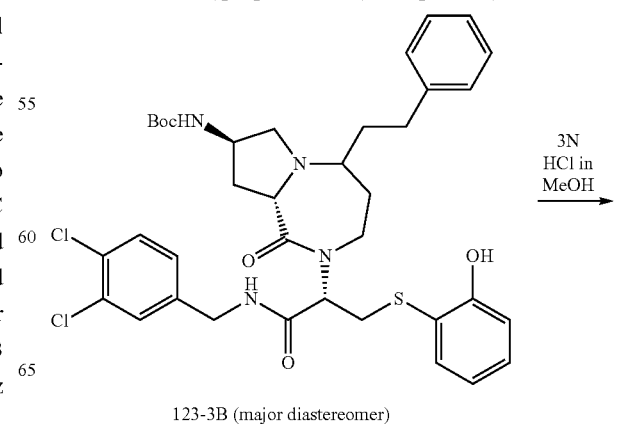

123-3B (major diastereomer)

3N HCl in MeOH

-continued

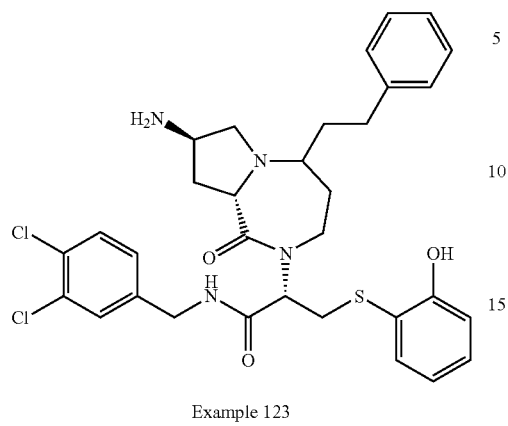

Example 123

A solution of Compound 123-3B (0.028 g, 0.038 mmol) in 3N methanolic HCl (1 mL) was stirred at room temperature for 3.5 h. The mixture was then concentrated in vacuo and the residue was purified by mass-directed preparative reversed-phase HPLC (C18, elution with 5-100% ACN/H2O, 0.25% formic acid) to provide 18 mg (74%) of Example 123. $^1$H NMR (400 MHz, CD$_3$OD): δ 7.49 (d, 1H), 7.43 (d, 1H), 7.30 (dd, 1H), 7.27-7.23 (m, 3H), 7.17-7.12 (m, 4H), 6.83 (dd, 1H), 6.79 (m, 1H), 5.17 (dd, 1H), 4.34 (ABq, 2H), 3.52 (dd, 1H), 3.45-3.22 (m partially obscured by solvent peak, 6H), 2.80 (m, 1H), 2.58 (m, 1H), 2.48 (m, 1H), 2.39 (m, 1H), 2.21 (m, 1H), 1.90 (m, 1H), 1.81 (m, 1H), 1.64 (m, 1H), 1.52 (m, 1H), 1.32 (m, 1H) ppm; LCMS (Method A): $t_R$=1.11 min, m/z 627.3/629.3 (M+H)$^+$ Example 124: (2S)-2-((8R,9aS)-8-amino-1-oxo-5-phenethylhexahydro-1H-pyrrolo[1,2-a][1,4]diazepin-2(3H)-yl)-N-(3,4-dichlorobenzyl)-3-((2-hydroxyphenyl)sulfonyl)propanamide.HCOOH Step 1: (8R,9aS)-8-((tert-butoxycarbonyl)amino)-2-((S)-1-((3,4-dichlorobenzyl)amino)-3-((2-hydroxyphenyl)sulfonyl)-1-oxopropan-2-yl)-1-oxo-5-phenethyldecahydropyrrolo[1,2-a][1,4]diazepine 6-oxide (Compound 124-1)

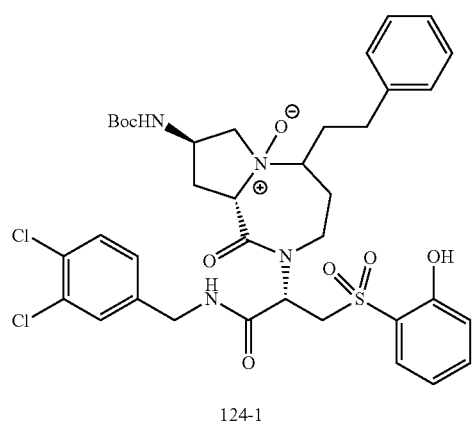

124-1

Compound 123-3B (50 mg, 0.069 mmol) was suspended in a mixture of 5:1 MeOH/H$_2$O (2 mL) and Oxone® (84 mg, 0.138 mmol) was added. The reaction mixture was stirred at room temperature for 1 h after which more Oxone® (84 mg, 0.138 mmol) was added. The reaction mixture was stirred at room temperature for an additional 16 h. The mixture was then concentrated in vacuo, diluted with H$_2$O and extracted with DCM (3×). The organic extracts were dried (MgSO$_4$), filtered and concentrated in vacuo to give 50 mg (93%) of Compound 124-1. LCMS (Method D): $t_R$=1.02 min, m/z 775.4/778.4 (M+H)$^+$.

Step 2: tert-butyl ((8R,9aS)-2-((S)-1-((3,4-dichlorobenzyl)amino)-3-((2-hydroxyphenyl)sulfonyl)-1-oxopropan-2-yl)-1-oxo-5-phenethyloctahydro-1H-pyrrolo[1,2-a][1,4]diazepin-8-yl)carbamate (Compound 124-2)

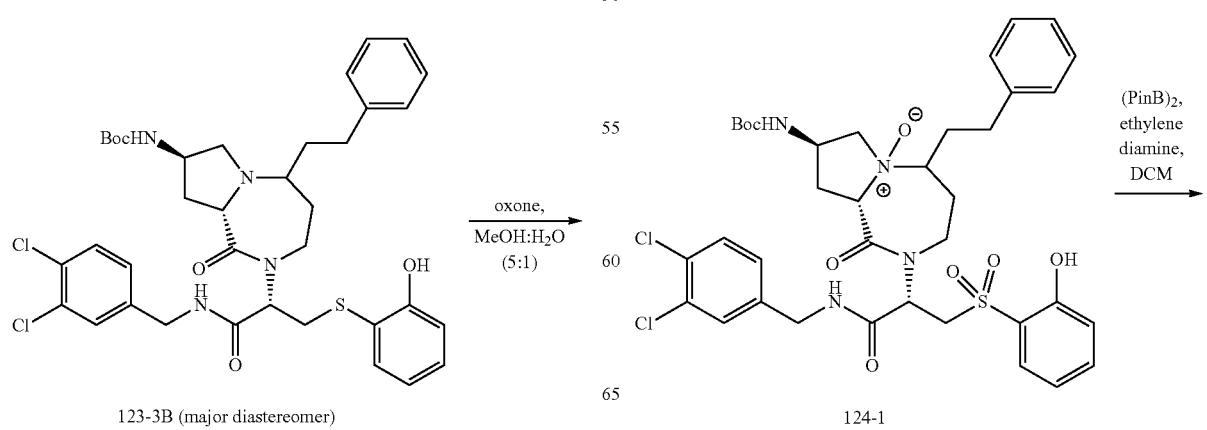

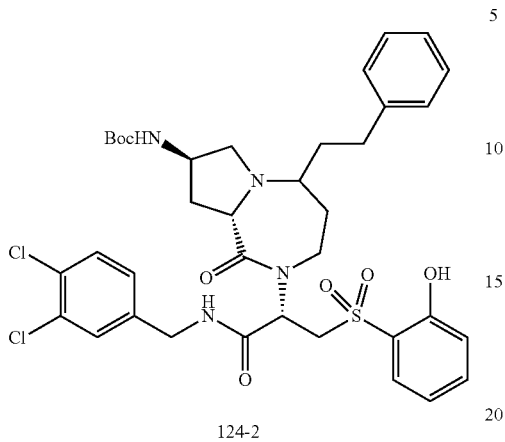

124-2

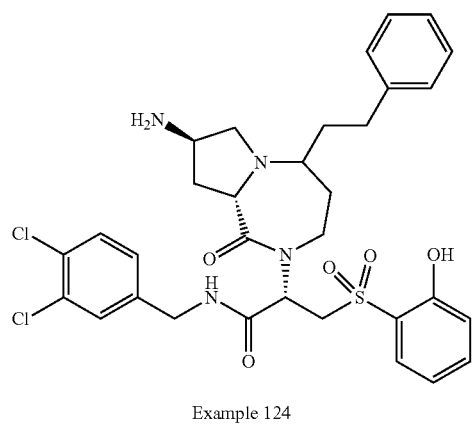

Example 124

To a solution of Compound 124-1 (50 mg, 0.064 mmol) in DCM (0.5 mL) was added Bis(pinacoloto)diboron (0.016 g, 0.064 mmol). The reaction mixture was stirred at room temperature for 3 h. The mixture was then quenched with ethylene diamine (0.086 mL, 1.29 mmol) and stirred at RT for 90 minutes. The mixture was diluted with DCM (2 mL) and filtered through an Isolute® HM-N cartridge (3 mL capacity) prewetted with brine (2 mL), rinsing with additional DCM (~5 mL). The eluent was collected by gravity filtration and concentrated in vacuo. The crude residue was purified by FCC (SiO$_2$, elution with 0-100% EtOAc/hexanes) to give 32 mg (66%) of Compound 124-2 as a clear oil. LCMS (Method D): $t_R$=1.15 min, m/z 759.4/762.4 (M+H)$^+$.

Step 3: (2S)-2-((8R,9aS)-8-amino-1-oxo-5-phenethylhexahydro-1H-pyrrolo[1,2-a][1,4]diazepin-2(3H)-yl)-N-(3,4-dichlorobenzyl)-3-((2-hydroxyphenyl)sulfonyl)propanamide (Example 124)

Example 124 was prepared from 124-2 (27 mg, 0.036 mmol) using the same general procedure described in step 5 for the preparation of Example 123 giving 17 mg (70%) as a white solid. $^1$H NMR (400 MHz, CD$_3$OD): δ 7.63 (dd, 1H), 7.51-7.46 (m, 2H), 7.42 (d, 1H), 7.27-7.21 (m, 3H), 7.17-7.12 (m, 3H), 6.96 (d, 1H), 6.90 (app t, 1H), 5.58 (dd, 1H), 4.32 (ABq, 2H), 4.09-3.97 (m, 2H), 3.43-3.31 (m partially obscured by solvent peak, 3H), 3.18 (dd, 1H), 2.71 (m, 1H), 2.56 (m, 2H), 2.45-2.32 (m, 2H), 2.20 (m, 1H), 1.91-1.78 (m, 2H), 1.61-1.45 (m, 2H), 1.26 (m, 1H) ppm; LCMS (Method A): $t_R$=1.02 min, m/z 659.3/661.3 (M+H)$^+$.

Example 125: (2R)-2-((8R,9aS)-8-amino-1-oxo-5-((phenylsulfinyl)methyl)hexahydro-1H-pyrrolo[1,2-a][1,4]diazepin-2(3H)-yl)-N-(3,4-dichlorobenzyl)-4-methylpentanamide.HCl Step 1: tert-butyl ((8R,9aS)-2-((R)-1-((3,4-dichlorobenzyl)amino)-4-methyl-1-oxopentan-2-yl)-1-oxo-5-((phenylsulfinyl)methyl)octahydro-1H-pyrrolo[1,2-a][1,4]diazepin-8-yl)carbamate (Compound 125-1)

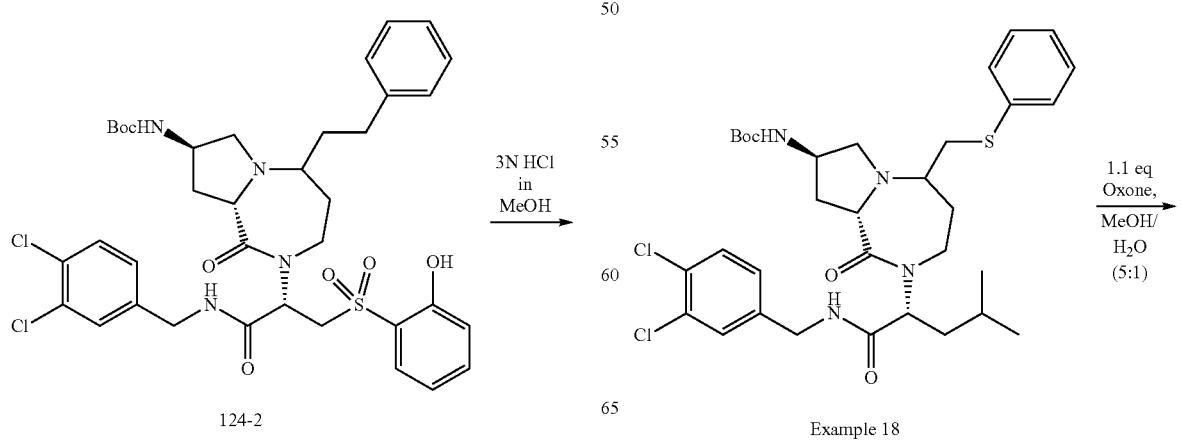

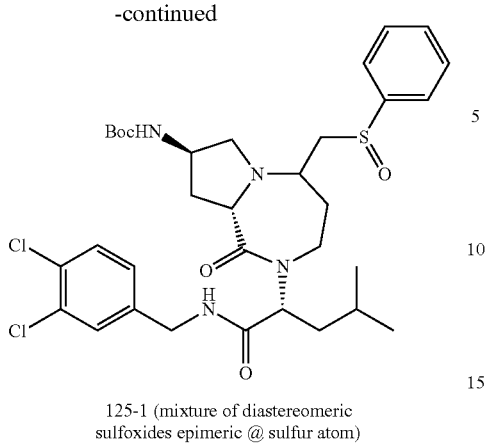

125-1 (mixture of diastereomeric sulfoxides epimeric @ sulfur atom)

To a solution of Example 18 (27 mg, 0.041 mmol) in 5:1 MeOH/H$_2$O (1 mL) was added ozone (14 mg, 0.045 mmol) and the reaction mixture was stirred at room temperature for 1 h. The reaction mixture was diluted with H$_2$O (10 mL) giving a white precipitate and extracted with 3:1 CHCl$_3$/i-PrOH (3×5 mL). The combined organic extracts were dried (MgSO$_4$), filtered and concentrated in vacuo. The residue was purified by FCC (SiO$_2$, elution with 0-100% EtOAc/hexanes) to provide 13 mg (46%) of first eluting, major diasteromer 125-1A and 6 mg (21%) of second eluting, minor diastereomer 125-1B. Data for Compound 125-1A (major diastereomer): $^1$H NMR (400 MHz, CD$_3$OD): δ 7.71-7.68 (m, 2H), 7.62-7.59 (m, 3H), 7.47 (d, 1H), 7.45 (d, 1H), 7.23 (dd, 1H), 5.14 (dd, 1H), 4.35 (ABq, 2H), 3.99 (m, 1H), 3.80 (dd, 1H), 3.67-3.51 (m, 2H), 3.33 (m partially obscured by solvent peak, 1H), 3.14 (dd, 1H), 3.05 (m, 1H), 2.77 (m, 1H), 2.68 (dd, 1H), 2.24 (app t, 1H), 2.13 (m, 1H), 1.79-1.59 (m, 4H), 1.46 (m partially obscured by singlet, 1H), 1.44 (s superimposed on multiplet, 9H), 0.96 (d, 3H), 0.90 (d, 3H) ppm; LCMS (Method A): t$_R$=1.38 min, m/z 679.3/681.3 (M+H)$^+$; HPLC: t$_R$=5.973 min. Data for Compound 125-1B (minor diastereomer): LCMS (Method A): t$_R$=1.38 min, m/z 679.3/681.3 (M+H)$^+$; HPLC: t$_R$=5.956 min.

Step 2A: (2R)-2-((8R,9aS)-8-amino-1-oxo-5-((phenylsulfinyl)methyl)hexahydro-1H-pyrrolo[1,2-a][1,4]diazepin-2(3H)-yl)-N-(3,4-dichlorobenzyl)-4-methylpentanamide.HCl (Example 125A)

Example 125A

Compound 125-1A (13 mg, 0.019 mmol) was treated with 3 N HCl in MeOH (1 mL) and the resultant solution was heated to 40° C. in a tightly capped reaction vial for 1 h. The reaction mixture was then cooled to room temperature and was diluted with H$_2$O (5 mL). The resultant solution was lyophilized to provide 11 mg (quantitative) of Example 125A as a tan solid. $^1$H NMR (400 MHz, CD$_3$OD): δ 7.71-7.68 (m, 2H), 7.62-7.59 (m, 3H), 7.47 (d, 1H), 7.44 (d, 1H), 7.24 (dd, 1H), 5.15 (app t, 1H), 4.34 (ABq, 2H), 4.30 (m, 1H), 3.84-3.44 (m, 5H), 3.18 (dd, 1H), 3.08-2.98 (m, 2H), 2.79 (m, 1H), 2.25 (m, 1H), 2.04 (m, 1H), 1.81 (m, 1H), 1.71-1.62 (m, 2H), 1.48 (m, 1H), 0.98 (d, 3H), 0.92 (d, 3H) ppm; LCMS (Method A): t$_R$=1.01 min, m/z 579.2/581.2 (M+H)$^+$.

Step 2B: (2R)-2-((8R,9aS)-8-amino-1-oxo-5-((phenylsulfinyl)methyl)hexahydro-1H-pyrrolo[1,2-a][1,4]diazepin-2(3H)-yl)-N-(3,4-dichlorobenzyl)-4-methylpentanamide.HCl (Example 125B)

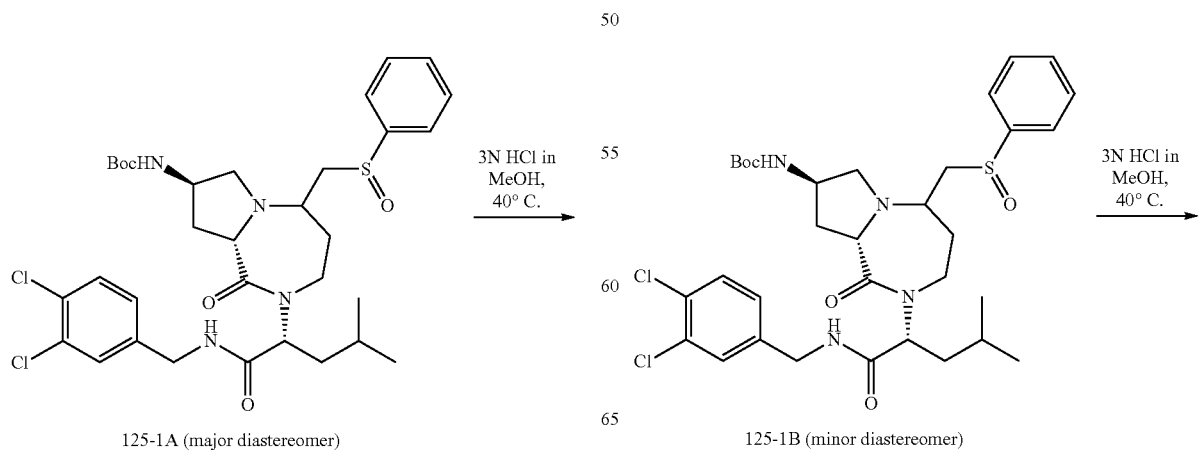

125-1A (major diastereomer)

125-1B (minor diastereomer)

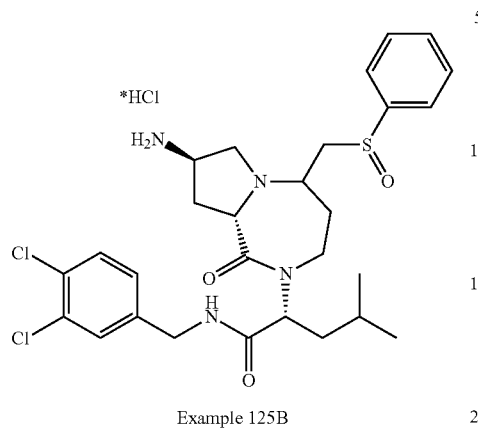

Example 125B

Compound 125-1B (6 mg, 0.009 mmol) was treated with 3N HCl in MeOH (1 mL) and the resultant solution was heated to 40° C. in a tightly capped reaction vial for 1 h. The reaction mixture was then cooled to room temperature and was diluted with $H_2O$ (5 mL). The resultant solution was lyophilized to provide 5 mg (quantitative) of Example 125B as a pale yellow solid. Data for Example 125B: LCMS (Method A): $t_R$=1.01 min, m/z 579.2/581.2 $(M+H)^+$.

Example 126: (2R)-2-((8R,9aS)-8-amino-1-oxo-5-((phenylsulfonyl)methyl)hexahydro-1H-pyrrolo[1,2-a][1,4]diazepin-2(3H)-yl)-N-(3,4-dichlorobenzyl)-4-methylpentanamide.HCl Steps 1 and 2: tert-butyl ((8R,9aS)-2-((R)-1-((3,4-dichlorobenzyl)amino)-4-methyl-1-oxopentan-2-yl)-1-oxo-5-((phenylsulfonyl)methyl)octahydro-1H-pyrrolo[1,2-a][1,4]diazepin-8-yl)carbamate (Compound 126-1)

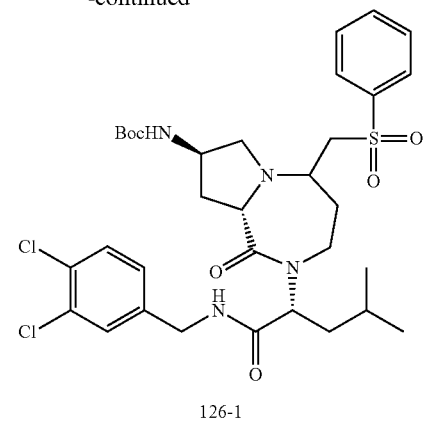

126-1

Compound 126-1 was prepared from Example 18 using the methods described in steps 1 and 2 for the preparation of Example 124. LCMS (Method A): $t_R$=1.44 min, m/z 695.3/697.3 $(M+H)^+$.

Step 3: (2R)-2-((8R,9aS)-8-amino-1-oxo-5-((phenylsulfonyl)methyl)hexahydro-1H-pyrrolo[1,2-a][1,4]diazepin-2(3H)-yl)-N-(3,4-dichlorobenzyl)-4-methylpentanamide.HCl (Example 126)

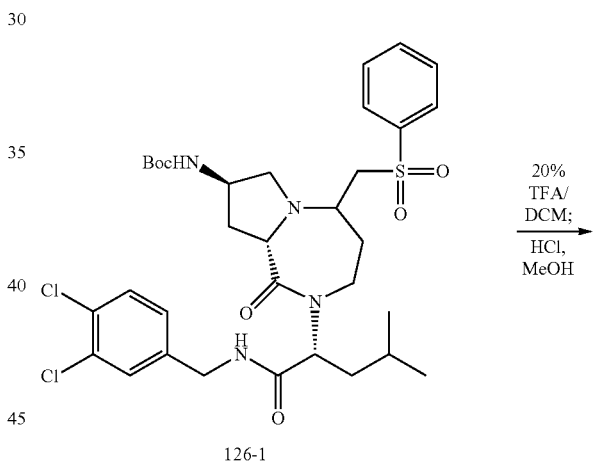

126-1

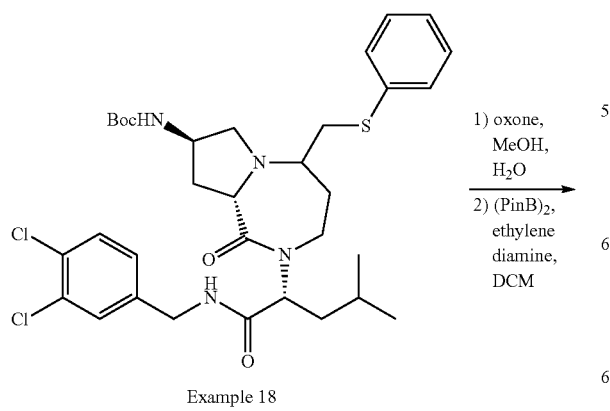

Example 18

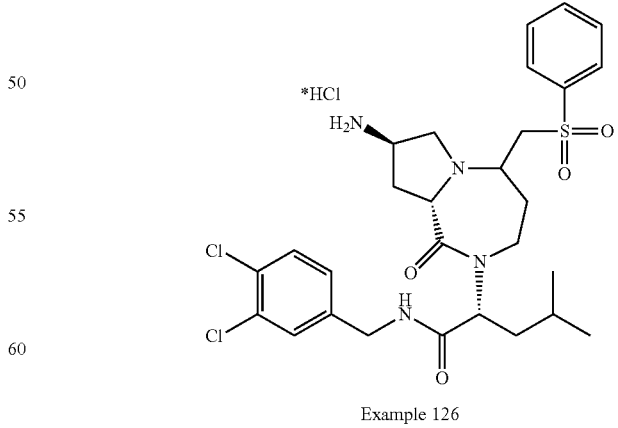

Example 126

Compound 126-1 (19 mg, 0.027 mmol) was treated with 20% TFA in DCM (1 mL) and stirred at room temperature for 1 h. The reaction mixture was concentrated in vacuo and the crude residue was purified by mass-directed, preparative reverse-phase HPLC (C18, elution with 5-100% ACN/H2O, 0.25% formic acid). The desired fractions were combined and concentrated in vacuo to remove most of the organic solvent. To this was added 3N HCl in MeOH (1 mL) and then the mixture was concentrated in vacuo. The treatment with HCl was repeated twice more to ensure the formation of HCl salt. The concentrate was diluted with H₂O and lyophilized to provide 11 mg (66%) of Example 126. ¹H NMR (400 MHz, CD₃OD): δ 7.99 (m, 2H), 7.78 (m, 1H), 7.68 (m, 2H), 7.44-7.42 (m, 2H), 7.22 (d, 1H), 5.12 (app t, 1H), 4.59 (m, 1H), 4.29 (ABq, 2H), 3.83 (m, 3H), 3.62 (m, 3H), 3.31-3.24 (m, 2H), 3.06 (m, 2H), 2.15 (m, 1H), 2.00 (m, 1H), 1.77 (m, 1H), 1.64 (m, 2H), 1.46 (m, 1H), 0.95 (d, 3H), 0.89 (d, 3H) ppm; LCMS (Method A): $t_R$=1.05 min, m/z 595.3/597.3 (M+H)⁺.

Example 127: (2R)-2-((8R,9aS)-8-acetamido-1-oxo-5-phenethylhexahydro-1H-pyrrolo[1,2-a][1,4]diazepin-2(3H)-yl)-N-(3,4-dichlorobenzyl)-4-methylpentanamide.HCl remaining solution was then treated once more with 3N HCl/MeOH as above and partially concentrated to ensure formation of the HCl salt. The concentrated mixture was diluted with H₂O and lyophilized to provide 14 mg (64%) of Example 127 as a fluffy white solid. ¹H NMR (400 MHz, CD₃OD): δ 7.50-7.47 (m, 2H), 7.33-7.20 (m, 6H), 5.23 (dd, 1H), 4.34 (s superimposed on multiplet, 2H), 4.34-4.29 (m partially obscured by singlet, 1H), 4.08 (dd, 1H), 3.92 (dd, 1H), 3.70 (dd, 1H), 3.52 (app t, 1H), 3.19 (m, 1H), 2.98 (m, 1H), 2.80 (m, 1H), 2.61 (m, 1H), 2.43 (dd, 1H), 2.20 (m, 2H), 2.05-1.95 (m partially obscured by singlet, 1H), 1.96 (s, 3H), 1.80 (m, 2H), 1.66 (m, 1H), 1.49 (m, 1H), 1.33-1.29 (m, 1H), 0.98 (s, 3H), 0.92 (s, 3H) ppm; LCMS (Method A): $t_R$=1.18 min, m/z 587.5/589.5 (M+H)⁺.

Example 128: (2R)—N-(3,4-dichlorobenzyl)-2-((8R,9aS)-8-(dimethylamino)-1-oxo-5-phenethyl-hexahydro-1H-pyrrolo[1,2-a][1,4]diazepin-2(3H)-yl)-4-methylpentanamide.HCl

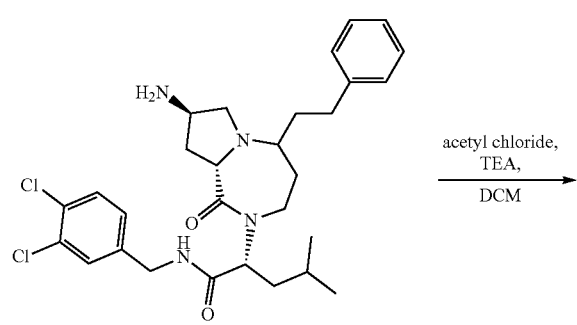

Example 1

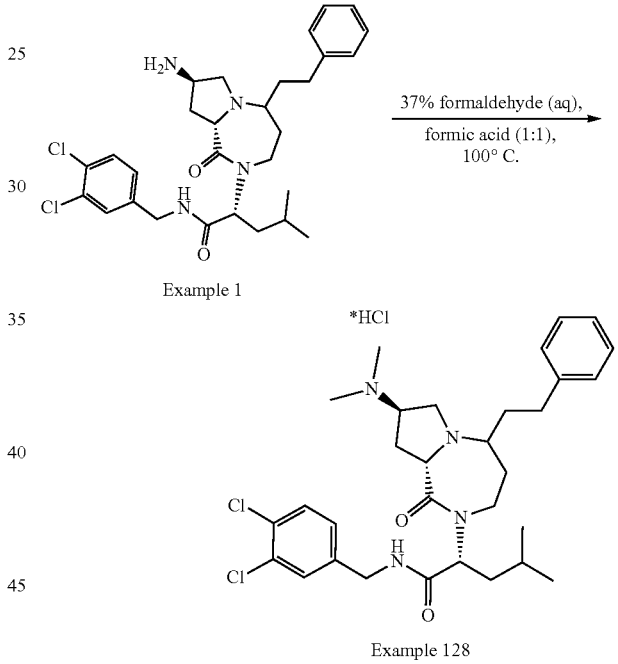

Example 1

Example 128

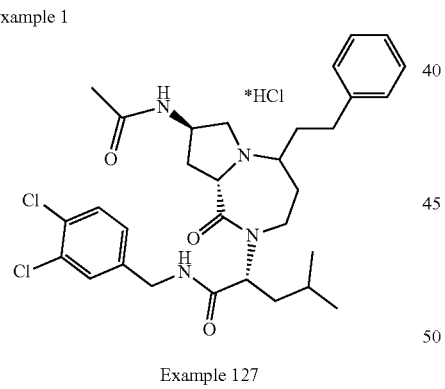

Example 127

To a solution of Example 1 (20 mg, 0.037 mmol) in DCM (1 mL) was added TEA (15 μL, 0.11 mmol) followed by acetyl chloride (5 μL, 0.07 mmol). The resultant solution was stirred at room temperature for 1 h. The mixture was then concentrated in vacuo and the residue was taken up in MeOH (~1 mL) and to this was added a small scoop of K₂CO₃. The mixture was stirred for 15 min then diluted with DCM and filtered to remove K₂CO₃. The filtrate was concentrated in vacuo and the residue was purified directly by mass-directed preparative reversed-phase HPLC (elution with 5-95% ACN/H₂O containing 0.25% formic acid). The desired fractions were combined and partially concentrated in vacuo and the concentrate was treated with 3N HCl/MeOH (~5 mL) and then partially concentrated again. The A solution of Example 1 (20 mg, 0.037 mmol) in 37% formaldehyde (aq) (1 mL) and formic acid (1 mL) was heated to 100° C. in a tightly capped reaction vial for 7 h. This was then cooled and the mixture was purified directly by mass-directed preparative reversed-phase HPLC (elution with 5-95% ACN/H₂O containing 0.25% formic acid). The desired fractions were combined and partially concentrated in vacuo and the concentrate was treated with 3N HCl/MeOH (~5 mL) and then partially concentrated again. The remaining solution was then treated once more with 3N HCl/MeOH as above and partially concentrated to ensure formation of the HCl salt. The concentrated mixture was diluted with H₂O and lyophilized to provide 14 mg (67%) of Example 128. ¹H NMR (400 MHz, CD₃OD): δ 7.53 (m, 1H), 7.48 (d, 1H), 7.32-7.18 (m, 6H), 5.22 (m, 1H), 5.06 (m, 1H), 4.35 (ABq superimposed on multiplet, 2H), 4.28 (m, partially obscured by AB quartet, 1H), 4.01 (m, 1H), 3.83-3.55 (m, 4H), 3.29 (m partially obscured by solvent peak, 1H), 3.00 (s, 6H), 2.76 (m, 1H), 2.57 (m, 2H), 2.36-2.21 (m, 2H), 1.98-1.80 (m, 2H), 1.72 (app t, 2H), 1.50 (m, 1H), 0.97 (d, 3H), 0.92 (d, 3H) ppm; LCMS (Method A): $t_R$=1.15 min, m/z 573.5/575.5 (M+H)$^+$.

Example 129: (2R)-2-((7R,8aS)-7-amino-1-oxo-4-phenethylhexahydropyrrolo[1,2-c]pyrazin-2(1H)-yl)-N-(3,4-dichlorobenzyl)-4-methylpentanamide.HCl Step 1: (R)—N-(3,4-dichlorobenzyl)-4-methyl-2-((2-oxo-4-phenylbutyl)amino)pentanamide (Compound 129-1)

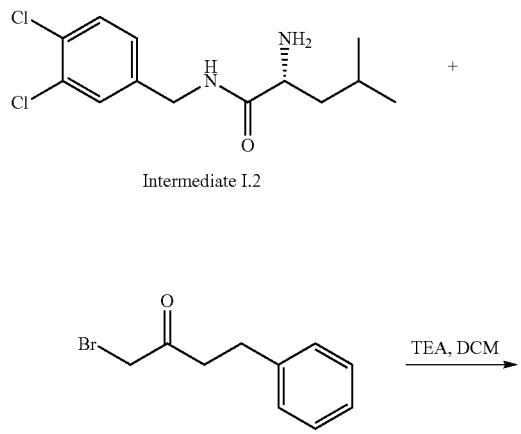

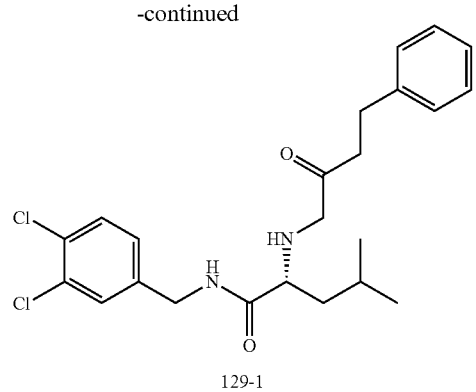

129-1

To a solution of Intermediate I.2 (67 mg, 0.23 mmol) in DCM (1 mL) was added 1-bromo-4-phenylbutan-2-one (50 mg, 0.22 mmol) followed by TEA (34 μL, 0.24 mmol). The reaction mixture was stirred at room temperature for 4 h. The mixture was then diluted with DCM and washed with sat. NaHCO$_3$ (aq) (2×). The organic layer was dried (MgSO$_4$), filtered and concentrated in vacuo. The residue was purified by FCC (SiO$_2$, elution with 0-100% EtOAc/hexanes) to provide 25 mg (26%) of 129-1 as a yellow semi-solid. $^1$H NMR (400 MHz, CDCl$_3$): δ 7.55 (br t, 1H, amide N—H), 7.38 (d, 1H), 7.33 (d, 1H), 7.30-7.26 (m partially obscured by solvent peak, 2H), 7.22-7.14 (m, 3H), 7.08 (dd, 1H), 4.36 (m, 2H), 3.37 (ABq, 2H), 3.05 (dd, 1H), 2.91 (t, 2H), 2.67 (t, 2H), 1.81-1.41 (m partially obscured by H$_2$O peak, 4H), 0.95 (d, 3H), 0.92 (d, 3H) ppm; LCMS (Method A): $t_R$=1.14 min, m/z 435.4/437.4 (M+H)$^+$.

Steps 2-4: tert-butyl ((7R,8aS)-2-((R)-1-((3,4-dichlorobenzyl)amino)-4-methyl-1-oxopentan-2-yl)-1-oxo-4-phenethyloctahydropyrrolo[1,2-c]pyrazin-7-yl)carbamate (Compound 129-3)

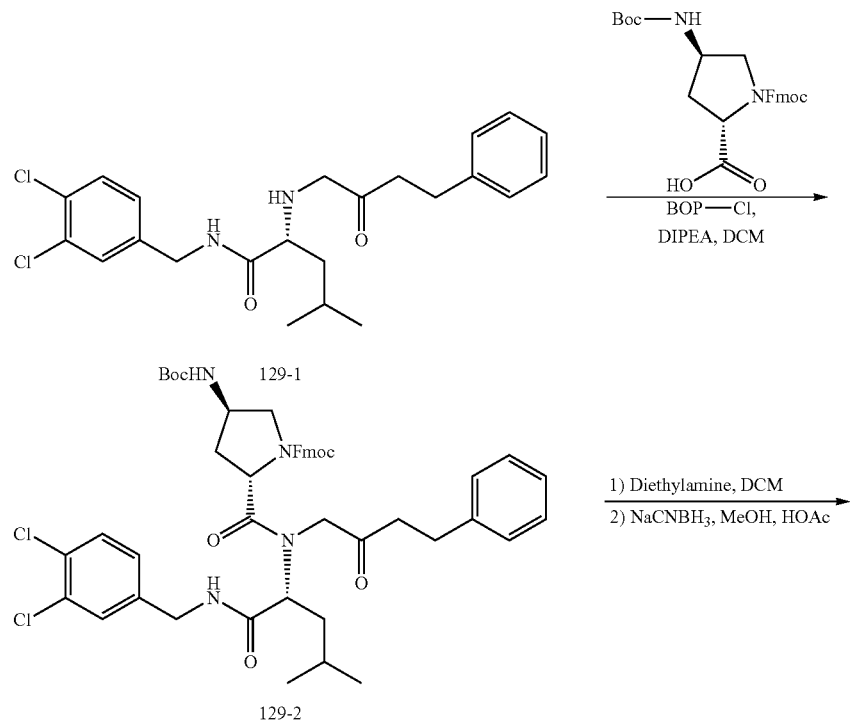

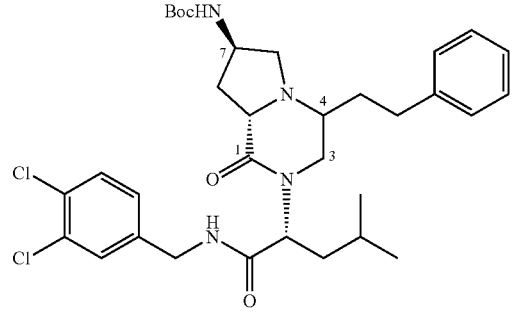

129-3 (mixture of diastereomers epimeric at C(4) of 6-ring)

Compound 129-3 was prepared from Compound 129-1 (92 mg, 0.21 mmol) using the same general procedures described for the preparation of compound 1-3 in steps 2-4 in Example 1. After work-up the crude product was purified by FCC (SiO$_2$, elution with 0-70% EtOAc/hexanes). Partial separation of the two diastereomers was achieved providing two fractions; one containing 29 mg of mainly the first eluting, major diastereomer (129-3A) and the other containing 17 mg of mainly the second eluting, minor diastereomer (129-3B). A small amount of the other diastereomer was present in each of the two fractions. The fraction containing mainly the minor diastereomer 129-3B was carried forward into the next step. Data for 129-3A (major diastereomer): LCMS (Method C): t$_R$=0.92 min, m/z 631.4/633.3 (M+H)$^+$. Data for 129-3B (minor diastereomer): LCMS (Method C): t$_R$=0.99 min, m/z 631.4/633.4 (M+H)$^+$.

Step 5: (2R)-2-((7R,8aS)-7-amino-1-oxo-4-phenethylhexahydropyrrolo[1,2-a]pyrazin-2(1H)-yl)-N-(3,4-dichlorobenzyl)-4-methylpentanamide (Example 129)

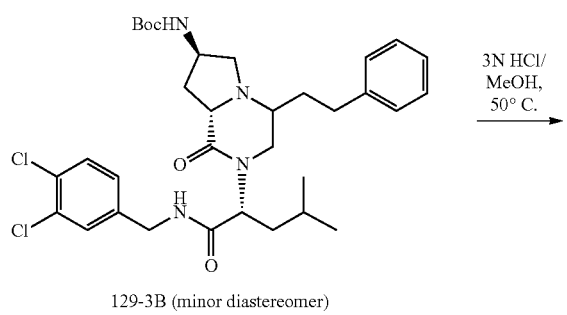

129-3B (minor diastereomer)

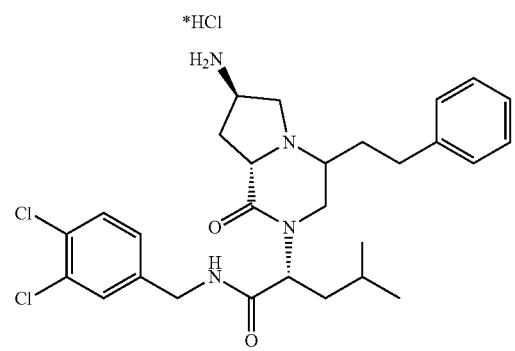

Example 129

Compound 129-3B (16 mg, 0.025 mmol) was taken up in 3 N HCl in MeOH (1 mL) and the resultant solution was stirred at 50° C. in a tightly capped reaction vial for 90 min. The reaction mixture was then cooled, concentrated in vacuo and the residue was purified directly by preparative reversed-phase HPLC (C18 column, elution with 5-95% ACN/H$_2$O). The desired fractions were combined and partially concentrated in vacuo. To this was added 3N HCl (~10 mL) and the volatiles were removed in vacuo. This treatment with 3N HCl was repeated to ensure formation of the HCl salt. The mixture was then concentrated in vacuo and the residue was taken up in H$_2$O and a small amount of ACN was added to provide a clear solution which was lyophilized to provide 11 mg (79%) of Example 129 as a white solid. $^1$H NMR (400 MHz, CD$_3$OD): δ 7.47 (d, 1H), 7.43 (d, 1H), 7.32-7.27 (m, 4H), 7.23-7.20 (m, 2H), 5.17 (dd, 1H), 4.55

(m, 1H), 4.33 (ABq, 2H), 4.10-3.42 (m, 6H), 2.90-2.76 (m, 3H), 2.45 (m, 1H), 2.15 (m, 1H), 2.00 (m, 1H), 1.81 (m, 1H), 1.66 (m, 1H), 1.45 (m, 1H), 1.01 (d, 3H), 0.94 (d, 3H) ppm; LCMS (Method A): $t_R$=1.13 min, m/z 531.5/533.5 (M+H)$^+$.

Example 130: N-((3R)-3-((8R,9aS)-8-amino-1-oxo-5-phenethylhexahydro-1H-pyrrolo[1,2-a][1,4]diazepin-2(3H)-yl)-4-((3,4-dichlorobenzyl)amino)-4-oxobutyl)cyclopropanecarboxamide.HCOOH Step 1: (R)-(9H-fluoren-9-yl)methyl (4-((3,4-dichlorobenzyl)amino)-4-oxo-3-((3-oxo-5-phenylpentyl)amino)butyl)carbamate (Compound 130-1)

To mixture of intermediate I.36 (319 mg, 0.64 mmol) and Intermediate II.1 (103 mg, 0.64 mmol) in DCM (3 mL) was added DIPEA (0.1 mL, 0.59 mmol) and the reaction mixture was stirred at room temperature for 16 h. The mixture was concentrated in vacuo and the crude residue was purified by FCC (SiO$_2$, elution with 0-5% MeOH/DCM) to provide 335 mg (79%) of Compound 130-1 as a tan solid. $^1$H NMR (400 MHz, CDCl$_3$): δ 8.04 (m, 1H), 7.76 (d, 1H), 7.59 (d, 1H), 7.43-7.37 (m, 4H), 7.32-7.28 (m, 4H), 7.20-7.14 (m, 5H), 5.27 (m, 1H), 4.42 (d, 2H), 4.37 (d, 1H), 4.21 (m, 1H), 3.44 (m, 1H), 3.24 (m, 1H), 3.12 (m, 1H), 2.93-2.84 (m, 3H), 2.81-2.63 (m, 5H), 2.56-2.51 (m, 2H), 1.93-1.73 (m, 2H) ppm. LCMS (Method B): $t_R$=1.28 min, m/z 658.5/660.5 (M+H)$^+$ Steps 2-4: tert-butyl ((8R,9aS)-2-((R)-4-amino-1-((3,4-dichlorobenzyl)amino)-1-oxobutan-2-yl)-1-oxo-5-phenethyloctahydro-1H-pyrrolo[1,2-a][1,4]diazepin-8-yl)carbamate (Compound 130-3)

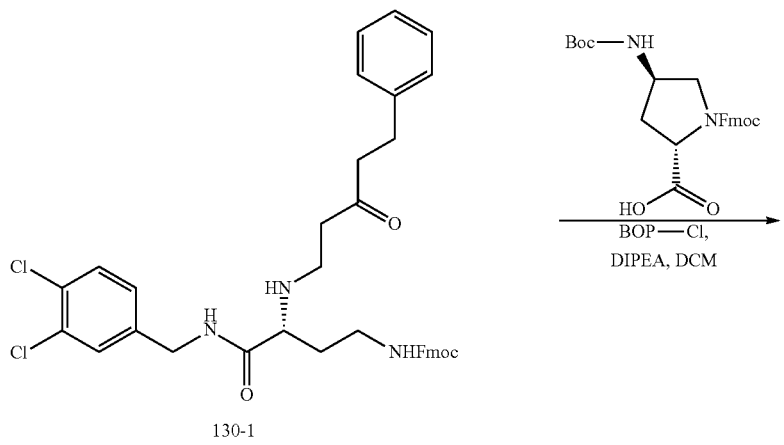

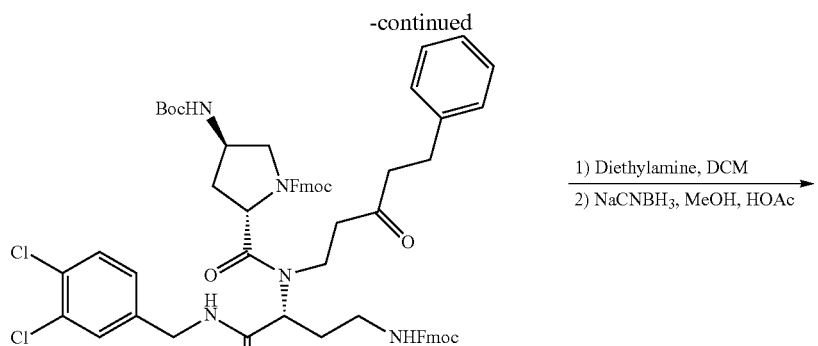

130-2

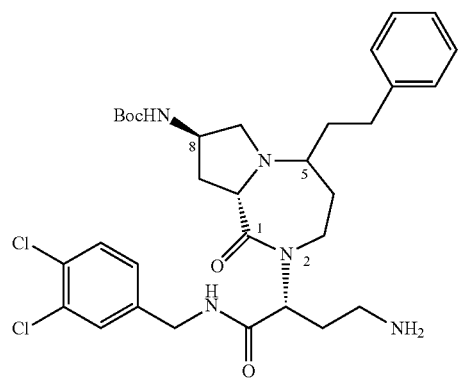

130-3 (mixture of diastereomers epimeric at C(5) of 7-ring)

Compound 130-3 was prepared from Compound 130-1 (160 mg, 0.24 mmol) using the same general procedures described for the preparation of Compound 1-3 in steps 2-4 in Example 1. After work-up the crude product was purified by FCC (SiO$_2$, elution with 0-10% MeOH/DCM). The second eluting, major diasteromer 130-3B was isolated and carried forward into the next step (the first eluting, minor diastereomer 130-3A was not isolated). Data for 130-3B (major diastereomer): LCMS (Method B): t$_R$=0.98 min, m/z 727.3/730.3 (M+H)$^+$.

Step 5 and step 6: N-((3R)-3-((8R,9aS)-8-amino-1-oxo-5-phenethylhexahydro-1H-pyrrolo[1,2-a][1,4]diazepin-2(3H)-yl)-4-(3,4-dichlorobenzyl)amino)-4-oxobutyl)cyclopropanecarboxamide.HCOOH (Example 130)

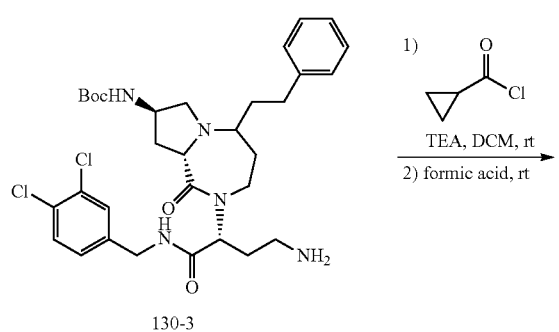

130-3

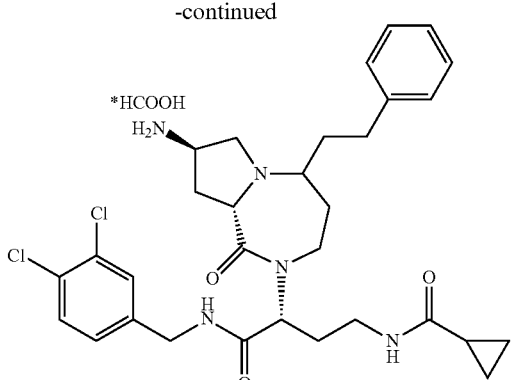

Example 130

To Compound 130-3 (25 mg, 0.040 mmol) in DCM (1 mL) was added TEA (8.1 mg, 11 µL, 0.08 mmol) at 0° C. followed by cyclopropane carbonyl chloride (6.2 mg, 0.059 mmol). The reaction mixture was warmed to room temperature and stirred for 2 h. The mixture was then quenched with sat. NaHCO$_3$ (aq) (5 mL) and extracted with DCM (3×). The combined organic extracts were dried (Na$_2$SO$_4$), filtered and concentrated in vacuo. The crude residue was taken as is in formic acid and stirred at room temperature in a tightly capped reaction vial for 5 h. The mixture was then cooled, concentrated in vacuo and the crude residue was purified directly by mass-directed, preparative reversed-phase HPLC (C18 column, elution with 5-95% ACN/H$_2$O containing 0.25% formic acid).). The desired fractions were combined and lyophilized to provide 8 mg (35% over two steps) of Example 130 as a white solid. $^1$H NMR (400 MHz, CD$_3$OD): δ 7.40 (d, 1H), 7.34 (d, 1H), 7.20-7.03 (m, 6H), 5.02 (m, 1H), 4.27 (ABq, 2H), 3.67 (m, 1H), 3.53-3.32 (m, 4H), 3.06 (m, 1H), 2.80 (m, 1H), 2.49 (m, 2H), 2.34 (m, 1H), 2.21 (m, 1H), 1.96 (m, 1H), 1.81 (m, 3H), 1.63 (m, 1H), 1.44 (m, 2H), 1.35-1.17 (m, 2H), 0.82-0.60 (m, 4H) ppm; LCMS (Method A): $t_R$=1.04 min, m/z 600.5/602.5 (M+H)$^+$; HPLC: $t_R$=5.984 min (100%).

Following the general method described above for the preparation of Example 130, and substituting the indicated reagent in step 5, the following examples set forth in Table 23 were prepared.

TABLE 23

| Example | Structure | Reagent | LCMS Method | $t_R$ (min) | (M + H)$^+$ observed |
|---------|-----------|---------|-------------|-------------|----------------------|
| 131 | 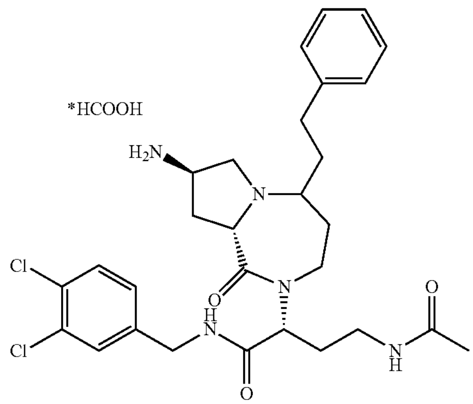 | Acetyl chloride | A | 0.95 | 574.5/576.5 |
| 132 | 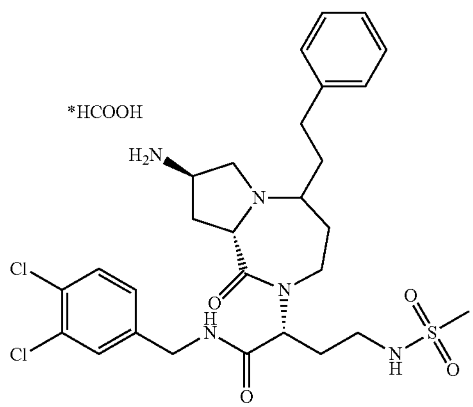 | Mesyl chloride | D | 0.85 | 610.5/612.5 |
| 133 | 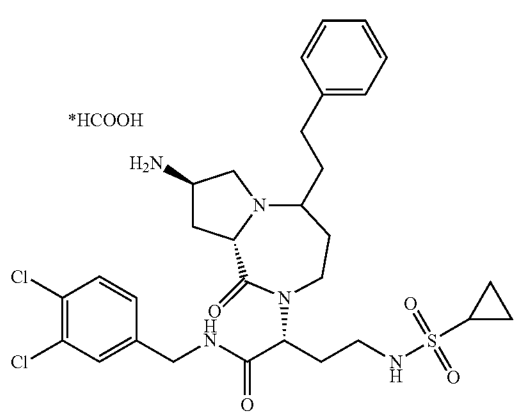 | Cyclopropanesulfonyl chloride | A | 1.01 | 636.6/638.5 |

Example 134: 2-(((2R)-2-((8R,9aS)-8-amino-1-oxo-5-phenethylhexahydro-1H-pyrrolo[1,2-a][1,4]diazepin-2(3H)-yl)-4-carboxybutanamido)methyl)-4,5-dichloropyridine 1-oxide.HCOOH

Steps 1-2: (2S,4R)-(9H-fluoren-9-yl)methyl 2-((R)-5-(tert-butoxy)-1-((5,6-dichloropyridin-2-yl)methyl)amino)-1,5-dioxopentan-2-yl)(3-oxo-5-phenylpentyl)carbamoyl)-4-((tert-butoxycarbonyl)amino)pyrrolidine-1-carboxylate (Compound 134-2)

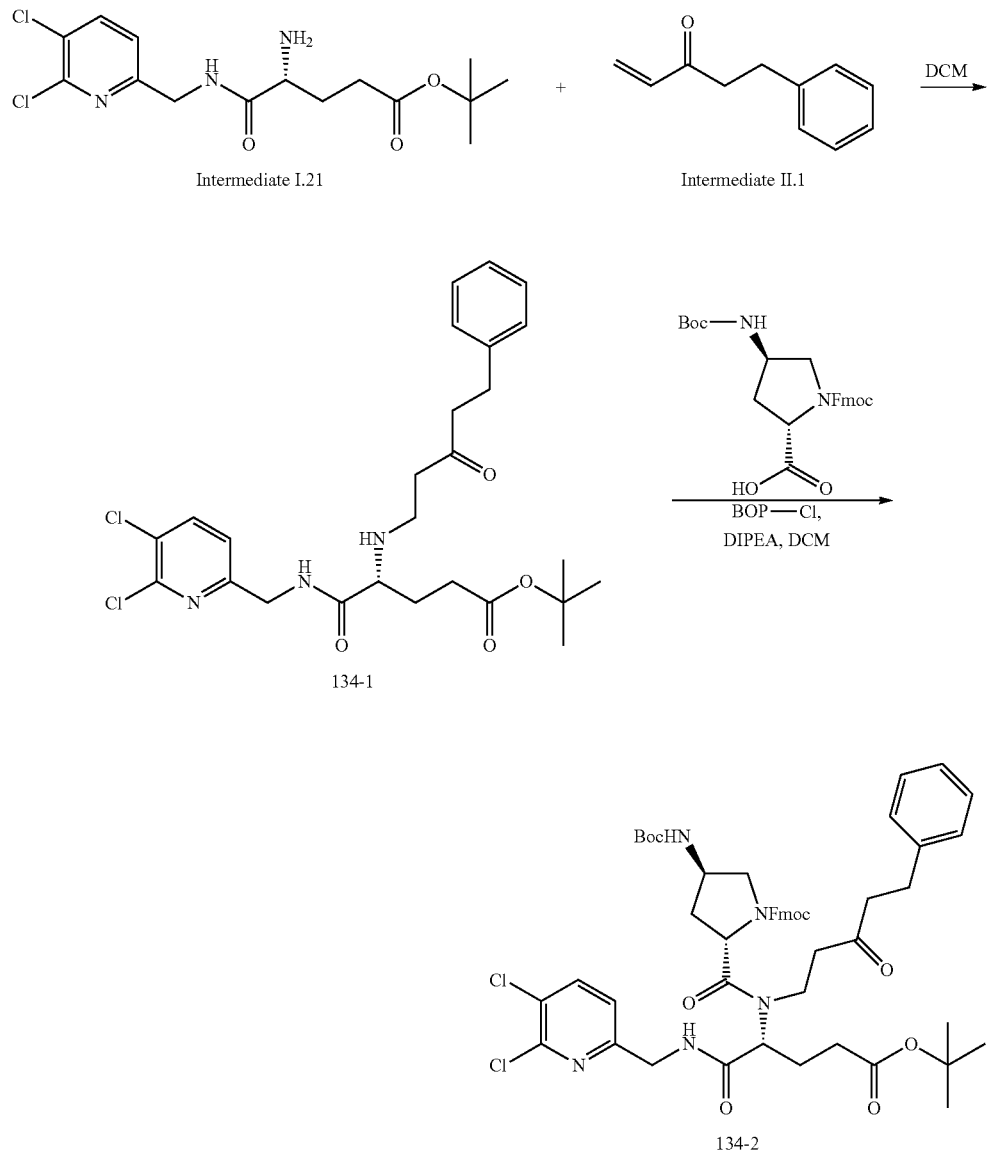

Compound 134-2 was prepared from Intermediate I.21 (231 mg, 0.64 mmol) and Intermediate II.1 (102 mg, 0.64 mmol) using the same general method described for the preparation of Compound 1-2 in steps 1-2 in Example 1. After work-up following the acylation reaction (step 2), the crude product was purified by FCC (SiO$_2$, elution with 0-100% EtOAc/hexanes) to provide 291 mg of Compound 134-2. Data for 134-2: $^1$H NMR (400 MHz, CDCl$_3$): δ 8.28 (s, 1H), 7.75 (t, 2H), 7.53 (d, 1H), 7.47-7.37 (m, 4H), 7.33-7.28 (m, 4H), 7.20-7.15 (m, 3H), 5.11 (t, 1H), 4.57-4.55 (m, 2H), 4.42-4.38 (m, 2H), 4.24-4.12 (m, 3H), 3.92-3.87 (m, 1H), 3.80-3.71 (m, 1H), 3.59-3.43 (m, 2H), 2.99-2.78 (m, 3H), 2.76-2.65 (m, 3H), 2.45-2.09 (m, 5H), 1.93-1.81 (m, 1H), 1.49 (s, 9H), 1.43 (s, 9H) ppm; LCMS (Method D): t$_R$=1.68 min, m/z 956.6/958.6 (M+H)$^+$.

Step 3: 6-(((R)-2-((2S,4R)-1-(((9H-fluoren-9-yl)methoxy)carbonyl)-4-((tert-butoxycarbonyl)amino)-N-(3-oxo-5-phenylpentyl)pyrrolidine-2-carboxamido)-5-(tert-butoxy)-5-oxopentanamido)methyl)-2,3-dichloropyridine 1-oxide (Compound 134-3)

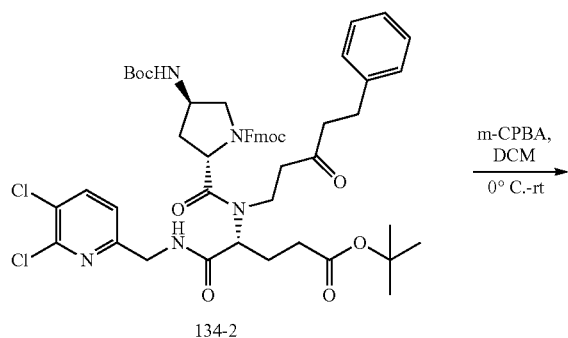

134-2

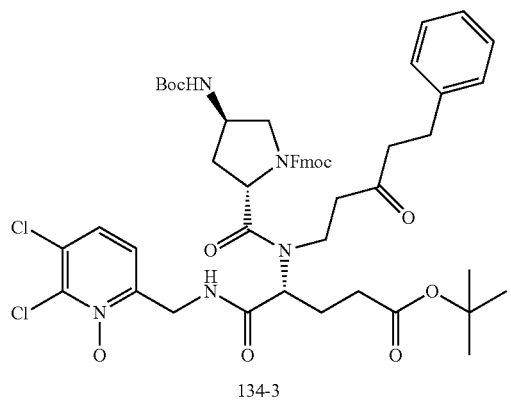

134-3

To a solution of Compound 134-2 (232 mg, 0.24 mmol) in DCM (2 mL) was added a solution of m-CPBA (50.3 mg, 0.29 mmol) in DCM (2 mL) at 0° C. and the mixture was warmed to ambient temperature and stirred for 3 d. The mixture was then concentrated in vacuo and the crude residue was taken up in DCM (10 mL). This was washed with sat. NaHCO₃ (aq) and brine. The organic layer was then dried (Na₂SO₄), filtered and concentrated in vacuo to provide 236 mg (quantitative) of Compound 134-3 which was used in the next step without further purification. LCMS (Method D) $t_R$=1.56 min, m/z 972.5/974.5 (M+H)⁺.

Steps 4: 2-(((2R)-5-(tert-butoxy)-2-((8R,9aS)-8-((tert-butoxycarbonyl)amino)-1-oxo-5-phenethylhexahydro-1H-pyrrolo[1,2-a][1,4]diazepin-2(3H)-yl)-5-oxopentanamido)methyl)-4,5-dichloropyridine-1-oxide (Compound 134-4)

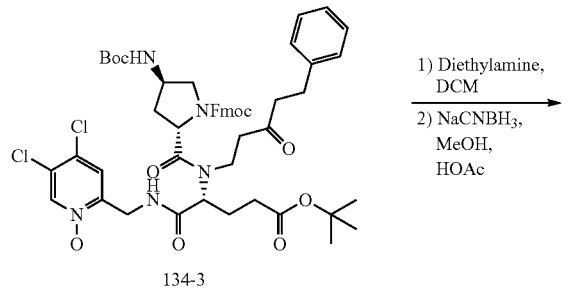

134-3

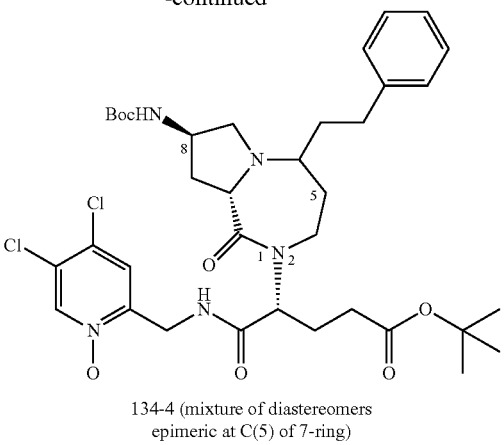

134-4 (mixture of diastereomers epimeric at C(5) of 7-ring)

Compound 134-4 was prepared from Compound 134-3 (236 mg, 0.24 mmol) using the same general methods for the preparation of Compound 1-3 described in steps 3-4 of Example 1. After work-up the crude product was purified by FCC (SiO₂, elution with 0-5% MeOH/DCM). The second eluting, major diastereomer 134-4B was isolated and carried forward into the next step (the first eluting, minor diastereomer 134-4A was not isolated). Data for 134-4B (major diastereomer): LCMS (Method A): $t_R$=1.22 min, m/z 734.5/736.5 (M+H)⁺.

Steps 5: 2-(((2R)-2-((8R,9aS)-8-amino-1-oxo-5-phenethylhexahydro-1H-pyrrolo[1,2-a][1,4]diazepin-2(3H)-yl)-4-carboxybutanamido)methyl)-4,5-dichloropyridine-1-oxide.HCOOH (Example 134)

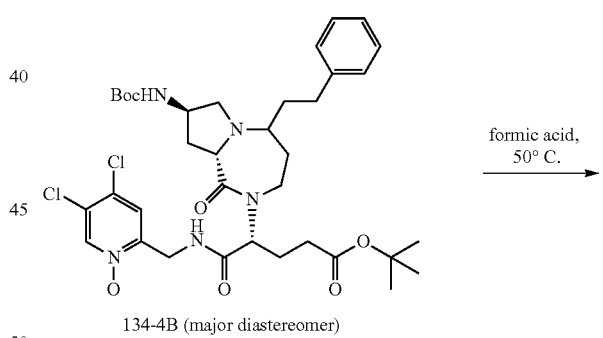

134-4B (major diastereomer)

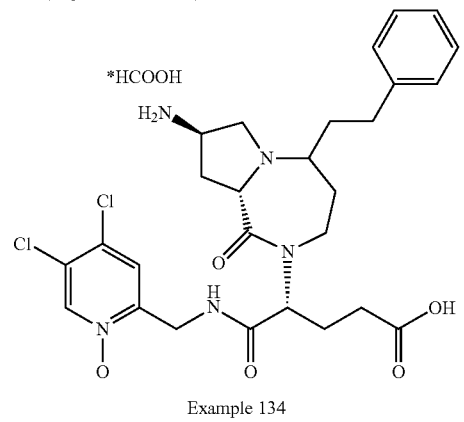

Example 134

Example 134 was prepared from Compound 134-4B (115 mg, 0.16 mmol) using the same general procedure described in step 5 for the preparation of Example 70 to give 61 mg (68%) product as a white solid. IE NMR (400 MHz, CD₃OD): δ 8.48 (s, 1H), 7.60 (s, 1H), 7.16 (t, 2H), 7.07 (d, 3H), 4.90 (m, 1H), 4.44 (ABq, 2H), 3.46 (dd, 1H), 3.56-3.53 (m, 3H), 3.44 (m, 1H), 2.94-2.87 (m, 1H), 2.56 (m, 2H), 2.47-2.37 (m, 1H), 2.33 (t, 1H), 2.13-2.06 (m, 3H), 2.05-1.96 (m, 1H), 1.90-1.74 (m, 3H), 1.56 (m, 2H) ppm; LCMS (Method A): $t_R$=0.83 min, m/z 578.4/580.4 (M+H)⁺. HPLC: $t_R$=4.013 min (100%).

Following the method described above for the preparation of Example 105, the following example set forth in Table 24 was prepared from Example 134 as the starting material.

TABLE 24

| Example | Structure | LCMS Method | $t_R$ (min) | (M + H)⁺ observed |
|---|---|---|---|---|
| 135 | 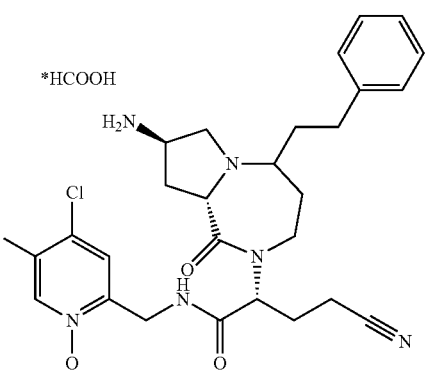 | A | 0.85 | 559.4/561.5 |

Following steps 1 and 2 and then step 4 (i.e. skip step 3) in the method described above for the preparation of Example 105, and substituting methylamine for ammonium chloride in step 2, the following example set forth in Table 25 was prepared.

TABLE 25

| Example | Structure | LCMS Method | $t_R$ (min) | (M + H)⁺ observed |
|---|---|---|---|---|
| 136 | 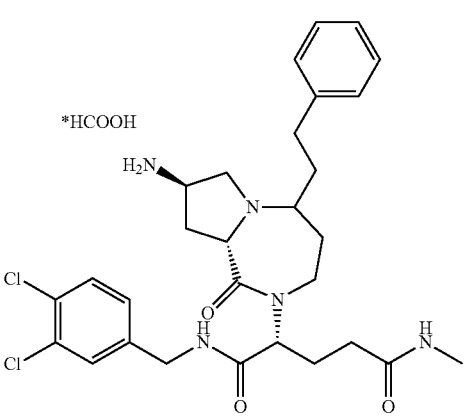 | A | 0.96 | 574.5/576.5 |

Following the methods described above for Examples 2, and using the corresponding intermediates in step 1, the examples set forth in Table 25 were prepared. The examples in Table 26 were prepared from the major diastereomer obtained in step 4 (intramolecular reductive amination) of the synthesis.

TABLE 26

| Example | Structure | Intermediates and reagents | LCMS Method | $t_R$ (min) | $(M + H)^+$ observed |
|---|---|---|---|---|---|
| 137 | 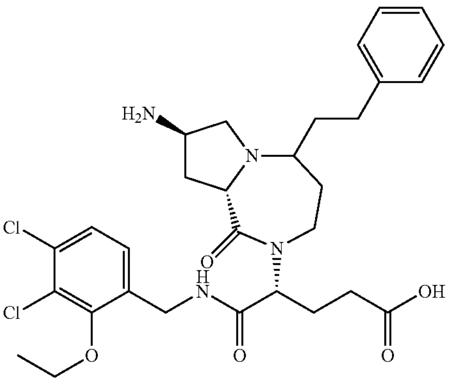 | I.37 and II.1 | A | 1.08 | 605.5/607.5 |
| 138 | 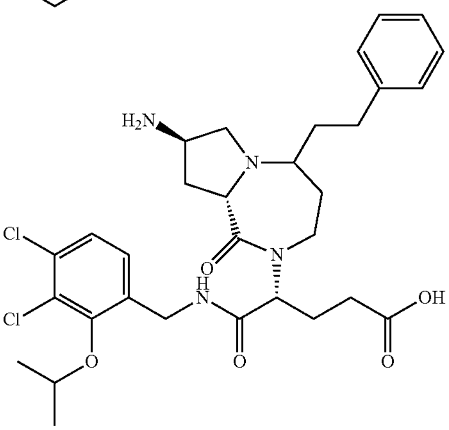 | I.38 and II.1 | A | 1.12 | 619.5/621.5 |

Example 139: (2R)-2-(4-(2-aminoethyl)-2-oxo-5-phenethyl-1,4-diazepan-1-yl)-N-(3,4-dichlorobenzyl)-4-methylpentanamide.HCl Steps 1-3: tert-butyl (2-(4-((R)-1-((3,4-dichlorobenzyl)amino)-4-methyl-1-oxopentan-2-yl)-3-oxo-7-phenethyl-1,4-diazepan-1-yl)ethyl)carbamate (Compound 139-2)

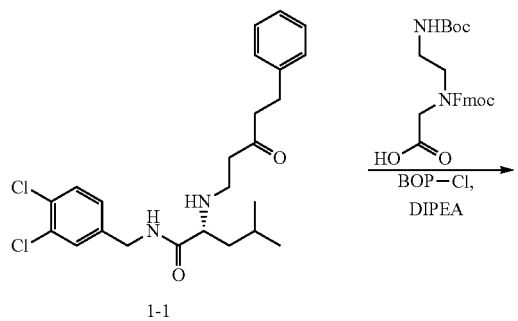

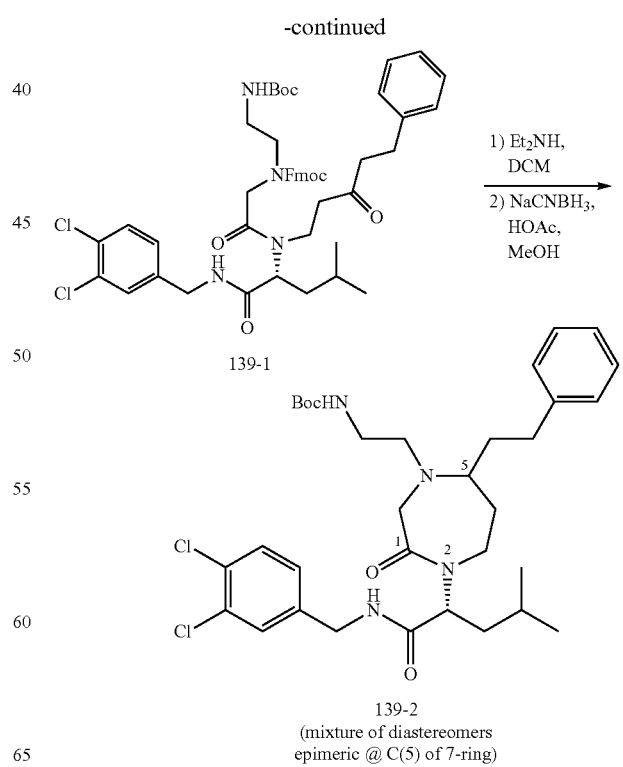

139-2
(mixture of diastereomers epimeric @ C(5) of 7-ring)

Compound 139-2 was prepared as a mixture of diastereomers (~1.2:1 ratio) epimeric at C(5) of the 7-ring from Compound 1-1 and Fmoc-N-(2-Boc-aminoethyl)-Gly-OH (Sigma-Aldrich) following the method described in steps 2-4 for the preparation of Example 1. LCMS (Method A): $t_R$=1.54 min (54%) and 1.55 min (46%), m/z 633.6/635.6 (M+H)$^+$.

Step 4: (2R)-2-(4-(2-aminoethyl)-2-oxo-5-phenethyl-1,4-diazepan-1-yl)-N-(3,4-dichlorobenzyl)-4-methylpentanamide.HCl (Example 139)

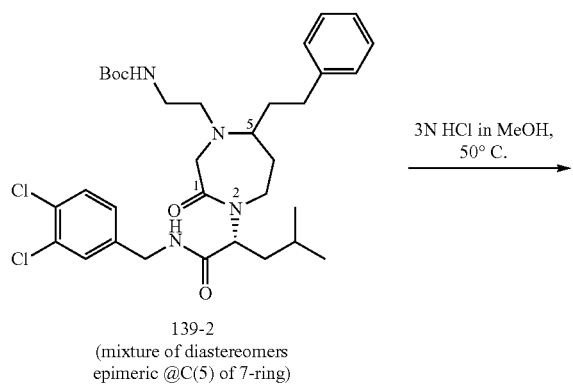

139-2
(mixture of diastereomers epimeric @C(5) of 7-ring)

3N HCl in MeOH, 50° C.

Example 139
(mixture of diastereomers epimeric @C(5) of 7-ring)

Compound 139-2 (100 mg, 0.158 mmol) was taken up in 3N HCl in MeOH (2 mL) and stirred in a tightly capped reaction vial at 50° C. for 2 h. The reaction mixture was then cooled, concentrated in vacuo and the crude residue was purified directly by mass-directed preparative reversed-phase HPLC (C18 column, elution with 5-95% ACN/H$_2$O containing 0.25% formic acid). The desired fractions were combined and concentrated in vacuo. To the residue was added 3N HCl in MeOH (~5 mL) and the volatiles were removed in vacuo. This treatment with 3N HCl was repeated to ensure formation of the hydrochloride salt. The mixture was then concentrated in vacuo and the residue was taken up in H$_2$O and a small amount of ACN was added to provide a clear solution which was then lyophilized to provide 74 mg (82%) of Example 139 as a white solid. $^1$H NMR (400 MHz, CD$_3$OD): δ 7.49-7.45 (m, 2H)), 7.30-7.15 (m, 6H), 5.14 (m, 1H), 4.42-4.21 (m, 2H), 4.05-3.39 (m, 4H), 3.21-2.62 (m, 7H), 2.06-1.46 (m, 7H), 0.98 (d, 3H), 0.95 (d, 3H) ppm; LCMS (Method A): $t_R$=1.16 min, m/z 533.4/535.4 (M+H)$^+$.

Additional Examples as set forth in Table 27 were prepared in accordance with the present invention.

TABLE 27

| Example | Structure | LCMS Method | $t_R$ (min) | (M + H)$^+$ observed |
|---|---|---|---|---|
| 140 | 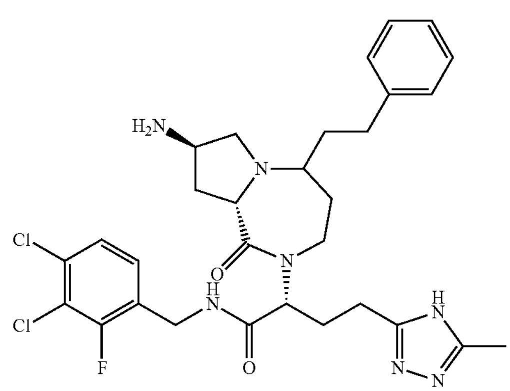 | A | 1.51 | 616.5/618.5 |

TABLE 27-continued

| Example | Structure | LCMS Method | $t_R$ (min) | $(M + H)^+$ observed |
|---|---|---|---|---|
| 141 | 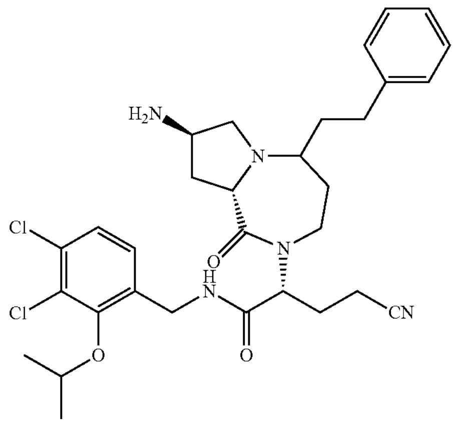 | A | 1.13 | 600.5/602.5 |
| 142 | 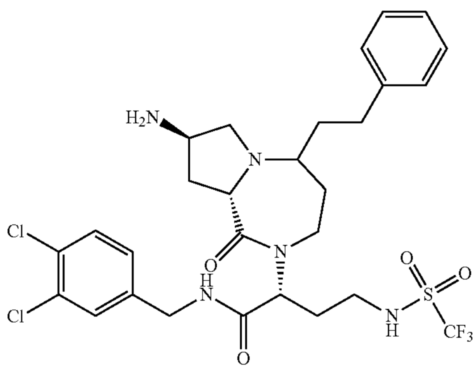 | D | 1.62 | 664.5/666.5 |
| 143 | 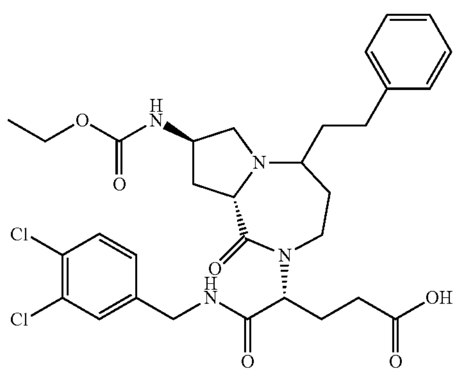 | A | 1.08 | 633.5/635.5 |
| 144 | 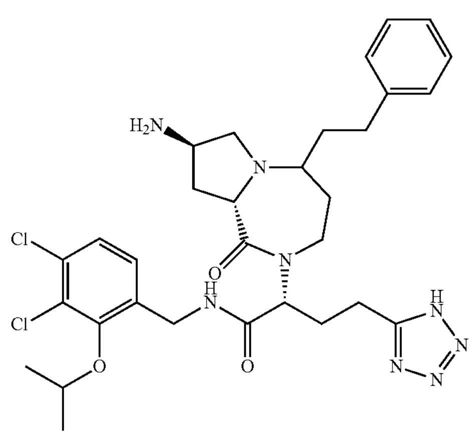 | A | 1.09 | 643.5/645.5 |

TABLE 27-continued

| Example | Structure | LCMS Method | $t_R$ (min) | $(M + H)^+$ observed |
|---|---|---|---|---|
| 145 | 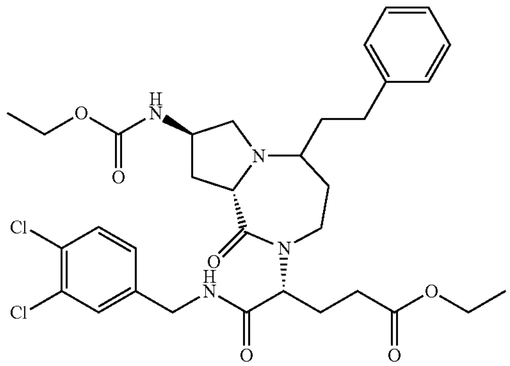 | D | 1.08 | 661.6/663.6 |
| 146 | 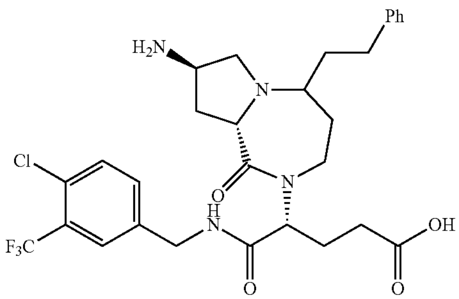 | A | 0.99 | 595.5/597.5 |

Example A TREX1 Exonuclease Assay

For human TREX1, the nucleotide sequence of the gene construct was codon optimized for expression in the bacterial host. The sequence was incorporated into the pMAL-c5e vector (NEB) downstream of a solubility-promoting MBP (maltose binding protein) fusion partner. The fusion protein product was expressed in *E. coli* strain BL21 (DE3) (Millipore) and purified in a series of chromatographic steps. Initial steps were conducted using a dextrin sepharose affinity column followed by a Q-sepharose ion exchange column (both GE Healthcare). After the second column the MBP partner was removed by incubation with enterokinase (NEB). Further purification was carried out with the second application of a Q-sepharose column followed by a Superdex 75 (GE Healthcare) size exclusion column. Finally, a heparin sepharose column (GE Healthcare) was applied to remove contaminating nucleotides. Similar methods were used in the preparation of the murine TREX1 enzyme and are described in Example B set forth below.

To evaluate the effect of compounds on TREX1 activity, test compounds were serially diluted (11-point, 3-fold) from 10 mM stock solutions and delivered to 384-well low-volume assay plates in 80 nL DMSO using an acoustic dispenser. Next, 4 μL of human TREX1 (0.5 nM), or murine TREX1 (1 nM), diluted in assay buffer (20 mM Tris pH 7.5, 5 mM $MgCl_2$, 100 μg/mL BSA, 0.002% Triton X-100, 2 mM DTT), was added to the assay plate. After incubating for 30 minutes, 4 μL of labeled DNA oligonucleotide (500 nM) in assay buffer was added to initiate TREX1 exonuclease activity. The reaction was allowed to proceed for 45 minutes at room temperature prior to the addition of 4 μL of 150 mM EDTA to halt TREX1 activity. Assay plates were equilibrated for an additional 30 minutes and read on an EnVision Plate Reader (Perkin Elmer) to measure fluorescence emission at 535 nm following excitation at 485 nm. Fluorescence was plotted as a function of log molar compound concentration and fit to a four-parameter dose-response equation to determine compound $IC_{50}$.

Compounds of the present invention were tested in the TREX1 Exonuclease assay described immediately above and the results shown in Table 28 below were obtained.

TABLE 28

| Example | Human TREX1 $IC_{50}$ (μM) |
|---|---|
| 1 | A |
| 2A | C |
| 2B | A |
| 3 | A |
| 4 | A |
| 5 | A |
| 6 | A |
| 7 | A |
| 8 | B |
| 9 | B |
| 10 | B |
| 11 | B |
| 12 | A |
| 13 | C |
| 14 | C |
| 15A | C |
| 15B | A |
| 16 | A |
| 17 | A |
| 18 | A |
| 19 | A |
| 20 | C |
| 21 | A |
| 22 | A |

TABLE 28-continued

| Example | Human TREX1 IC$_{50}$ (μM) |
|---|---|
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | B |
| 41 | C |
| 43 | B |
| 44 | A |
| 45 | B |
| 46 | B |
| 47 | B |
| 48 | B |
| 49 | A |
| 50 | B |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | B |
| 63 | A |
| 63 | A |
| 64 | A |
| 65 | A |
| 66 | B |
| 67 | B |
| 68 | C |
| 69 | B |
| 70 | A |
| 71 | B |
| 72 | B |
| 73 | B |
| 74 | A |
| 75 | A |
| 76 | A |
| 77 | A |
| 78 | A |
| 79 | A |
| 80 | B |
| 81 | A |
| 82 | B |
| 83 | A |
| 84 | C |
| 85 | C |
| 86 | B |
| 87 | C |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125A | A |
| 125B | A |
| 126 | B |
| 127 | B |
| 128 | C |
| 129 | C |
| 130 | A |
| 131 | A |
| 132 | A |
| 133 | A |
| 134 | A |
| 135 | A |
| 136 | A |
| 137 | A |
| 138 | A |
| 139 | B |
| 140 | A |
| 141 | A |
| 142 | A |
| 143 | C |
| 144 | A |
| 145 | C |
| 146 | A |

A: IC$_{50}$ < 1.00 μM;
B: IC$_{50}$ = 1.00 μM – 9.99 μM;
C: IC$_{50}$ = 10.0 μM – 100 μM;

Example B TREX1 Thermal Shift Binding Assay

The thermal shift assays used recombinant protein corresponding to human and murine TREX1. The protein encoding plasmid contained a N-terminal MBP (maltose binding protein) tag followed by the TREX1 coding sequence within the pMAL-c5E vector. The plasmid was transfected into a BL21 (DE3) *E. coli* expression strain. Protein was purified from the bacterial lysate using an Amylose resin column. The MBP tag was cleaved from the purified protein using recombinant enterokinase (EMD Millipore #69066-3). The cleaved TREX1 protein was further purified on a Q-Sepharose column followed by a heparin column.

Binding of compounds to both human and murine TREX1 were measured by protein thermal shift assays. (Huynh K, Partch C L. Current Protocols in Protein Science: Analysis of protein stability and ligand interactions by thermal shift assay. *Current protocols in protein science/editorial board*, John E Coligan. [et al]. 2015; 79:28.9.1-28.9.14. doi: 10.1002/0471140864.ps2809s79.). Thermal shift assays were conducted in sealed 96-well PCR plates containing 5 μM TREX1 protein, 100 μM compound, and 2 μM BODIPY FL-cystine (Sigma) in either 20 μL assay buffer (20 mM Tris, 7.5, 5 mM MgCl$_2$, 0.002% Triton X-100) or 20 μL phosphate buffered saline (PBS). Using a RT-qPCR machine (Mx3005P, Stratagene) changes in fluorescence (excitation at 492 nm and emission at 516 nm) were monitored as temperature was increased from 25° C. to 96° C. at a rate of 1° C. every 2 minutes. T. values were calculated from the first derivative plot of fluorescence intensity versus temperature. The results shown in Table 29 indicate the examples bind to human TREX1 and murine TREX1. ND indicates assay was not done.

TABLE 29

| Example number | Thermal shift cleaved human TREX1, ($\Delta$Tm ° C.) | | Thermal shift cleaved mouse TREX1, ($\Delta$Tm ° C.) | |
| --- | --- | --- | --- | --- |
| | PBS | Assay buffer | PBS | Assay buffer |
| Example 1 | A | A | B | B |
| Example 2B | A | A | B | B |
| Example 3 | A | A | B | B |
| Example 5 | A | A | B | B |
| Example 15B | ND | A | A | ND |

A: $\Delta T_m > 8°$ C.;
B: $8°$ C. $\geq \Delta T_m \geq 4°$ C.

Example C THP1 Monocyte Assay

A cell-based assay was established using THP1 Dual™ cells (Invivogen), a human monocyte cell line that has stable integration of an Interferon Stimulated Response Element (ISRE) Lucia reporter gene. The Lucia gene encodes a secreted luciferase reporter protein, under the control of an ISG54 minimal promoter in conjunction with five IFN-stimulated response elements. Activation of the cGAS-STING pathway in these cells leads to enhanced luciferase secretion. The assay was conducted in standard 384-well white tissue culture plates. Cells (25,000 in 25 μL RPMI 1640 containing 10% Heat-Inactivated FBS, 1× Glutagro, 10 mM HEPES, 1 mM sodium pyruvate, 1×Pen/Strep, 100 μg/mL Normocin, 100 μg/mL Zeocin, 10 μg/mL Blasticidin) were added to the plate followed by 25 μL of compound in the same media+0.2% DMSO. The assay was incubated for 48 hours at 37° C. in 5% CO$_2$. An aliquot of 5 μl was removed to combine with 12.5 μL of the luciferase detection reagent, QUANTI-Luc™ Gold (Invivogen) in a white 384-well plate. The luminescent signal was then read using an EnVision plate reader (Perkin Elmer). The fold activation was calculated by dividing the signal in wells containing test compound by the signal in the control wells without compound (see Table 30).

TABLE 30

| Example compound | Fold activation @ 10 μM |
| --- | --- |
| Example 15 | 12 |
| Example 16 | 2 |
| Example 4 | 4 |
| Example 118 | 7 |

Example D RT-qPCR Assay

The RT-qPCR assay was used to assess the ability of TREX1 inhibitors to enhance the expression of interferon stimulated genes (ISGs) in cells transfected with double-stranded DNA. The double stranded DNA used to transfect cells was VACV-70 (Invivogen), a 70 base pair oligonucleotide containing viral DNA motifs (Unterholzner L. et al., 2010. IFI16 is an innate immune sensor for intracellular DNA. Nat Immunol. 11(11):997-1004). Human THP1 Dual™ cells (Invivogen), were treated with test compound in the presence or absence of 1,200 ng/mL VACV-70, or with VACV-70 alone, for 24 hours. Cells were harvested by centrifugation and washed with phosphate buffer saline. Total RNA was isolated using Qiagen RNeasy mini kit. Genomic DNA was degraded using Thermo Scientific DNase 1 kit. Total RNA was quantified using a Nanodrop spectrophotometer. Using equal amounts of RNA, cDNA was synthesized using Invitrogen Superstrand III First Strand synthesis kit. Target and reference gene expression levels were determined by RT-qPCR using TaqMan gene expression assays and a Stratagene Mx3005P QPCR system (all reagents were from TaqMan, Applied Biosystems). Data were analyzed by the Comparative $C_T$ method. GAPDH was used for normalization. Target genes that were analyzed included interferon stimulated genes (INF-β, CXCL10, IFIT1, IFIT2, IFIT3, IFI44, and IFI44L). The data are shown in Table 31.

TABLE 31

| | IFN-β | CXCL10 | IFIT1 | IFIT2 | IFIT3 | IFI44 | IFI44L |
| --- | --- | --- | --- | --- | --- | --- | --- |
| Unstimulated control | 1 | 1 | 1 | 1 | 1 | 1 | 1 |
| Unstimulated control | 1 | 1 | 1 | 1 | 1 | 1 | 1 |
| VACV70 alone | 732 | 185 | 813 | 518 | 355 | 827 | 2076 |
| (Example 15) alone | 7 | 2 | 19 | 44 | 25 | 54 | 65 |
| (Example 15) + VACV70 | 2725 | 729 | 3580 | 7928 | 2297 | 2929 | 5263 |
| (Example 16) alone | 5 | 1 | 10 | 32 | 20 | 20 | 20 |
| (Example 16) + VACV70 | 3449 | 712 | 4373 | 9581 | 3348 | 3969 | 3348 |
| (Example 4) alone | 6 | 2 | 11 | 41 | 25 | 14 | 15 |
| (Example 4) + VACV70 | 3692 | 1941 | 3676 | 8218 | 2729 | 3618 | 2729 |
| (Example 118) alone | 3 | 2 | 8 | 26 | 16 | 20 | 16 |

Example E Human Cellular EC50 Reporter Assay

Example E is a cell-based assay for TREX1 inhibitors using THP1 Dual™ cells (Invivogen), a human monocyte cell line that has stable integration of an Interferon Stimulated Response Element (ISRE) Lucia reporter gene. The Lucia gene encodes a secreted luciferase reporter protein, under the control of an ISG54 minimal promoter in conjunction with five IFN-stimulated response elements. Activation of the cGAS-STING pathway in THP1 Dual™ cells leads to enhanced luciferase secretion and increased luminescence.

Human Cellular Reporter Assay

A cell-based assay was established using THP1 Dual™ cells (InvivoGen), a human monocyte cell line that has stable integration of an Interferon Stimulated Response Element (ISRE) Lucia reporter gene. The Lucia gene encodes a secreted luciferase reporter protein, under the control of an ISG54 minimal promoter in conjunction with five IFN-stimulated response elements. Activation of the cGAS-STING pathway in these cells leads to enhanced luciferase secretion. Three days prior to the assay, cells were transferred to a T75 flask at a density of $3.0\times10^5$ cells/ml in 20 ml of serum-starved media (RPMI 1640 containing 1% Heat-Inactivated FBS, 1× Glutagro, 10 mM HEPES, 1 mM sodium pyruvate, 1×Pen/Strep, 100 µg/ml Normocin, 100 µg/ml Zeocin, 10 µg/ml Blasticidin). On the day of assay cells were collected by centrifugation, washed in 1×DPBS, and resuspended in the 1% serum media at $3.3\times10^5$ cells/ml. An aliquot of an aqueous solution of the DNA oligonucleotide G3-YSD (InvivoGen) at 1 mg/ml was diluted 100-fold into the transfection reagent LyoVec (InvivoGen) and incubated at ambient temperature for 50 min to allow complex formation. Test compounds in DMSO were transferred to a standard 96-well tissue culture plate via acoustic dispense of 0.54 µl per well. Serum-starved cells were batch transfected with complex at a final DNA concentration of 10 ng/ml for 60 min at ambient temperature before dispensing 180 ul (60,000 cells) per well into the assay plate. The assay plate was then incubated in a humidified chamber at 37° C. in 5% $CO_2$ for three days. An aliquot of 10 µl was removed from each well to combine with 10 µl of the luciferase detection reagent, QUANTI-Luc™ Gold (InvivoGen) in a white 384-well plate. The luminescent signal was then read using an EnVision plate reader (Perkin Elmer). An $EC_{50}$ for each compound was determined by plotting the signal as a function of log molar concentration and fitting to a four parameter logistic equation. (see Table 32).

TABLE 32

| Example | EC50 |
|---|---|
| 22 | A |
| 30 | B |
| 119 | A |
| 120 | B |
| 137 | A |
| 138 | A |

A = <1 µM
B = 1-10 µM

Example F MB49-Luc Tumor Bearing Mice Treated with Example 15B

The efficacy of the TREX1 inhibitors of the present invention can also be measured in a variety of in vivo assays. Exemplary mammals that can provide models to test the effectiveness of the TREX1 inhibitors of the present invention as anticancer agents include, but are not limited to, mice. Models of tumor growth and other tumor measurements can be used to assess the effectiveness of the anticancer agents described in the current invention. Example F describes an in vivo model of tumor growth in C57BL/6 mice. Compounds of the present invention can be tested in this model for their ability to inhibit growth of tumors. Compounds of the present invention can be used in combinatorial strategies to maximizing the immunogenicity of radiation therapy (Vanpouille-Box (2017) Nature Commun. 8, 81658). Demonstration of efficacy in this model supports the utility of TREX1 inhibitors of the present invention for treatment of oncological diseases.

Ten week old female C57BL/6 mice were purchased from Jackson Laboratory (www.jax.org). During the study, the care and use of animals was conducted in accordance with the regulations of the Association for Assessment and Accreditation of Laboratory 15 Animal Care (AAALAC). The protocol and any amendment(s) or procedures involving the care and use of animals in the study was reviewed and approved by the Institutional Animal Care and Use Committee (IACUC) of Invivotek prior the initiation of the study. Mice were acclimated for 72 hours before subcutaneous implantation of cells. Mice were group housed (n=5/cage) and maintained on a 12 hour light: dark schedule. Reverse osmosis chlorinated water and irradiated food Purina rodent diet #5053 (Fisher Feeds, Bound Brook, N.J.) were available ad libitum.

MB49-luc cells were maintained in vitro as a monolayer culture in DMEM+10% heat-inactivated FBS and harvested at passage. Mice were inoculated subcutaneously with 0.5× 106 MB49-Luc tumor cells in 100 µL serum-free RPMI 1640 Media on the lower right flank. Tumors were measured in two dimensions using calipers. Tumor volumes were calculated using the formula: volume (mm3)=(length× width2)/2. Animals were euthanized when the tumor volume reached 2,000 mm3.

Tumors grew for 4 days to an average size of 100 mm3. Animals were randomized by tumor volume and body weight into groups of ten mice per treatment group on Day 0. Mice receiving radiotherapy were treated by irradiation with 10 Gy using a Small Animal Radiation Research Platform (xstrahl) on Day 0. Mice were treated by intratumoral injection of 100 µg of Example 15B in 30 µL of PBS containing 10% Solutol or PBS containing 10% Solutol alone on Days 1, 3, 6, and 9. All vehicle treated animals achieved 2,000 mm³ tumor size and were euthanized. By Day 20, mice treated with Example 15B and vehicle and 10 Gy radiation had reduced tumor volumes compare to mice treated with vehicle alone, 10 Gy radiation and vehicle, or Example 15B and vehicle. The results are shown in FIG. 1.

The invention claimed is:
1. A compound of Formula I:

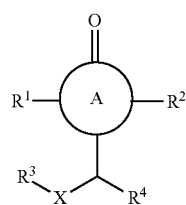

or a pharmaceutically acceptable salt, solvate, stereoisomer, or tautomer thereof,
wherein:

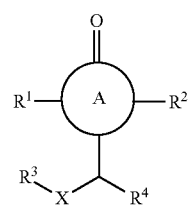

is

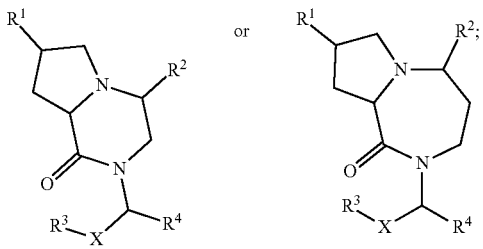

X is —$C_1$-$C_6$ alkylene-NR$^5$C(O)—, —$C_1$-$C_6$ alkylene-NR$^5$S(O)$_2$—, —C(O)NR$^5$—, —C(O)NR$^5$S(O)$_2$—, —C(O)NHet-, or a 5-membered heteroarylene;
  wherein NHet is a monocyclic 5- to 7-membered heterocyclylene or a bicyclic 9- to 12-membered heterocyclylene;
  wherein NHet contains at least 1 nitrogen heteroatom;
  wherein NHet is bonded to —C(O)— via a nitrogen atom;
  wherein NHet is optionally substituted with 1 or more substituents independently selected from the group consisting of halo, CN, $C_1$-$C_4$ alkyl, $C_1$-$C_4$ haloalkyl, OH, O$C_1$-$C_4$ alkyl, O$C_1$-$C_4$ haloalkyl, and =O; and
  wherein the 5-membered heteroarylene contains at least 1 nitrogen heteroatom;
$R^1$ is $C_1$-$C_6$ alkylene-NR$^5$R$^6$ or NR$^5$R$^6$;
$R^2$ is $C_1$-$C_6$ alkyl, $C_1$-$C_6$ alkylene-O—$C_6$-$C_{10}$ aryl, $C_1$-$C_6$ alkylene-O-5- to 10-membered heteroaryl, $C_1$-$C_6$ alkylene-S—$C_6$-$C_{10}$ aryl, $C_1$-$C_6$ alkylene-S-5- to 10-membered heteroaryl, $C_1$-$C_6$ alkylene-S(O)—$C_6$-$C_{10}$ aryl, $C_1$-$C_6$ alkylene-S(O)-5- to 10-membered heteroaryl, $C_1$-$C_6$ alkylene-S(O)$_2$—$C_6$-$C_{10}$ aryl, $C_1$-$C_6$ alkylene-S(O)$_2$-5- to 10-membered heteroaryl, $C_1$-$C_6$ alkylene-$C_6$-$C_{10}$ aryl, or $C_1$-$C_6$ alkylene-5- to 10-membered heteroaryl, wherein any $C_6$-$C_{10}$ aryl or 5- to 10-membered heteroaryl is optionally and independently substituted with 1 or more substituents independently selected from the group consisting of halo, CN, $C_1$-$C_4$ alkyl, $C_1$-$C_4$ haloalkyl, OH, O$C_1$-$C_4$ alkyl, and O$C_1$-$C_4$ haloalkyl;
$R^3$ is $C_1$-$C_6$ alkyl, $C_1$-$C_6$ alkylene-$C_3$-$C_6$ cycloalkyl, $C_1$-$C_6$ alkylene-$C_6$-$C_{10}$ aryl, $C_1$-$C_6$ alkylene-5- to 10-membered heteroaryl, or $C_6$-$C_{10}$ aryl, wherein any $C_3$-$C_6$ cycloalkyl, $C_6$-$C_{10}$ aryl, or 5- to 10-membered heteroaryl is optionally and independently substituted with 1 or more substituents independently selected from the group consisting of halo, CN, $C_1$-$C_4$ alkyl, $C_1$-$C_4$ haloalkyl, OH, O$C_1$-$C_4$ alkyl, and O$C_1$-$C_6$ haloalkyl;
$R^4$ is $C_1$-$C_6$ alkyl;
  wherein the $C_1$-$C_6$ alkyl is optionally substituted with 1 or more substituents independently selected from the group consisting of CN, C(O)NR$^8$R$^9$, C(O)NR$^8$S(O)$_2$R$^9$, C(O)NR$^8$S(O)$_2$NR$^{28}$R$^{29}$, C(O)OH, C(O)OR$^{27}$, NR$^8$R$^9$, NR$^{28}$C(NH)NR$^8$R$^9$, NR$^{28}$C(O)NR$^8$R$^9$, NR$^{28}$C(O)NR$^8$S(O)$_2$R$^9$, NR$^8$S(O)$_2$R$^9$, OH, ONR$^8$R$^9$, SR$^9$, S(O)R$^9$, S(O)$_2$R$^9$, S(O)$_2$NR$^8$R$^9$, S(O)$_2$OH, $C_6$-$C_{10}$ aryl, and a 5-membered heteroaryl, wherein each 5-membered heteroaryl independently contains at least 1 nitrogen heteroatom; and
  wherein any $C_6$-$C_{10}$ aryl or 5-membered heteroaryl is optionally and independently substituted with 1 or more substituents independently selected from the group consisting of halo, CN, $C_1$-$C_4$ alkyl, $C_1$-$C_4$ haloalkyl, OH, =O, O$C_1$-$C_4$ alkyl, and O$C_1$-$C_4$ haloalkyl; or X and $R^4$, taken together with the carbon atom to which they are attached, form a monocyclic 5- to 7-membered heterocyclyl, wherein the monocyclic 5- to 7-membered heterocyclyl is optionally substituted with 1 or more substituents independently selected from the group consisting of C(O)R$^{25}$, S(O)$_2$R$^{25}$, =O, and R$^{25}$;

each $R^5$ is independently H, $C_1$-$C_6$ alkyl, or $C_1$-$C_6$ haloalkyl;

each $R^6$ is independently H, $C_1$-$C_6$ alkyl, $C_1$-$C_6$ haloalkyl, or C(O)R$^7$;

each $R^7$ is independently $C_1$-$C_6$ alkyl or O$C_1$-$C_6$ alkyl;

each $R^8$ is independently H, $C_1$-$C_4$ alkyl, $C_1$-$C_4$ haloalkyl, C(O)$C_1$-$C_4$ alkyl, O$C_1$-$C_4$ alkyl, or O$C_1$-$C_4$ haloalkyl;

each $R^9$ is independently H, $C_1$-$C_4$ alkyl, OH, O$C_1$-$C_4$ alkyl, $C_3$-$C_6$ cycloalkyl, or $C_6$-$C_{10}$ aryl, wherein each $C_1$-$C_4$ alkyl, O$C_1$-$C_4$ alkyl, $C_3$-$C_6$ cycloalkyl, and $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, =O, O$C_1$-$C_4$ alkyl, and O$C_1$-$C_4$ haloalkyl;

$R^{25}$ is $C_1$-$C_6$ alkylene-$C_3$-$C_6$ cycloalkyl, $C_1$-$C_6$ alkylene-$C_6$-$C_{10}$ aryl, $C_1$-$C_6$ alkylene-5- to 10-membered heteroaryl, or $C_6$-$C_{10}$ aryl;
  wherein the $C_3$-$C_6$ cycloalkyl of the $C_1$-$C_6$ alkylene-$C_3$-$C_6$ cycloalkyl, $C_6$-$C_{10}$ aryl of the $C_1$-$C_6$ alkylene-$C_6$-$C_{10}$ aryl, 5- to 10-membered heteroaryl of the $C_1$-$C_6$ alkylene-5- to 10-membered heteroaryl, or $C_6$-$C_{10}$ aryl is substituted with 1 or more substituents independently selected from the group consisting of halo, CN, $C_1$-$C_6$ alkyl, $C_1$-$C_4$ haloalkyl, OH, O$C_1$-$C_4$ alkyl, and O$C_1$-$C_6$ haloalkyl; and
  wherein each $C_1$-$C_6$ alkyl substituent is optionally and independently substituted with 1 or more substituents independently selected from the group consisting of CN, C(O)NR$^8$R$^9$, C(O)NR$^8$S(O)$_2$R$^9$, C(O)NR$^8$S(O)$_2$NR$^{28}$R$^{29}$, C(O)OH, C(O)OR$^{27}$, NR$^8$R$^9$, NR$^{28}$C(O)NR$^8$R$^9$, NR$^{28}$C(O)NR$^8$S(O)$_2$R$^9$, NR$^8$S(O)$_2$R$^9$, OH, ONR$^8$R$^9$, SR$^9$, S(O)R$^9$, S(O)$_2$R$^9$, S(O)$_2$NR$^8$R$^9$, S(O)$_2$OH, and $C_6$-$C_{10}$ aryl;

$R^{27}$ is $C_1$-$C_6$ alkyl or $C_1$-$C_6$ alkylene-C(O)NR$^8$R$^9$;

each $R^{28}$ is independently H, $C_1$-$C_4$ alkyl, $C_1$-$C_4$ haloalkyl, O$C_1$-$C_4$ alkyl, or O$C_1$-$C_4$ haloalkyl; and each $R^{29}$ is independently H, $C_1$-$C_4$ alkyl, $C_1$-$C_4$ haloalkyl, O$C_1$-$C_4$ alkyl, or O$C_1$-$C_4$ haloalkyl;

with the provisos that:
  (1) if X is NHet, wherein NHet is a bicyclic dichloro-substituted heterocyclyl, then $R^3$ is additionally H; and
  (2) if X and $R^4$, taken together with the carbon atom to which they are attached, form a monocyclic 5- to 7-membered heterocyclyl, wherein the monocyclic 5- to 7-membered heterocyclyl is optionally substituted with 1 or more substituents independently selected from the group consisting of C(O)R$^{25}$, S(O)$_2$R$^{25}$, =O, and R$^{25}$, then $R^3$ is additionally H.

2. The compound of claim 1, wherein the compound is of the following formula:

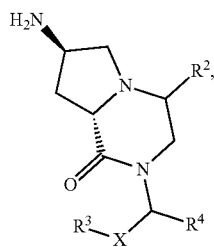

or a pharmaceutically acceptable salt, solvate, or tautomer thereof.

3. The compound of claim 1, wherein the compound is of the following formula:

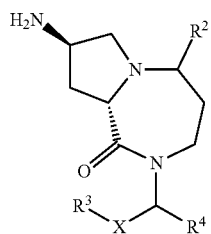

or a pharmaceutically acceptable salt, solvate, or tautomer thereof.

4. The compound of claim 3, or a pharmaceutically acceptable salt, solvate, or tautomer thereof, wherein X is —C(O)NR$^5$—, —C(O)NR$^5$S(O)$_2$—, or —C(O)NHet-.

5. The compound of claim 3, or a pharmaceutically acceptable salt, solvate, or tautomer thereof, wherein R$^2$ is C$_1$-C$_6$ alkylene-C$_6$-C$_{10}$ aryl or C$_1$-C$_6$ alkylene-5- to 10-membered heteroaryl, wherein the C$_6$-C$_{10}$ aryl or 5-to 10-membered heteroaryl is optionally substituted with 1 or more substituents independently selected from the group consisting of halo, CN, C$_1$-C$_4$ alkyl, C$_1$-C$_4$ haloalkyl, OH, OC$_1$-C$_4$ alkyl, and OC$_1$-C$_4$ haloalkyl.

6. The compound of claim 5, or a pharmaceutically acceptable salt, solvate, or tautomer thereof, wherein R$^2$ is CH$_2$CH$_2$-phenyl.

7. The compound of claim 6, or a pharmaceutically acceptable salt, solvate, or tautomer thereof, wherein:
X is —C(O)NH—; and
R$^3$ is:

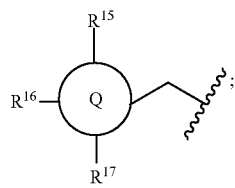

wherein:
Q is phenyl or pyridinyl;
R$^{15}$ is H, halo, C$_1$-C$_4$ alkyl, C$_1$-C$_4$ haloalkyl, OC$_1$-C$_4$ alkyl, and OC$_1$-C$_6$ haloalkyl;
R$^{16}$ is H, halo, C$_1$-C$_4$ alkyl, C$_1$-C$_4$ haloalkyl, OC$_1$-C$_4$ alkyl, and OC$_1$-C$_6$ haloalkyl; and
R$^{17}$ is H, halo, C$_1$-C$_4$ alkyl, C$_1$-C$_4$ haloalkyl, OC$_1$-C$_4$ alkyl, and OC$_1$-C$_6$ haloalkyl.

8. The compound of claim 3, or a pharmaceutically acceptable salt, solvate, or tautomer thereof, wherein R$^4$ is C$_1$-C$_6$ alkyl, wherein the C$_1$-C$_6$ alkyl is optionally substituted with 1 substituent selected from the group consisting of CN, C(O)NR$^8$R$^9$, C(O)OH, C(O)OR$^{27}$, NHC(NH)NH$_2$, and NR$^8$S(O)$_2$R$^9$.

9. The compound of claim 8, or a pharmaceutically acceptable salt, solvate, or tautomer thereof, wherein:
R$^8$ is H, CH$_3$, or CH$_2$CH$_3$;
R$^9$ is H, C$_1$-C$_4$ alkyl, or C$_3$-C$_6$ cycloalkyl; and
R$^{27}$ is C$_1$-C$_6$ alkyl or CH$_2$C(O)NR$^8$R$^9$.

10. The compound of claim 3, or a pharmaceutically acceptable salt, solvate, or tautomer thereof, wherein X and R$^4$, taken together with the carbon atom to which they are attached, form a monocyclic 5- to 7-membered heterocyclyl, wherein the monocyclic 5- to 7-membered heterocyclyl is optionally substituted with 1 or more substituents independently selected from the group consisting of C(O)R$^{25}$, S(O)$_2$R$^{25}$, =O, and R$^{25}$.

11. The compound of claim 10, or a pharmaceutically acceptable salt, solvate, or tautomer thereof, wherein R$^{25}$ is C$_1$-C$_6$ alkylene-C$_6$-C$_{10}$ aryl or C$_6$-C$_{10}$ aryl, wherein the C$_6$-C$_{10}$ aryl is substituted with 1 or more substituents independently selected from the group consisting of halo, CN, C$_1$-C$_4$ alkyl, C$_1$-C$_4$ haloalkyl, OH, OC$_1$-C$_4$ alkyl, and OC$_1$-C$_6$ haloalkyl.

12. The compound of claim 1, or a pharmaceutically acceptable salt, solvate, stereoisomer, or tautomer thereof, wherein:
X is —C$_1$-C$_6$ alkylene-NR$^5$C(O)—, —C$_1$-C$_6$ alkylene-NR$^5$S(O)$_2$—, —C(O)NR$^5$—, —C(O)NR$^5$S(O)$_2$—, or a 5-membered heteroarylene, wherein the 5-membered heteroarylene contains at least 1 nitrogen heteroatom; and
R$^4$ is C$_1$-C$_6$ alkyl;
wherein the C$_1$-C$_6$ alkyl is optionally substituted with 1 or more substituents independently selected from the group consisting of CN, C(O)NR$^8$R$^9$, C(O)NR$^8$S(O)$_2$R$^9$, C(O)NR$^8$S(O)$_2$NR$^{28}$R$^{29}$, C(O)OH, NR$^8$R$^9$, NR$^{28}$C(O)NR$^8$R$^9$, NR$^{28}$C(O)NR$^8$S(O)$_2$R$^9$, NR$^8$S(O)$_2$R$^9$, OH, ONR$^8$R$^9$, SR$^9$, S(O)R$^9$, S(O)$_2$R$^9$, S(O)$_2$NR$^8$R$^9$, S(O)$_2$OH, C$_6$-C$_{10}$ aryl, and a 5-membered heteroaryl, wherein each 5-membered heteroaryl independently contains at least 1 nitrogen heteroatom; and
wherein any C$_6$-C$_{10}$ aryl or 5-membered heteroaryl is optionally and independently substituted with 1 or more substituents independently selected from the group consisting of halo, CN, C$_1$-C$_4$ alkyl, C$_1$-C$_4$ haloalkyl, OH, =O, OC$_1$-C$_4$ alkyl, and OC$_1$-C$_4$ haloalkyl.

13. The compound of claim 12, or a pharmaceutically acceptable salt, solvate, stereoisomer, or tautomer thereof, wherein:
X is —C$_1$-C$_6$ alkylene-NR$^5$C(O)—, —C(O)NR$^5$—, —C(O)NR$^5$S(O)$_2$—, or a 5-membered heteroarylene, wherein the 5-membered heteroarylene contains at least 1 nitrogen heteroatom;
R$^2$ is C$_1$-C$_6$ alkyl, C$_1$-C$_6$ alkylene-O—C$_6$-C$_{10}$ aryl, C$_1$-C$_6$ alkylene-O-5- to 10-membered heteroaryl, C$_1$-C$_6$ alkylene-S—C$_6$-C$_{10}$ aryl, C$_1$-C$_6$ alkylene-S-5- to 10-membered heteroaryl, C$_1$-C$_6$ alkylene-S(O)—C$_6$-C$_{10}$ aryl, C$_1$-C$_6$ alkylene-S(O)-5- to 10-membered heteroaryl, C$_1$-C$_6$ alkylene-S(O)$_2$—C$_6$-C$_{10}$ aryl, C$_1$-C$_6$ alkylene-S(O)$_2$—5- to 10-membered heteroaryl, or C$_1$-C$_6$ alkylene-C$_6$-C$_{10}$ aryl, wherein any C$_6$-C$_{10}$ aryl or 5- to 10-membered heteroaryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_4$ haloalkyl;

$R^4$ is $C_1$-$C_6$ alkyl;

wherein the $C_1$-$C_6$ alkyl is optionally substituted with 1 or more substituents independently selected from the group consisting of CN, $C(O)NR^8R^9$, $C(O)OH$, OH, $C_6$-$C_{10}$ aryl, and a 5-membered heteroaryl, wherein each 5-membered heteroaryl independently contains at least 1 nitrogen heteroatom; and wherein any $C_6$-$C_{10}$ aryl or 5-membered heteroaryl is optionally and independently substituted with 1 or more substituents independently selected from the group consisting of halo, CN, $C_1$-$C_4$ alkyl, $C_1$-$C_4$ haloalkyl, OH, =O, $OC_1$-$C_4$ alkyl, and $OC_1$-$C_4$ haloalkyl;

each $R^8$ is independently H, $C_1$-$C_4$ alkyl, $C_1$-$C_4$ haloalkyl, or $OC_1$-$C_4$ alkyl; and each $R^9$ is independently H, $C_1$-$C_4$ alkyl, $C_1$-$C_4$ haloalkyl, or $OC_1$-$C_4$ alkyl.

14. The compound of claim 12, or a pharmaceutically acceptable salt, solvate, stereoisomer, or tautomer thereof, wherein:

X is —$C_1$-$C_6$ alkylene-$NR^5C(O)$—, —$C(O)NR^5$—, or a 5-membered heteroarylene, wherein the 5-membered heteroarylene contains at least 1 nitrogen heteroatom;

$R^2$ is $C_1$-$C_6$ alkyl, $C_1$-$C_6$ alkylene-O—$C_6$-$C_{10}$ aryl, $C_1$-$C_6$ alkylene-S—$C_6$-$C_{10}$ aryl, or $C_1$-$C_6$ alkylene-$C_6$-$C_{10}$ aryl, wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_4$ haloalkyl;

$R^3$ is $C_1$-$C_6$ alkyl, $C_1$-$C_6$ alkylene-$C_6$-$C_{10}$ aryl, $C_1$-$C_6$ alkylene-5-membered heteroaryl, or $C_6$-$C_{10}$ aryl, wherein any $C_6$-$C_{10}$ aryl or 5-membered heteroaryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_6$ haloalkyl;

$R^4$ is $C_1$-$C_6$ alkyl;

wherein the $C_1$-$C_6$ alkyl is optionally substituted with 1 or more substituents independently selected from the group consisting of CN, $C(O)NR^8R^9$, $C(O)OH$, OH, $C_6$-$C_{10}$ aryl, and a 5-membered heteroaryl, wherein each 5-membered heteroaryl independently contains at least 1 nitrogen heteroatom; and wherein any $C_6$-$C_{10}$ aryl or 5-membered heteroaryl is optionally and independently substituted with 1 or more substituents independently selected from the group consisting of halo, CN, $C_1$-$C_4$ alkyl, $C_1$-$C_4$ haloalkyl, OH, =O, $OC_1$-$C_4$ alkyl, and $OC_1$-$C_4$ haloalkyl;

each $R^8$ is independently H, $C_1$-$C_4$ alkyl, $C_1$-$C_4$ haloalkyl, or $OC_1$-$C_4$ alkyl; and each $R^9$ is independently H, $C_1$-$C_4$ alkyl, $C_1$-$C_4$ haloalkyl, or $OC_1$-$C_4$ alkyl.

15. The compound of claim 12, or a pharmaceutically acceptable salt, solvate, stereoisomer, or tautomer thereof, wherein:

X is —$C_1$-$C_6$ alkylene-$NR^5C(O)$— or —$C(O)NR^5$—;

$R^2$ is $C_1$-$C_6$ alkyl, $C_1$-$C_6$ alkylene-O—$C_6$-$C_{10}$ aryl, or $C_1$-$C_6$ alkylene-$C_6$-$C_{10}$ aryl, wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_4$ haloalkyl;

$R^3$ is $C_1$-$C_6$ alkyl, $C_1$-$C_6$ alkylene-$C_6$-$C_{10}$ aryl, or $C_6$-$C_{10}$ aryl, wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_6$ haloalkyl;

$R^4$ is $C_1$-$C_6$ alkyl;

wherein the $C_1$-$C_6$ alkyl is optionally substituted with 1 or more substituents independently selected from the group consisting of CN, $C(O)NR^8R^9$, $C(O)OH$, OH, and $C_6$-$C_{10}$ aryl; and wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_4$ haloalkyl;

each $R^8$ is independently H, $C_1$-$C_4$ alkyl, $C_1$-$C_4$ haloalkyl, or $OC_1$-$C_4$ alkyl; and each $R^9$ is independently H, $C_1$-$C_4$ alkyl, $C_1$-$C_4$ haloalkyl, or $OC_1$-$C_4$ alkyl.

16. The compound of claim 12, or a pharmaceutically acceptable salt, solvate, stereoisomer, or tautomer thereof, wherein:

X is —$C_1$-$C_6$ alkylene-$NR^5C(O)$— or —$C(O)NR^5$—;

$R^2$ is $C_1$-$C_6$ alkyl or $C_1$-$C_6$ alkylene-$C_6$-$C_{10}$ aryl, wherein the $C_6$-$C_{10}$ aryl is optionally substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_4$ haloalkyl;

$R^3$ is $C_1$-$C_6$ alkyl, $C_1$-$C_6$ alkylene-$C_6$-$C_{10}$ aryl, or $C_6$-$C_{10}$ aryl, wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_6$ haloalkyl;

$R^4$ is $C_1$-$C_6$ alkyl;

wherein the $C_1$-$C_6$ alkyl is optionally substituted with 1 or more substituents independently selected from the group consisting of $C(O)NR^8R^9$, $C(O)OH$, OH, and $C_6$-$C_{10}$ aryl; and wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_4$ haloalkyl;

each $R^5$ is independently H or $C_1$-$C_6$ alkyl;

each $R^6$ is independently H, $C_1$-$C_6$ alkyl, or $C(O)R^7$;

each $R^8$ is independently H, $C_1$-$C_4$ alkyl, or $C_1$-$C_4$ haloalkyl; and each $R^9$ is independently H, $C_1$-$C_4$ alkyl, or $C_1$-$C_4$ haloalkyl.

17. The compound of claim 12, or a pharmaceutically acceptable salt, solvate, stereoisomer, or tautomer thereof, wherein:

X is —$C(O)NR^5$—;

$R^1$ is $NR^5R^6$;

$R^2$ is $C_1$-$C_6$ alkyl or $C_1$-$C_6$ alkylene-$C_6$-$C_{10}$ aryl, wherein the $C_6$-$C_{10}$ aryl is optionally substituted with 1 or more substituents independently selected from the group consisting of halo, CN, $C_1$-$C_4$ alkyl, $C_1$-$C_4$ haloalkyl, and OH;

$R^3$ is $C_1$-$C_6$ alkyl, $C_1$-$C_6$ alkylene-$C_6$-$C_{10}$ aryl, or $C_6$-$C_{10}$ aryl, wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, and OH;

$R^4$ is $C_1$-$C_6$ alkyl;

wherein the $C_1$-$C_6$ alkyl is optionally substituted with 1 or more substituents independently selected from the group consisting of C(O)OH, OH, and $C_6$-$C_{10}$ aryl; and wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, and OH;

each $R^5$ is independently H or $C_1$-$C_6$ alkyl; and each $R^6$ is independently H, $C_1$-$C_6$ alkyl, or C(O)$R^7$.

18. A pharmaceutical composition comprising a pharmaceutically acceptable carrier and a compound of claim 1, or a pharmaceutically acceptable salt, solvate, stereoisomer, or tautomer thereof, alone or in combination with another therapeutic agent.

19. The pharmaceutical composition of claim 18, wherein the other therapeutic agent is selected from the group consisting of an anti-cancer agent, an anti-viral compound, an adjuvant, an antigen, a biotherapeutic agent, a cell transfected with a gene that encodes an immune stimulating cytokine, a checkpoint inhibitor, a chemotherapeutic agent, a cytotoxic agent, an immunogenic agent, an immunomodulatory cell line, a lipid, a liposome, and a peptide.

20. A method for treating bladder cancer in a subject, wherein the method comprises administering to the subject in need thereof a therapeutically effective amount of a compound of claim 1, or a pharmaceutically acceptable salt, solvate, stereoisomer, or tautomer thereof.

21. The method of claim 20, wherein the bladder cancer is non-muscle invasive bladder cancer with bacillus Calmette-Guérin (BCG) resistance.

22. A method for treating bladder cancer in a subject, wherein the method comprises administering to the subject in need thereof a therapeutically effective amount of the pharmaceutical composition of claim 18.

* * * * *